US008153813B2

(12) United States Patent
Black et al.

(10) Patent No.: US 8,153,813 B2
(45) Date of Patent: Apr. 10, 2012

(54) BENZOTHIAZOLE AND BENZOOXAZOLE DERIVATIVES AND METHODS OF USE

(75) Inventors: Lawrence A. Black, Libertyville, IL (US); Marlon D. Cowart, Round Lake Beach, IL (US); Gregory A. Gfesser, Lindenhurst, IL (US); Brian D. Wakefield, Vernon Hills, IL (US); Robert J. Altenbach, Chicago, IL (US); Huaqing Liu, Buffalo Grove, IL (US); Chen Zhao, Libertyville, IL (US); Gin C. Hsieh, Long Grove, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 12/337,433

(22) Filed: Dec. 17, 2008

(65) Prior Publication Data

US 2009/0163464 A1    Jun. 25, 2009

Related U.S. Application Data

(60) Provisional application No. 61/015,513, filed on Dec. 20, 2007.

(51) Int. Cl.
A61K 31/454     (2006.01)
A61K 31/4545    (2006.01)
C07D 417/04     (2006.01)
C07D 417/14     (2006.01)

(52) U.S. Cl. ........ 548/162; 514/367; 514/321; 514/374; 514/233.8; 514/252.06; 514/318; 544/135; 544/333; 544/238; 546/193; 546/198

(58) Field of Classification Search .................... 548/162
See application file for complete search history.

(56) References Cited

U.S. PATENT DOCUMENTS

| 3,654,296 | A | 4/1972 | Bolhofer |
| 2004/0224952 | A1 | 11/2004 | Cowart et al. |
| 2007/0078133 | A1 | 4/2007 | Liu et al. |

FOREIGN PATENT DOCUMENTS

| JP | 02/306916 | A | * | 12/1990 |
| JP | 2306916 | | | 12/1990 |
| WO | WO-0177092 | A1 | | 10/2001 |
| WO | WO-2004043458 | A1 | | 5/2004 |
| WO | WO2006066173 | A2 | | 6/2006 |
| WO | WO2006103537 | A2 | | 10/2006 |
| WO | WO2006103546 | A2 | | 10/2006 |
| WO | WO2007038074 | A1 | | 4/2007 |

OTHER PUBLICATIONS

An English translation of JP 02-306916, Dec. 20, 1990.*
Arrang et al., "Auto-inhibition of brain histamine release mediated by a novel class (H.sub.3) of histamine receptor," Nature, vol. 302, pp. 832-837, 1983.
Arrang et al., "Highly potent and selective ligands for histamine H.sub.3-receptors," Nature, vol. 327, pp. 117-123, 1987.
Arrang et al., "Histamine H.sub.3 receptor binding sites in rat brain membranes: modulations by guanine nucleotides and divalent cations," European Journal of Pharmacology, vol. 188, pp. 219-227, 1990.
Barbier, A .J. et al., "Acute wake-promoting actions of JNJ-5207852, a novel, diamine-based H.sub.3 antagonist," Br. J. of Pharm., vol. 143, pp. 649-661, 2004.
Baudoin, O., et al., "Palladium-Catalyzed Borylation of Ortho-Substituted Phenyl Halides and Application to the One-Pot Synthesis of 2,2'-Disubstituted Biphenyls," J. Org. Chem., vol. 65, pp. 9268-9271, 2000.
Benaglia, M., et al., "Synthesis of Pyridylstannanes from Halopyridines and Hexamethyldistannane with Catalytic Palladium," Tetrahedron Ltrs., vol. 38 (27), pp. 4737-4740, 1997.
Bernaerts, P. et al., "Histamine H3 antagonist thioperamide dose-dependently enhances memory consolidation and reverse amnesia induced by dizocilpine or scopolamine in a one-trail inhibitory avoidance task in mice," Beh. Brain Res., vol. 154, pp. 211-219, 2004.
Bjenning C., et al., Peripherally Administered Ciproxifan Elevates Hypothalamic Histamine And Potently Reduces Food Intake in the Sprague Dawley Rat, Histamine Research In The New Mellennium, 2001, pp. 449-450.
Black, W. C. et al., "2, 3-Diarylcyclopentenones as Orally Active, Highly Selective Cyclooxygenase.2 Inhibitors," Journal of Medicinal Chemistry, vol. 42, pp. 1274-1281, 1999.
Browman K.E., et al., "Enhancement of prepulse inhibition of startle in mice by the H3 receptor antagonists thioperamide and ciproxifan," Behavioural Brain Research, vol. 153 (1), pp. 69-76, 2004.
Burns et al., "PET ligands for assessing receptor occupancy in vivo," Annual Reports in Medicinal Chemistry, vol. 36, pp. 267-276, 2001.
Burns et al., "Positron emission tomography neuroreceptor imaging as a tool in drug discovery, research and development," Current Opinion in Chemical Biology, vol. 3 (4), pp. 388-394, 1999.
Carroll, F. I. et al., "Synthesis, Nicotinic Acetylcholine Receptor Binding, and Antinociceptive Properties of 2- exo '2-(2'-Substituted 5'-pyridinyl)-7-azabicyclo[2.2.1]heptanes. Epibatidine Analogues," J. Med. Chem., vol. 44, pp. 2229-2237, 2001.
Chaplan S. R. et al., "Quantitative assessment of tactile allodynia in the rat paw," Journal of Neuroscience Methods, 1994, vol. 53, pp. 55-63.

(Continued)

*Primary Examiner* — Laura L. Stockton
(74) *Attorney, Agent, or Firm* — Nancy J. Gettel; Portia Chen

(57) ABSTRACT

Compounds of formula (I)

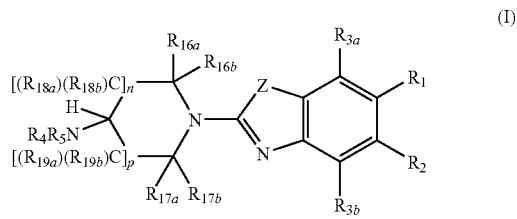

are useful in treating conditions or disorders prevented by or ameliorated by histamine-3 receptor ligands. Also disclosed are pharmaceutical compositions of compounds of formula (I), methods for using such compounds and compositions, and a process for preparing the compounds.

16 Claims, No Drawings

OTHER PUBLICATIONS

Ueno, Chemistry Letters, 1984, pp. 2125-2128.
Chen et al., "Effects of histamine on MK-801-induced memory deficits in radial maze performance in rats," Brain Research, vol. 839, pp. 186-189, 1999.
Chen, Z. et al., "Pharmacological effects of carcinine on histaminergic neurons in the brain," British J. of Pharmacology, vol. 143, pp. 573-580, 2004.
Cheng,Y. et al., "Relationship Between the Inhibition Constant (KI) and the Concentration of Inhibitor Which Causes 50 Per Cent Inhibition (I.sub.50) of An Enzymatic Reaction," Biochemical Pharmacology, vol. 22, pp. 3099-3108, 1973.
Clapham, J. et al., "Thioperamide, the selective histamine H3 receptor antagonist, attenuates stimulant induced locomotor activity in the mouse," European Journal of Pharmacology, vol. 259 (2), pp. 107-114, 1994.
Cowart, et al., "4-(2-[2-(2(R)- Methylpyrrolidin-1-yl) ethyl] benzofuran-5yl) benzonitrile and Related 2-Aminoethylbenzofuran H3 Receptor Antagonists Potently Enhance Cognition and Attention," J. Med. Chem., vol. 48, pp. 38-55, 2005.
De Almeida, et al., "Memory Facilitation by Histamine," Arch. Int. Pharmacodyn, vol. 283, pp. 193-198, 1986.
DeLaunois et al., "Modulation of acetylcholine, capsaicin and substance P effects by histamine H.sub.3 receptors in isolated perfused rabbit lungs," European Journal of Pharmacology, vol. 277, pp. 243-250, 1995.
Dimitriadou et al., "Functional relationship between mast cells and C-sensitive nerve fibres evidenced by histamine H.sub.3 -receptor modulation in rat lung and spleen," Clinical Science, vol. 87, pp. 151-163, 1994.
Dixon W. J. et al., "Efficient analysis of experimental observations," Annual Review of Pharmacology and Toxicology, 1980, vol. 20, pp. 441-462.
Dumery et al., "Development of Amygdaloid Cholinergic Mediation of Passive Avoidance Learning in the Rat," Exp. Brain. Res., vol. 67, pp. 61-69, 1987.
Dvorak, C. et al., "4-Phenoxypiperidines: Potent, Conformationally Restricted, non-Imidazole Histamine H3 Antagonists," Journal of Medicinal Chemistry, vol. 48, pp. 2229-2238, 2005.
Eastwood, "A versatile synthesis of 4-aryl tetrahydropyridines via palladium mediated Suzuki cross-coupling with cyclic vinyl boronates," Tetrahedron Letters, vol. 41 (19), pp. 3705-3708, 2000.
Esbenshade et al., "Pharmacological and behavioral properties of A-349821, a selective and potent human histamine H3 receptor antagonist", Biochemical Pharmacology, 2004, 68, 933-945.
Esbenshade, et al., "Pharmacological Properties of ABT-239 [4-(2-{2-[(2R)-2- Methylpyrrolidinyl]ethyl}-benzofuran-5-yObenzonitrile]: I. Potent and Selective Histamine H3 Receptor Antagonist with Drug-Like Properties," Journal of Pharmacology and Experiment Ther. vol. 313 (1), pp. 165-175, 2005.
Fitzsimons, C.H. et al., "Histamine receptors signaling in epidermal tumor cell lines with H-ras gene alterations," Inflammation Research, vol. 47 Suppl. 1, pp. S50-S51, 1998.
Fox et al., "Effects of Histamine H3 Receptor Ligands GT2331 and Ciproxifan in a Repeated Acquisition Response in the Spontaneously Hypertensive Rat Pup," Behavioural Brain Research, vol. 131, pp. 151-161, 2002.
Fox G.B. et al., Pharmacological Properties of ABT-239 [4-(2-{2-[(2R)-2- Methylpyrrolidinty]ethy1}-benzofuran-5-yl)benzonitrile]- : II Neurophysiological Characterization and Broad Preclinical Efficacy in Cognition and Schizophrenia of a Potent and Selective Histamine H3 Receptor Antagonist, J. of Pharm. & Exp. Ther., 2005, 313 (1), pp. 176-190.
Fox, G.B. et al. , "Identification of novel H3 receptor (H3R) antagonists with cognition enhancing properties in rats," Inflammation Research, vol. 52 (1), pp. S31-S32, 2003.
Fox, G.B. et al. , "Two Novel and Selective Nonimidazole H3 Receptor Antagonists A-304121 and A-317920: II. In Vivo Behavioral and Neurophysiological Characterization," Journal of Pharmacology and Experimental Therapeutics, vol. 305 (3), pp. 897-908, 2003.
Furniss B. S. et al, "Practical Organic Chemistry", 5th Ed., Longman Scientific & Technical & John Wiley & Sons, Inc., Table of Contents, 1989.
Gaffield et al., "Chiroptical Properties of N-Nitrosopyrrolidines and N-Nitrosamino Acids," Tetrahedron, vol. 37, pp. 1861-1869, 1981.
Gerhard Vogel G. et al., Drug Discovery and Evaluation, 2nd edition, 2002, Springer-Verlag, New York, 702-706.
Glase, S.A. et al., "Attention deficit hyperactivity disorder: Pathophysiology and Design of New Treatments," Annual Reports in Medicinal Chemistry, vol. 37, pp. 11-20, 2002.
Goher et al., "Synthesis, structural characterisation, and Monte Carlo simulation of the magnetic properties of the 3D-stacked honeycomb Cs(n)," Chemistry, 2000, pp. 778-784, vol. 6 (5).
Gronowitz et al., "On the synthesis of various thienyl- and selenienylpyrimidines," Chem. Scr, 1986, pp. 305-309, vol. 26 (2).
Haas,H. et al., "Subcortical Modulation of Synaptic Plasticity in the Hippocampus," Behavioural Brain Research, vol. 66, pp. 41-44, 1995.
Halpern, M.T., "GT-2331," Current Opinion in Central and Peripheral Nervous System Investigational Drugs, vol. 1, pp. 524-527, 1999.
Hancock, A. A., "Antiobesity effects of A-331440, a novel nonimidazole histamine H3 receptor antagonist," European Journal of Pharmacology, vol. 487, pp. 183-197, 2004.
Hancock, A. A., "Histamine H3 antagonists in models of obesity," Inflammatory Research, vol. 53 Suppl. 1, pp. S47-S48, 2004.
Harada, C. et al., "Inhibitory effect of iodophenpropit, a selective histamine H3 antagonist, on amygdaloid kindled seizures," Brain Research Bulletin, vol. 63, pp. 143-146, 2004.
Hietala, J.F., "Ligand-receptor interactions as studied by PET: implications for drug development," Annals of Medicine (Helsinki), vol. 31 (6), pp. 438-443, 1999.
Hriscu, A., "Experimental evaluation of the analgesic efficacy of some antihistamines as proof of the histaminergic receptor involvement in pain," Famacia, vol. 49 (2), pp. 23-30, 2001.
Huang, Y .W., et al., "Effect of the histamine H.sub.3-antagonist clobenpropit on spatial memory deficits induced by MK-801 as evaluated by radial maze in Sprague-Dawley rats," Beh. Brain Res., vol. 151, pp. 287-293 , 2004.
International Search Report for application No. PCT/US2008/087413, Mailed on Mar. 26, 2009, 3 pages.
Ishiyama, T., et al., "Palladium(0)-Catalyzed Cross-Coupling Reaction of Alkoxydiboron with Haloarenes: A Direct Procedure for Arylboronic Esters ," J. Org. Chem., vol. 60, pp. 7508-7510, 1995.
Ishiyama, T., et al., "Synthesis of pinacol arylboronates via cross-coupling reaction of bis(pinacolato)diboron with chloroarenes catalyzed by palladium(0)-tricyclohexylphosphine complexes," Tetradedron, vol. 57, pp. 9813-9816, 2001.
Itoh et al., "Thioperamide, A Histamine H.sub.3 Receptor Antagonist, Powerfully Suppresses Peptide YY-Induced Food Intake in Rats," Biol. Psychiatry, vol. 45, pp. 475-481, 1999.
IUPAC Commission on Nomenclature of Organic Chemistry: Rules for the Nomenclature of Organic Chemistry Section E: Stereochemistry, Pure Appl Chem, 1976, 45, 13-30.
Joshi et al., "Animal models of pain for drug discovery", Expert Opinion on Drug Discovery, 2006, 1, 341-352.
Schinazi, Journal of Organic Chemistry, 1985, pp. 841-847, vol. 50 (6).
Kamei et al., Jpn. J. Pharmacol., 1991, vol. 57. , 473-482.
Kamei, C. et al., "Influence of Certain H.sub.1 -Blockers on the Step-Through Active Avoidance Response in Rats," Psychopharmacology, vol. 102, pp. 312-318, 1990.
Kim et al., Bioorg. Med. Chem.Lett., vol. 6 (1), pp. 71-76, 1996.
Kim S. H. et al., "An experimental model for peripheral neuropathy produced by segmental spinal nerve ligation in the rat," Pain, 1992, vol. 50 (3), pp. 355-363.
Komater, V.A., et al., "H3 receptor blockade by thioperamide enhances cognition in rats without inducing locomotor sensitization," Psychopharmacology (Berlin, Germany), vol. 167 (4), pp. 363-372, 2003.
Krische, M.J.,Lehn, J.-M., "Molecular-Recognition-Directed Self-Assembly of Pleated Sheets from 2-Aminopyrimidine Hydrogen-Bonding Motifs," Helv. Chemica Acta, vol. 81, pp. 1909-1920, 1998.
Krueger K.M. et al., "G Protein-Dependent Pharmacology of Histamine H.sub.3 Receptor ligands: Evidence for Heterogeneous Active State Receptor Conformations", Journal of Pharmacology and Experimental Therapeutics, 2005, 314 (1), 271-281.

Lamberti, C. et al., "Antidepressant-like effects of endogenous histamine and of two histamine H 1 receptor agonists in the mouse forced swim test," British Journal of Pharmacology, vol. 123, pp. 1331-1336, 1998.

Letsinger, R.L. et al., "Organoboron Compounds. IX. 8-Quinolineboronic Acid, its Preparation and Influence on Reactions of Chlorohydrins," J. Amer. Chem. Soc., vol. 81, pp. 498-501, 1959.

Leurs et al., "Histamine Homologues Discriminating between Two Functional $H_3$-Receptor Assays. Evidence for $H_3$ Receptor," Journal of Pharmacology and Experimental Therapeutics, vol. 276 (3), pp. 1009-1015, 1996.

Leurs et al., "The Histamine $H_3$-Receptor: A Target for Developing New Drugs," Progress in Drug Research vol. 39, pp. 127-165, 1992.

Leurs et al., "The Histamine H3 Receptor: A Target for New Drugs," 1998, vol. 30, Elsevier. Content Page Only.

Leurs et al., "The medicinal chemistry and therapeutic potential of ligands of the histamine $H_3$ receptor," Progress in Drug Research, vol. 45, pp. 170-165, vol. 45.

Leurs et al., "The Medicinal Chemistry and Therapeutic Potentials of Ligands of the Histamine $H_3$ Receptor," Progress in Drug Research, vol. 45, pp. 107-165, 1995.

Ligneau, X., et al., "Neurochemical and Behavioral Effects of Ciproxifan, a Potent Histamine H3-Receptor Antagonist," Journal of Pharmacology and Experimental Therapeutics, vol. 287 (2), pp. 658-666, 1998.

Lin et al., "Involvement of histaminergic neurons in arousal mechanisms demonstrated with $H_3$ -receptor ligands in the cat," Brain Research, vol. 523, pp. 325-330, 1990.

Littke, A.F., et al., "Pd/P(t -Bu)$_3$: A Mild and General Catalyst for Stille Reactions of Aryl Chlorides and Aryl Bromides," J. Am. Chem. Soc., vol. 124, pp. 6343-6348, 2002.

Lozada, A.F. et al., "Plasticity of histamine $H_3$ receptor expression and binding in the vestibular nuclei after labyrinthectomy in rat," BioMed Centr. Neurosci., vol. 5, pp. 32, 2004.

Malmberg Aiello, P. et al., "Role of histamine in rodent antinociception," British Journal of Pharmacology, vol. 111 (4), pp. 1269-1279, 1994.

Mazurkiewicz Kwilecki et al., "Changes in the regional brain histamine and histidine levels in postmortem brains of Alzheimer patients," Can J Physiol Pharmacol, vol. 67, pp. 75-78, 1989.

McLeod R. L, et al., "Combined Histamine H1 and H3 Receptor Blockade Produces Nasal Decongestion in an Experimental Model of Nasal Congestion," American Journal of Rhinology, vol. 13 (5), pp. 391-399, 1999.

McLeod R.L., et al., "Histamine $H_3$ Antagonists," Progress in Resp. Research, vol. 31, pp. 133-134, 2001.

Medhurst et al., "Novel histamine $H_3$ receptor antagonists GSK189254 and GSK334429 are efficacious in surgically-induced and virally-induced rat models of neuropathic pain," Pain , 2008, pp. 61-69, vol. 138.

Medhurst et al., "Structurally novel histamine H3 receptor antagonists GSK207040 and GSK334429 improve scopolamine-induced memory impairment and capsaicin-induced secondary allodynia in rats," Biochemical Pharmacology, vol. 73, pp. 1182-1194 , 2007.

Meguro et al., "Effects of Thioperamide, a Histamine H3 Antagonist, on the Step-Through Passive Avoidance Response and Histidine Decarboxylase Activity in Senescence-Accelerated Mice," Pharmacology, Biochemistry and Behavior, vol. 50 (3), pp. 321-325 , 1995.

Mitchell, T.N., "Palladium-Catalysed Reactions of Organotin Compounds," Synthesis, pp. 803-815, 1992.

Monti et al., "Effects of selective activation or blockade of the histamine $H_3$ receptor on sleep and wakefulness," Journal of Pharmacology, vol. 205, pp. 283-287, 1991.

Monti, J. et al., "Sleep and Waking During Acute Histamine $H_3$ Agonist BP2.94 or $H_3$ Antagonist Carboperamide (MR 16155) Administration in Rats," Neuropsychopharmacology, vol. 15 (1), pp. 31-35, 1996.

Morisset, S., et al., "Atypical Neuroleptics Enhance Histamine Turnoer in Brain Via 5-Hydroxytryptamino$_{2A}$ Receptor Blockade," J. of Pharmacol. & Exp. Ther., vol. 288 (2), pp. 590-596, 1999.

Murakami et al., "AQ-0145, A Newly Developed Histamine $H_3$ Antagonist, Decreased Seizure Susceptibility of Electrically Induced Convulsions in Mice," Meth. Find. Exp. Clin. Pharmacol., vol. 17 ©, pp. 70-73, 1995.

O'Neill, A.B., et al., "Pharmacological Evaluation of the In Vivo Model of Vestibular Dysfunction in the Rat," Meth. Find Exp. Clin. Pharmacol., vol. 21 (4), pp. 285-289, 1999.

O'Neill, B.T., et al., "Total Synthesis of (±)-Cytisine," Organic Letters, vol. 2 (26), pp. 4201-4206, 2000.

Onodera et al., "Neuropharmacology of the Histaminergic Neuron System in the Brain and Its Relationship With Behavioral Disorders," Progress in Neurobiology, vol. 42, pp. 685-702, 1994.

Onodera, K., et al., "Improvement by FUB 181, a novel histamine H 3 -receptor antagonist, of learning and memory in the elevated plus-maze test in mice," Naunyn-Schmiedebergs' Arch Pharmacol, vol. 357, pp. 508-513, 1998.

Pan et al., "Histaminergic Ligands Attenuate Barrel Rotation in Rats Following Unilateral Labyrinthectomy," Meth. Find Exp. Clin. Pharmacol, vol. 20 (9), pp. 771-777, 1998.

Panula et al., Neuroscience, vol. 44, pp. 465-481 , 1998.

Panula, P. et al., "Neuronal Histamine Deficit in Alzheimer's Disease," Neurosci. vol. 82 (4), pp. 993-997, 1998.

Parry et al., "Functionalized pyridylboronic acids and their Suzuki cross-coupling reactions to yield novel heteroarylpyridines," J Org Chem, 2002, pp. 7541-7543, vol. 67 (21).

Parry et al., Brian, Department of Chemistry, Synthesis, 2003, pp. 1035-1038, vol. 7.

Passani et al., "Central histaminergic system and cognition," Neuroscience and Biobehavioral Reviews, vol. 24, pp. 107-113, 2000.

Perez Garcia et al., "Effects of Histamine $H_3$ Receptor Ligands in Experimental Models of Anxiety and Depression," Psychopharmacology, vol. 142 Issue 2, pp. 215-220, 1999.

Prast, H., et al., "Histaminergic neurons facilitate social memory in rats," Brain Res., vol. 734, pp. 316-318, 1996.

Poste et al., "Lipid Vesicles as Carriers for Introducing Biologically Active Materials into Cells," Methods in Cell Biology, 1976, vol. 14, Academic Press, pp. 33-71.

Pu, et al., "A Facile and Scaleable Synthesis of ABT-239, A Benzofuranoid H3 Antagonist," Organic Process Research and Development, vol. 9, pp. 45-50, 2005.

Rodrigues, A. A, et al., "Interaction of clozapine with the histamine H3 receptor in rat brain," British Journal of Pharmacology, vol. 114 (8), pp. 1523-1524, 1995.

Sakai et al., "Effects of Thioperamide, A Histamine H3 Receptor Antagonist, On Locomotor Activity and Brain Histamine Content in Mast Cell-Deficient WIWv Mice," Life Sciences, vol. 48, pp. 2397-2404, 1991.

Sakata, T., et al., "Hypothalamic neuronal histamine modulates ad libitum feeding by rats," Brain research, vol. 537 (1-2), pp. 303-306, 1990.

Sanchez Lemus, E., et al. , "Histamine $H_3$ receptor activation inhibits dopamine $D_1$ receptor-induced camp accumulation in rat striatal slices," Neurosci. Ltrs., vol. 364, pp. 179-184, 2004.

Sato et al., Heterocycles, 2001, pp. 851-854, vol. 55.

Schwartz,J. et al. , "Histamine," Psychopharmacology: The Fourth Generation of Progress, pp. 397-405, 1995.

Schweitzer, J.B, "Drugs under investigation for attention-deficit hyperactivity disorder," Curr. Opin. In Invest. Drugs, vol. 3 (8), pp. 1207-1211, 2002.

Shaywitz et al., "Dopaminergic But Not Noradrenergic Mediation of Hyperactivity and Performance Deficits in the Developing Rat Pup," Psychopharmacology, vol. 82, pp. 73-77, 1984.

Sindkhedkar, M.D., et al., "Aromatic Interactions of the Synthesis and Conformation of Two Collapsible Tetracationic Cyclophanes," Tetrahedron, vol. 57, pp. 2991-2996, 2000.

Skopenko V. N. et al., "Ukrainskii Khimicheskii Zhurnal (Russian Edition) ," 1977, pp. 518-521, vol. 43 (5).

Smith et al. , "Reactions, mechanisms, and structure," Advanced organic chemistry, 2001, pp. 850-859, Ed. 5, John Wiley & Sons.

Southam E. et al. , "Preclinical investigations into the antipsychotic potential of the novel histamine $H_3$ receptor antagonist GSK207040," Psychopharmacology , 2009, pp. 483-494, vol. 201.

Stille, J.K., "The Palladium-Catalyzed Cross-Coupling Reactions of Organotin Reagents with Organic Electrophiles," Angew. Chem. Int. Ed. Engl., vol. 25, pp. 508-524 , 1986.

Szelag, A., "Role of Histamine H.sub.3 -Receptors in the Proliferation Neoplastic Cells in Vitro," Med. Sci. Monit. , vol. 4 (5), pp. 747-755, 1998.

Takagi, J., et al., "Iridium-catalyzed C-H coupling reaction of heteroaromatic compounds with bis(pinacolato)diboron: regioselective synthesis of heteroarylboronates," Tetrahedron Ltrs., vol. 43, pp. 5649-5651, 2002.

Tedford et al., "Abstracts," Society for Neuroscience, 1996, pp. 22 , vol. 22 Part. 1., 18.3.

Tedford et al., "Pharmacological Characterization of GT-2016, A Non-Thiourea-Containing Histamine H.sub.3 Antagonist: In Vitro and In Vivo Studies," The Journal of Pharmacology and Experimental Therapeutics, vol. 275 (2), pp. 598-604, 1995.

Testaferri L. et al., Synthesis , 1983, pp. 751-755.

Tietje et al. , "Preclinical Characterization of A-582941: A Novel .alpha.7 Neuronal Nicotinic Receptor Agonist with Broad Spectrum Cognition-Enhancing Properties," CNS Neuroscience and Therapeutics , 2008, pp. 65-82, vol. 14.

Tozer, M., et al., "Histamine H3 Receptor Antagonists," Expert Opinion Therapeutic Patents, vol. 10 (7), pp. 1045-1055, 2000.

Vohara, D., et al., "Thioperamide, A Selective Histamine H.sub.3 Receptor Antagonist, Protects Against PTZ-Induced Seizures in Mice," Life Sci., vol. 66 (22), pp. 297-301, 2000.

Wada, H. et al., "Is the Histaminergic Neuron System a Regulatory Center for Whole-Brain Activity?," Trends in Neurosciences, vol. 14 (9), pp. 415-418, 1991.

Walczynski, K .et al., "Non-imidazolehistamine h3 ligands, part 2: new2-substituted benzothiazoles as histamineh3 antagonists,XP001097557," Archiv der pharmazie, vchverlagsgesellschaft mbh, weinheim, de vol. 332 (11), pp. 389-398, 1999.

Yates, S.L., et al., "Effects of a novel histamine H3 receptor antagonist, GT2394, on food intake and weight gain in Sprague-Dawley rats," Society for Neuroscience, vol. 102 (10), pp. 219, 2000. , Abstract Only .

Yawata et al., "Role of histaminergic neurons in development of epileptic seizures in EL mice," Molecular Brain Research, vol. 132, pp. 13-17, 2004.

Yokoyama et al., "Effect of Thioperamide, a Histamine H.sub.3 Receptor Antagonist, on Electrically Induced Convulsions in Mice," Journal of Pharmacology, vol. 234 (1), pp. 129-133, 1993.

Yokoyama et al., "Histamine and Seizures Implications for the Treatment of Epilepsy" CNS Drugs, vol. 5 (5), pp. 321-330, 1996.

Zhang et al., "6-Aryl-1,4-dihydro-benzo[d][1,3]oxazin- 2-ones: a novel class of potent, selective, and orally active nonsteroidal progesterone receptor antagonists," J. Med Chem, 2002, pp. 4379-4382, vol. 45 (20).

Zhu et al., J. Heterocyclic Chem, 2005, pp. 727-730, vol. 42.

Yates, S.L., et al., "Identification and Pharmacological Characterization of a Series of New 1H-4-Substituted-Imidazoyl Histamine H3 Receptor Ligands," Journal of Pharmacology and Experimental Therapeutics, vol. 289, pp. 1151-1159, 1999.

Yokoyama, H., et al., "Clobenpropit (VUF-9153), a new histamine H3 receptor antagonist, inhibits electrically induced convulsions in mice," European Journal of Pharmacology vol. 260, pp. 23-28, 1994.

* cited by examiner

BENZOTHIAZOLE AND BENZOOXAZOLE DERIVATIVES AND METHODS OF USE

CROSS-REFERENCE TO RELATED APPLICATION

This application claims priority to provisional application Ser. No. 61/015,513, filed on Dec. 20, 2007, which is herein incorporated by reference.

BACKGROUND OF THE INVENTION

1. Technical Field

The invention relates to heterocyclic compounds such as benzothiazole and benzooxazole derivatives, compositions comprising such compounds, methods for making the compounds, and methods of treating conditions and disorders using such compounds and compositions.

2. Description of Related Technology

Histamine is a well-known modulator of neuronal activity. At least four types of histamine receptors have been reported in the literature, typically referred to as histamine-1, histamine-2, histamine-3, and histamine-4. The class of histamine receptor known as histamine-3 receptors is believed to play a role in neurotransmission in the central nervous system.

The histamine-3 ($H_3$) receptor was first characterized pharmacologically on histaminergic nerve terminals (Nature, 302: 832-837 (1983)), where it regulates the release of neurotransmitters in both the central nervous system and peripheral organs, particularly the lungs, cardiovascular system and gastrointestinal tract. $H_3$ receptors are thought to be disposed presynaptically on histaminergic nerve endings, and also on neurons possessing other activity, such as adrenergic, cholinergic, serotoninergic, and dopaminergic activity. The existence of $H_3$ receptors has been confirmed by the development of selective $H_3$ receptor agonists and antagonists ((Nature, 327:117-123 (1987); Leurs and Timmerman, ed. "The History of $H_3$ Receptor: a Target for New Drugs," Elsevier (1998)).

The activity at the $H_3$ receptors can be modified or regulated by the administration of $H_3$ receptor ligands. The ligands can demonstrate antagonist, inverse agonist, agonist, or partial agonist activity. For example, $H_3$ receptors have been linked to conditions and disorders related to memory and cognition processes, neurological processes, cardiovascular function, and regulation of blood sugar, among other systemic activities. Although various classes of compounds demonstrating $H_3$ receptor-modulating activity exist, it would be beneficial to provide additional compounds demonstrating activity at the $H_3$ receptors that can be incorporated into pharmaceutical compositions useful for therapeutic methods.

SUMMARY OF THE INVENTION

The invention is directed to benzothiazoles and benzooxazoles and, more particularly, 2-diamino-benzothiazole and 2-diamino-benzooxazole derivatives having a compound of formula (I):

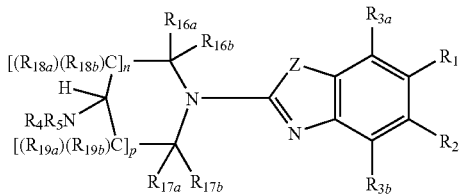

or a pharmaceutically acceptable salt, ester, amide, or radiolabelled form thereof, wherein:

Z is an atom selected from sulfur and oxygen;
n is an integer from 0 to 2;
p is an integer from 0 to 1;
one of $R_1$ and $R_2$ is hydrogen, acyl, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkylthio, alkynyl, amido, carboxy, cyano, cycloalkyl, fluoroalkoxy, haloalkoxy, haloalkyl, halogen, hydroxy, hydroxyalkoxy, hydroxyalkyl, —$NR_AR_B$, ($NR_AR_B$)carbonyl-, —$SO_2N(R_{14a})(R_{14b})$, —$N(R_{14a})SO_2(R_{14b})$, a group of the formula -L-$R_6$, or a group of the formula -$L_{2a}$-$R_{6a}$-$L_{2b}$-$R_{6b}$;
the other of $R_1$ and $R_2$ is selected from hydrogen, chloro, cyano, alkoxy, alkoxyalkyl, alkyl, alkylthio, cycloalkyl, fluoro, fluoroalkyl, fluoroalkoxy, hydroxyalkoxy, —$SO_2N(R_{14a})(R_{14b})$, and —$N(R_{14a})SO_2(R_{14b})$;
$R_{3a}$ and $R_{3b}$ are each independently selected from hydrogen, cyano, halogen, alkyl, cycloalkyl, fluoroalkyl, alkoxy, alkoxyalkyl, fluoroalkoxy, alkylthio, —$SO_2N(R_{14a})(R_{14b})$, and —$N(R_{14a})SO_2(R_{14b})$;
$R_4$ and $R_5$ are each independently selected from alkyl, fluoroalkyl, hydroxyalkyl, alkoxyalkyl, and cycloalkyl; or $R_4$ and $R_5$ taken together with the nitrogen atom to which each is attached form a non-aromatic ring of the formula:

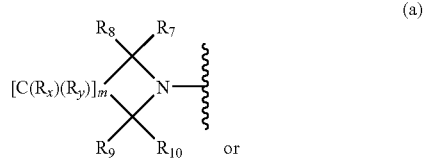

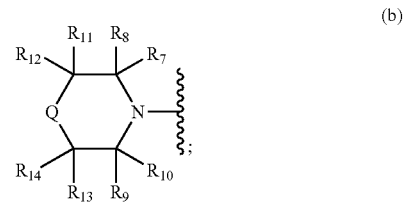

$R_7$, $R_8$, $R_9$, and $R_{10}$ at each occurrence are each independently selected from hydrogen, hydroxyalkyl, fluoroalkyl, cycloalkyl, and alkyl;
$R_{11}$, $R_{12}$, $R_{13}$, and $R_{14}$ are each independently selected from hydrogen, hydroxyalkyl, alkyl, and fluoroalkyl;
$R_x$ and $R_y$ at each occurrence are independently selected from the group consisting of hydrogen, hydroxy, hydroxyalkyl, alkyl, alkoxy, alkylamino, fluoro, and dialkylamino;
Q is selected from O and S;
m is an integer from 1 to 5;
$R_6$ is selected from aryl, a 5- to 6-membered heteroaryl ring, an 8- to 12-membered bicyclic heteroaryl ring, and a 4- to 12-membered heterocyclic ring when L is a bond, —O—, alkylene, —C(=O)—, —S—, —$SO_2N(R_{14a})$—, —$N(R_{14a})$ $SO_2$—, —$C(O)N(R_{14a})$—, —$N(R_{14a})C(O)$—, or —$N(R_{15})$—; or $R_6$ is bromo when L is a bond;

$R_{6a}$ is selected from a divalent 5- to 6-membered heteroaryl ring, a divalent cyanophenyl, a divalent 8- to 12-membered bicyclic heteroaryl ring, and a divalent 4- to 12-membered heterocyclic ring;

$R_{6b}$ is selected from hydrogen, a 5- to 6-membered heteroaryl ring, an aryl ring, an 8- to 12-membered bicyclic heteroaryl ring, and a 4- to 12-membered heterocyclic ring;

L, $L_{2a}$, and $L_{2b}$ are each independently selected from a bond, —O—, alkylene, —C(=O)—, —S—, —$SO_2N(R_{14a})$—, —$N(R_{14a})SO_2$—, —$C(O)N(R_{14a})$—, —$N(R_{14a})C(O)$—, and —$N(R_{15})$—;

$R_{14a}$ and $R_{14b}$ are each independently selected at each occurrence from hydrogen, alkyl, and cycloalkyl;

$R_{15}$ is selected from hydrogen, alkyl, acyl, alkoxycarbonyl and $(R_{14a})(R_{14b})NC(O)$—;

$R_{16a}$, $R_{16b}$, $R_{17a}$, $R_{17b}$, $R_{18a}$, $R_{18b}$, $R_{19a}$, and $R_{19b}$ are independently selected at each occurrence from hydrogen and lower alkyl; and $R_A$ and $R_B$ are independently selected from hydrogen, alkyl, haloalkyl, alkoxycarbonyl, cycloalkyl, hydroxyalkyl, and formyl.

Another aspect of the invention relates to pharmaceutical compositions comprising compounds of the invention. Such compositions can be administered in accordance with a method of the invention, typically as part of a therapeutic regimen for treatment or prevention of conditions and disorders related to $H_3$ receptor activity.

Yet another aspect of the invention relates to a method of selectively modulating $H_3$ receptor activity. The method is useful for treating, or preventing conditions and disorders related to $H_3$ receptor modulation in mammals. More particularly, the method is useful for treating or preventing conditions and disorders related to memory and cognition processes, neurological processes, cardiovascular function, and body weight. Accordingly, the compounds and compositions of the invention are useful as a medicament for treating or preventing $H_3$ receptor modulated disease.

Yet another aspect of the invention relates to radiolabelled pharmaceutical compositions useful as a radioligand. Radiolabelled forms of compounds of formula (I) can be provided as compositions of the invention and administered in accordance with a method of the invention, typically for assessing or diagnosing conditions and disorders related to $H_3$ receptor activity, for example in medical imaging. More particularly, positron-emitting isotopes of compounds of the invention may be used for medical imaging in PET (positron emitting tomography), wherein the localization of histamine $H_3$ receptors, and the extent to which these receptors are occupied by ligands, can be determined. In this use, the compounds of the invention possess at least one atom of a positron-emitting isotope selected from $^{11}C$, $^{18}F$, $^{15}O$, and $^{13}N$. Compounds of the invention may also incorporate isotopes that useful for sPECT imaging, for example $^{123}I$.

The compounds, compositions comprising the compounds, methods for making the compounds, methods for treating or preventing conditions and disorders by administering the compounds, radiolabelled forms of the compounds, and compositions containing radiolabelled forms of the compounds are further described herein.

DETAILED DESCRIPTION OF THE INVENTION

Definition of Terms

Certain terms as used in the specification are intended to refer to the following definitions, as detailed below.

The term "acyl" as used herein means an alkyl group, as defined herein, appended to the parent molecular moiety through a carbonyl group, as defined herein. Representative examples of acyl include, but are not limited to, acetyl, 1-oxopropyl, 2,2-dimethyl-1-oxopropyl, 1-oxobutyl, and 1-oxopentyl.

The term "acyloxy" as used herein means an acyl group, as defined herein, appended to the parent molecular moiety through an oxygen atom. Representative examples of acyloxy include, but are not limited to, acetyloxy, propionyloxy, and isobutyryloxy.

The term "alkenyl" as used herein means a straight or branched chain hydrocarbon containing from 2 to 10 carbons, and preferably 2, 3, 4, 5, or 6 carbons, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl" as used herein means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein means an alkoxy group, as defined herein, appended to the parent molecular moiety through a carbonyl group, as defined herein. Representative examples of alkoxycarbonyl include, but are not limited to, methoxycarbonyl, ethoxycarbonyl, isopropoxycarbonyl, and tert-butoxycarbonyl.

The term "alkoxyimino" as used herein means an alkoxy group, as defined herein, appended to the parent molecular moiety through an imino group, as defined herein. Representative examples of alkoxyimino include, but are not limited to, ethoxy(imino)methyl and methoxy(imino)methyl.

The term "alkoxysulfonyl" as used herein means an alkoxy group, as defined herein, appended to the parent molecular moiety through a sulfonyl group, as defined herein. Representative examples of alkoxysulfonyl include, but are not limited to, methoxysulfonyl, ethoxysulfonyl, and propoxysulfonyl.

The term "alkyl" as used herein means a straight or branched chain hydrocarbon containing from 1 to 10 carbon atoms, and preferably 1, 2, 3, 4, 5, or 6 carbons. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. Each of the carbon atoms of the alkyl group is substituted with hydrogen or with 0, 1, or 2 substituents selected from acyl, acyloxy, alkoxy, alkoxyalkoxy, alkoxyalkyl, alkoxycarbonyl, alkoxyimino, alkoxysulfonyl, alkylcarbonyl, alkylsulfonyl, amido, carboxy, cyano, cycloalkyl, fluoroalkoxy, formyl, haloalkoxy, haloalkyl, halogen, hydroxy, hydroxyalkyl, mercapto, nitro, oxo, alkylthio, —NR$_A$R$_B$, (NR$_A$R$_B$)carbonyl-, and (NR$_A$R$_B$)sulfonyl.

The term "alkylene" means a divalent group derived from a straight or branched chain hydrocarbon of from 1 to 10 carbon atoms. Representative examples of alkylene include, but are not limited to, —CH$_2$—, —CH(CH$_3$)—, —C(CH$_3$)$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkylamino" as used herein means an alkyl group, as defined herein, appended to the parent molecular moiety through a NH group. Representative examples of alkylamino include, but are not limited to, methylamino, ethylamino, isopropylamino, and butylamino.

The term "alkylcarbonyl" as used herein means an alkyl group, as defined herein, appended to the parent molecular moiety through a carbonyl group, as defined herein. Representative examples of alkylcarbonyl include, but are not limited to, methylcarbonyl, ethylcarbonyl, isopropylcarbonyl, n-propylcarbonyl, and the like.

The term "alkylsulfonyl" as used herein means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio.

The term "alkynyl" as used herein means a straight or branched chain hydrocarbon group containing from 2 to 10 carbon atoms, and preferably 2, 3, 4, or 5 carbons, and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "amido" as used herein means an amino, alkylamino, haloalkylamino or dialkylamino group appended to the parent molecular moiety through a carbonyl group, as defined herein. Representative examples of amido include, but are not limited to, aminocarbonyl, methylaminocarbonyl, dimethylaminocarbonyl, ethylaminocarbonyl, isopropylaminocarbonyl, 2-fluoroethylaminocarbonyl, and ethylmethylaminocarbonyl.

The term "amino" as used herein means an —NH$_2$ group.

The term "aryl," as used herein, means phenyl, a bicyclic aryl, or a tricyclic aryl. The bicyclic aryl is attached to the parent molecular moiety through any carbon atom contained within the bicyclic aryl. Representative examples of the bicyclic aryl include, but are not limited to, dihydroindenyl, indenyl, naphthyl, dihydronaphthalenyl, and tetrahydronaphthalenyl. The tricyclic aryl is a tricyclic aryl ring system such as anthracene or phenanthrene, a bicyclic aryl fused to a cycloalkyl, a bicyclic aryl fused to a cycloalkenyl, or a bicyclic aryl fused to a phenyl. The tricyclic aryl is attached to the parent molecular moiety through any carbon atom contained within the tricyclic aryl. Representative examples of tricyclic aryl ring include, but are not limited to, anthracenyl, phenanthrenyl, azulenyl, dihydroanthracenyl, fluorenyl, and tetrahydrophenanthrenyl.

The carbon atoms of the aryl groups of this invention are substituted with hydrogen or are optionally substituted with one or more substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkyl, fluoroalkoxy, formyl, haloalkoxy, haloalkyl, halogen, hydroxy, hydroxyalkyl, mercapto, nitro, alkylthio, —NR$_A$R$_B$, (NR$_A$R$_B$)carbonyl-, —SO$_2$N(R$_{14a}$)(R$_{14b}$), and —N(R$_{14a}$)SO$_2$(R$_{14b}$). Where the aryl group is a phenyl group, the number of substituents is 0, 1, 2, 3, 4, or 5. Where the aryl group is a bicyclic aryl, the number of substituents is 0, 1, 2, 3, 4, 5, 6, 7, 8, or 9. Where the aryl group is a tricyclic aryl, the number of substituents is 0, 1, 2, 3, 4, 5, 6, 7, 8, or 9.

The term "arylalkyl" as used herein means an aryl group, as defined herein, appended to the parent molecular moiety through an alkyl group, as defined herein. Representative examples of arylalkyl include, but are not limited to, benzyl, 2-phenylethyl and 3-phenylpropyl.

The term "carbonyl" as used herein means a —C(=O)— group.

The term "carboxy" as used herein means a —CO$_2$H group.

The term "cyano" as used herein means a —CN group, attached to the parent molecular moiety through the carbon.

The term "cyanophenyl" as used herein means a —CN group appended to the parent molecular moiety through a phenyl group, including, but not limited to, 4-cyanophenyl, 3-cyanophenyl, and 2-cyanophenyl.

The term "cycloalkyl" as used herein means a saturated cyclic hydrocarbon group containing from 3 to 8 carbons. Examples of cycloalkyl include cyclopropyl, cyclobutyl, cyclopentyl, cyclohexyl, cycloheptyl, and cyclooctyl.

Each of the carbon atoms of the cycloalkyl groups of the invention is substituted with 0, 1, or 2 substituents selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkyl, fluoroalkoxy, formyl, haloalkoxy, haloalkyl, halogen, hydroxy, hydroxyalkyl, mercapto, nitro, alkylthio, —NR$_A$R$_B$, (NR$_A$R$_B$)carbonyl-, —SO$_2$N(R$_{14a}$)(R$_{14b}$), and —N(R$_{14a}$)SO$_2$(R$_{14b}$).

The term "cycloalkylcarbonyl" as used herein means a cycloalkyl group, as defined herein, appended to the parent molecular moiety through a carbonyl group, as defined herein. Representative examples of cycloalkylcarbonyl include, but are not limited to, cyclopropylcarbonyl, cyclopentylcarbonyl, cyclohexylcarbonyl, and cycloheptylcarbonyl.

The term "dialkylamino" as used herein means two independent alkyl groups, as defined herein, appended to the parent molecular moiety through a nitrogen atom. Representative examples of dialkylamino include, but are not limited to, dimethylamino, diethylamino, ethylmethylamino, and butylmethylamino.

The term "fluoro" as used herein means —F.

The term "fluoroalkyl" as used herein means at least one fluoro group, as defined herein, appended to the parent molecular moiety through an alkyl group, as defined herein. Representative examples of fluoroalkyl include, but are not limited to, fluoromethyl, difluoromethyl, trifluoromethyl, pentafluoroethyl, and 2,2,2-trifluoroethyl.

The term "fluoroalkoxy" as used herein means at least one fluoro group, as defined herein, appended to the parent molecular moiety through an alkoxy group, as defined herein. Representative examples of fluoroalkoxy include, but are not limited to, fluoromethoxy, difluoromethoxy, trifluoromethoxy, pentafluoroethoxy, heptafluoropropyloxy, and 2,2,2-trifluoroethoxy.

The term "formyl" as used herein means a —C(O)H group.

The term "halo" or "halogen" as used herein means Cl, Br, I, or F.

The term "haloalkoxy" as used herein means at least one halogen, as defined herein, appended to the parent molecular moiety through an alkoxy, as defined herein. Representative examples of haloalkoxy include, but are not limited to, 2-fluoroethoxy, trifluoromethoxy, and pentafluoroethoxy.

The term "haloalkyl" as used herein means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl", as used herein, refers to an aromatic ring containing one or more heteroatoms independently selected from nitrogen, oxygen, or sulfur, or a tautomer thereof. Such rings can be monocyclic or bicyclic as further described herein. Heteroaryl rings are connected to the parent molecular moiety, or to L, $L_{2a}$, or $L_{2b}$, wherein L, $L_{2a}$, or $L_{2b}$ are defined in formula (I), through a carbon or nitrogen atom.

The terms "monocyclic heteroaryl" or "5- or 6-membered heteroaryl ring", as used herein, refer to 5- or 6-membered aromatic rings containing 1, 2, 3, or 4 heteroatoms independently selected from nitrogen, oxygen, or sulfur, or a tautomer thereof. Examples of such rings include, but are not limited to, a ring wherein one carbon is replaced with an O or S atom; one, two, or three N atoms are arranged in a suitable manner to provide an aromatic ring; or a ring wherein two carbon atoms in the ring are replaced with one O or S atom and one N atom. Such rings can include, but are not limited to, a six-membered aromatic ring wherein one to four of the ring carbon atoms are replaced by nitrogen atoms, five-membered rings containing a sulfur, oxygen, or nitrogen in the ring; five-membered rings containing one to four nitrogen atoms; and five-membered rings containing an oxygen or sulfur and one to three nitrogen atoms. Representative examples of 5- to 6-membered heteroaryl rings include, but are not limited to, furyl, imidazolyl, isoxazolyl, isothiazolyl, oxazolyl, pyrazinyl, pyrazolyl, pyridazinyl, pyridinyl, pyrimidinyl, pyrrolyl, tetrazolyl, [1,2,3]thiadiazolyl, [1,2,3]oxadiazolyl, thiazolyl, thienyl, [1,2,3]triazinyl, [1,2,4]triazinyl, [1,3,5]triazinyl, [1,2,3]triazolyl, [1,2,4]triazolyl.

The term "bicyclic heteroaryl" or "8- to 12-membered bicyclic heteroaryl ring", as used herein, refers to an 8-, 9-, 10-, 11-, or 12-membered bicyclic aromatic ring containing at least 3 double bonds, and wherein the atoms of the ring include one or more heteroatoms independently selected from oxygen, sulfur, and nitrogen. Representative examples of bicyclic heteroaryl rings include indolyl, benzothienyl, benzofuranyl, indazolyl, benzimidazolyl, benzothiazolyl, benzoxazolyl or benzooxazolyl, benzoisothiazolyl, benzoisoxazolyl, quinolinyl, isoquinolinyl, quinazolinyl, quinoxalinyl, phthalazinyl, pteridinyl, purinyl, naphthyridinyl, cinnolinyl, thieno[2,3-d]imidazole, 1,5-dihydro-benzo[b][1,4]diazepin-2-on-yl, and pyrrolopyrimidinyl.

Heteroaryl groups of the invention, whether monocyclic or bicyclic, may be substituted with hydrogen, or optionally substituted with one or more substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkyl, fluoroalkoxy, formyl, haloalkoxy, haloalkyl, halogen, hydroxy, hydroxyalkyl, mercapto, nitro, alkylthio, —$NR_AR_B$, ($NR_AR_B$)carbonyl-, —$SO_2N(R_{14a})(R_{14b})$, and —$N(R_{14a})SO_2(R_{14b})$. Monocyclic heteroaryl or 5- or 6-membered heteroaryl rings are substituted with 0, 1, 2, 3, 4, or 5 substituents. Bicyclic heteroaryl or 8- to 12-membered bicyclic heteroaryl rings are substituted with 0, 1, 2, 3, 4, 5, 6, 7, 8, or 9 substituents. Heteroaryl groups of the present invention may be present as tautomers.

The terms "heterocyclic ring" and "heterocycle", as used herein, refer to a 4- to 12-membered monocyclic or bicyclic ring containing one, two, three, four, or five heteroatoms independently selected from the group consisting of nitrogen, oxygen, and sulfur, and also containing either at least one carbon atom attached to four other atoms or one carbon atom substituted with an oxo group and attached to two other atoms. Four- and five-membered rings may have zero or one double bond. Six-membered rings may have zero, one, or two double bonds. Seven- and eight-membered rings may have zero, one, two or three double bonds. The non-aromatic heterocycle groups of the invention can be attached through a carbon atom or a nitrogen atom. The non-aromatic heterocycle groups may be present in tautomeric form. Representative examples of nitrogen-containing heterocycles include, but are not limited to, azepanyl, azetidinyl, aziridinyl, azocanyl, dihydropyridazinyl, dihydropyridinyl, dihydropyrimidinyl, oxazolidinyl, imidazolidinyl, morpholinyl, piperazinyl, piperidinyl, pyrrolidinyl, pyrrolinyl, dihydrothiazolyl, dihydropyridinyl, and thiomorpholinyl. Representative examples of non-nitrogen containing non-aromatic heterocycles include, but are not limited to, dioxanyl, dithianyl, tetrahydrofuryl, dihydropyranyl, tetrahydropyranyl, and [1,3]dioxolanyl.

The non-aromatic heterocycles of the invention are substituted with hydrogen, or optionally substituted with 0, 1, 2, 3, 4, 5, 6, 7, 8, or 9 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkyl, fluoroalkoxy, formyl, haloalkoxy, haloalkyl, halogen, hydroxy, hydroxyalkyl, mercapto, nitro, oxo, alkylthio, —$NR_AR_B$, ($NR_AR_B$)carbonyl, —$SO_2N(R_{14a})(R_{14b})$, and —$N(R_{14a})SO_2(R_{14b})$.

Additional representative examples of heterocycles include, but are not limited to, azetidin-2-one, azepan-2-one, isoindoline-1,3-dione, (Z)-1H-benzo[e][1,4]diazepin-5(4H)-one, pyridazin-3(2H)-one, pyridin-4(1H)-one, pyrimidin-2(1H)-one, pyrimidine-2,4(1H,3H)-dione, pyrrolidin-2-one, benzo[d]thiazol-2(3H)-one, pyridin-4(1H)-one, imidazolidin-2-one, 1H-imidazol-2(3H)-one, piperidin-2-one, morpholin-2-one, morpholin-3-one, 3H-quinazolin-4-one, 8-trifluoromethyl-3H-quinazolin-4-one, quinazoline-dione, tetrahydropyrimidin-2(1H)-one, thiadiazinone, oxadiazolone, oxadiazinone, oxazolidin-2-one, and 1H-benzo[d]imidazol-2(3H)-one.

The term "hydroxy" as used herein means an —OH group.

The term "hydroxyalkyl" as used herein means at least one hydroxy group, as defined herein, appended to the parent molecular moiety through an alkyl group, as defined herein. Representative examples of hydroxyalkyl include, but are not limited to, hydroxymethyl, 2-hydroxyethyl, 2-methyl-2-hydroxyethyl, 3-hydroxypropyl, 2,3-dihydroxypentyl, and 2-ethyl-4-hydroxyheptyl.

The term "hydroxy-protecting group" means a substituent which protects hydroxyl groups against undesirable reactions during synthetic procedures. Examples of hydroxy-protecting groups include, but are not limited to, methoxymethyl, benzyloxymethyl, 2-methoxyethoxymethyl, 2-(trimethylsilyl)ethoxymethyl, benzyl, triphenylmethyl, 2,2,2-trichloroethyl, t-butyl, trimethylsilyl, t-butyldimethylsilyl, t-butyldiphenylsilyl, methylene acetal, acetonide benzylidene acetal, cyclic ortho esters, methoxymethylene, cyclic carbonates, and cyclic boronates. Hydroxy-protecting groups are appended onto hydroxy groups by reaction of the compound that contains the hydroxy group with a base, such as triethylamine, and a reagent selected from an alkyl halide, alkyl triflate, trialkylsilyl halide, trialkylsilyl triflate, aryldialkylsilyltriflate, or an alkylchloroformate, $CH_2I_2$, or a dihaloboronate ester, for example with methyliodide, benzyl iodide, triethylsilyltriflate, acetyl chloride, benzylchloride, or dimethylcarbonate. A protecting group also may be appended onto a hydroxy group by reaction of the compound that contains the hydroxy group with acid and an alkyl acetal.

The term "imino" as defined herein means a —C(=NH)— group.

The term "mercapto" as used herein means a —SH group.

The term "$(NR_AR_B)$alkyl" as used herein means an —$NR_AR_B$ group, wherein $R_A$ and $R_B$ are independently selected from hydrogen, alkyl, haloalkyl, alkoxycarbonyl, cycloalkyl, hydroxyalkyl, and formyl, appended to the parent molecular moiety through an alkyl group, as defined herein. Representative examples of $(NR_AR_B)$alkyl include, but are not limited to, 2-(methylamino)ethyl, 2-(dimethylamino)ethyl, 2-(amino)ethyl, 2-(ethylmethylamino)ethyl, and the like.

The term "$(NR_AR_B)$carbonyl-" as used herein means an —$NR_AR_B$ group, as defined herein, appended to the parent molecular moiety through a carbonyl group, as defined herein. Representative examples of $(NR_AR_B)$carbonyl- include, but are not limited to, aminocarbonyl, (methylamino)carbonyl, (dimethylamino)carbonyl, (ethylmethylamino)carbonyl, ethylaminocarbonyl, isopropylaminocarbonyl, 2-fluoroethylaminocarbonyl, 2-hydroxy-2-methylpropylaminocarbonyl, and the like.

The term "$(NR_AR_B)$sulfonyl-" as used herein means a —$NR_AR_B$ group, as defined herein, appended to the parent molecular moiety through a sulfonyl group, as defined herein. Representative examples of $(NR_AR_B)$sulfonyl- include, but are not limited to, aminosulfonyl, (methylamino)sulfonyl, (dimethylamino)sulfonyl and (ethylmethylamino)sulfonyl.

The term "—$N(R_{14a})SO_2(R_{14b})$" as used herein means an amino group attached to the parent moiety to which is further appended with an $R_{14a}$ group, wherein $R_{14a}$ is hydrogen, alkyl, or cycloalkyl, and a $SO_2$ group to which is appended an ($R_{14b}$) group, wherein $R_{14b}$ is hydrogen, alkyl, or cycloalkyl. Representative examples of —$N(R_{14a})SO_2(R_{14b})$ include, but are not limited to, N-methylmethanesulfonamide.

The term "—$SO_2N(R_{14a})(R_{14b})$" as used herein means a —$N(R_{14a})(R_{14b})$ group, wherein $R_{14a}$ and $R_{14b}$ are each independently hydrogen, alkyl, or cycloalkyl, attached to a $SO_2$ group, appended to the parent moiety through the sulfonyl group. Representative examples of —$SO_2N(R_{14a})(R_{14b})$ include, but are not limited to (dimethylamino)sulfonyl and N-cyclohexyl-N-methylsulfonyl.

The term "nitro" as used herein means a —$NO_2$ group.

The term "nitrogen protecting group" as used herein means those groups intended to protect a nitrogen atom against undesirable reactions during synthetic procedures. Nitrogen protecting groups comprise carbamates, amides, N-benzyl derivatives, and imine derivatives. Preferred nitrogen protecting groups are acetyl, benzoyl, benzyl, benzyloxycarbonyl (Cbz), formyl, phenylsulfonyl, pivaloyl, tert-butoxycarbonyl (Boc), tert-butylacetyl, trifluoroacetyl, and triphenylmethyl (trityl). Nitrogen-protecting groups are appended onto primary or secondary amino groups by reacting the compound that contains the amine group with base, such as triethylamine, and a reagent selected from an alkyl halide, an alkyl triflate, a dialkyl anhydride, for example as represented by an alkyl anhydride (alkyl-C=O)$_2$O, an alkoxy anhydride, a diaryl anhydride, for example as represented by (aryl-C=O)$_2$O, an acyl halide, an alkylchloroformate, or an alkylsulfonylhalide, an arylsulfonylhalide, or halo-CON(alkyl)$_2$, for example acetylchloride, benzoylchloride, benzylbromide, benzyloxycarbonylchloride, formylfluoride, phenylsulfonylchloride, pivaloylchloride, (tert-butyl-O—C=O)$_2$O, trifluoroacetic anhydride, and triphenylmethylchloride.

The term "oxo" as used herein means (=O).

The term "sulfonyl" as used herein means a —$S(O)_2$— group.

As used herein, the term "antagonist" encompasses and describes compounds that prevent receptor activation by an $H_3$ receptor agonist alone, such as histamine, and also encompasses compounds known as "inverse agonists". Inverse agonists are compounds that not only prevent receptor activation by an $H_3$ receptor agonist, such as histamine, but also inhibit intrinsic $H_3$ receptor activity.

As used herein, the term "radiolabel" refers to a compound of the invention in which at least one of the atoms is a radioactive atom or radioactive isotope, wherein the radioactive atom or isotope spontaneously emits gamma rays or energetic particles, for example alpha particles or beta particles, or positrons. Examples of such radioactive atoms include, but are not limited to, $^3H$ (tritium), $^{14}C$, $^{11}C$, $^{15}O$, $^{18}F$, $^{35}S$, $^{123}I$, and $^{125}I$.

COMPOUNDS OF THE INVENTION

Compounds of the invention can have the formula (I) as described in the Summary of the Invention.

In compounds of formula (I), n is an integer from 0 to 2 and p is an integer from 0 to 1. Preferably, n is 1 or 2. Preferably, p is 0. Most preferably, n is 1 and p is 0.

Z is an atom selected from sulfur and oxygen.

L is independently selected from a bond, —O—, alkylene, —C(=O)—, —S—, —$SO_2N(R_{14a})$—, —$N(R_{14a})SO_2$—, —$C(O)N(R_{14a})$—, —$N(R_{14a})C(O)$—, and —$N(R_{15})$—. L is preferably a bond.

One of $R_1$ and $R_2$ in a compound of formula (I) is hydrogen, acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkyl, fluoroalkoxy, haloalkoxy, haloalkyl, halogen, hydroxy, hydroxyalkyl, mercapto, nitro, alkylthio, —$NR_AR_B$, ($NR_AR_B$)carbonyl-, —$N(R_A)$alkylsulfonyl, ($NR_{14a}R_{14b}$)sulfonyl-, or a group of the formula -L-$R_6$ or -$L_{2a}$-$R_{6a}$-$L_{2b}$-$R_{6b}$. The other group represented by $R_1$ or $R_2$ is hydrogen, cyano, halogen, alkyl, cycloalkyl, fluoroalkyl, alkoxy, alkoxyalkyl, fluoroalkoxy, alkylthio, —$SO_2N(R_{14a})(R_{14b})$, or —$N(R_{14a})SO_2(R_{14b})$, wherein $R_{14a}$ and $R_{14b}$ are each independently hydrogen, alkyl, or cycloalkyl, and more preferably are hydrogen or alkyl, particularly methyl. When $R_1$ or $R_2$ is not -L-$R_6$ or -$L_{2a}$-$R_{6a}$-$L_{2b}$-$R_{6b}$, the preferred group is hydrogen.

In one embodiment, $R_1$ is -L-$R_6$ or -$L_{2a}$-$R_{6a}$-$L_{2b}$-$R_{6b}$ and $R_2$ is hydrogen, cyano, halogen, alkyl, cycloalkyl, fluoroalkyl, alkoxy, alkoxyalkyl, and fluoroalkoxy. More preferably, $R_1$ is -L-$R_6$.

In another embodiment, $R_2$ is -L-$R_6$ or -$L_{2a}$-$R_{6a}$-$L_{2b}$-$R_{6b}$ and $R_1$ is hydrogen, cyano, halogen, alkyl, cycloalkyl, fluoroalkyl, alkoxy, alkoxyalkyl, and fluoroalkoxy. More preferably, $R_2$ is -L-$R_6$.

In one embodiment, $R_6$ is selected from aryl, a 5- to 6-membered heteroaryl ring, an 8- to 12-membered bicyclic heteroaryl ring, and a 4- to 12-membered heterocyclic ring when L is a bond, —O—, alkylene, —C(=O)—, —S—, —$SO_2N(R_{14a})$—, —$N(R_{14a})SO_2$—, —$C(O)N(R_{14a})$—, —$N(R_{14a})C(O)$—, or —$N(R_{15})$—. In another embodiment, $R_6$ is bromo and L is a bond. In particular, $R_6$ is bromo, aryl, heteroaryl, or heterocycle. Preferably, $R_6$ is phenyl, optionally substituted with cyano. More preferably, $R_6$ is heteroaryl or heterocycle. Examples of suitable heteroaryl for $R_6$ include, but are not limited to, furyl, imidazolyl, isoxazolyl, isothiazolyl, oxazolyl, pyrazinyl, pyrazolyl, pyridazinyl, pyridinyl, pyrimidinyl, pyrrolyl, tetrazolyl, thiazolyl, thienyl, indolyl, benzothienyl, benzofuranyl, indazolyl, benzimidazolyl, benzothiazolyl, benzoxazolyl, benzoisothiazolyl, benzoisoxazolyl, quinolinyl, isoquinolinyl, quinazolinyl, quinoxalinyl, phthalazinyl, pteridinyl, purinyl, naphthyridinyl, cinnolinyl, thieno[2,3-d]imidazole, [1,2,3]thiadiazolyl, [1,2,3]oxadiazolyl, [1,2,3]triazinyl, [1,2,4]triazinyl, [1,3,5]triazinyl, [1,2,3]triazolyl, and [1,2,4]triazolyl and pyrrolopyrimidinyl. Preferred heteroaryl rings are, for example, pyrimidinyl, pyridinyl, pyridazinyl, thiazolyl, and pyrazolyl. Each of the heteroaryl rings is independently unsubstituted or substituted with substituents as described herein, for example as in the Examples or the Definitions. Examples of heterocyclic rings suitable for $R_6$ include, but are not limited to, azepanyl, azetidinyl, aziridinyl, azocanyl, dihydropyridazinyl, dihydropyridinyl, dihydropyrimidinyl, morpholinyl, piperazinyl, piperidinyl, pyrrolidinyl, pyrrolinyl, dihydrothiazolyl, dihydropyridinyl, thiomorpholinyl, dioxanyl, dithianyl, tetrahydrofuryl, dihydropyranyl, tetrahydropyranyl, [1,3]dioxolanyl, azetidin-2-onyl, azepan-2-onyl, isoindolin-1,3-dionyl, (Z)-1H-benzo[e][1,4]diazepin-5(4H)-onyl, pyridazin-3(2H)-onyl, pyridin-2(1H)-onyl, pyrimidin-2(1H)-onyl, pyrimidin-2,4(1H,3H)-dionyl, pyrrolidin-2-onyl, benzo[d]thiazol-2(3H)-onyl, pyridin-4(1H)-onyl, imidazolidin-2-onyl, 1H-imidazol-2(3H)-onyl, piperidin-2-onyl, tetrahydropyrimidin-2(1H)-onyl, [1,2,4]thiadiazolonyl, [1,2,5]thiadiazolonyl, [1,3,4]thiadiazinonyl, [1,2,4]oxadiazolonyl, [1,2,5]oxadiazolonyl, [1,3,4]oxadiazinonyl, oxazolidin-2-onyl, quinazoline-4-onyl and 1H-benzo[d]imidazol-2(3H)-onyl. Preferred heterocyclic rings are pyridazin-3(2H)-onyl, pyrrolidin-2-onyl, pyrrolidinyl, morpholinyl, quinazoline-4-onyl and oxazolidin-2-onyl. Each of the heterocyclic rings is independently unsubstituted or substituted with substituents as described herein, for example as in the Examples or the Definitions.

$L_{2a}$ and $L_{2b}$ are each independently selected from a bond, —O—, alkylene, —C(=O)—, —S—, —SO$_2$N(R$_{14a}$)—, —N(R$_{14a}$)SO$_2$—, —C(O)N(R$_{14a}$)—, —N(R$_{14a}$)C(O)—, and —N(R$_{15}$)—, wherein $R_{14a}$, $R_{14b}$, and $R_{15}$ are as described for formula (I) in the Summary of the Invention. Preferably, $L_{2a}$ is a bond. $L_{2b}$ also is preferred to be a bond.

$R_{3a}$ and $R_{3b}$ are each independently hydrogen, cyano, halogen, alkyl, cycloalkyl, fluoroalkyl, alkoxy, alkoxyalkyl, fluoroalkoxy, alkylthio, —SO$_2$N(R$_{14a}$)(R$_{14b}$), or —N(R$_{14a}$)SO$_2$(R$_{14b}$), wherein $R_{14a}$, and $R_{14b}$ are as described for formula (I) in the Summary of the Invention. $R_{3a}$ and $R_{3b}$ are both preferred to be hydrogen.

In one embodiment, $R_4$ and $R_5$ are each independently alkyl, fluoroalkyl, hydroxyalkyl, alkoxyalkyl, or cycloalkyl. In this embodiment, $R_4$ and $R_5$ are preferably alkyl or hydroxyalkyl, and more particularly methyl, ethyl, propyl, and hydroxyethyl. Groups selected for $R_4$ and $R_5$ need not be the same.

Alternatively, and more preferably, $R_4$ and $R_5$ are taken together with the nitrogen atom to which each is attached form a non-aromatic ring. The non-aromatic ring form can be any nitrogen-containing non-aromatic ring. Examples of non-aromatic rings suitable for the embodiment wherein $R_4$ and $R_5$ are taken together to form a ring include, but are not limited to, non-aromatic rings having the formulas:

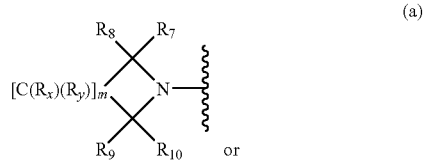

(a)

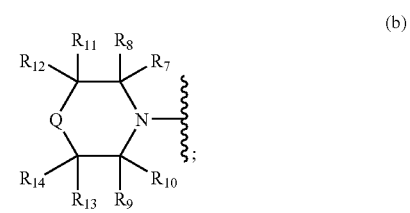

(b)

wherein $R_7$, $R_8$, $R_9$, and $R_{10}$ at each occurrence are each independently selected from hydrogen, hydroxyalkyl, fluoroalkyl, cycloalkyl, and alkyl;

$R_{11}$, $R_{12}$, $R_{13}$, and $R_{14}$ are each independently selected from hydrogen, hydroxyalkyl, alkyl, and fluoroalkyl;

$R_x$ and $R_y$ at each occurrence are independently selected from the group consisting of hydrogen, hydroxy, hydroxyalkyl, alkyl, alkoxy, alkylamino, fluoro, and dialkylamino; and Q is O or S.

Preferred for $R_7$, $R_8$, $R_9$, and $R_{10}$ is hydrogen. Preferred for $R_{11}$, $R_{12}$, $R_{13}$, and $R_{14}$ is hydrogen.

Groups of formula (a) are preferred for $R_4$ and $R_5$ when taken together to form a non-aromatic ring. The preferred groups for $R_4$ and $R_5$ when taken together with the nitrogen atom to which each is attached to form a group of formula (a) are pyrrolidine, piperidine and azepane.

Another embodiment of the invention is compounds of the formula (II):

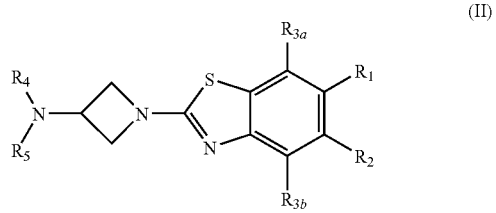

(II)

wherein $R_1$, $R_2$, $R_{3a}$, $R_{3b}$, $R_4$, and $R_5$ are as described for compounds of formula (I). In one embodiment, $R_1$ is -L-$R_6$, $R_2$ is hydrogen, $R_{3a}$ and $R_{3b}$ are both hydrogen, and $R_4$ and $R_5$ taken together form a non-aromatic ring. In another embodiment, $R_1$ is hydrogen, $R_2$ is -L-$R_6$, $R_{3a}$ and $R_{3b}$ are both hydrogen, and $R_4$ and $R_5$ taken together form a non-aromatic ring.

Another embodiment of the invention is compounds of the formula (III):

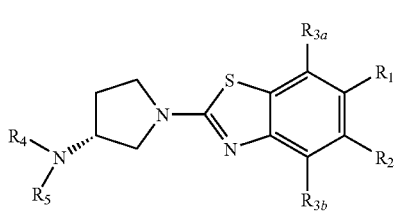

(III)

wherein $R_1$, $R_2$, $R_{3a}$, $R_{3b}$, $R_4$, and $R_5$ are as described for compounds of formula (I). In one embodiment, $R_1$ is -L-$R_6$, $R_2$ is hydrogen, $R_{3a}$ and $R_{3b}$ are both hydrogen, and $R_4$ and $R_5$ taken together form a non-aromatic ring. In another embodiment, $R_1$ is hydrogen, $R_2$ is -L-$R_6$, $R_{3a}$ and $R_{3b}$ are both hydrogen, and $R_4$ and $R_5$ taken together form a non-aromatic ring.

Another embodiment of the invention is compounds of the formula (IV):

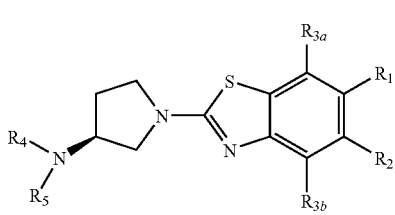

(IV)

wherein $R_1$, $R_2$, $R_{3a}$, $R_{3b}$, $R_4$, and $R_5$ are as described for compounds of formula (I). In one embodiment, $R_1$ is -L-$R_6$, $R_2$ is hydrogen, $R_{3a}$ and $R_{3b}$ are both hydrogen, and $R_4$ and $R_5$ taken together form a non-aromatic ring. In another embodiment, $R_1$ is hydrogen, $R_2$ is -L-$R_6$, $R_{3a}$ and $R_{3b}$ are both hydrogen, and $R_4$ and $R_5$ taken together form a non-aromatic ring.

Another embodiment of the invention is compounds of the formula (V):

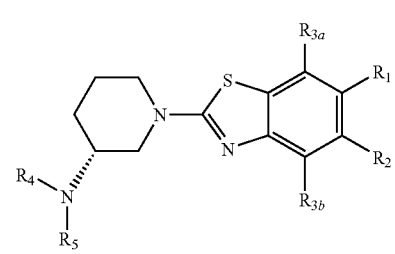

(V)

wherein $R_1$, $R_2$, $R_{3a}$, $R_{3b}$, $R_4$, and $R_5$ are as described for compounds of formula (I). In one embodiment, $R_1$ is -L-$R_6$, $R_2$ is hydrogen, $R_{3a}$ and $R_{3b}$ are both hydrogen, and $R_4$ and $R_5$ taken together form a non-aromatic ring. In another embodiment, $R_1$ is hydrogen, $R_2$ is -L-$R_6$, $R_{3a}$ and $R_{3b}$ are both hydrogen, and $R_4$ and $R_5$ taken together form a non-aromatic ring.

Another embodiment of the invention is compounds of the formula (VI):

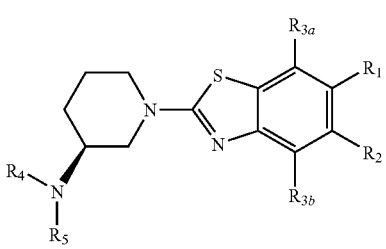

(VI)

wherein $R_1$, $R_2$, $R_{3a}$, $R_{3b}$, $R_4$, and $R_5$ are as described for compounds of formula (I). In one embodiment, $R_1$ is -L-$R_6$, $R_2$ is hydrogen, $R_{3a}$ and $R_{3b\ b}$ are both hydrogen, and $R_4$ and $R_5$ taken together form a non-aromatic ring. In another embodiment, $R_1$ is hydrogen, $R_2$ is -L-$R_6$, $R_{3a}$ and $R_{3b}$ are both hydrogen, and $R_4$ and $R_5$ taken together form a non-aromatic ring.

Another embodiment of the invention is compounds of the formula (VII):

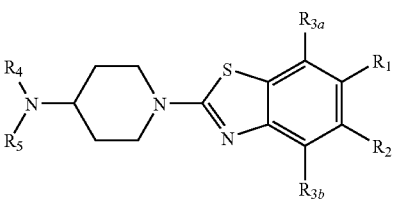

(VII)

wherein $R_1$, $R_2$, $R_{3a}$, $R_{3b}$, $R_4$, and $R_5$ are as described for compounds of formula (I). In one embodiment, $R_1$ is -L-$R_6$, $R_2$ is hydrogen, $R_{3a}$ and $R_{3b}$ are both hydrogen, and $R_4$ and $R_5$ taken together form a non-aromatic ring. In another embodiment, $R_1$ is hydrogen, $R_2$ is -L-$R_6$, $R_{3a}$ and $R_{3b}$ are both hydrogen, and $R_4$ and $R_5$ taken together form a non-aromatic ring.

Suitable groups for each position in compounds of formula (I), for example, $R_1$, $R_2$, $R_{3a}$, $R_{3b}$, $R_4$, and $R_5$, and the integers represented by m, n, and p in all embodiments, each can be determined independently of substitutions in other positions of the compound. It is contemplated that a preferred group represented by one variable, for example $R_1$ is -L$R_6$ wherein L is a defined for $R_1$ and $R_6$ is heterocycle, can be incorporated into compounds of formula (I) with a preferred group for another variable, for example wherein $R_4$ and $R_5$ is a group of formula (a) as previously described from $R_4$ and $R_5$.

One embodiment contemplated as part of the invention includes, but is not limited to, compounds of formula (I) wherein n is 1; p is 0; —$NR_4R_5$ is piperidine; L is a bond; and $R_6$ is a heterocycle.

One embodiment contemplated as part of the invention includes, but is not limited to, compounds of formula (I) wherein n is 1; p is 0; —$NR_4R_5$ is pyrrolidine; L is a bond; and $R_6$ is a heterocycle.

One embodiment contemplated as part of the invention includes, but is not limited to, compounds of formula (I) wherein n is 2; p is 0; —$NR_4R_5$ is azepane; L is a bond; and $R_6$ is a heterocycle.

Another embodiment of preferred compounds are compounds of formula (I) wherein $R_1$ is -$LR_6$, L is a bond, and $R_6$ is a structure of formula (c):

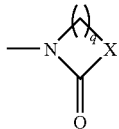
(c)

wherein X is selected from oxygen, $NR_{20}$, and $CR_{21}R_{22}$; q is an integer from 1 to 4; $R_{20}$ is selected from hydrogen and lower alkyl; $R_{21}$ and $R_{22}$ are each independently selected from hydrogen, hydroxy, alkoxy, lower alkyl and lower haloalkyl; and all other variables are as defined for compounds of formula (I).

Another embodiment of the invention is compounds of the formula (VIII),

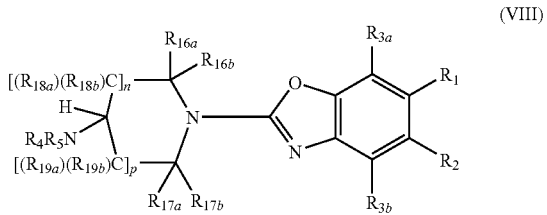
(VIII)

or a pharmaceutically acceptable salt, ester, amide, or radiolabelled form thereof, wherein $R_1$, $R_2$, $R_{3a}$, $R_{3b}$, $R_4$, $R_5$, $R_{16a}$, $R_{16b}$, $R_{17a}$, $R_{17b}$, $R_{18a}$, $R_{18b}$, $R_{19a}$, and $R_{19b}$ are as described for formula (I) in the Summary of the Invention.

Another embodiment of the invention is compounds of the formula (IX):

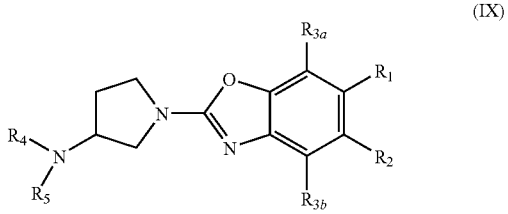
(IX)

wherein $R_1$, $R_2$, $R_{3a}$, $R_{3b}$, $R_4$, and $R_5$ are as described for compounds of formula (I). In one embodiment, $R_1$ is $(NR_AR_B)$carbonyl-, $R_2$ is hydrogen, $R_{3a}$ and $R_{3b}$ are both hydrogen, and $R_4$ and $R_5$ taken together form a non-aromatic ring. In another embodiment, $R_1$ is hydrogen, $R_2$ is $(NR_AR_B)$carbonyl-, $R_{3a}$ and $R_{3b}$ are both hydrogen, and $R_4$ and $R_5$ taken together form a non-aromatic ring.

Another embodiment of the invention is compounds of the formula (X):

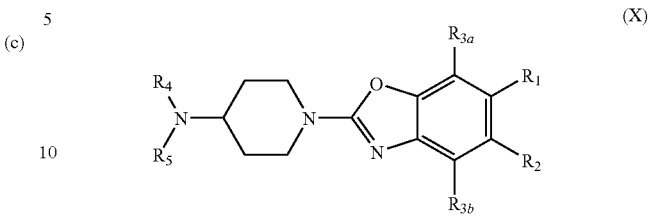
(X)

wherein $R_1$, $R_2$, $R_{3a}$, $R_{3b}$, $R_4$, and $R_5$ are as described for compounds of formula (I). In one embodiment, $R_1$ is $(NR_AR_B)$carbonyl- or alkoxycarbonyl, $R_2$ is hydrogen, $R_{3a}$ and $R_{3b}$ are both hydrogen, and $R_4$ and $R_5$ taken together form a non-aromatic ring. In another embodiment, $R_1$ is hydrogen, $R_2$ is $(NR_AR_B)$carbonyl- or alkoxycarbonyl, $R_{3a}$ and $R_{3b}$ are both hydrogen, and $R_4$ and $R_5$ taken together form a non-aromatic ring.

Specific embodiments contemplated as part of the invention also include, but are not limited to, compounds of formula (I), as defined, for example:

6-(1-methyl-1H-pyrazol-4-yl)-2-(3-(piperidin-1-yl)azetidin-1-yl)benzo[d]thiazole;
6-(1-methyl-1H-pyrazol-4-yl)-2-(3-(pyrrolidin-1-yl)azetidin-1-yl)benzo[d]thiazole;
2-(3-(azepan-1-yl)azetidin-1-yl)-6-(1-methyl-1H-pyrazol-4-yl)benzo[d]thiazole;
(R)-6-(1-methyl-1H-pyrazol-4-yl)-2-(3-(2-methylpyrrolidin-1-yl)azetidin-1-yl)benzo[d]thiazole;
6-(1-methyl-1H-pyrazol-4-yl)-2-(3-(2-methylpiperidin-1-yl)azetidin-1-yl)benzo[d]thiazole;
N-ethyl-N-methyl-1-(6-(1-methyl-1H-pyrazol-4-yl)benzo[d]thiazol-2-yl)azetidin-3-amine;
2-(ethyl(1-(6-(1-methyl-1H-pyrazol-4-yl)benzo[d]thiazol-2-yl)azetidin-3-yl)amino)ethanol;
(S)-(1-(1-(6-(1-methyl-1H-pyrazol-4-yl)benzo[d]thiazol-2-yl)azetidin-3-yl)pyrrolidin-2-yl)methanol;
6-bromo-2-(3-(piperidin-1-yl)azetidin-1-yl)benzo[d]thiazole;
(R)-6-bromo-2-(3-(2-methylpyrrolidin-1-yl)azetidin-1-yl)benzo[d]thiazole;
4-(2-((2R,3'R)-2-methyl-1,3'-bipyrrolidin-1'-yl)benzo[d]thiazol-6-yl)benzonitrile;
(R)-4-(2-(1,3'-bipyrrolidin-1'-yl)benzo[d]thiazol-6-yl)benzonitrile;
(R)-4-(2-(3-(piperidin-1-yl)pyrrolidin-1-yl)benzo[d]thiazol-6-yl)benzonitrile;
(R)-6-bromo-2-(3-(piperidin-1-yl)pyrrolidin-1-yl)benzo[d]thiazole;
(R)-6-(2-methoxypyrimidin-5-yl)-2-(3-(piperidin-1-yl)pyrrolidin-1-yl)benzo[d]thiazole;
(R)-2-(3-(piperidin-1-yl)pyrrolidin-1-yl)-6-(pyrimidin-5-yl)benzo[d]thiazole;
(R)-6-(1-methyl-1H-pyrazol-4-yl)-2-(3-(piperidin-1-yl)pyrrolidin-1-yl)benzo[d]thiazole;
(R)-6-(2,6-dimethylpyridin-3-yl)-2-(3-(piperidin-1-yl)pyrrolidin-1-yl)benzo[d]thiazole;
(R)-6-(6-methoxypyridin-3-yl)-2-(3-(piperidin-1-yl)pyrrolidin-1-yl)benzo[d]thiazole;
(R)-2-(2-(3-(piperidin-1-yl)pyrrolidin-1-yl)benzo[d]thiazol-6-yl)pyridazin-3(2H)-one;
(R)-3-(2-(3-(piperidin-1-yl)pyrrolidin-1-yl)benzo[d]thiazol-6-yl)oxazolidin-2-one;
(S)-3-hydroxy-1-(2-((R)-3-(piperidin-1-yl)pyrrolidin-1-yl)benzo[d]thiazol-6-yl)pyrrolidin-2-one;

4-(2-((3S)-3-(2-methylpiperidin-1-yl)pyrrolidin-1-yl)benzo[d]thiazol-6-yl)benzonitrile;
(S)-4-(2-(3-(piperidin-1-yl)pyrrolidin-1-yl)benzo[d]thiazol-6-yl)benzonitrile;
(S)-4-(2-(3-(azepan-1-yl)pyrrolidin-1-yl)benzo[d]thiazol-6-yl)benzonitrile;
4-(2-((3'S)-2-methyl-1,3'-bipyrrolidin-1'-yl)benzo[d]thiazol-6-yl)benzonitrile;
(S)-4-(2-(1,3'-bipyrrolidin-1'-yl)benzo[d]thiazol-6-yl)benzonitrile;
4-(2-((2S,3'S)-2-(hydroxymethyl)-1,3'-bipyrrolidin-1'-yl)benzo[d]thiazol-6-yl)benzonitrile;
(S)-4-(2-(3-(diethylamino)pyrrolidin-1-yl)benzo[d]thiazol-6-yl)benzonitrile;
(S)-4-(2-(3-(ethyl(methyl)amino)pyrrolidin-1-yl)benzo[d]thiazol-6-yl)benzonitrile;
(S)-4-(2-(3-(isopropyl(methyl)amino)pyrrolidin-1-yl)benzo[d]thiazol-6-yl)benzonitrile;
(S)-2-(1,3'-bipyrrolidin-1'-yl)-6-bromobenzo[d]thiazole;
(S)-2-(2-(1,3'-bipyrrolidin-1'-yl)benzo[d]thiazol-6-yl)pyridazin-3(2H)-one;
(R)-2-(3-(azetidin-1-yl)piperidin-1-yl)-6-bromobenzo[d]thiazole;
(R)-6-bromo-2-(3-(pyrrolidin-1-yl)piperidin-1-yl)benzo[d]thiazole;
(R)-2-(1,3'-bipiperidin-1'-yl)-6-bromobenzo[d]thiazole;
(R)-4-(1-(6-bromobenzo[d]thiazol-2-yl)piperidin-3-yl)morpholine;
(R)-2-(3-(azepan-1-yl)piperidin-1-yl)-6-bromobenzo[d]thiazole;
(S)-2-(3-(azetidin-1-yl)piperidin-1-yl)-6-bromobenzo[d]thiazole;
(S)-6-bromo-2-(3-(pyrrolidin-1-yl)piperidin-1-yl)benzo[d]thiazole;
(S)-2-(1,3'-bipiperidin-1'-yl)-6-bromobenzo[d]thiazole;
(S)-4-(1-(6-bromobenzo[d]thiazol-2-yl)piperidin-3-yl)morpholine;
(S)-2-(3-(azepan-1-yl)piperidin-1-yl)-6-bromobenzo[d]thiazole;
6-bromo-2-(4-(pyrrolidin-1-yl)piperidin-1-yl)benzo[d]thiazole;
2-(1,4'-bipiperidin-1'-yl)-6-bromobenzo[d]thiazole;
(R)-6-methoxy-2-(3-(piperidin-1-yl)pyrrolidin-1-yl)benzo[d]thiazole;
(R)-2-(3-(piperidin-1-yl)pyrrolidin-1-yl)benzo[d]thiazol-6-ol;
(R)-6-(2-(3-(piperidin-1-yl)pyrrolidin-1-yl)benzo[d]thiazol-6-yloxy)nicotinamide;
(R)—N-methyl-5-(2-(3-(piperidin-1-yl)pyrrolidin-1-yl)benzo[d]thiazol-6-yloxy)pyrazine-2-carboxamide;
(R)-5-bromo-2-(3-(piperidin-1-yl)pyrrolidin-1-yl)benzo[d]thiazole;
(R)-2-(2-(3-(piperidin-1-yl)pyrrolidin-1-yl)benzo[d]thiazol-5-yl)pyridazin-3(2H)-one;
(R)-ethyl 2-(3-(piperidin-1-yl)pyrrolidin-1-yl)benzo[d]thiazole-6-carboxylate;
(R)-2-(3-(piperidin-1-yl)pyrrolidin-1-yl)benzo[d]thiazole-6-carboxylic acid;
(R)-morpholino(2-(3-(piperidin-1-yl)pyrrolidin-1-yl)benzo[d]thiazol-6-yl)methanone;
(R)—N-methyl-2-(3-(piperidin-1-yl)pyrrolidin-1-yl)benzo[d]thiazole-6-carboxamide;
((S)-3-hydroxypyrrolidin-1-yl)(2-((R)-3-(piperidin-1-yl)pyrrolidin-1-yl)benzo[d]thiazol-6-yl)methanone;
(R)—N-(2-hydroxy-2-methylpropyl)-2-(3-(piperidin-1-yl)pyrrolidin-1-yl)benzo[d]thiazole-6-carboxamide;
(R)—N-ethyl-N-methyl-2-(3-(piperidin-1-yl)pyrrolidin-1-yl)benzo[d]thiazole-6-carboxamide;
(R)—N,N-dimethyl-2-(3-(piperidin-1-yl)pyrrolidin-1-yl)benzo[d]thiazole-6-carboxamide;
(R)—N-ethyl-2-(3-(piperidin-1-yl)pyrrolidin-1-yl)benzo[d]thiazole-6-carboxamide;
(R)—N-isopropyl-2-(3-(piperidin-1-yl)pyrrolidin-1-yl)benzo[d]thiazole-6-carboxamide;
(R)—N-(2-fluoroethyl)-2-(3-(piperidin-1-yl)pyrrolidin-1-yl)benzo[d]thiazole-6-carboxamide;
(R)-isopropyl 6-(2-(3-(piperidin-1-yl)pyrrolidin-1-yl)benzo[d]thiazol-6-yl)picolinate;
(R)-6-(2-(3-(piperidin-1-yl)pyrrolidin-1-yl)benzo[d]thiazol-6-yl)picolinic acid;
(R)-methyl 6-(2-(3-(piperidin-1-yl)pyrrolidin-1-yl)benzo[d]thiazol-6-yl)picolinate;
(R)-methyl 5-(2-(3-(piperidin-1-yl)pyrrolidin-1-yl)benzo[d]thiazol-6-yl)picolinate;
(R)-6-(6-methoxypyridazin-3-yl)-2-(3-(piperidin-1-yl)pyrrolidin-1-yl)benzo[d]thiazole;
(R)—N-methyl-6-(2-(3-(piperidin-1-yl)pyrrolidin-1-yl)benzo[d]thiazol-6-yl)picolinamide;
(R)—N-methyl-2-(2-(3-(piperidin-1-yl)pyrrolidin-1-yl)benzo[d]thiazol-6-yl)isonicotinamide;
(R)—N-methyl-6-(2-(3-(piperidin-1-yl)pyrrolidin-1-yl)benzo[d]thiazol-6-yl)nicotinamide;
(R)-6-(2-(3-(piperidin-1-yl)pyrrolidin-1-yl)benzo[d]thiazol-6-yl)pyridazin-3-ol;
(R)-5-(2-(3-(piperidin-1-yl)pyrrolidin-1-yl)benzo[d]thiazol-6-yl)pyrimidin-2-ol;
(R)-5-(2-(3-(piperidin-1-yl)pyrrolidin-1-yl)benzo[d]thiazol-6-yl)pyridin-2-ol;
(R)—N-methyl-5-(2-(3-(piperidin-1-yl)pyrrolidin-1-yl)benzo[d]thiazol-6-yl)picolinamide;
(R)—N-methyl-2-(2-(3-(piperidin-1-yl)pyrrolidin-1-yl)benzo[d]thiazol-6-yl)thiazole-5-carboxamide;
(R)—N-methyl-5-(2-(3-(piperidin-1-yl)pyrrolidin-1-yl)benzo[d]thiazol-6-yl)nicotinamide;
(R)—N-methyl-6-(2-(3-(piperidin-1-yl)pyrrolidin-1-yl)benzo[d]thiazol-6-yloxy)nicotinamide;
(R)—N-methyl-6-(2-(3-(piperidin-1-yl)pyrrolidin-1-yl)benzo[d]thiazol-6-yloxy)picolinamide;
(R)—N-methyl-2-(2-(3-(piperidin-1-yl)pyrrolidin-1-yl)benzo[d]thiazol-6-yloxy)isonicotinamide;
(R)—N-methyl-5-(2-(3-(piperidin-1-yl)pyrrolidin-1-yl)benzo[d]thiazol-6-yloxy)picolinamide;
(R)—N-methyl-2-(2-(3-(piperidin-1-yl)pyrrolidin-1-yl)benzo[d]thiazol-6-yloxy)thiazole-5-carboxamide;
(R)-6-(6-methoxypyridazin-3-yloxy)-2-(3-(piperidin-1-yl)pyrrolidin-1-yl)benzo[d]thiazole;
(R)-6-(6-methoxypyridin-2-yloxy)-2-(3-(piperidin-1-yl)pyrrolidin-1-yl)benzo[d]thiazole;
(R)-6-(2-(3-(piperidin-1-yl)pyrrolidin-1-yl)benzo[d]thiazol-6-yloxy)pyridazin-3-ol;
3-[2-((R)-3-piperidin-1-yl-pyrrolidin-1-yl)-benzothiazol-6-yl]-3H-pyrimidin-4-one;
6-methyl-3-[2-((R)-3-piperidin-1-yl-pyrrolidin-1-yl)-benzothiazol-6-yl]-3H-pyrimidin-4-one;
4- [2-((R)-3-piperidin-1-yl-pyrrolidin-1-yl)-benzothiazol-6-yl]-morpholin-3-one;
2-methyl-3-[2-((R)-3-piperidin-1-yl-pyrrolidin-1-yl)-benzothiazol-6-yl]-3H-quinazolin-4-one;
2,8-dimethyl-3-[2-((R)-3-piperidin-1-yl-pyrrolidin-1-yl)-benzothiazol-6-yl]-3H-quinazolin-4-one;
2-methyl-3-[2-((R)-3-piperidin-1-yl-pyrrolidin-1-yl)-benzothiazol-6-yl]-8-trifluoromethyl-3H-quinazolin-4-one;
(R)—N,N-dimethyl-2-(3-(piperidin-1-yl)pyrrolidin-1-yl)benzo[d]oxazole-6-carboxamide;
(R)—N-ethyl-2-(3-(piperidin-1-yl)pyrrolidin-1-yl)benzo[d]oxazole-6-carboxamide;
methyl 2-(1,4'-bipiperidin-1'-yl)benzo[d]oxazole-5-carboxylate; and
2-(1,4'-bipiperidin-1'-yl)-N-ethylbenzo[d]oxazole-5-carboxamide.

Compound names are assigned by using AUTONOM naming software, which is provided by MDL Information Systems GmbH (formerly known as Beilstein Informationssysteme) of Frankfurt, Germany, and is part of the CHEMDRAW® ULTRA v. 6.0.2 software suite or Struct=Name naming algorithm as part of CHEMDRAW® ULTRA v. 9.0.7.

Compounds of the invention may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Compounds of the invention may exist as cis or trans isomers, wherein substituents on a ring may attached in such a manner that they are on the same side of the ring (cis) relative to each other, or on opposite sides of the ring relative to each other (trans). For example, cyclobutanes may be present in the cis or trans configuration, and may be present as a single isomer or a mixture of the cis and trans isomers. Individual cis or trans isomers of compounds of the invention may be prepared synthetically from commercially available starting materials using selective organic transformations, or by prepared in single isomeric form by purification of mixtures of the cis and trans isomers. Such methods are well-known to those of ordinary skill in the art, and may include separation of isomers by recrystallization or chromatography.

It should be understood that the compounds of the invention may possess tautomeric forms, as well as geometric isomers, and that these also constitute an aspect of the invention. It is also understood that the compounds of the invention may exist as isotopomers, wherein atoms may have different weights; for example, hydrogen and deuterium, or $^{12}C$ and $^{13}C$.

Methods for Preparing Compounds of the Invention

The compounds of the invention can be better understood in connection with the following synthetic schemes and methods which illustrate a means by which the compounds can be prepared.

Abbreviations which have been used in the descriptions of the schemes and the examples that follow are: Ac for acetyl; OAc for acetoxy; Boc for t-butyloxycarbonyl; Bu for butyl; cyc-Hex for cyclohexyl; DIEA for N,N-diisopropylethylamine; DMSO for dimethyl sulfoxide; EDTA for ethylenediaminetetraacetic acid; Et for ethyl; HPLC for high pressure liquid chromatography; Me for methyl; Ms for methanesulfonyl; Ph for phenyl; tBu for tert-butyl; rt or RT for "room temperature" or ambient temperature suitably ranging 20-30° C.; TEA for triethylamine; TFA for trifluoroacetic acid; TLC for thin layer chromatography; TE buffer for Tris and EDTA buffer; and Tris for trishydroxymethylaminomethane. Microwave heating was accomplished in a commercial microwave apparatus.

The compounds of this invention can be prepared by a variety of synthetic procedures. Representative procedures are shown in, but are not limited to, Schemes 1-11.

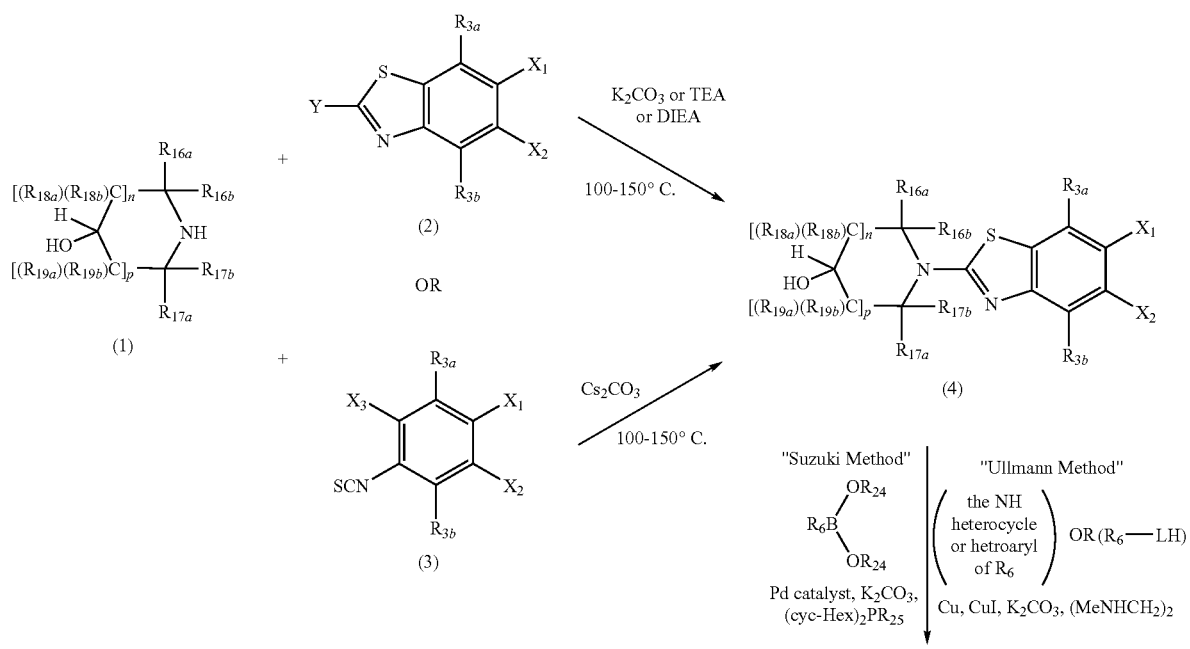

-continued

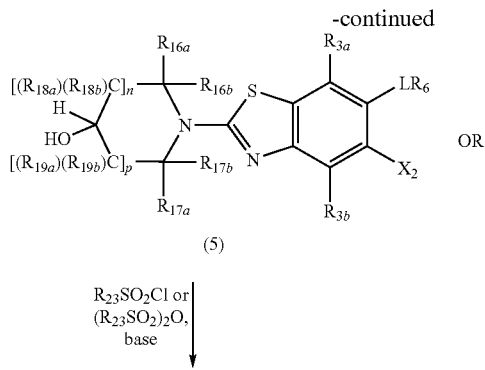

(5)

OR

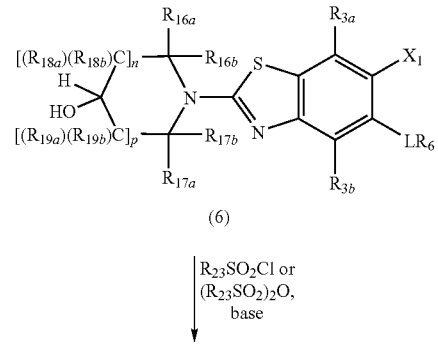

(6)

↓ R₂₃SO₂Cl or (R₂₃SO₂)₂O, base

↓ R₂₃SO₂Cl or (R₂₃SO₂)₂O, base

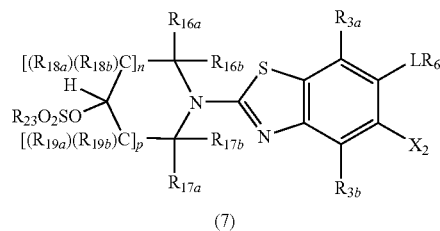

(7)

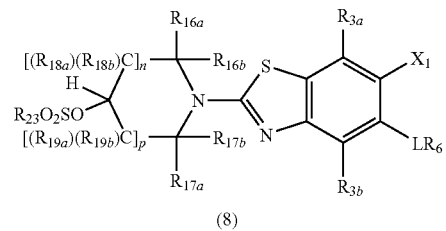

(8)

↓ R₄R₅NH, K₂CO₃

↓ R₄R₅NH, K₂CO₃

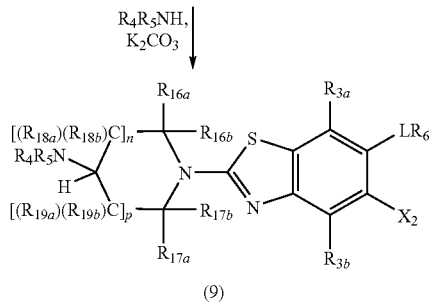

(9)

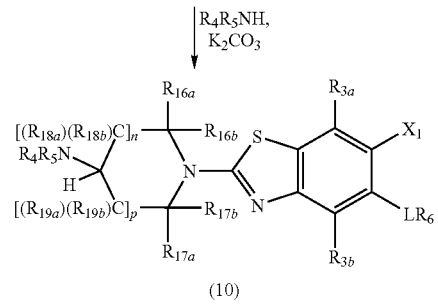

(10)

Compounds of formula (9) and (10) can be prepared as described in Scheme 1, wherein n, p, $R_1$, $R_2$, $R_{3a}$, $R_{3b}$, $R_4$, $R_5$, $R_6$, $R_{16a}$, $R_{16b}$, $R_{17a}$, $R_{17b}$, $R_{18a}$, $R_{18b}$, $R_{19a}$, and $R_{19b}$ are as defined in formula (I), wherein L is selected from a bond, O, S, and —N($R_{15}$);

$X_2$ is selected from hydrogen, chloro, cyano, alkoxy, alkoxyalkyl, alkyl, alkylthio, cycloalkyl, fluoro, fluoroalkyl, fluoroalkoxy, hydroxyalkoxy, —SO₂N($R_{14a}$)($R_{14b}$), and —N($R_{14a}$)SO₂($R_{14b}$) in compound (9); and $X_1$ is selected from hydrogen, chloro, cyano, alkoxy, alkoxyalkyl, alkyl, alkylthio, cycloalkyl, fluoro, fluoroalkyl, fluoroalkoxy, hydroxyalkoxy, —SO₂N($R_{14a}$)($R_{14b}$), and —N($R_{14a}$)SO₂($R_{14b}$) in compound (10); and $R_{14a}$, $R_{14b}$, and $R_{15}$ are as defined for compounds of formula (I).

$X_3$ in compound (3) is selected from fluoro, chloro, and bromo.

Y in compound (2) is selected from chloro and —SO₂CH₃.

Hydroxy-substituted, cyclic amines of formula (1), purchased (see Table 1) or prepared using methodologies known to those of ordinary skill in the art, when treated either with compounds of formula (2) and a base, or with compounds of formula (3) and a base, particularly Cs₂CO₃, will provide intermediates of formula (4).

There are many suitable and readily available hydroxy-substituted amines of formula (1). Examples of such hydroxy-substituted amines are exemplified, but not limited to, those shown in Table 1.

TABLE 1

Examples of readily available hydroxy-substituted amines of formula (1).

| Amines | Structures | Commercial Source, Chemical Abstracts Number (CAS#), or Literature Reference |
|---|---|---|
| azetidin-3-ol hydrochloride | HO—▱—NH·HCl | CAS# 18621-18-6, Aldrich |
| (S)-pyrrolidin-3-ol | (structure) | CAS# 100243-39-8, Fluka |
| (R)-pyrrolidin-3-ol | (structure) | CAS# 2799-21-5, Aldrich |
| (S)-piperidin-3-ol hydrochloride | (structure) | CAS# 475058-41-4, Fluorochem Wesley Street Old Glossop, Derbyshire, SK13 7RY United Kingdom |

TABLE 1-continued

Examples of readily available hydroxy-substituted amines of formula (1).

| Amines | Structures | Commercial Source, Chemical Abstracts Number (CAS#), or Literature Reference |
|---|---|---|
| (R)-piperidin-3-ol hydrochloride | 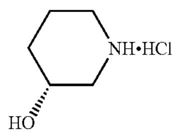 | CAS# 198976-43-1, Aldrich |
| piperidin-4-ol | 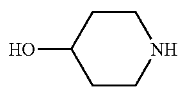 | CAS# 5382-16-1, Fluka |

Compounds of the formula (2) when Y is chloro, can be purchased such as 6-bromo-2-chlorobenzo[d]thiazole (CAS #80945-86-4, Aldrich) and 5-bromo-2-chlorobenzo[d]thiazole (CAS #824403-26-1, Nanjing Daxian Chemical Institute Ltd., Nanjing, People's Republic of China), or when Y is —SO$_2$CH$_3$, prepared from the appropritely substituted, commercially available anilines of formula (11) using methodologies known to those of ordinary skill in the art (see Scheme 2).

Scheme 2

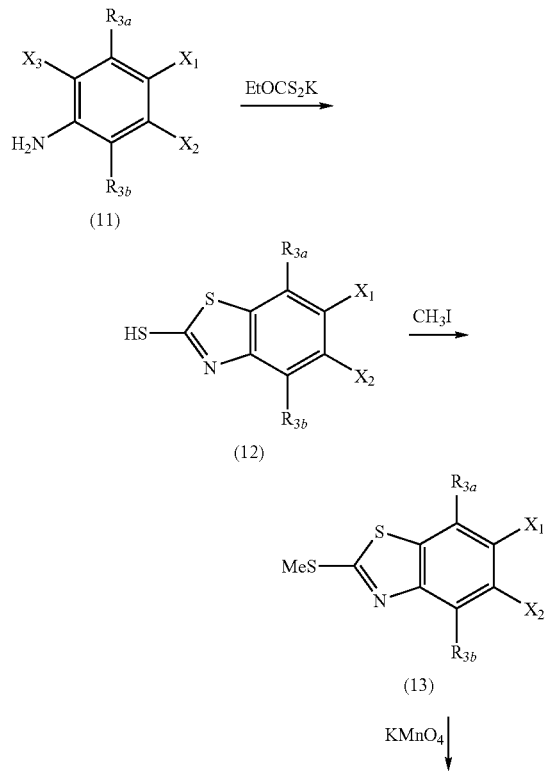

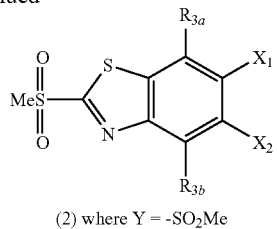

(2) where Y = -SO$_2$Me

Thus, compounds of formula (11) when treated with potassium ethylxanthogenate (CAS #140-89-6, Aldrich) in a solvent such as N,N-dimethylformamide and heated to approximately 95° C. (*J. Het. Chem.* 2005, 42(4), 727-730) affords compounds of formula (12). Treatment of compounds of formula (12) with methyl iodide in the presence of base, such as potassium carbonate provides compounds of formula (13). Oxidation of the methylthio group in compounds of formula (13) with an oxidant such as potassium permanganate (*Chemistry Letters* 1984, 2125-2128) gives compounds of formula (2) where Y=SO$_2$Me. Examples of such appropriately substituted anilines are exemplified, but not limited to, those shown in Table 2.

TABLE 2

Examples of readily available anilines of formula (11).

| Anilines | Structures | Commercial Source, Chemical Abstracts Number (CAS#), or Literature Reference |
|---|---|---|
| 4-bromo-2-fluoroaniline | 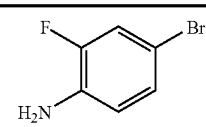 | CAS# 367-24-8, Aldrich |
| 2-fluoro-4-iodoaniline | 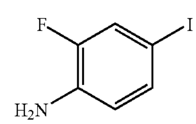 | CAS# 29632-74-4, Aldrich |
| 2,4-dibromoaniline | 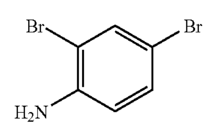 | CAS# 615-57-6, Aldrich |
| 4-bromo-2-chloroaniline | 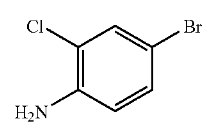 | CAS# 38762-41-3, Aldrich |
| 4-bromo-2-fluoro-6-(trifluoromethyl)aniline | | CAS# 875664-46-3, Manchester Organics Ltd. Unit 2, Clifton Lane Ashville Industrial Estate Sutton Weaver, Runcorn, Cheshire, WA73FP United Kingdom |
| 4-bromo-2-fluoro-5-methylaniline | 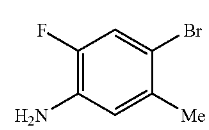 | CAS# 418762-26-2, Fluorochem Ltd. Wesley Street Old Glossop, Derbyshire, SK13 7RY United Kingdom |

TABLE 2-continued

Examples of readily available anilines of formula (11).

| Anilines | Structures | Commercial Source, Chemical Abstracts Number (CAS#), or Literature Reference |
|---|---|---|
| 4-Bromo-2,5-difluoroaniline | F, Br, $H_2N$, F substituted benzene | CAS# 112279-60-4, Aldrich |
| 4-Bromo-2-fluoro-5-(trifluoromethyl)aniline | F, Br, $H_2N$, $CF_3$ substituted benzene | CAS# 104460-70-0, Fluorochem Ltd. Wesley Street Old Glossop, Derbyshire, SK13 7RY United Kingdom |
| 4-Bromo-2,6-difluoroaniline | F, Br, $H_2N$, F substituted benzene | CAS# 67567-26-4, Aldrich |
| 2,6-Difluoro-4-iodoaniline | F, I, $H_2N$, F substituted benzene | CAS# 141743-49-9, SynQuest Laboratories, Inc. P O Box 309 Alachua, FL, 32616-0309 |
| 2-Chloro-4-bromo-6-trifluoromethoxyaniline | Cl, Br, $H_2N$, $OCF_3$ substituted benzene | CAS# 885266-98-8, Focus Synthesis LLC 10929 Technology Place, Suite B San Diego, CA, 92127 |

Returning to Scheme 1, compounds of formula (3) can also be purchased such as 4-bromo-2-fluoro-1-isothiocyanatobenzene (CAS #81171-71-3, Aldrich) and 4-bromo-3-chloro-2-fluorophenyl isothiocyanate (CAS #886501-37-7, Oakwood Products, Inc. 1741 Old Dunbar Rd., West Columbia, S.C., 29172) or prepared from the approprietly substituted, commercially available anilines (see Table 2) by treatment with thiophosgene (Bioorg. Med. Chem. Lett. 2006, 16, 3975-80), with O,O-di(pyridin-2-yl)carbonothioate (J. Org. Chem. 1986, 51(13), 2613-5), or first with carbondisulfide in the presence of triethylamine, followed by addition of ethylchloroformate (J. Fluorine Chem. 2006, 127, 182-6).

For the ultimate preparation of compounds of formula (9), intermediates of formula (4) have $X_1$ selected from Cl or, more preferably, Br or I and $X_2$ selected from hydrogen, chloro (except when $X_1$ is Cl), cyano, alkoxy, alkoxyalkyl, alkyl, alkylthio, cycloalkyl, fluoro, fluoroalkyl, fluoroalkoxy, hydroxyalkoxy, —$SO_2N(R_{14a})(R_{14b})$, and —$N(R_{14a})SO_2(R_{14b})$. Such appropriately substituted compounds of formula (4) may be converted to compounds of formula (5) by the "Suzuki Method," the "Ullmann Method," or the "Stille Method".

The "Suzuki Method" in which a boronic acid ($R_{24}$=H) or boronate (each $R_{24}$=methyl or alkyl or both $R_{24}$ combined=picolinyl) that is either purchased or prepared using methodologies known to those of ordinary skill in the art (see Table 3), reacts at the site of the halogen, $X_1$, in the presence of a palladium catalyst such as, but not limited to, palladium diacetate, dichlorobis(triphenylphosphine)palladium (II), or tetrakis(triphenylphosphine)palladium, optionally with a palladium ligand added such as (cyc-Hex)$_2PR_{25}$ (where $R_{25}$ is aryl or biphenyl, e.g. 2-(dicyclohexylphosphino)biphenyl), tri-t-butylphosphine, or tris(2-furyl)phosphine and a base such as, but not limited to aqueous $K_3PO_4$ or $Na_2CO_3$, or KF provides compounds of formula (5) in which L is a bond.

There are many aryl, heteroaryl, and heterocyclic boronic acids and boronic acid esters that are available commercially or that can be prepared as described in the scientific literature of synthetic organic chemistry. Typical examples of boronic acid and boronic acid ester reagents for the synthesis of compounds of formula (I) are shown in Table 3.

TABLE 3

Examples of Boronic Acid and Boronic Acid Ester Reagents

| Boronic Acid or Boronic Acid Ester | Commercial Source, Chemical Abstracts Number (CAS #), or Literature Reference |
|---|---|
| 2-pyrimidinone-5-boronic acid | CAS #373384-19-1 |
| 2-methoxypyrimidine-5-boronic acid | Frontier Scientific, Inc., Logan, UT, USA |
| 1H-pyrimidine-2,4-dione-5-boranic acid | Specs, Flemingslaan, the Netherlands CAS #70523-22-7; Schinazi, Raymond F.; Prusoff, William H., Synthesis of 5-(dihydroxyboryl)-2'-deoxyuridine and related boron-containing pyrimidines, Journal of Organic Chemistry (1985), 50(6), 841-7. |
| pyridine-3-boronic acid | CAS #1692-25-7, Frontier Scientific, Inc., Logan, UT, USA |
| 2,4-dimethoxypyrimidine-5-boronic acid | CAS #89641-18-9, Frontier Scientific, Inc., Logan, UT, USA |
| 2-methoxy-5-pyridine boronic acid | Digital Specialty Chemicals, Dublin, NH; CAS #163105-89-3; New shelf-stable halo- and alkoxy-substituted pyridylboronic acids and their Suzuki cross-coupling reactions to yield heteroarylpyridines, Parry, Paul R.; Bryce, Martin R.; Tarbit, Brian, Department of Chemistry, Synthesis (2003), (7), 1035-1038; Functionalized Pyridylboronic Acids and Their Suzuki Cross-Coupling Reactions To Yield Novel Heteroarylpyridines, Parry, Paul R.; |

TABLE 3-continued

Examples of Boronic Acid and Boronic Acid Ester Reagents

| Boronic Acid or Boronic Acid Ester | Commercial Source, Chemical Abstracts Number (CAS #), or Literature Reference |
|---|---|
| pyrimidine-5-boronic acid | Wang, Changsheng; Batsanov, Andrei S.; Bryce, Martin R.; Tarbit, Brian, Journal of Organic Chemistry (2002), 67(21), 7541-7543. CAS #109299-78-7, S. Gronowitz, et al., "On the synthesis of various thienyl- and selenienylpyrimidines", Chem. Scr. 26(2): 305-309 (1986). |
| pyrimidine-5-boronic acid, pinacol ester | Umemoto, et al., Angew. Chem. Int. Ed. 40(14): 2620-2622 (2001). |
| 2-methylpyridine-5-boronic acid hydrate | SYNCHEM OHG Heinrich-Plett-Strassse 40; Kassel, D-34132; Germany; CAS #659742-21-9 |
| 2H-Pyran, 3,6-dihydro-4-(4,4,5,5-tetramethyl-1,3,2-dioxaborolan-2-yl) | CAS #287944-16-5; Murata, Miki; Oyama, Takashi; Watanabe, Shinji; Masuda, Yuzuru, Synthesis of alkenylboronates via palladium-catalyzed borylation of alkenyl triflates (or iodides) with pinacolborane. Synthesis(2000), (6), 778-780. |
| 1(2H)-Pyridinecarboxylic acid, 3,6-dihydro-4-(4,4,5,5-tetramethyl-1,3,2-dioxaborolan-2-yl)-, 1,1-dimethylethyl ester | CAS #286961-14-6; A versatile synthesis of 4-aryltetrahydropyridines via palladium mediated Suzuki cross-coupling with cyclic vinyl boronates, Eastwood, Paul R., Discovery Chemistry, Aventis Pharma, Essex, UK., Tetrahedron Letters (2000), 41(19), 3705-3708. |
| (5-cyano-3-pyridinyl)-boronic acid | CAS #497147-93-0; Chemstep Institut du PIN - University Bordeaux 1 351 cours de la liberation Talence Cedex, 33450 France |
| Thianthrene-1-boronic acid | Aldrich Chemical Company, Inc. |
| Benzoxazole-5-boronic acid | Cat # 110831, Asymchem Laboratories, Inc. |
| Benzothiazole-5-boronic acid | Cat # 1464, Digital Specialty Chemicals, Inc. |
| 4-Methyl-7-(4,4,5,5-tetramethyl-1,3,2-dioxaborolan-2-yl)-3,4-dihydro-2H-1,4-benzoxazine | Cat # CC13539CB, Acros Organics USA |
| 10-Methyl-3-(4,4,5,5-tetramethyl-[1,3,2]dioxaborolan-2-yl)-10H-phenothiazine | Kraemer, C. S.; et. al. Synthesis 2002, 9, 1163-1170. |
| (1,4-Dihydro-4,4-dimethyl-2-oxo-2H-3,1-benzoxazin-6-yl)boronic acid | Zhang, P.; et. al. J. Med. Chem. 2002, 45, 4379-4382. |

Boronic acids or boronic acid esters of formula $R_6$—B$(OR_{24})_2$ and

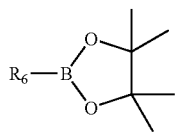

can be prepared from corresponding halides or triflates of $R_6$, wherein $R_6$ is aryl, a 5- to 6-membered heteroaryl ring, or an 8- to 12-membered bicyclic heteroaryl ring, via either: (1) metal exchange with an organo lithium agent followed with addition of alkyl borate or pinacolborate or, (2) cross coupling with a reagent such as, but not limited to, bis(pinacolato) diboron (CAS #73183-34-3) or bis(pinacolato)borane. References describing the first method are: B. T. O'Neill, et al., Organic Letters, 2:4201 (2000); M. D. Sindkhedkar, et al., Tetrahedron, 57:2991 (2001); W. C. Black, et al., J. Med. Chem., 42:1274 (1999); R. L. Letsinger et al., J. Amer. Chem. Soc., 81:498-501 (1959); and F. I. Carroll et al., J. Med. Chem., 2229-2237 (2001). References describing the second method are: T. Ishiyama et al., Tetrahedron, 57:9813-9816 (2001); T. Ishiyama et al., J. Org. Chem., 60:7508-7510 (1995); and Takagi et al., Tetrahedron Letters, 43:5649-5651 (2002).

Other methods for preparing boronic acids and boronic acid esters is described in O. Baudoin, et al., J. Org. Chem., 65:9268-9271 (2000), wherein an aryl or heteroaryl halides or triflate are treated with a dialkyloxyborane such as pinacolborane, in the presence of triethylamine and palladium (II) acetate in dioxane.

The "Ullmann Method" in which copper/copper(1) iodide catalysis, typically in a coordinating solvent such as pyridine and/or in the presence of a copper chelator such as N,N'-dimethylethylenediamine with base such as sodium carbonate, mediates the coupling to a nitrogen of a $R_6$ NH-containing heterocycle or heteroaryl to the site of the halogen, $X_1$, on compounds of formula (4) to provide compounds of formula (5) in which L is a bond. NH-containing $R_6$ heterocycle or heteroaryl compounds that are readily available are exemplified, but not limited to, examples in Table 4.

TABLE 4

Examples of readily available NH-containing $R_6$ heterocycle or heteroaryl compounds.

| Heterocycle or heteroaryl compound | Structures | Commercial Source, Chemical Abstracts Number (CAS#), or Literature Reference |
|---|---|---|
| azetidine | 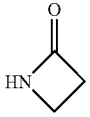 | CAS# 503-29-7, Aldrich |
| 2-pyrrolidinone | 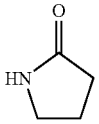 | CAS# 616-45-5, Aldrich |
| (S)-3-hydroxy-pyrrolidin-2-one | 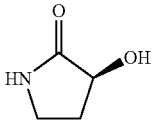 | CAS# 34368-52-0, Oakwood Products, Inc. 1741 Old Dunbar Rd. West Columbia, SC, 29172 USA |
| 2-oxazolidinone | 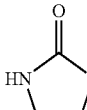 | CAS# 497-25-6, Aldrich |
| 2-imidazolidinone | 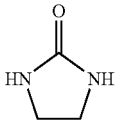 | CAS# 120-93-4, Aldrich |
| 1-methyl-2-imidazolidinone | 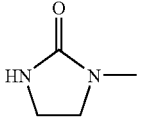 | CAS# 694-32-6, Acros |
| delta-valerolactam | 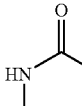 | CAS# 675-20-7, Aldrich |
| morpholin-3-one | 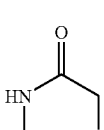 | CAS# 109-11-5, AK Scientific, Inc 897-4G Independence Ave. Mountain View, CA, 94043 USA |
| N,N'-trimethyleneurea | 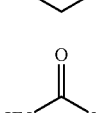 | CAS# 1852-17-1, Aldrich |
| 3-(S)-amino-2-piperidone | 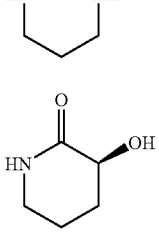 | CAS# 74954-71-5, Small Molecules, Inc. 38 Jackson Street Hoboken, NJ, 07030 USA |

TABLE 4-continued

Examples of readily available NH-containing $R_6$ heterocycle or heteroaryl compounds.

| Heterocycle or heteroaryl compound | Structures | Commercial Source, Chemical Abstracts Number (CAS#), or Literature Reference |
|---|---|---|
| 3-(R)-amino-2-piperidone | 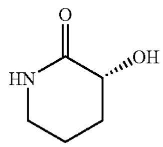 | CAS# 220928-01-8, Small Molecules, Inc. 38 Jackson Street Hoboken, NJ, 07030 USA |
| 2-hydroxypyridine | 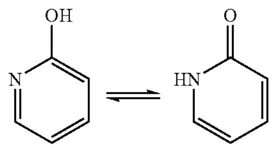 | CAS# 1852-17-1, Aldrich |
| 3(2H)-pyridazinone | 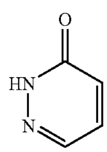 | CAS# 504-30-3, Fluka |

The "Ullmann Method" will also provide compounds of formula (5) in which L is O, if compounds of formula (4) are coupled to a hydroxy-substituted aryl or heteroaryl compound ($R_6$-LH=$R_6$—OH) either purchased or prepared using methodologies known to those of ordinary skill in the art. The "Ullmann Method" will also provide compounds of formula (5) in which L is S, if compounds of formula (4) are coupled to a mercapto-substituted aryl or heteroaryl compound ($R_6$-LH=$R_6$—SH) either purchased or prepared using methodologies known to those of ordinary skill in the art. The "Ullmann Method" will also provide compounds of formula (5) in which L is —N($R_{15}$), if compounds of formula (4) are coupled to a H($R_{15}$)N-substituted aryl or heteroaryl compound ($R_6$-LH=$R_6$—N($R_{15}$)) either purchased or prepared using methodologies known to those of ordinary skill in the art.

Alternatively, utilizing other coupling methods such as Stille coupling, compounds of formula (4), can be converted into compounds of formula (5) by treatment with organostannanes of formula $R_6Sn(R_{x''})_3$ in the presence of a palladium source such as tris(dibenzylidineacetone)-dipalladium (CAS #52409-22-0) or palladium diacetate (CAS #3375-31-3), and a ligand such as tri(2-furyl)phosphine (CAS #5518-52-5) or triphenylarsine (CAS #603-32-7). The reaction can be performed in a solvent such as N,N-dimethylformamide at a temperature from about 25° C. to about 150° C. Such methods are described, for instance, in J. K. Stille Angew. Chem. Int. Ed. 25:508(1986) and T. N. Mitchell, Synthesis, 803(1992).

While many stannanes are commercially available or described in the literature, it is also possible to prepare new stannanes from arylhalides, aryltriflates, heteroarylhalides, and heteroaryltriflates by reaction with hexa-alkyl distannanes of formula (($R_{x''})_3Sn)_2$ wherein $R_{x''}$ is alkyl or aryl, with aryl, heteroaryl, or heterocyclic halides and triflates in the presence of a palladium source like tetrakis(triphenylphosphine)palladium. Example of hexa-alkyl distannanes include, but not limited to, hexamethyldistannane (CAS #661-69-8). Such methods are described, for instance in Krische, et. al., Helvetica Chimica Acta 81(11):1909-1920 (1998), and in Benaglia, et al., Tetrahedron Letters 38:4737-4740 (1997).

Alternatively, aryl, heteroaryl, or heterocyclic organolithium and magnesium reagents can be treated with tributyltin chloride to provide Stille reagents. These reagents can be reacted with compounds of formula (4) to provide compounds of formula (5) under Stille conditions. A reference describing the Stille reaction is A. F. Littke et al., J. Amer. Chem. Soc. 124:6343-6348 (2002).

For the ultimate preparation of compounds of formula (10), intermediates of formula (4) have $X_2$ selected from Cl or, more preferably, Br or I and $X_1$ selected from hydrogen, chloro (except when $X_2$ is Cl), cyano, alkoxy, alkoxyalkyl, alkyl, alkylthio, cycloalkyl, fluoro, fluoroalkyl, fluoroalkoxy, hydroxyalkoxy, —SO$_2$N($R_{14a}$)($R_{14b}$), and —N($R_{14a}$)SO$_2$($R_{14b}$). Such appropriately substituted compounds of formula (4) may be converted to compounds of formula (6) by the "Suzuki Method" or the "Ullmann Method" or the "Stille Method" in a fashion analogous to the above description for the conversion of compounds of formula (4) to compounds of formula (5).

The alcohols (5) or (6) when treated with sulfonyl chlorides $R_{23}SO_2Cl$ (where $R_{23}$ is alkyl, fluoroalkyl, or aryl) such as mesyl chloride, tosyl chloride, or nosyl chloride or with sulfonic anhydrides ($R_{23}SO_2)_2O$ such as triflic anhydride, in the presence of base such as but not limited to potassium carbonate, triethylamine, diisopropylethylamine and the like, provide compounds of formulae (7) and (8), respectively.

The sulfonates (7) or (8) when treated with an amine of formula $R_4R_5$NH (see Table 5), in the presence of base such as but not limited to potassium carbonate or in the presence of excess $R_4R_5$NH, provide compounds (9) and (10), respectively, which are representative of the compounds of the present invention. When the sulfonate (7) is a single enantiomer, the resultant compound (9) will have the opposite configuration, due to inversion at the chiral center during the amine displacement. Likewise, when the sulfonate (8) is a single enantiomer, the resultant compound (10) will have the opposite configuration.

There are many suitable and readily available amines of formula $R_4R_5$NH, wherein $R_4$ and $R_5$ are as defined in formula (I).

TABLE 5

Examples of readily available amines of formula $R_4R_5NH$.

| Amines | Structures | Commercial Source, Chemical Abstracts Number (CAS#), or Literature Reference |
|---|---|---|
| azetidine | 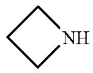 | CAS# 503-29-7, Aldrich |
| pyrrolidine | 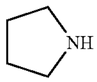 | CAS# 123-75-1, Aldrich |
| 2-(R)-methylpyrrolidine L-tartrate | 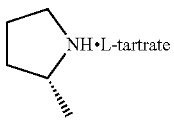 | International Publication No. WO 2004043458; Y. Pu et al., Organic Process Research & Development, 9(1), 45-50, 2005 |
| 2-(S)-methylpyrrolidine L-tartrate | 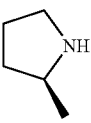 | Kim, Mahn-Joo, et al., Bioorg. Med. Chem. Lett. 6(1):71-76 (1996); Tetrahedron, 37:1861-1869 (1981). |
| L-pyrolinol | 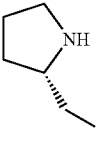 | CAS# 23356-96-9, Aldrich |
| S-(+)-2-fluoromethylpyrrolidine | 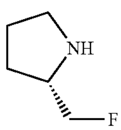 | CAS# 460748-85-0, prepared according to the procedure described in: International Publication No. WO 2004043458 |
| piperidine | 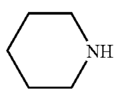 | CAS# 110-89-4, Aldrich |
| 2-methylpiperidine | 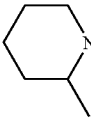 | CAS# 109-05-7, Aldrich |
| 2-(R)-methylpiperidine | 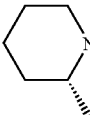 | Clariant Life Science Molecules Sandycroft Deeside Clwyd CH5 2PX UNITED KINGDOM |
| 4-fluoropiperidine hydrochloride | 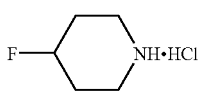 | ABCR GmbH & CO. KG P.O. Box 21 01 35 76151 Karlsruhe GERMANY |
| (R)-3-hydroxypiperidine hydrochloride | 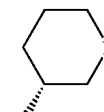 | CAS# 198976-43-1, Aldrich |
| hexamethyleneimine | 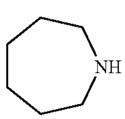 | CAS# 100-97-0, Aldrich |

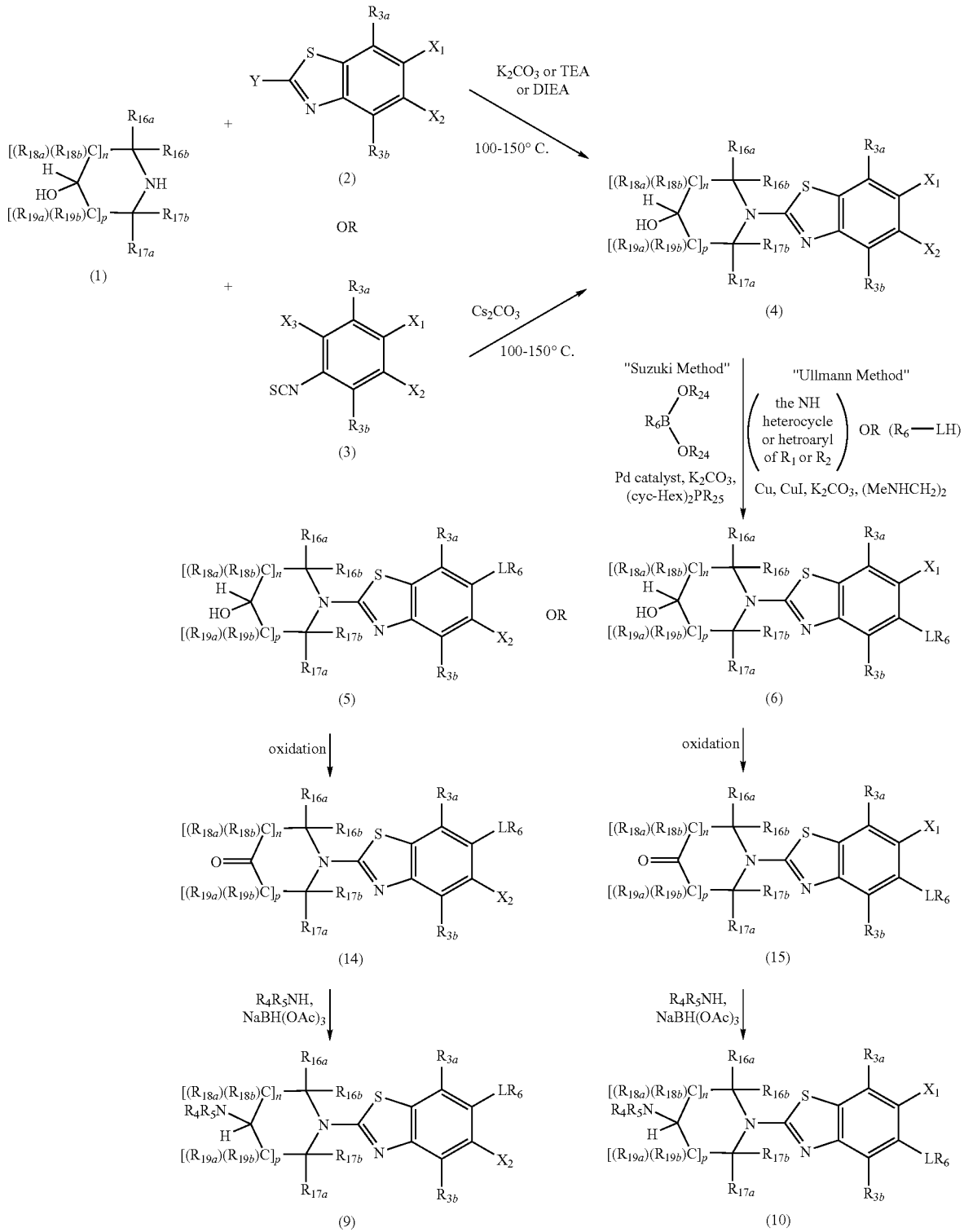

Scheme 3

Another alternative approach to the preparation of compounds of formulae (9) and (10) is outlined in Scheme 3 above, where substituent definitions are the same as in Scheme 1. Hydroxy-substituted, cyclic amines of formula (1), purchased (see Table 1) or prepared using methodologies known to those of ordinary skill in the art, when treated either with compounds of formula (2) and a base, or with compounds of formula (3) and a base, particularly $Cs_2CO_3$, will provide intermediates of formula (4). For the ultimate preparation of compounds of formula (9), intermediates of formula (4) have $X_1$ selected from Cl or, more preferably, Br or I and $X_2$ selected from hydrogen, chloro (except when $X_1$ is Cl), cyano, alkoxy, alkoxyalkyl, alkyl, alkylthio, cycloalkyl, fluoro, fluoroalkyl, fluoroalkoxy, hydroxyalkoxy, —$SO_2N(R_{14a})(R_{14b})$, and —$N(R_{14a})SO_2(R_{14b})$. Such appropriately substituted compounds of formula (4) may be converted to compounds of formula (5) by the "Suzuki Method," the "Ullmann Method," or the "Stille Method" as described above for the approach depicted by Scheme 1. Similarly, for the ultimate preparation of compounds of formula (10), intermediates of formula (4) have $X_2$ selected from Cl or, more preferably, Br or I and $X_1$ selected from hydrogen, chloro (except when $X_2$ is Cl), cyano, alkoxy, alkoxyalkyl, alkyl, alkylthio, cycloalkyl, fluoro, fluoroalkyl, fluoroalkoxy, hydroxyalkoxy, —$SO_2N(R_{14a})(R_{14b})$, and —$N(R_{14a})SO_2(R_{14b})$. Such appropriately substituted compounds of formula (4) may be converted to compounds of formula (6) by the "Suzuki Method," the "Ullmann Method," or the "Stille Method" as described above for the approach depicted by Scheme 1. Compounds of formulae (5) and (6) may then be converted to the corresponding keto derivatives of formulae (14) and (15) respectively by treatment with an oxidizing agent such as, but not limited to, the Dess-Martin periodinane (1,1,1-tris(acetyloxy)-1,1-dihydro-1,2-benziodoxol-3-(1H)-one, CAS #87413-09-0). Keto derivatives of formulae (14) and (15) are then converted to compounds of formulae (9) and (10) respectively by reductive amination employing the amines of formula $R_4R_5NH$ and a reducing agent such as sodium triacetoxyborohydride or sodium cyanoborohydride.

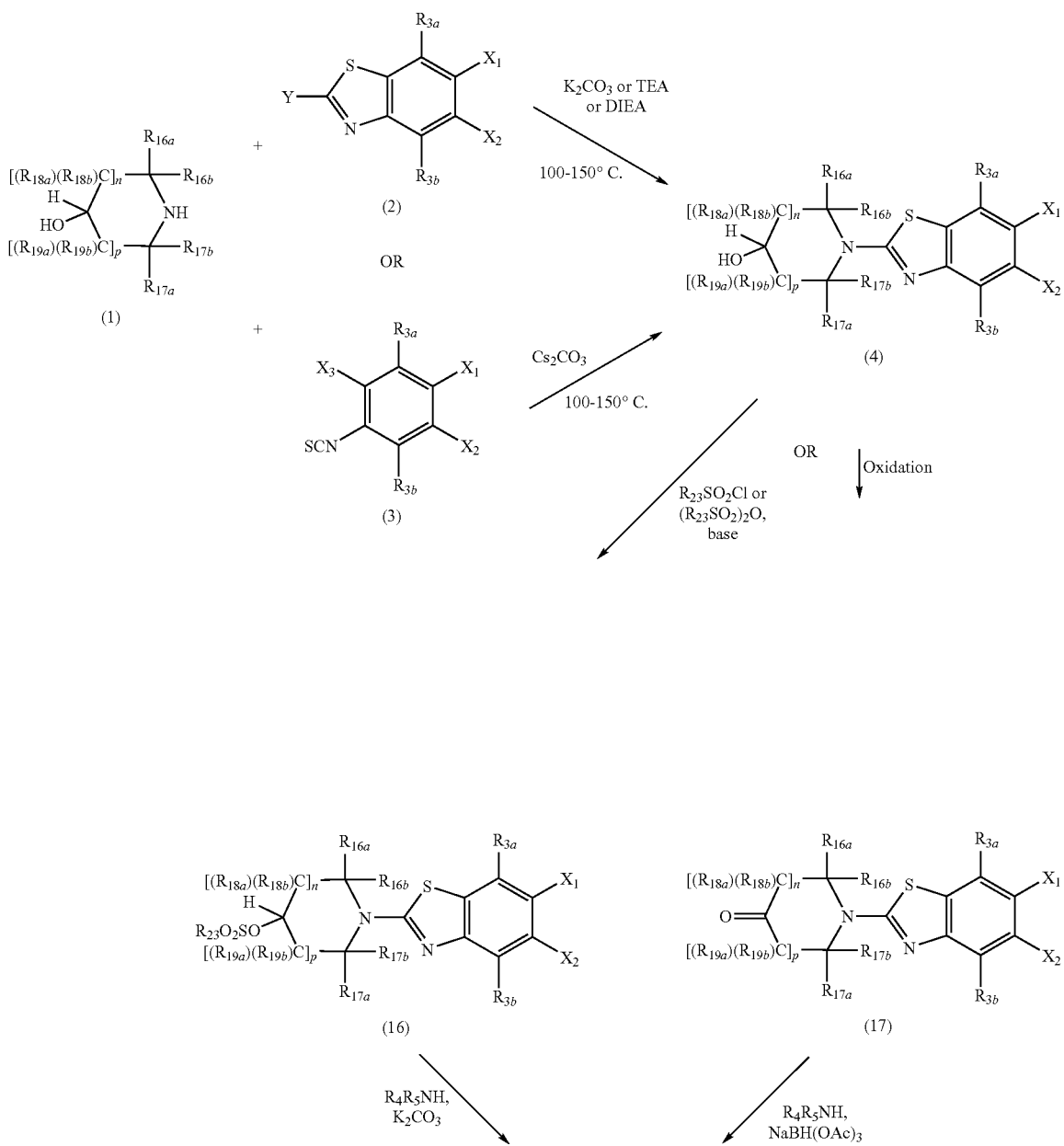

Scheme 4

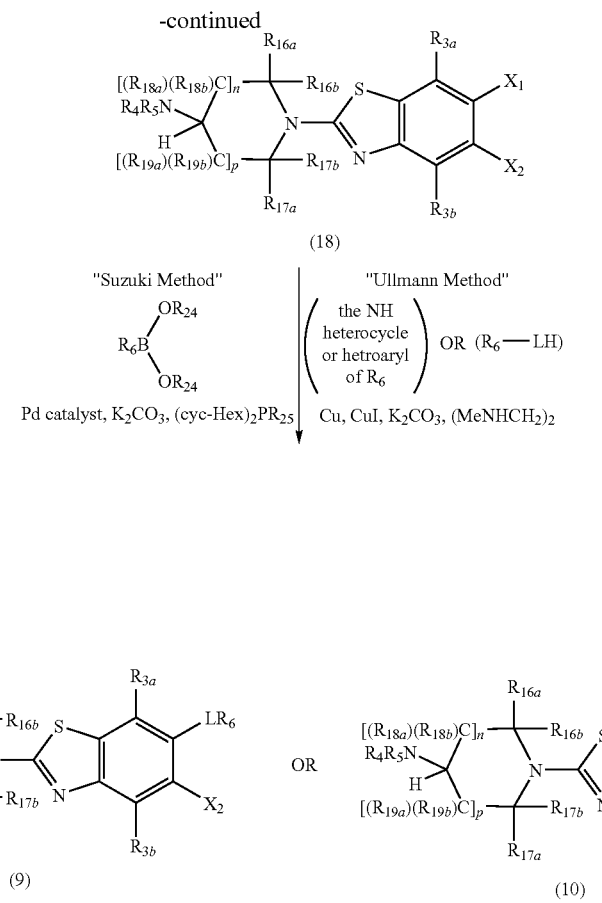

Another alternative approach to the preparation of compounds of formulae (9) and (10) is summarized in Scheme 4 above, where substituent definitions are the same as in Scheme 1. As with the approaches outlined in Schemes 1 and 3, the synthesis begins with reaction of hydroxy-substituted, cyclic amines of formula (1), purchased (see Table 1) or prepared using methodologies known to those of ordinary skill in the art, either with compounds of formula (2) and a base, or with compounds of formula (3) and a base, particularly $Cs_2CO_3$, to provide intermediates of formula (4). In a departure from the approaches depicted in Schemes 1 and 3, compounds of formula (4) in this scheme are next subjected to one of two routes.

In the first, the alcohols of formula (4) when treated with sulfonyl chlorides $R_{23}SO_2Cl$ (where $R_{23}$ is alkyl, fluoroalkyl, or aryl) such as mesyl chloride, tosyl chloride, or nosyl chloride or with sulfonic anhydrides $(R_{23}SO_2)_2O$ such as triflic anhydride, in the presence of base such as but not limited to potassium carbonate, triethylamine, diisopropylethylamine and the like, provide compounds of formula (16). The sulfonates of formula (16) when treated with an amine of formula $R_4R_5NH$ (see Table 5), in the presence of base such as but not limited to potassium carbonate or in the presence of excess $R_4R_5NH$, provide compounds of formula (18). When the sulfonates of formula (16) are a single enantiomer, the resultant compounds of formula (18) will have the opposite configuration, due to inversion at the chiral center during the amine displacement.

In the second route, compounds of formula (4) may be converted to the corresponding keto derivatives of formula (17) by treatment with an oxidizing agent such as, but not limited to, the Dess-Martin periodinane (1,1,1-tris(acetyloxy)-1,1-dihydro-1,2-benziodoxol-3-(1H)-one, CAS #87413-09-0). The keto derivatives of formula (17) are then converted to compounds of formula (18) by reductive amination employing the amines of formula $R_4R_5NH$ and a reducing agent such as sodium triacetoxyborohydride or sodium cyanoborohydride.

For the ultimate preparation of compounds of formula (9), intermediates of formula (18) have $X_1$ selected from Cl or, more preferably, Br or I and $X_2$ selected from hydrogen, chloro (except when $X_1$ is Cl), cyano, alkoxy, alkoxyalkyl, alkyl, alkylthio, cycloalkyl, fluoro, fluoroalkyl, fluoroalkoxy, hydroxyalkoxy, —$SO_2N(R_{14a})(R_{14b})$, and —$N(R_{14a})SO_2$ $(R_{14b})$. Such appropriately substituted compounds of formula (18) may be converted to compounds of formula (9) by the "Suzuki Method," the "Ullmann Method," or the "Stille Method".

The "Suzuki Method" in which a boronic acid ($R_{24}$=H) or boronate (each $R_{24}$=methyl or alkyl or both $R_{24}$ combined=picolinyl) that is either purchased or prepared using methodologies known to those of ordinary skill in the art, reacts with compounds of formula (18) at the site of the halogen, $X_1$, in the presence of a palladium catalyst such as, but not limited to, palladium diacetate, dichlorobis(triphenylphosphine)palladium (II), or tetrakis(triphenylphosphine)palladium, optionally with a palladium ligand added such as (cyc-Hex)$_2PR_{25}$ (where $R_{25}$ is aryl or biphenyl, e.g. 2-(dicyclohexylphosphino)biphenyl), tri-t-butylphosphine, or tris(2-furyl)phosphine and a base such as, but not limited to aqueous K₃PO₄ or Na₂CO₃, or KF provides compounds of formula (9) in which L is a bond.

There are many aryl, heteroaryl, and heterocyclic boronic acids and boronic acid esters that are available commercially or that can be prepared as described in the scientific literature of synthetic organic chemistry. Typical examples of boronic acid and boronic acid ester reagents for the synthesis of compounds of formula (I) are shown in Table 3 above.

Boronic acids or boronic acid esters of formula $R_6$—B(OR)₂ and

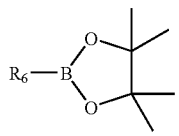

can be prepared from corresponding halides or triflates of $R_6$ via either: (1) metal exchange with an organo lithium agent followed with addition of alkyl borate or pinacolborate or, (2) cross coupling with a reagent such as, but not limited to, bis(pinacolato)diboron (CAS #73183-34-3) or bis(pinacolato)borane. References describing the first method are: B. T. O'Neill, et al., Organic Letters, 2:4201 (2000); M. D. Sindkhedkar, et al., Tetrahedron, 57:2991 (2001); W. C. Black, et al., J. Med. Chem., 42:1274 (1999); R. L. Letsinger et al., J. Amer. Chem. Soc., 81:498-501 (1959); and F. I. Carroll et al., J. Med. Chem., 2229-2237 (2001). References describing the second method are: T. Ishiyama et al., Tetrahedron, 57:9813-9816 (2001); T. Ishiyama et al., J. Org. Chem., 60:7508-7510 (1995); and Takagi et al., Tetrahedron Letters, 43:5649-5651 (2002).

Other methods for preparing boronic acids and boronic acid esters is described in O. Baudoin, et al., J. Org. Chem., 65:9268-9271 (2000), wherein an aryl or heteroaryl halides or triflate are treated with a dialkyloxyborane such as pinacolborane, in the presence of triethylamine and palladium (II) acetate in dioxane.

The "Ullmann Method" in which copper/copper(I) iodide catalysis, typically in a coordinating solvent such as pyridine and/or in the presence of a copper chelator such as N,N'-dimethylethylenediamine with base such as sodium carbonate, mediates the coupling between a nitrogen of a $R_6$NH-containing heterocycle or heteroaryl and compounds of formula (18) at the site of the halogen, $X_1$, to provide compounds of formula (9) in which L is a bond. The "Ullmann Method" will also provide compounds of formula (9) in which L is O, if compounds of formula (18) are coupled to a hydroxy-substituted aryl or heteroaryl compound ($R_6$-LH=$R_6$—OH) either purchased or prepared using methodologies known to those of ordinary skill in the art. The "Ullmann Method" will also provide compounds of formula (9) in which L is S, if compounds of formula (18) are coupled to a mercapto-substituted aryl or heteroaryl compound ($R_6$-LH=$R_6$—SH) either purchased or prepared using methodologies known to those of ordinary skill in the art. The "Ullmann Method" will also provide compounds of formula (9) in which L is —N($R_{15}$), if compounds of formula (18) are coupled to a H($R_{15}$)N-substituted aryl or heteroaryl compound ($R_6$-LH=$R_6$—N($R_{15}$)) either purchased or prepared using methodologies known to those of ordinary skill in the art.

Alternatively, utilizing other coupling methods such as Stille coupling, appropriately substituted compounds of formula (18), can be converted into compounds of formula (9) by treatment with organostannanes of formula $R_6Sn(R_{x''})_3$, wherein $R_{x''}$ is alkyl, aryl, or halogen, in the presence of a palladium source such as tris(dibenzylidineacetone)-dipalladium (CAS #52409-22-0) or palladium diacetate (CAS #3375-31-3), and a ligand such as tri(2-furyl)phosphine (CAS #5518-52-5) or triphenylarsine (CAS #603-32-7). The reaction can be performed in a solvent such as N,N-dimethylformamide at a temperature from about 25° C. to about 150° C. Such methods are described, for instance, in J. K. Stille Angew. Chem. Int. Ed. 25:508(1986) and T. N. Mitchell, Synthesis, 803(1992).

While many stannanes are commercially available or described in the literature, it is also possible to prepare new stannanes from arylhalides, aryltriflates, heteroarylhalides, and heteroaryltriflates by reaction with hexa-alkyl distannanes of formula $((R_{x''})_3Sn)_2$ wherein $R_{x''}$ is alkyl, aryl, or halogen, with aryl, heteroaryl, or heterocyclic halides and triflates in the presence of a palladium source like tetrakis (triphenylphosphine)palladium. Example of hexa-alkyl distannanes include, but not limited to, hexamethyldistannane (CAS #661-69-8). Such methods are described, for instance in Krische, et. al., Helvetica Chimica Acta 81(11):1909-1920 (1998), and in Benaglia, et al., Tetrahedron Letters 38:4737-4740 (1997). Alternatively, aryl, heteroaryl, or heterocyclic organolithium and magnesium reagents can be treated with tributyltin chloride to provide Stille reagents. These reagents can be reacted with appropriately substituted compounds of formula (18) to provide compounds of formula (9) under Stille conditions. A reference describing the Stille reaction is A. F. Littke et al., J. Amer. Chem. Soc. 124:6343-6348 (2002).

Similarly, for the ultimate preparation of compounds of formula (10), intermediates of formula (18) have $X_2$ selected from Cl or, more preferably, Br or I and $X_1$ selected from hydrogen, chloro (except when $X_2$ is Cl), cyano, alkoxy, alkoxyalkyl, alkyl, alkylthio, cycloalkyl, fluoro, fluoroalkyl, fluoroalkoxy, hydroxyalkoxy, —SO₂N($R_{14a}$)($R_{14b}$), and —N($R_{14a}$)SO₂($R_{14b}$). Such appropriately substituted compounds of formula (18) may be converted to compounds of formula (10) by the "Suzuki Method," the "Ullmann Method," or the "Stille Method" as described above.

Scheme 5
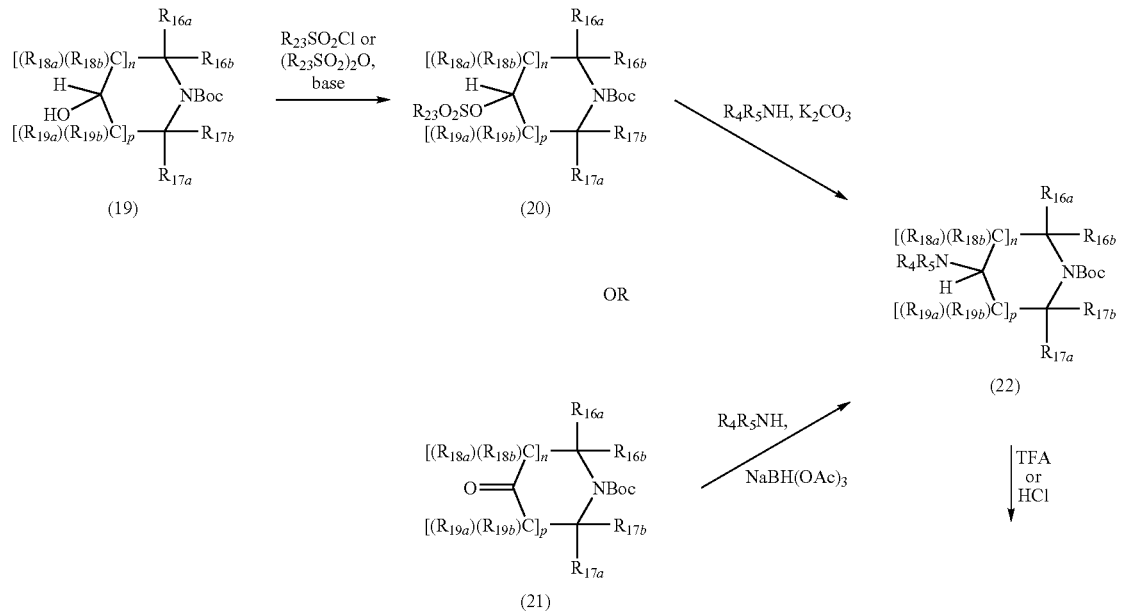
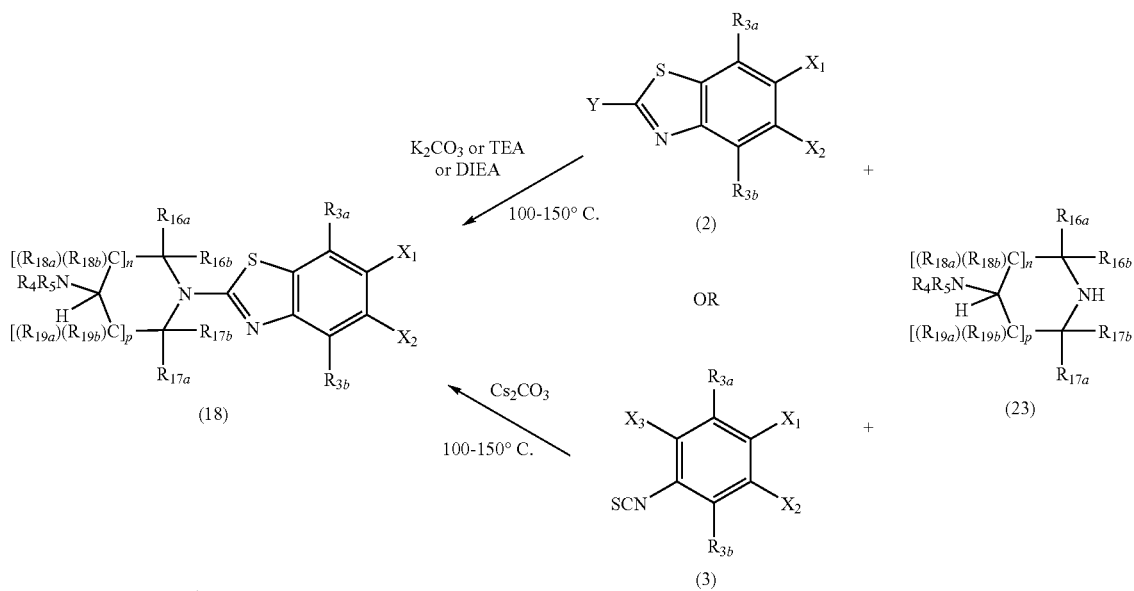
"Suzuki Method"
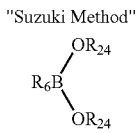
Pd catalyst, K$_2$CO$_3$, (cyc-Hex)$_2$PR$_{25}$
"Ullmann Method"
(the NH heterocycle or hetroaryl of R$_6$) OR (R$_6$—LH)
Cu, CuI, K$_2$CO$_3$, (MeNHCH$_2$)$_2$

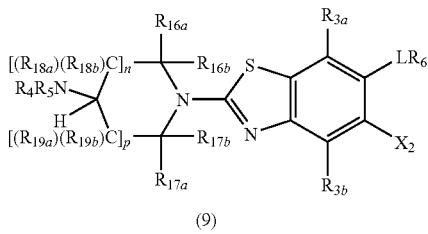

(9)

OR

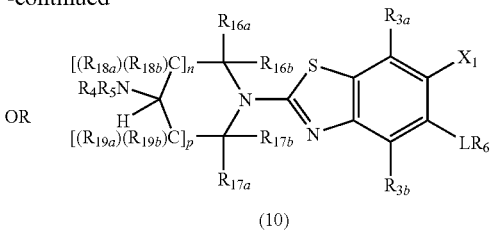

(10)

Alternatively, compounds of formulae (9) and (10) can be prepared by first preparing the diamine intermediate of formula (23) by converting N-protected, hydroxy-substituted, cyclic amines of formula (19), purchased (see Table 6) or prepared using methodologies known to those of ordinary skill in the art, to the sulfonate of formula (20). Subsequent displacement with an amine of formula $R_4R_5NH$, in the presence of base such as but not limited to potassium carbonate or in the presence of excess $R_4R_5NH$, provides compounds of the formula (22), which upon deprotection of the nitrogen with acid, for example hydrochloric acid or trifluoroacetic acid, yields the desired diamine intermediate of formula (23). The protected diamine of formula (22) may also be prepared by reductive amination of ketoamines of formula (21) that are commercially available such as 1-Boc-4-piperidone (CAS #79099-07-3, Aldrich) or 1-Boc-3-azetidinone (CAS #398489-26-4, Alfa-Aesar), prepared by oxidation of the N-protected version of the hydroxy-substituted, cyclic amines of formula (1) as in Table 6, using methodologies known to those of ordinary skill in the art.

TABLE 6

Examples of readily available N-protected, hydroxy-substituted cyclic amines of formula (19).

| N-Protected, hydroxy-substituted cyclic amines | Structures | Commercial Source, Chemical Abstracts Number (CAS#), or Literature Reference |
| --- | --- | --- |
| 1-Boc-3-hydroxyazetidine | HO—▱—NBoc | CAS# 141699-55-0, CNH Technologies, Inc. 10A Henshaw Street Woburn, MA, 01801 USA |
| (R)-(−)-N-Boc-3-pyrrolidinol | 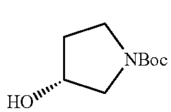 | CAS# 109431-87-0, Aldrich |
| (S)-(+)-N-Boc-3-pyrrolidinol | 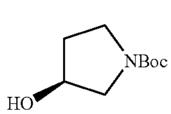 | CAS# 101469-92-5, Aldrich |
| 1-Boc-4-hydroxypiperidine | 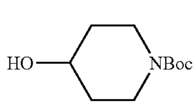 | CAS# 109384-19-2, Aldrich |

TABLE 6-continued

Examples of readily available N-protected, hydroxy-substituted cyclic amines of formula (19).

| N-Protected, hydroxy-substituted cyclic amines | Structures | Commercial Source, Chemical Abstracts Number (CAS#), or Literature Reference |
| --- | --- | --- |
| (R)-1-Boc-3-hydroxypiperidine | 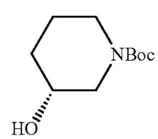 | CAS# 143900-43-0, Waterstone Technology 12202 Hancock Street Carmel, IN, 46032 USA |
| (S)-1-Boc-3-hydroxypiperidine | 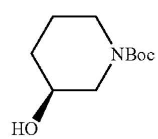 | CAS# 143900-44-1, Waterstone Technology 12202 Hancock Street Carmel, IN, 46032 USA |

The diamine intermediate of formula (23) thus obtained when treated either with compounds of formula (2) and a base, or with compounds of formula (3) and $Cs_2CO_3$, will provide intermediates of formula (18).

For the ultimate preparation of compounds of formula (9), intermediates of formula (18) have $X_1$ selected from Br or I and $X_2$ selected from hydrogen, chloro, cyano, alkoxy, alkoxyalkyl, alkyl, alkylthio, cycloalkyl, fluoro, fluoroalkyl, fluoroalkoxy, hydroxyalkyl, —$SO_2N(R_{14a})(R_{14b})$, and —$N(R_{14a})SO_2(R_{14b})$. Such appropriately substituted compounds of formula (18) may be converted to compounds of formula (9) by the "Suzuki Method" or the "Ullmann Method" or the "Stille Method" as described above for Scheme 4.

For the ultimate preparation of compounds of formula (10), intermediates of formula (18) have $X_2$ selected from Br or I and $X_1$ selected from hydrogen, chloro, cyano, alkoxy, alkoxyalkyl, alkyl, alkylthio, cycloalkyl, fluoro, fluoroalkyl, fluoroalkoxy, hydroxyalkyl, —$SO_2N(R_{14a})(R_{14b})$, and —$N(R_{14a})SO_2(R_{14b})$. Such appropriately substituted compounds of formula (18) may be converted to compounds of formula (10) by the "Suzuki Method" or the "Ullmann Method" or the "Stille Method" in a fashion analogous to the above description for the conversion of compounds of formula (18) to compounds of formula (9).

Scheme 6

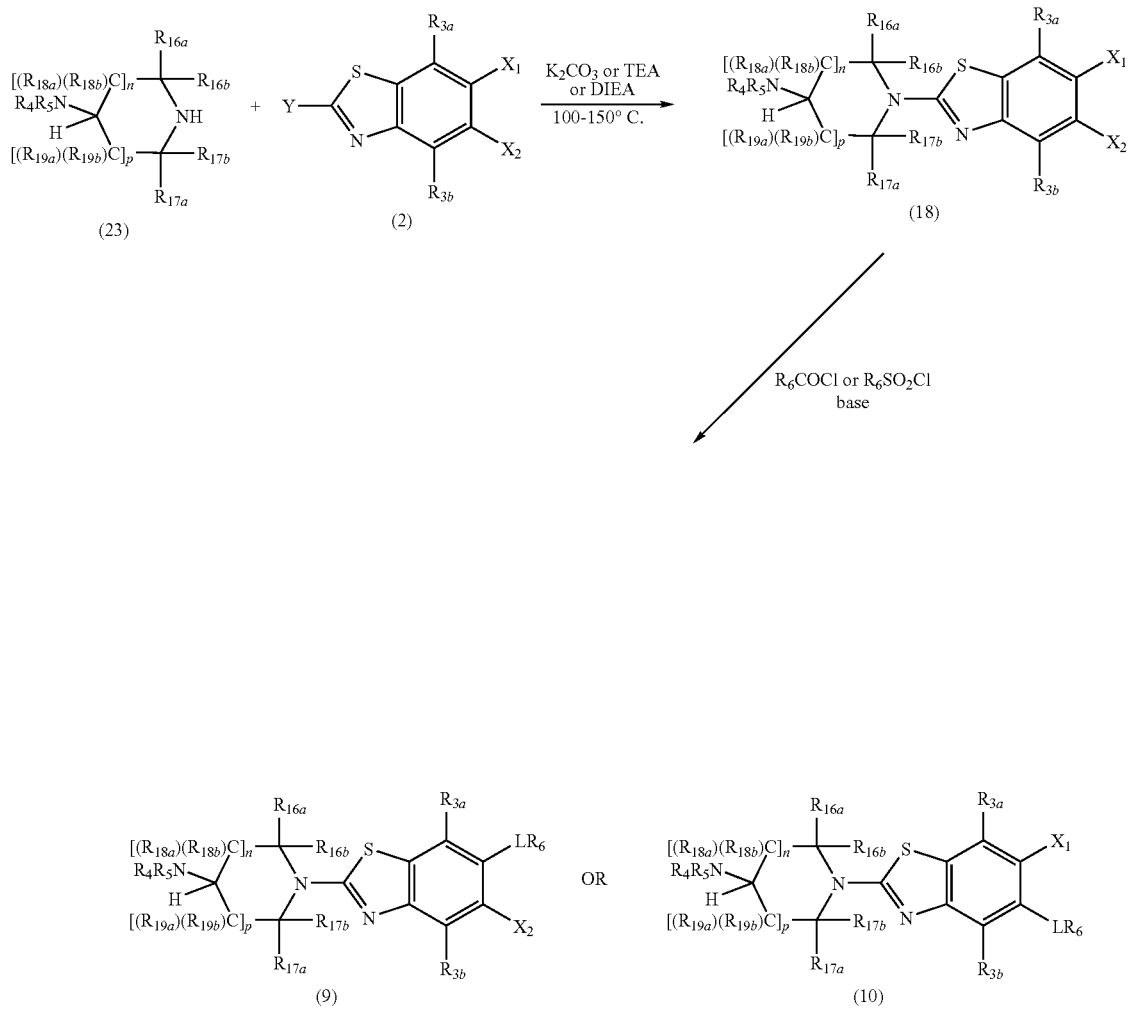

Compounds of formulae (9) and (10), where L is —N(R$_{14a}$)CO— or —N(R$_{14a}$)SO$_2$— can be prepared as described in Scheme 6, where substituent definitions are the same as in Scheme 1.

For the ultimate preparation of compounds of formula (9), the previously described diamine of formula (23) is reacted with a compound of formula (2) where X$_1$=NH$_2$ and Y=Cl (such as 2-chlorobenzothiazol-6-ylamine, CAS #2406-90-8, KaironKem, BP29, 23 Avenue Bocoumajour, Carry le Rouet, 13620, France) to provide compounds of structure (18) where X$_1$=NH$_2$. Reaction of compounds of formula (18) where X$_1$=NH$_2$ with R$_6$COCl in the presence of base or with R$_6$CO$_2$H and an amide coupling reagent yields compounds of formula (9) in which L is —N(R$_{14a}$)CO— and R$_{14a}$ is H. Other R$_{14a}$ groups can be introduced via reductive amination of compounds of formula (18) where X$_1$=NH$_2$ and subsequent amide coupling. Reaction of compounds of formula (18) where X$_1$=NH$_2$ with R$_6$SO$_2$Cl in the presence of base yields compounds of formula (9) in which L is —N(R$_{14a}$) SO$_2$— and R$_{14a}$ is H. Other R$_{14a}$ groups can be introduced via reductive amination of compounds of formula (18) where X$_1$=NH$_2$ and subsequent sulfonamide formation.

For the ultimate preparation of compounds of formula (10), the previously described diamine of formula (23) is reacted with a compound of formula (2) where X$_2$=NH$_2$ and Y=Cl (such as 2-chloro-5-benzothiazolamine, CAS #80945-82-0, Chemstep, 20 Avenue Victor Hugo, Carbon Blanc, 33560, France) to provide compounds of structure (18) where X$_2$=NH$_2$. Reaction of compounds of formula (18) where X$_2$=NH$_2$ with R$_6$COCl in the presence of base or with R$_6$CO$_2$H and amide coupling reagent yields compounds of formula (10) in which L is —N(R$_{14a}$)CO— and R$_{14a}$ is H. Other R$_{14a}$ groups can be introduced via reductive amination of compounds of formula (18) where X$_2$=NH$_2$ and subsequent amide coupling. Reaction of compounds of formula (18) where X$_2$=NH$_2$ with R$_6$SO$_2$Cl in the presence of base yields compounds of formula (10) in which L is —N(R$_{14a}$) SO$_2$— and R$_{14a}$ is H. Other R$_{14a}$ groups can be introduced via reductive amination of compounds of formula (18) where X$_2$=NH$_2$ and subsequent sulfonamide formation.

Scheme 7

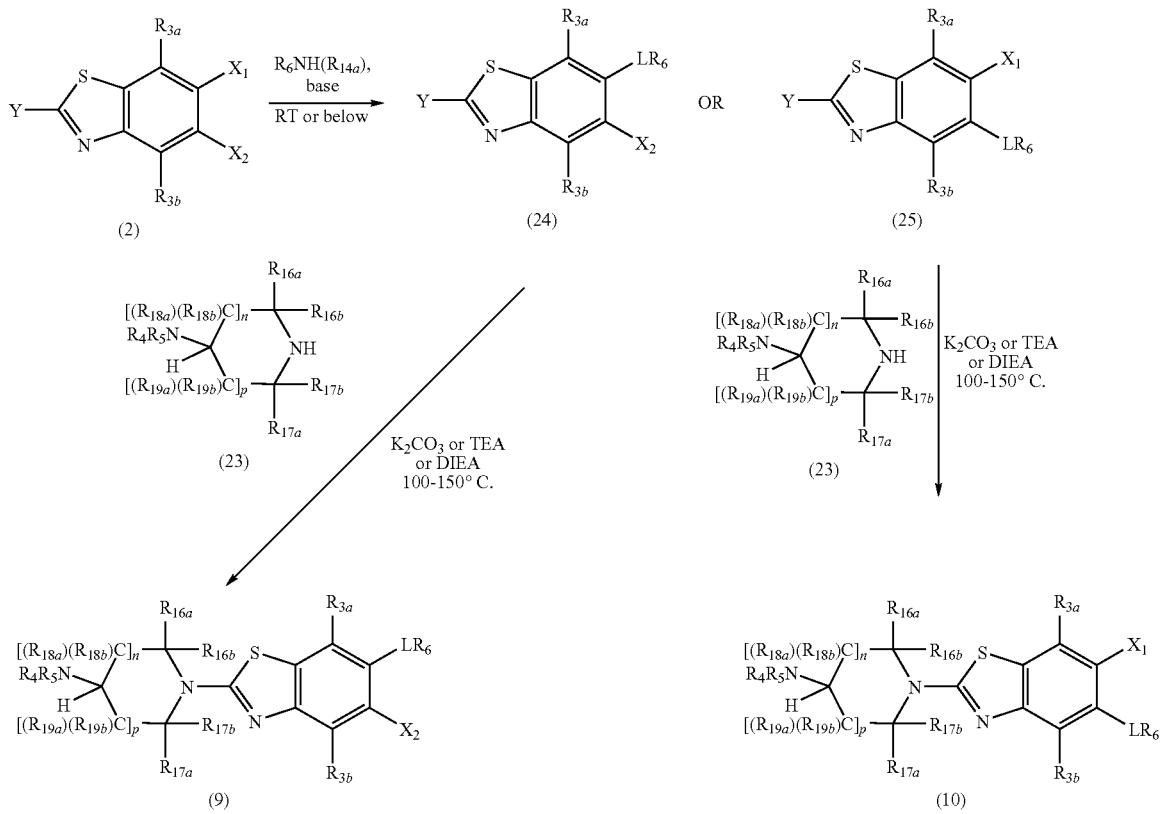

Compounds of formulae (9) and (10), where L is —CON(R$_{14a}$)— or —SO$_2$N(R$_{14a}$)— can be prepared as described in Scheme 7. For the ultimate preparation of compounds of formula (9) where L=-CON(R$_{14a}$)—, a compound of formula (2) where X$_1$=COCl and Y=Cl (such as 2-chloro-6-benzothiazolecarbonyl chloride, CAS #37525-59-0, prepared as in U.S. Pat. No. 3,654,296) is reacted with one equivalent of an amine of formula R$_6$NH(R$_{14a}$) and a non-nucleophilic base, first at 0 to 5° C., then at room temperature, to provide compounds of formula (24) where Y=Cl and L=-CON(R$_{14a}$)—. Subsequent reaction of compounds of formula (24) where Y=Cl and L=-CON(R$_{14a}$)— with one equivalent of the previously described diamine of formula (23) in the presence of base while heating between 100 and 150° C. yields compounds of formula (9) where L is —CON(R$_{14a}$)—.

Analogously, for the ultimate preparation of compounds of formula (10) where L=-CON(R$_{14a}$)—, a compound of formula (2) where X$_2$=COCl and Y=Cl (such as 2-chloro-5-benzothiazolecarbonyl chloride, CAS #2049-06-1, prepared as in U.S. Pat. No. 3,654,296) is reacted with one equivalent of an amine of formula R$_6$NH(R$_{14a}$) and a non-nucleophilic base, first at 0 to 5° C., then at room temperature, to provide compounds of formula (25) where Y=Cl and L=-CON(R$_{14a}$)—. Subsequent reaction of compounds of formula (25) where Y=Cl and L=-CON(R$_{14a}$)— with one equivalent of the previously described diamine of formula (23) in the presence of base while heating between 100 and 150° C. yields compounds of formula (10) where L is —CON(R$_{14a}$)—.

For the ultimate preparation of compounds of formula (9) where L=-SO$_2$N(R$_{14a}$)—, a compound of formula (2) where X$_1$=SO$_2$Cl and Y=Cl (such as 2-chloro-6-benzothiazolesulfonyl chloride, CAS #6608-50-0, prepared by the treatment of 2-chlorobenzothiazole, CAS #615-20-3, Aldrich, with chlorosulfonic acid, CAS #7790-94-5, Aldrich, as in International Publication No. WO2001/77092) is reacted with one equivalent of an amine of formula R$_6$NH(R$_{14a}$) and a non-nucleophilic base, first at 0 to 5° C., then at room temperature, to provide compounds of formula (24) where Y=Cl and L=-SO$_2$N(R$_{14a}$)—. Subsequent reaction of compounds of formula (24) where Y=Cl and L=-SO$_2$N(R$_{14a}$)— with one equivalent of the previously described diamine of formula (23) in the presence of base while heating between 100 and 150° C. yields compounds of formula (9) where L is —SO$_2$N(R$_{14a}$)—.

Analogously, for the ultimate preparation of compounds of formula (10) where L=-SO$_2$N(R$_{14a}$)—, a compound of formula (2) where X$_2$=SO$_2$Cl and Y=Cl (such as 2-chloro-5-benzothiazolesulfonyl chloride, CAS #6608-49-7, prepared as in Skopenko, V. N., et al., *Ukrainskii Khimicheskii Zhurnal (Russian Edition)* 1977, 43(5), 518-21) is reacted with one equivalent of an amine of formula R$_6$NH(R$_{14a}$) and a non-nucleophilic base, first at 0 to 5° C., then at room temperature, to provide compounds of formula (25) where Y=Cl and L=-SO$_2$N(R$_{14a}$)—. Subsequent reaction of compounds of formula (25) where Y=Cl and L=-SO$_2$N(R$_{14a}$)— with one equivalent of the previously described diamine of formula (23) in the presence of base while heating between 100 and 150° C. yields compounds of formula (10) where L is —SO$_2$N(R$_{14a}$)—.

Scheme 8

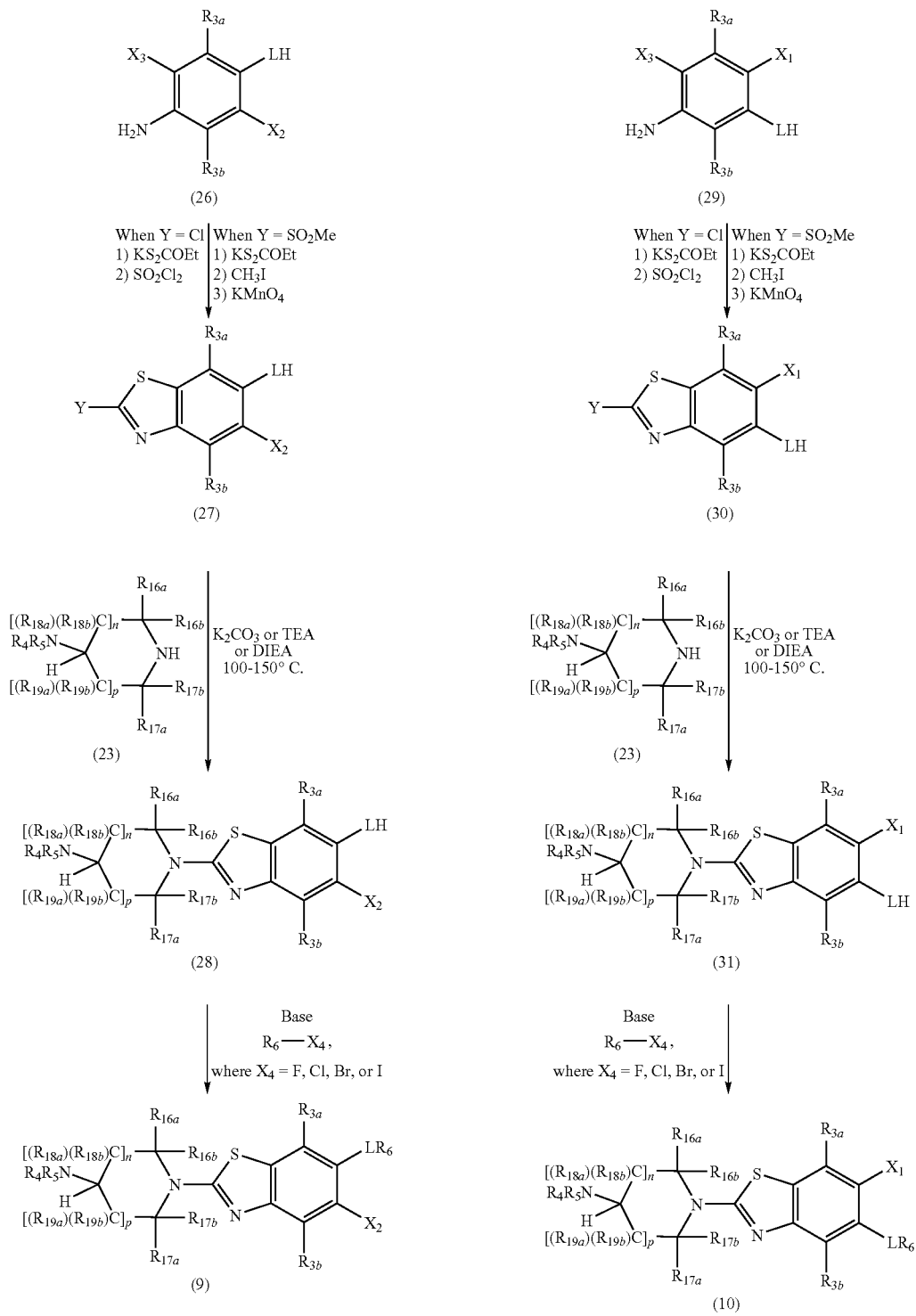

An alternative approach to the "Ullmann Method" described for the preparation of compounds of formulae (9) and (10) in which L=O, $NR_{15}$, or S in Scheme 4 above, involves the conversion of compounds of formulae (28) and (31) in which L=O, $NR_{15}$, or S into compounds of formulae (9) and (10) in which L=O, $NR_{15}$, or S in Scheme 8 above, by the reaction with a base and compounds $R_6$—$X_4$, where $X_4$=F, Cl, Br, or I, and $R_6$ is activated for a $S_NAr$ reaction (Smith, M. B. and March, J., *March's advanced organic chemistry: reactions, mechanisms, and structure*, 5th edition, John Wiley & Sons, New York, N.Y., 2001, pp 850-859) by virtue of its structure and substituents. The compounds of formulae (28) and (31) may be prepared by reacting the diamines of formula (23) in the presence of a base such as, but not limited to, potassium carbonate, triethylamine, or diisopropylethylamine, with compounds of formulae (27) and (30), respectively.

Compounds of formula (27), or their precursors, may be purchased (Table 7) or prepared using methodologies known to those of ordinary skill in the art, by reacting the appropriately substituted anilines of formula (26) (Table 8) with potassium ethylxanthogenate (CAS #140-89-6, Aldrich) to first give the 2-mercapto-benzothiazole of formula (27) where Y=SH, followed by either a) reaction with sulfuryl chloride (CAS #7791-25-5, Aldrich) to provide compounds of formula (27) where Y=Cl (Zhu, L.; et al.; *J. Heterocyclic Chem.* 2005, 42, 727-730) or by b) reaction with iodomethane (CAS #74-88-4, Aldrich) to provide the intermediates of formula (27) where Y=CH$_3$S—, followed by oxidation with an oxidizing agent such as potassium permanganate (CAS #7722-64-7, Aldrich) to provide compounds of formula (27) where Y=CH$_3$SO$_2$—. When LH=SH in compounds of formula (26), approach a) is preferred.

Scheme 9

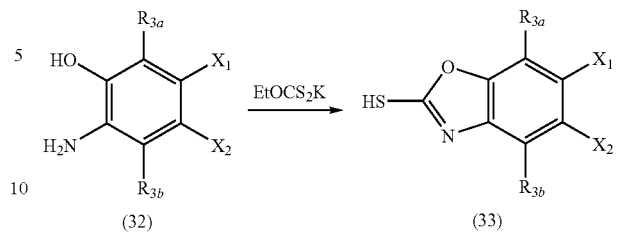

Compounds of formula (32) when treated with potassium ethylxanthogenate (CAS #140-89-6, Aldrich) in a solvent such as pyridine and heated to reflux affords compounds of formula (33) where Y=SH.

Scheme 10

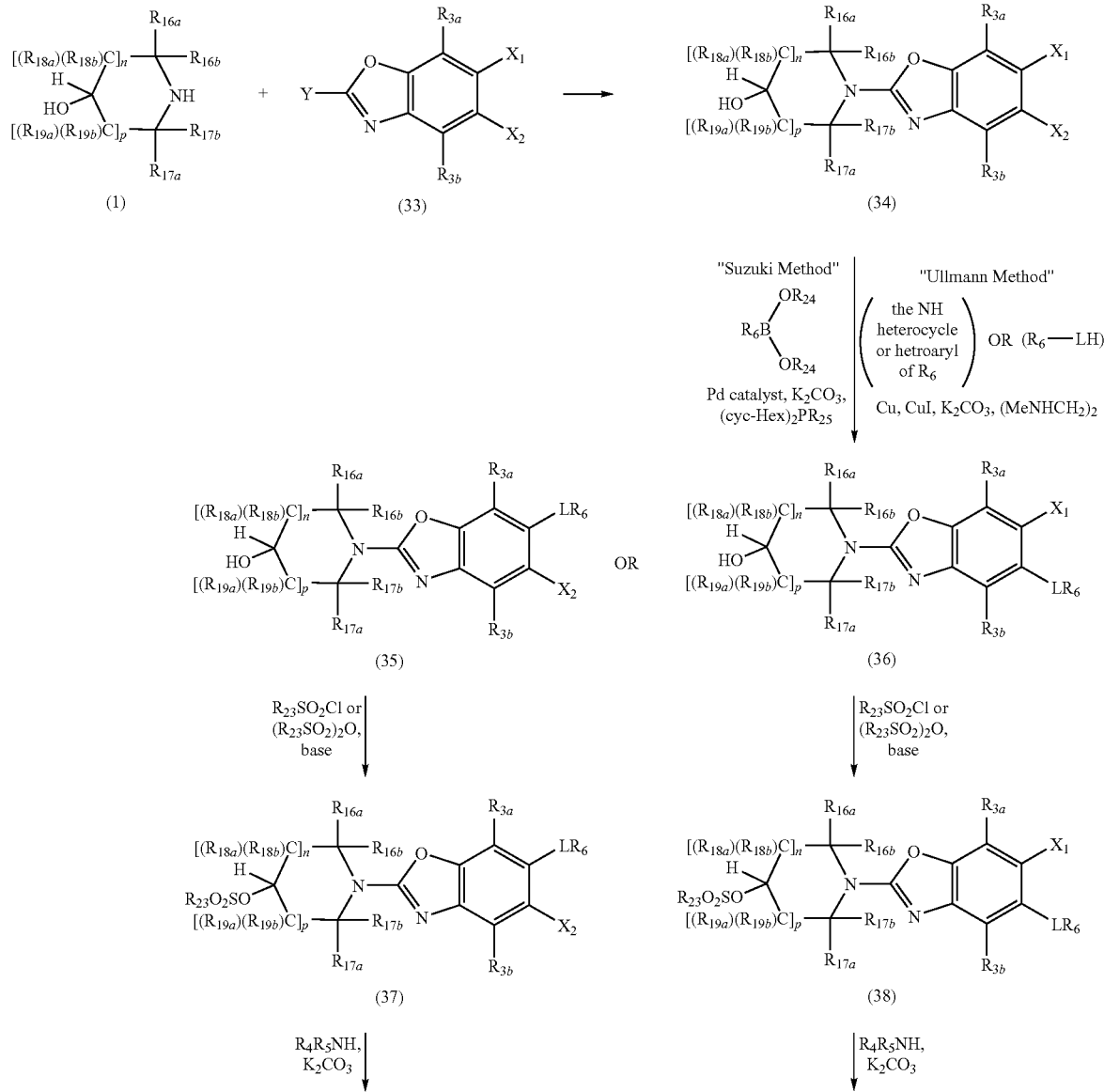

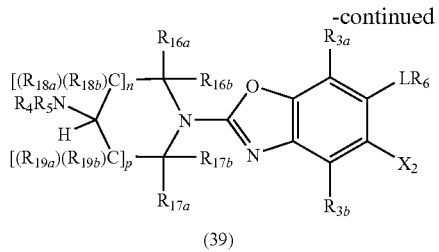

(39)

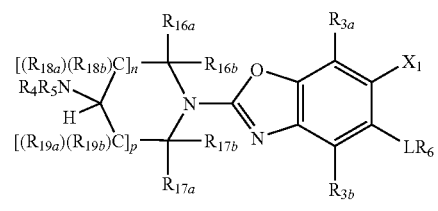

(40)

Compounds of formula (39) and (40) can be prepared as described in Scheme 10, wherein n, p, $R_1$, $R_2$, $R_{3a}$, $R_{3b}$, $R_4$, $R_5$, $R_6$, $R_{16a}$, $R_{16b}$, $R_{17a}$, $R_{17b}$, $R_{18a}$, $R_{18b}$, $R_{19a}$, and $R_{19b}$ are as defined in formula (I), wherein:

L is selected from a bond, O, S, and —N($R_{15}$);

$X_2$ is selected from hydrogen, chloro, cyano, alkoxy, alkoxyalkyl, alkyl, alkylthio, cycloalkyl, fluoro, fluoroalkyl, fluoroalkoxy, hydroxyalkoxy, —SO$_2$N($R_{14a}$)($R_{14b}$), and —N($R_{14a}$)SO$_2$($R_{14b}$) in compound (39); and $X_1$ is selected from hydrogen, chloro, cyano, alkoxy, alkoxyalkyl, alkyl, alkylthio, cycloalkyl, fluoro, fluoroalkyl, fluoroalkoxy, hydroxyalkoxy, —SO$_2$N($R_{14a}$)($R_{14b}$), and —N($R_{14a}$)SO$_2$($R_{14b}$) in compound (40); and $R_{14a}$, $R_{14b}$, and $R_{15}$ are as defined for compounds of formula (I).

Y in compound (33) is SH.

Hydroxy-substituted, cyclic amines of formula (1), purchased (see Table 1) or prepared using methodologies known to those of ordinary skill in the art, when treated with compounds of formula (33) in xylene and heated to 150° C., will provide intermediates of formula (34).

There are many suitable and readily available hydroxy-substituted amines of formula (1). Examples of such hydroxy-substituted amines are exemplified, but not limited to, those shown in Table 1.

For the ultimate preparation of compounds of formula (39), intermediates of formula (34) have $X_1$ selected from Cl or, more preferably, Br or I and $X_2$ selected from hydrogen, chloro (except when $X_1$ is Cl), cyano, alkoxy, alkoxyalkyl, alkyl, alkylthio, cycloalkyl, fluoro, fluoroalkyl, fluoroalkoxy, hydroxyalkoxy, —SO$_2$N($R_{14a}$)($R_{14b}$), and —N($R_{14a}$)SO$_2$($R_{14b}$). Such appropriately substituted compounds of formula (34) may be converted to compounds of formula (35) by the "Suzuki Method," the "Ullmann Method," or the "Stille Method" as described in Scheme 1.

For the ultimate preparation of compounds of formula (40), intermediates of formula (34) have $X_2$ selected from Cl or, more preferably, Br or I and $X_1$ selected from hydrogen, chloro (except when $X_2$ is Cl), cyano, alkoxy, alkoxyalkyl, alkyl, alkylthio, cycloalkyl, fluoro, fluoroalkyl, fluoroalkoxy, hydroxyalkoxy, —SO$_2$N($R_{14a}$)($R_{14b}$), and —N($R_{14a}$)SO$_2$($R_{14b}$). Such appropriately substituted compounds of formula (34) may be converted to compounds of formula (36) by the "Suzuki Method" or the "Ullmann Method" or the "Stille Method" in a fashion analogous to the above description for the conversion of compounds of formula (34) to compounds of formula (35).

The alcohols (35) or (36) can be converted to compounds (39) and (40) according to methods described for Scheme 1.

Scheme 11

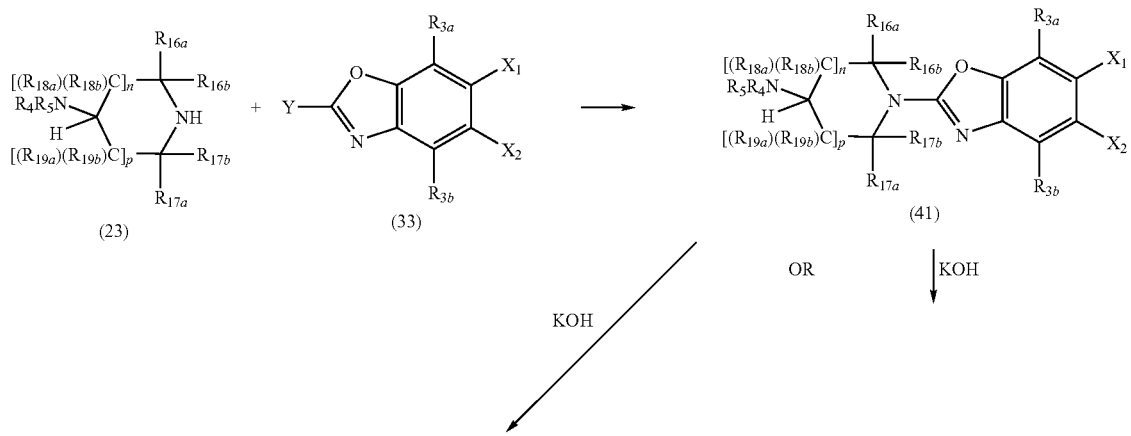

-continued

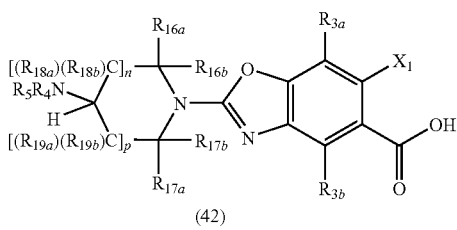
(42)

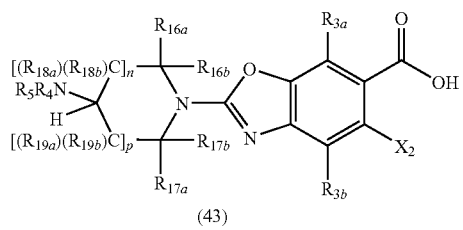
(43)

↓ ↓

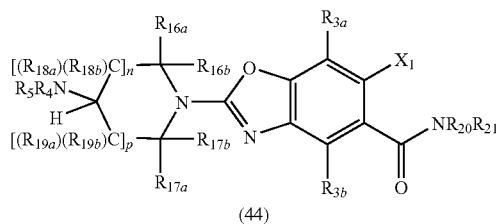
(44)

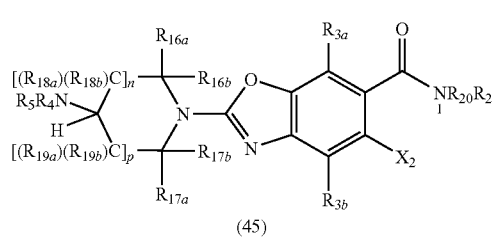
(45)

Compounds of formula (44) and (45) can be prepared by combining (33) and (23) together as described in Scheme 11, where one of $X_1$ or $X_2$ is carbomethoxy [C(O)OMe]. The ester can be hydrolyzed to the carboxylic acid followed by amide bond formation to form compounds (44) and (45) according to methods known to one skilled in the art of organic synthesis.

TABLE 7

Examples of readily available benzothiazoles of formula (27).

| Benzothiazole | Structures | Commercial Source, Chemical Abstracts Number (CAS#), or Literature Reference |
|---|---|---|
| 2-chloro-6-methoxy-benzothiazole | [structure with $OCH_3$] | CAS# 2605-14-3, Aldrich (After reaction with diamines of formula (23) to give compounds of formula (28) where LH = $OCH_3$ and $R_{3a}$, $R_{3b}$, and $X_2$ = H, these intermediates can be converted to the necessary compounds of formula (28) where LH = OH by treatment with $BBr_3$. |
| 2-chloro-benzothiazol-6-yl amine | [structure with $NH_2$] | CAS# 2406-90-8, Kairon Kem BP 29 23 avenue Bocoumajour Carry le Rouet, 13620 France |
| 6-bromo-2-chloro-benzothiazole | [structure with Br] | CAS# 80945-86-4, Aldrich (After reaction with diamines of formula (23) to give compounds of formula (28) where LH = Br and $R_{3a}$, $R_{3b}$, and $X_2$ = H, these intermediates can be converted to the necessary compounds of formula (28) where LH = SH by treatment with $CH_3SK$ and heat (Testaferri, L.; et al., Synthesis 1983, 751-5) or by treatment first with Mg, then with sulfur (Sato, R.; et al., Heterocycles 2001, 55, 851-854). |

TABLE 8

Examples of readily available anilines of formula (26).

| Anilines | Structures | Commercial Source, Chemical Abstracts Number (CAS#), or Literature Reference |
|---|---|---|
| 4-amino-3-fluorophenol | [structure: F, OH, H₂N on benzene] | CAS# 399-95-1, Matrix |
| 2-fluoro-4-nitroaniline | [structure: F, NO₂, H₂N on benzene] | CAS# 369-35-7, Aldrich (After conversion to compounds of formula (27) where LH = NO$_2$, reaction with the diamines of formula (23) to give compounds of formula (28) where LH = NO$_2$. Reduction of the aromatic nitro group by catalytic hydrogenation or with zinc, for example, provides the desired compounds of formula (28) where LH = NH$_2$.) |
| 2-Fluoro-4-thioaniline | [structure: F, SH, H₂N on benzene] | CAS# 15178-48-0, Apollo Scientific Ltd. Whitefield Rd. Bredbury, Stockport, Cheshire, SK6 2QR United Kingdom |

Compounds of formula (30), or their precursors, may be purchased (Table 9) or prepared using methodologies known to those of ordinary skill in the art, by reacting the appropriately substituted anilines of formula (29) (Table 10) with potassium ethylxanthogenate (CAS #140-89-6, Aldrich) to first give the 2-mercapto-benzothiazole of formula (30) where Y=SH, followed by either a) reaction with sulfuryl chloride (CAS #7791-25-5, Aldrich) to provide compounds of formula (30) where Y=Cl (Zhu, L.; et al.; *J. Heterocyclic Chem.* 2005, 42, 727-730) or by b) reaction with iodomethane (CAS #74-88-4, Aldrich) to provide the intermediates of formula (30) where Y=CH$_3$S—, followed by oxidation with an oxidizing agent such as potassium permanganate (CAS #7722-64-7, Aldrich) to provide compounds of formula (30) where Y=CH$_3$SO$_2$—. When LH=SH in compounds of formula (29), approach a) is preferred.

TABLE 9

Examples of readily available benzothiazoles of formula (30).

| Benzothiazole | Structures | Commercial Source, Chemical Abstracts Number (CAS #), or Literature Reference |
|---|---|---|
| 2-chloro-5-methoxy-benzothiazole | [structure: Cl-benzothiazole-OCH₃] | CAS# 3507-28-6, Daxian Chemical Institute #179, 10169 New Hampshire Ave. Silver Spring, MD, 20903 USA (After reaction with diamines of formula (23) to give compounds of formula (28) where LH = OCH$_3$ and R$_{3a}$, R$_{3b}$, and X$_2$ = H, these intermediates can be converted to the necessary compounds of formula (28) where LH = OH by treatment with BBr$_3$. |
| 2-chloro-5-nitro-benzothiazole | [structure: Cl-benzothiazole-NO₂] | CAS# 3622-38-6, Daxian Chemical Institute #179, 10169 New Hampshire Ave. Silver Spring, MD, 20903 USA (After conversion to compounds of formula (30) where LH = NO$_2$, reaction with the diamines of formula (23) give compounds of formula (31) where LH = NO$_2$. Reduction of the aromatic nitro group by catalytic hydrogenation or with zinc, for example, provides the desired compounds of formula (31) where LH = NH$_2$). |

TABLE 9-continued

Examples of readily available benzothiazoles of formula (30).

| Benzothiazole | Structures | Commercial Source, Chemical Abstracts Number (CAS #), or Literature Reference |
|---|---|---|
| 2-chloro-5-benzothiazolamine | 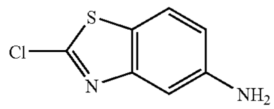 | CAS# 80945-82-0, Chemstep 20 Avenue Victor Hugo Carbon Blanc, 33560 France |
| 2,5-Benzothiazoledithiol | 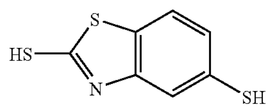 | CAS# 854060-35-8, ChemPacific Corp 6200 Freeport Center Baltimore, MD, 21224 USA |

TABLE 10

Examples of readily available anilines of formula (29).

| Anilines | Structures | Commercial Source, Chemical Abstracts Number (CAS#), or Literature Reference |
|---|---|---|
| 3-amino-4-fluorophenol | 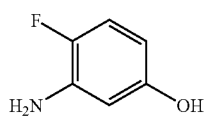 | CAS# 62257-16-3, Waterstone Technology 12202 Hancock Street Carmel, IN 46032 USA |
| (3-Amino-4-fluoro-phenyl)-carbamic acid tert-butyl ester | 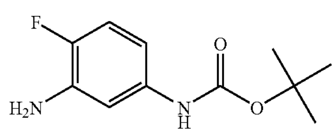 | CAS# 361548-95-0, J & W PharmLab LLC 2000 Hartel Street, Suite B Levittown, PA, 19057 USA (After conversion to compounds of formula (30) where LH = NHBoc, and subsequent treatment with that intermediate with the diamine of formula (23), compounds of formula (31) are obtained where LH = NHBoc. Such compounds of formula (31) can be converted to the desired compounds of formula (31) where LH = $NH_2$ by treatment with excess HCl or trifluoroacetic acid). |

Compounds of formula $R_6$—$X_4$, or their precursors, may be purchased (Table 11) or prepared using methodologies known to those of ordinary skill in the art.

TABLE 11

Examples of readily available compounds of formula $R_6\text{-}X_4$.

| Compounds | Structures | Commercial Source, Chemical Abstracts Number (CAS#), or Literature Reference |
|---|---|---|
| Methyl 6-chloro-pyridine-3-carboxylate | 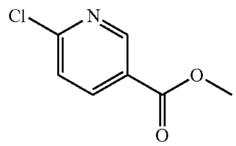 | CAS# 73781-91-6, Aldrich (Precursor compound provides compounds of formulae (9) and (10) where the ester can be hydrolyzed to the acid, the acid activated as an acid chloride with oxalyl chloride or thionyl chloride, and the acid chloride converted to the desired amide by treatment with the appropriate amine). |
| 6-Chloronicotinoyl chloride | 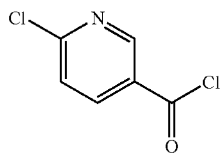 | CAS# 66608-11-5, Aldrich (Precursor compound that can be converted to the desired amide by treatment with the appropriate amine to give $R_6\text{-}X_4$ = a 5-carboxamido-2-pyridinyl chloride). |
| 6-Chloro-N-methyl-3-pyridinecarboxamide | 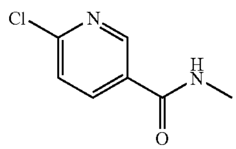 | CAS# 54189-82-1, ChemPacific Corp 6200 Freeport Center Baltimore, MD, 21224 USA |
| 6-Chloronicotinamide | 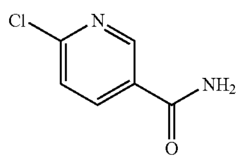 | CAS# 6271-78-9, Aldrich |
| Methyl 5-chloro-2-pyridazinecarboxylate | 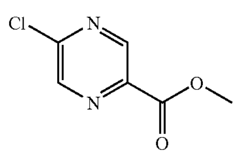 | CAS# 33332-25-1, ChemPacific Corp 6200 Freeport Center Baltimore, MD, 21224 USA (Precursor compound provides compounds of formulae (9) and (10) where the ester can be hydrolyzed to the acid, the acid activated as an acid chloride with oxalyl chloride or thionyl chloride, and the acid chloride converted to the desired amide by treatment with the appropriate amine). |

The compounds and intermediates of the invention may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

The compounds of the invention have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, or hydroxybutyric acid, camphorsulfonic, malic, phenylacetic, aspartic, glutamic, and the like.

Compositions of the Invention

The invention also provides pharmaceutical compositions comprising a therapeutically effective amount of a compound of formula (I) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral injection or for rectal administration.

The term "pharmaceutically acceptable carrier", as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally", as used herein, refers to modes of administration which include intravenous, intramuscular, intraperitoneal, intrasternal, subcutaneous, intraarticular injection and infusion.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of materials which can be useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants, which can be required. Opthalmic formulations, eye ointments, powders and solutions are contemplated as being within the scope of this invention. Aqueous liquid compositions comprising compounds of the invention also are contemplated.

The compounds of the invention can be used in the form of pharmaceutically acceptable salts or esters, or amides derived from inorganic or organic acids. The term "pharmaceutically acceptable salts and esters and amides", as used herein, refer to carboxylate salts, amino acid addition salts, zwitterions, and esters and amides of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid. An example of a suitable salt is a hydrochloride salt.

Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Preferred salts of the compounds of the invention are the tartrate and hydrochloride salts.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid, and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylammonium, dimethylammonium, trimethylammonium, triethylammonium, diethylammonium, ethylammonium and the like. Other representative organic amines useful for the formation of base addition salts include ethylenediamine, ethanolamine, diethanolamine, piperidine, and piperazine.

The term "pharmaceutically acceptable ester", as used herein, refers to esters of compounds of the invention which hydrolyze in vivo and include those that break down readily in the human body to leave the parent compound or a salt thereof. Examples of pharmaceutically acceptable, non-toxic esters of the invention include $C_1$-to-$C_6$ alkyl esters and $C_5$-to-$C_7$ cycloalkyl esters, although $C_1$-to-$C_4$ alkyl esters are preferred. Esters of the compounds of formula (I) may be prepared according to conventional methods. For example, such esters may be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, alkyl triflate, for example with methyl iodide, benzyl iodide, cyclopentyl iodide. They also may be prepared by reaction of the compound with an acid such as hydrochloric acid and an alcohol such as methanol or ethanol.

The term "pharmaceutically acceptable amide", as used herein, refers to non-toxic amides of the invention derived from ammonia, primary $C_1$-to-$C_6$ alkyl amines and secondary $C_1$-to-$C_6$ dialkyl amines. In the case of secondary amines, the amine may also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula (I) may be prepared according to conventional methods. Pharmaceutically acceptable amides are prepared from compounds containing primary or secondary amine groups by reaction of the compound that contains the amino group with an alkyl anhydride, aryl anhydride, acyl halide, or aryl halide. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. They also may be prepared by reaction of the compound with an acid such as sulfuric acid and an alkylcarboxylic acid such as acetic acid, or with acid and an arylcarboxylic acid such as benzoic acid under dehydrating conditions as with molecular sieves added. The composition can contain a compound of the invention in the form of a pharmaceutically acceptable prodrug.

The invention contemplates pharmaceutically active compounds either chemically synthesized or formed by in vivo biotransformation to compounds of formula (I).

Methods of the Invention

The compounds and compositions of the invention are useful for treating and preventing certain diseases and disorders in humans and animals. As an important consequence of the ability of the compounds of the invention to modulate the effects of histamine-3 receptors in cells, the compounds described in the invention can affect physiological processes in humans and animals. In this way, the compounds and compositions described in the invention are useful for treating and preventing diseases and disorders modulated by histamine-3 receptors. Typically, treatment or prevention of such diseases and disorders can be effected by selectively modulating the histamine-3 receptors in a mammal, by administering a compound or composition of the invention, either alone or in combination with another active agent as part of a therapeutic regimen.

The compounds of the invention, including but not limited to those specified in the examples, possess an affinity for the histamine-3 receptors and therefore, the compounds of the invention may be useful for the treatment and prevention of diseases or conditions such as attention-deficit hyperactivity disorder (ADHD), deficits in attention, dementia, and diseases with deficits of memory, learning, schizophrenia, cognitive deficits of schizophrenia, cognitive deficits and dysfunction in psychiatric disorders, Alzheimer's disease, mild cognitive impairment, epilepsy, seizures, allergic rhinitis, and asthma, motion sickness, dizziness, Meniere's disease, vestibular disorders, vertigo, obesity, diabetes, type II diabetes, Syndrome X, insulin resistance syndrome, metabolic syndrome, pain, including neuropathic pain, osteoarthritis pain, neuropathy, sleep disorders, narcolepsy, pathological sleepiness, jet lag, drug abuse, mood alteration, bipolar disorder, depression, obsessive compulsive disorder, Tourette's syndrome, Parkinson's disease, and medullary thyroid carcinoma, melanoma, and polycystic ovary syndrome. The ability of histamine-3 receptor modulators, and consequently the compounds of the invention, to prevent or treat such disorders is demonstrated by examples found in the following references.

The ability of the compounds of the invention, including, but not limited to, those specified in the examples, to treat attention-deficit hyperactivity disorder (ADHD), and deficits in attention, may be demonstrated by Cowart, et al. *J. Med. Chem.* 2005, 48, 38-55; Fox, G. B., et al. "Pharmacological Properties of ABT-239: II. Neurophysiological Characterization and Broad Preclinical Efficacy in Cognition and Schizophrenia of a Potent and Selective Histamine $H_3$ Receptor Antagonist", Journal of Pharmacology and Experimental Therapeutics (2005) 313, 176-190; "Effects of histamine $H_3$ receptor ligands GT-2331 and ciproxifan in a repeated acquisition avoidance response in the spontaneously hypertensive rat pup." Fox, G. B., et al. Behavioural Brain Research (2002), 131(1,2), 151-161; Yates, et al. JPET (1999) 289, 1151-1159 "Identification and Pharmacological Characterization of a Series of New 1H-4-Substituted-Imidazoyl Histamine $H_3$ Receptor Ligands"; Ligneau, et al. Journal of Pharmacology and Experimental Therapeutics (1998), 287, 658-666; Tozer, M. Expert Opinion Therapeutic Patents (2000) 10, p. 1045; M. T. Halpern, "GT-2331" Current Opinion in Central and Peripheral Nervous System Investigational Drugs (1999) 1, pages 524-527; Shaywitz et al., Psychopharmacology, 82:73-77 (1984); Dumery and Blozovski, Exp. Brain Res., 67:61-69 (1987); Tedford et al., J. Pharmacol. Exp. Ther., 275:598-604 (1995); Tedford et al., Soc. Neurosci. Abstr., 22:22 (1996); and Fox, et al., Behav. Brain Res., 131:151-161 (2002); Glase, S. A., et al. "Attention deficit hyperactivity disorder: pathophysiology and design of new treatments." Annual Reports in Medicinal Chemistry (2002), 37 11-20; Schweitzer, J. B., and Holcomb, H. H. "Drugs under investigation for attention-deficit hyperactivity disorder" Current Opinion in Investigative Drugs (2002) 3, p. 1207.

The ability of the compounds of the invention, including, but not limited to, those specified in the examples, to treat dementia, and diseases with deficits of memory and learning, may be demonstrated by "Two novel and selective nonimidazole $H_3$ receptor antagonists A-304121 and A-317920: II. In vivo behavioral and neurophysiological characterization." Fox, G. B., et al. Journal of pharmacology and experimental therapeutics (June 2003), 305(3), 897-908; "Identification of novel $H_3$ receptor ($H_3R$) antagonist with cognition enhancing properties in rats." Fox, G. B.; Inflammation Research (2003), 52(Suppl. 1), S31-S32; Bernaerts, P., et al. "Histamine $H_3$ antagonist thioperamide dose-dependently enhances memory consolidation and reverses amnesia induced by dizocilpine or scopolamine in a one-trial inhibitory avoidance task in mice" Behavioural Brain Research 154 (2004) 211-219; Onodera, et al. Nauyn-Schmiedebergs' Arch. Pharmacol. (1998), 357, 508-513; Prast, et al. Brain Research (1996) 734, 316-318; Chen, et al. Brain Research (1999) 839, 186-189 "Effects of histamine on MK-801-induced memory deficits in radial maze performance in rats"; Passani, et al. "Central histaminergic system and cognition" Neuroscience and Biobehavioral Reviews (2000) 24, p 107-113.

The ability of the compounds of the invention, including, but not limited to, those specified in the examples, to treat schizophrenia, cognitive deficits of schizophrenia, and cognitive deficits, may be demonstrated by Fox, G. B., et al. "Pharmacological Properties of ABT-239: II. Neurophysiological Characterization and Broad Preclinical Efficacy in Cognition and Schizophrenia of a Potent and Selective Histamine $H_3$ Receptor Antagonist", Journal of Pharmacology and Experimental Therapeutics (2005) 313, 176-190 and by "Enhancement of prepulse inhibition of startle in mice by the $H_3$ receptor antagonists thioperamide and ciproxifan." Browman, Kaitlin E., et al. Behavioural Brain Research (2004), 153(1), 69-76; "$H_3$ receptor blockade by thioperamide enhances cognition in rats without inducing locomotor sensitization."; Komater, V. A., et al. Psychopharmacology (Berlin, Germany) (2003), 167(4), 363-372; A A Rodrigues, F P Jansen, R Leurs, H Timmerman and G D Prell "Interaction of clozapine with the histamine $H_3$ receptor in rat brain" British Journal of Pharmacology (1995), 114(8), pp. 1523-1524; Passani, et al. "Central histaminergic system and cognition" Neuroscience and Biobehavioral Reviews (2000) 24, p 107-113; Morriset, S., et al. "Atypical Neuroleptics Enhance Histamine Turnover in Brain Via 5-Hydroxytryptamine$_{2A}$ Receptor Blockade" Journal of Pharmacology and Experimental Therapeutics (1999) 288, pages 590-596; and Southam, E. et al. "Preclinical investigations into the antipsychotic potential of the novel histamine $H_3$ receptor antagonist GSK207040" Psychopharmacology (2009) 201, pages 483-494.

The ability of the compounds of the invention, including, but not limited to, those specified in the examples, to treat dysfunction in psychiatric disorders, Alzheimer's disease, and mild cognitive impairment may be demonstrated by Meguro, et al. Pharmacology, Biochemistry and Behavior (1995) 50(3), 321-325; Esbenshade, T., et al. "Pharmacological and behavioral properties of A-349821, a selective and potent human histamine H3 receptor antagonist" Biochemical Pharmacology 68 (2004) 933-945; Huang, Y.-W., et al. "Effect of the histamine H3-antagonist clobenpropit on spatial memory deficits induced by MK-801 as evaluated by radial maze in Sprague-Dawley rats" Behavioural Brain Research 151 (2004) 287-293; Mazurkiewicz-Kwilecki and Nsonwah, Can. J. Physiol. Pharmacol. (1989) 67, p. 75-78; P. Panula, et al., Neuroscience (1997) 82, 993-997; Haas, et al., Behav. Brain Res. (1995) 66, p. 41-44; De Almeida and Izquierdo, Arch. Int. Pharmacodyn. (1986), 283, p. 193-198; Kamei et al., Psychopharmacology, (1990) 102, p. 312-318; Kamei and Sakata, Jpn. J. Pharmacol. (1991), 57, p. 437-482; Schwartz et al., Psychopharmacology, The Fourth Generation of Progress. Bloom and Kupfer (eds). Raven Press, NewYork, (1995) 397; and Wada, et al., Trends in Neurosci. (1991) 14, p. 415.

The ability of the compounds of the invention, including, but not limited to, those specified in the examples, to treat epilepsy, and seizures, may be demonstrated by Harada, C., et al. "Inhibitory effect of iodophenpropit, a selective histamine H3 antagonist, on amygdaloid kindled seizures" Brain Research Bulletin (2004) 63 p, 143-146; as well as by Yokoyama, et al., Eur. J. Pharmacol. (1993) 234, p. 129-133; Yokoyama, et al. European Journal of Pharmacology (1994) 260, p. 23; Yokoyama and Iinuma, CNS Drugs (1996) 5, p. 321; Vohora, Life Sciences (2000) 66, p. 297-301; Onodera et al., Prog. Neurobiol. (1994) 42, p. 685; Chen, Z., et al. "Pharmacological effects of carcinine on histaminergic neurons in the brain" British Journal of Pharmacology (2004) 143, 573-580; R. Leurs, R. C. Vollinga and H. Timmerman, "The medicinal chemistry and therapeutic potential of ligands of the histamine $H_3$ receptor", Progress in Drug Research (1995) 45, p. 170-165; Leurs and Timmerman, Prog. Drug Res. (1992) 39, p. 127; H. Yokoyama and K. Iinuma, "Histamine and Seizures: Implications for the treatment of epilepsy", CNS Drugs, 5(5): 321-330 (1995); and K. Hurukami, H. Yokoyama, K. Onodera, K. Iinuma and T. Watanabe, "AQ-0145, A newly developed histamine $H_3$ antagonist, decreased seizure susceptibility of electrically induced convulsions in mice", Meth. Find. Exp. Clin. Pharmacol., 17(C):70-73 (1995); Yawata, et al. "Role of histaminergic neurons in development of epileptic seizures in EL mice" Molecular Brain Research 132 (2004) 13-17; and Schwartz, J.-C. and Lecomte, J.-M., "Treatment of epilepsy with non-imidazole alkylamine histamine $H_3$-receptor ligands", International Publication No. WO 2006/103537 A2.

The ability of the compounds of the invention, including, but not limited to, those specified in the examples, to treat allergic rhinitis, and asthma, may be demonstrated by McLeod, R. L., Mingo, G. G., Herczku, C., DeGennaro-Culver, F., Kreutner, W., Egan, R. W., Hey, J. A., "Combined histamine H1 and H3 receptor blockade produces nasal decongestion in an experimental model of nasal congestion" Am. J. Rhinol. (1999a) 13, p. 391-399; McLeod, Robbie L.; Egan, Robert W.; Cuss, Francis M.; Bolser, Donald C.; Hey, John A. (Allergy, Schering-Plough Research Institute, Kenilworth, N.J., USA. ) Progress in Respiratory Research (2001), 31 (in New Drugs for Asthma, Allergy and COPD), pp. 133-136; A. Delaunois A., et al., "Modulation of acetylcholine, capsaicin and substance P effects by histamine $H_3$ receptors in isolated perfused rabbit lungs," European Journal of Pharmacology (1995) 277, p. 243-250; Dimitriadou, et al., "Functional relationship between mast cells and C-sensitive nerve fibres evidenced by histamine $H_3$-receptor modulation in rat lung and spleen," Clinical Science (1994), 87, p. 151-163.

The ability of the compounds of the invention, including, but not limited to, those specified in the examples, to treat motion sickness, dizziness, Meniere's disease, vestibular disorders, and vertigo, may be demonstrated by Pan, et al. Methods and Findings in Clinical Pharmacology (1998), 20(9), 771-777; O'Neill, et al. Methods and Findings in Clinical Pharmacology (1999) 21(4), 285-289; and by R. Leurs, R. C. Vollinga and H. Timmerman, "The medicinal chemistry and therapeutic potential of ligands of the histamine $H_3$ receptor," Progress in Drug Research (1995), 45, p. 170-165, Lozada, et al. "Plasticity of histamine $H_3$ receptor expression and binding in the vestibular nuclei after labyrinthectomy in rat" BioMedCentral Neuroscience 2004, 5:32.

The ability of the compounds of the invention, including, but not limited to, those specified in the examples, to treat obesity, diabetes, type II diabetes, Syndrome X, insulin resistance syndrome, and metabolic syndrome, may be demonstrated by Hancock, A. A. "Antiobesity effects of A-331440, a novel non-imidazole histamine H3 receptor antagonist" European Journal of Pharmacology (2004) 487, 183-197; Hancock, A. A., et al. "Histamine $H_3$ antagonists in models of obesity" Inflamm. res. (2004) 53, *Supplement* 1 S47-S48; as well as by E. Itoh, M. Fujimiay, and A. Inui, "Thioperamide, A histamine $H_3$ receptor antagonist, powerfully suppresses peptide YY-induced food intake in rats," Biol. Psych. (1999) 45(4), p. 475-481; S. I. Yates, et al., "Effects of a novel histamine $H_3$ receptor antagonist, GT-2394, on food intake and weight gain in Sprague-Dawley rats," Abstracts, Society for Neuroscience, 102.10:219 (November, 2000); and C. Bjenning, et al., "Peripherally administered ciproxifan elevates hypothalamic histamine levels and potently reduces food intake in the Sprague Dawley rat," Abstracts, International Sendai Histamine Symposium, Sendai, Japan, # P39 (November, 2000); Sakata T; et al. "Hypothalamic neuronal histamine modulates ad libitum feeding by rats." Brain research (1990 Dec. 24), 537(1-2), 303-6.

The ability of the compounds of the invention, including, but not limited to, those specified in the examples, to treat pain, including neuropathic pain and neuropathy, has been demonstrated by diverse research labs, including Malmberg-Aiello, Petra; Lamberti, Claudia; Ghelardini, Carla; Giotti, Alberto; Bartolini, Alessandro. British Journal of Pharmacology (1994), 111(4), 1269-1279; Hriscu, Anisoara; Gherase, Florenta; Pavelescu, M.; Hriscu, E. "Experimental evaluation of the analgesic efficacy of some antihistamines as proof of the histaminergic receptor involvement in pain." Farmacia, (2001), 49(2), 23-30, 76. Recently, additional demonstrations of the efficacy of H3 antagonists in neuropathic pain have appeared, including Medhurst, A. D.; et al.; "Structurally novel histamine $H_3$ receptor antagonists GSK207040 and GSK334429 improve scopolamine-induced memory impairment and capsaicin-induced secondary allodynia in rats", Biochemical Pharmacology (2007), 73(8), 1182-1194; and Medhurst, S. J.; et al.; "Novel histamine $H_3$ receptor antagonists GSK189254 and GSK334429 are efficacious in surgically-induced and virally-induced rat models of neuropathic pain", Pain (2008), vol. 138, pp. 61-69.

The ability of the compounds of the invention, including, but not limited to, those specified in the examples, to treat sleep disorders, including narcolepsy and pathological sleepiness, and jet lag, may be demonstrated by Barbier, A. J., et al. "Acute wake-promoting actions of JNJ-5207852, a novel, diamine-based $H_3$ antagonist" British Journal of Pharmacology (2004) 1-13; Monti et al., Neuropsychopharmacology (1996) 15, 31-35; Lin et al., Brain Res. (1990) 523, p. 325-330; Monti, et al., Neuropsychopharmacology (1996) 15, p. 31-35; Ligneau, et al. Journal of Pharmacology and Experimental Therapeutics (1998), 287, 658-666; Sakai, et al., Life Sci. (1991) 48, p. 2397-2404; Mazurkiewicz-Kwilecki and Nsonwah, Can. J. Physiol. Pharmacol., (1989) 67, p. 75-78; P. Panula, et al., Neuroscience (1998) 44, 465-481; Wada, et al., Trends in Neuroscience (1991) 14, p. 415; and Monti, et al., Eur. J. Pharmacol. (1991), 205, p. 283; Dvorak, C., et al. "4-Phenoxypiperidines: Potent, Conformationally Restricted, Non-Imidazole Histamine $H_3$ Antagonists" Journal of Medicinal Chemistry (2005) 48, 2229-2238; and Schwartz, J.-C. and Lecomte, J.-M., "Treatment of Parkinson's disease, obstructive sleep apnea, dementia with Lewy bodies, and vascular dementia with non-imidazole alkylamine histamine $H_3$-receptor ligands", International Publication No. WO 2006/103546 A2.

The ability of the compounds of the invention, including, but not limited to, those specified in the examples, to treat drug abuse. Amphetamine is an abused stimulant in humans. It, and similar abused drugs stimulate locomotor activity in animals, and it has been found that the $H_3$ antagonist thioperamide suppresses the locomotor stimulation induced by amphetamine; therefore $H_3$ antagonists are likely to be useful for treating drug abuse as may be demonstrated by Clapham J.; Kilpatrick G. J. "Thioperamide, the selective histamine $H_3$ receptor antagonist, attenuates stimulant-induced locomotor activity in the mouse", European journal of pharmacology (1994), 259(2), 107-14.

The ability of the compounds of the invention, including, but not limited to, those specified in the examples, to treat mood alteration, bipolar disorder, depression, obsessive compulsive disorder, and Tourette's syndrome, may be demonstrated by Lamberti, et al. British Journal of Pharmacology (1998) 123, 1331-1336; Perez-Garcia C, et. al., Psychopharmacology (Berlin) (1999) 142(2): 215-20.

The ability of the compounds of the invention, including, but not limited to, those specified in the examples, to treat Parkinson's disease (a disease wherein patients have deficits in ability to initiate movements, and patients' brain have low dopamine levels) may be demonstrated by Sánchez-Lemus, E., et al. "Histamine $H_3$ receptor activation inhibits dopamine $D_1$ receptor-induced cAMP accumulation in rat striatal slices" Neuroscience Letters (2004) 364, p. 179-184; Sakai, et al., Life Sci. (1991) 48, 2397-2404; Fox, G. B., et al. "Pharmacological Properties of ABT-239: II. Neurophysiological Characterization and Broad Preclinical Efficacy in Cognition and Schizophrenia of a Potent and Selective Histamine $H_3$ Receptor Antagonist" Journal of Pharmacology and Experimental Therapeutics, 313:176-190, 2005; Chen, Z., et al. "Pharmacological effects of carcinine on histaminergic neurons in the brain" British Journal of Pharmacology (2004) 143, 573-580; and Schwartz, J.-C. and Lecomte, J.-M., "Treatment of Parkinson's disease, obstructive sleep apnea, dementia with Lewy bodies, and vascular dementia with non-imidazole alkylamine histamine $H_3$-receptor ligands", International Publication No. WO 2006/103546 A2.

The ability of the compounds of the invention, including, but not limited to, those specified in the examples, to treat medullary thyroid carcinoma, melanoma, polycystic ovary syndrome, may be demonstrated by Polish Med. Sci. Mon. (1998) 4(5): 747; Adam Szelag, "Role of histamine $H_3$-receptors in the proliferation of neoplastic cells in vitro," Med. Sci. Monitor (1998) 4(5): 747-755; and C. H. Fitzsimons, et al., "Histamine receptors signalling in epidermal tumor cell lines with H-ras gene alterations," Inflammation Res. (1998) 47 (Suppl 1):S50-S51.

Compounds of the invention are particularly useful for treating and preventing a condition or disorder affecting memory or cognition, for example Alzheimer's disease, attention-deficit hyperactivity disorder, schizophrenia, or the cognitive deficits of schizophrenia.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salt or ester, or amide form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

For treatment or prevention of disease, the total daily dose of the compounds of this invention administered to a human or lower animal may range from about 0.0003 to about 30 mg/kg/day. For purposes of oral administration, more preferable doses can be in the range of from about 0.0003 to about 1 mg/kg/day. If desired, the effective daily dose can be divided into multiple doses for purposes of administration; consequently, single dose compositions may contain such amounts or submultiples thereof to make up the daily dose.

Compounds and compositions of the invention also are useful as diagnostic tools. The ability of PET (positron emitting tomography) and sPECT to probe the degree of receptor occupancy in humans and animals by endogenous ligands (such as histamine for the histamine $H_3$ receptor) or drugs (such with a clinically used drug that affects brain histamine levels) is widely recognized. This constitutes the use of PET as a biomarker to assess efficacy of pharmacological interventions with drugs. The topic and use of positron-emitting ligands for these purposes has been generally reviewed, for example in "PET ligands for assessing receptor occupancy in vivo" Burns, et al. Annual Reports in Medicinal Chemistry (2001), 36, 267-276; "Ligand-receptor interactions as studied by PET: implications for drug development" by Jarmo Hietala, Annals of Medicine (Helsinki) (1999), 31(6), 438-443; "Positron emission tomography neuroreceptor imaging as a tool in drug discovery, research and development" Burns, et al. Current Opinion in Chemical Biology (1999), 3(4), 388-394. The compounds of the invention, synthesized with $^{11}C$, $^{18}F$, or other positron-emitting isotopes are suitable ligand tools for PET; a number of positron-emitting reagents have been synthesized, are available, and are known to those skilled in the art. Especially suitable compounds of the invention for this use are those wherein a $^{11}CH_3$ group can be incorporated in by reaction with $^{11}CH_3I$. Also, especially suitable compounds of the use are those wherein a $^{18}F$ group can be incorporated into the compound by reaction with $^{18}F$-fluoride anion. The incorporation of $^{11}CH_3I$ can be carried out by substituting $^{11}CH_3I$ for the $^{12}CH_3I$. For example, compounds of formula (I), wherein $R_6$, $R_{6a}$, or $R_{6b}$ are pyrazol-4-yl or pyrazol-2-yl can be treated with base and $^{11}CH_3I$ to prepare ligands for use in PET studies. For incorporation of $^{18}F$ into compounds or compositions of the invention, compounds of formula (I), wherein $R_4R_5N$ is 4-hydroxypiperidine or 4-hydroxymethylpyrrolidine, can be treated with methanesulfonic anhydride or triflic anhydride and a base in an inert solvent such as dichloromethane, and the resulting compound (a methanesulfonate or triflate) can be treated with $^{18}F$-fluoride by methods well known to skilled in the art of synthetic organic chemistry or medicinal chemistry. Among compounds of the invention that are suitable for use as ligands for PET studies are $^{18}F$ and $^{11}C$ isotopes of compounds of the invention, including, but not limited to:

(R)-6-(1-($^{11}C$)Methyl-1H-pyrazol-4-yl)-2-(3-(piperidin-1-yl)pyrrolidin-1-yl)benzo[d]thiazole;

(R)-6-(1-Methyl-1H-pyrazol-4-yl)-2-(3-(4-($^{18}F$)fluoro-piperidin-1-yl)pyrrolidin-1-yl)benzo[d]thiazole;

(R)-2-(2-(3-(4-($^{18}F$)Fluoro-piperidin-1-yl)pyrrolidin-1-yl)benzo[d]thiazol-6-yl)pyridazin-3 (2H)-one;

(R)-3-(2-(3-(4-($^{18}F$)Fluoro-piperidin-1-yl)pyrrolidin-1-yl)benzo[d]thiazol-6-yl)oxazolidin-2-one;

(S)-3-Hydroxy-1-(2-((R)-3-(4-($^{18}F$)fluoro-piperidin-1-yl)pyrrolidin-1-yl)benzo[d]thiazol-6-yl)pyrrolidin-2-one; and (R)—N-(2-($^{18}F$)fluoroethyl)-2-(3-(piperidin-1-yl)pyrrolidin-1-yl)benzo[d]thiazole-6-carboxamide.

The compounds and processes of the invention will be better understood by reference to the following examples, which are intended as an illustration of and not a limitation upon the scope of the invention.

REFERENCE EXAMPLES

Reference Example 1

1-(6-bromobenzo[d]thiazol-2-yl)azetidin-3-ol 2,4-Dibromophenylisothiocyanate (CAS #13037-63-3, 3.02 g, 0.0103 mole), and 3-hydroxyazetidine hydrochloride (CAS #18621-18-6, 1.18 g, 10.8 mmol) were suspended in acetonitrile (35 mL). Triethylamine (1.53 mL, 0.011 mole) was added dropwise to the stirred suspension. After 20 minutes of stirring at room temperature, the reaction mixture had become a light yellow solution. After another 10 minutes of stirring at room temperature, the isothiocyanate was consumed and the intermediate, N-(2,4-dibromophenyl)-3-hydroxyazetidine-1-carbothioamide had formed. Although not necessary, this intermediate thiourea was isolated and purified by partitioning between 1:1 hexane/ethyl acetate (150 mL) and 1 M aqueous $KH_2PO_4$ (35 mL). The organic layer was washed with saturated aqueous sodium bicarbonate (10 mL) and dried ($Na_2SO_4$). The filtrate was partially concentrated at which point the thiourea crystallized. The crystals were collected by filtration and dried under vacuum to provide N-(2,4-dibromophenyl)-3-hydroxyazetidine-1-carbothioamide.

N-(2,4-Dibromophenyl)-3-hydroxyazetidine-1-carbothioamide (0.366 g, 1.0 mmol) and $Cs_2CO_3$ (0.489 g, 1.5 mmol) were suspended in acetonitrile (10 mL), and the stirred reaction mixture was heated under microwave irradiation at 150° C. for 12 minutes. The reaction mixture was filtered and the filtrate was concentrated under reduced pressure. The resulting residue was purified by silica gel chromatography (2:1 to 1:2 hexane/ethyl acetate) to provide 1-(6-bromobenzo[d]

thiazol-2-yl)azetidin-3-ol. ¹H NMR (300 MHz, DMSO-d$_6$) δ ppm 3.85-3.91 (m, 2H), 4.29-4.36 (m, 2H), 4.61-4.72 (m, 1H), 5.90 (d, J=8 Hz, 1H), 7.36-7.44 (m, 2H), 8.02-8.03 (m, 1H); MS (DCI/NH$_3$) m/z 285 (M+H)$^+$.

Reference Example 2

1-(6-(1-methyl-1H-pyrazol-4-yl)benzo[d]thiazol-2-yl)azetidin-3-ol

A mixture of 1-(6-bromobenzo[d]thiazol-2-yl)azetidin-3-ol (Reference Example 1, 1.426 g, 5.0 mmol), 1-methyl-4-(4,4,5,5-tetramethyl-1,3,2-dioxaborolan-2-yl)-1H-pyrazole (CAS #761446-44-0, 1.248 g, 6.0 mmol), dichlorobis(triphenylphosphine)palladium (II) (0.140 g, 0.20 mmol), and (2-biphenyl)dicyclohexylphosphine (0.070 g, 0.20 mmol) in 1:1 dioxane/ethanol (12 mL) was treated with deoxygenated 1 M aqueous Na$_2$CO$_3$ (6.0 mL). The reaction mixture was then heated under microwave irradiation at 150° C. for 10 minutes. The reaction mixture was then diluted with dichloromethane (30 mL) and filtered through a pad of diatomaceous earth that was subsequently rinsed with 9:1 dichloromethane/methanol. The filtrate was concentrated under reduced pressure and the residue was treated with acetonitrile (20 mL) to provide a slurry that was filtered. The filter cake was treated with 4:1 methanol/water (5 mL) and the resulting slurry was filtered. The filter cake was rinsed with 4:1 methanol/water (3 mL), then dried under vacuum to provide 1-(6-(1-methyl-1H-pyrazol-4-yl)benzo[d]thiazol-2-yl)azetidin-3-ol. ¹H NMR (300 MHz, DMSO-d$_6$) δ ppm 3.82-3.91 (m, 2H), 3.85 (s, 3H), 4.31 (t, J=8 Hz, 2H), 4.62-4.72 (m, 1H), 5.86-5.91 (m, 1H), 7.43 d, J=8 Hz, 1H), 7.48 (dd, J=1, 8 Hz, 1H), 7.82 (d, J=1 Hz, 1H), 7.96 (d, J=1 Hz, 1H), 8.07 (s, 1H); MS (DCI/NH$_3$) m/z 287 (M+H)$^+$.

Reference Example 3

1-(6-(1-methyl-1H-pyrazol-4-yl)benzo[d]thiazol-2-yl)azetidin-3-yl 4-nitrobenzenesulfonate A suspension of 1-(6-(1-methyl-1H-pyrazol-4-yl)benzo[d]thiazol-2-yl)azetidin-3-ol (Reference Example 2, 0.143 g, 0.50 mmol), N,N-diisopropylethylamine (0.105 mL, 0.60 mmol), and 1-(4-nitrophenylsulfonyl)-1H-1,2,4-triazole (0.178 g, 0.70 mmol) in dichloromethane (5.0 mL) was stirred a few hours and then triethylamine (0.14 mL, 1.0 mmol) was added. After the mixture had been stirred overnight additional 1-(4-nitrophenylsulfonyl)-1H-1,2,4-triazole (0.076 g, 0.30 mmol) was added. The mixture was stirred another day and then placed directly onto a column of silica and purified chromatographically (100% CH$_2$Cl$_2$ to 80:20 CH$_2$Cl$_2$/ethyl acetate) to give 1-(6-(1-methyl-1H-pyrazol-4-yl)benzo[d]thiazol-2-yl)azetidin-3-yl 4-nitrobenzenesulfonate. ¹H NMR (300 MHz, CD$_3$OD) δ ppm 3.91 (s, 3H), 4.20-4.25 (m, 2H), 4.46-4.52 (m, 2H), 5.41-5.50 (m, 1H), 7.46 (d, J=8 Hz, 1H), 7.52 (dd, J=1, 8 Hz, 1H), 7.79 (s, 1H), 7.87 (s, 1H), 7.92 (s, 1H) 8.24 (d, J=9 Hz, 2H), 8.51 (d, J=9 Hz, 2H); MS (ESI) m/z 472 (M+H)$^+$.

Reference Example 4

1-(6-(1-methyl-1H-pyrazol-4-yl)benzo[d]thiazol-2-yl)azetidin-3-one

A suspension of 1-(6-(1-methyl-1H-pyrazol-4-yl)benzo[d]thiazol-2-yl)azetidin-3-ol (Reference Example 2, 0.143 g, 0.50 mmol) and Dess-Martin periodinane (1,1,1-tris(acetyloxy)-1,1-dihydro-1,2-benziodoxol-3-(1H)-one, CAS #87413-09-0, 0.636 g, 1.50 mmol) was stirred in 15:1 acetone/dimethyl sulfoxide (15 mL/1 mL). The reaction mixture was heated to near reflux for 4 hours, then additional Dess-Martin periodinane (0.212 g, 0.50 mmol) was added. The reaction was cooled to room temperature after an additional 3 hours of heating at near reflux. The reaction mixture was diluted with diethyl ether (15 mL) and insoluble material was removed by filtration. The filtrate was concentrated under reduced pressure to remove all but the dimethyl sulfoxide. This residue was partitioned between 9:1 CH$_2$Cl$_2$/hexane (20 mL) and water (10 mL). The organic layer was dried (Na$_2$SO$_4$) and filtered. The filtrate was concentrated under reduced pressure and the residue was purified by silica gel chromatography (90:10 to 40:60 CH$_2$Cl$_2$/ethyl acetate). Fractions containing product were combined and concentrated under reduced pressure to give a gummy solid, which after trituration with diethyl ether, provided 1-(6-(1-methyl-1H-pyrazol-4-yl)benzo[d]thiazol-2-yl)azetidin-3-one as a solid. ¹H NMR (300 MHz, CDCl$_3$) δ ppm 3.95 (s, 3H), 5.00(s, 4H), 7.46 (dd, J=2, 8 Hz, 1H), 7.59 (s, 1H), 7.64 (d, J=8 Hz, 1H), 7.74 (d, J=2 Hz, 1H), 7.75 (s, 1H); MS (DCI/NH$_3$) m/z 285 (M+H)$^+$.

Reference Example 5

(R)-1-(pyrrolidin-3-yl)piperidine dihydrochloride

Reference Example 5a (S)-tert-butyl 3-(methylsulfonyloxy)pyrrolidine-1-carboxylate To a stirred, 0° C. solution of (S)-tert-butyl 3-hydroxypyrrolidine-1-carboxylate (10.4 g, 55.5 mmol) and triethylamine (15.5 mL, 0.1111 mole) in CH$_2$Cl$_2$ (150 mL) was added dropwise methanesulfonyl chloride (5.2 mL, 0.06665 mole). When the addition was complete, the reaction mixture was allowed to warm to room temperature, then stirred overnight. The reaction mixture was concentrated under reduced pressure to give a residue that was partitioned between ethyl acetate and saturated aqueous sodium carbonate. The organic layer was dried (MgSO$_4$) and filtered. The filtrate was concentrated under reduced pressure and the residue was purified by silica gel chromatography (100% hexane to 70:30 hexane/ethyl acetate). Fractions containing product were combined and concentrated under reduced pressure to give (S)-tert-butyl 3-(methylsulfonyloxy)pyrrolidine-1-carboxylate. ¹H NMR (300 MHz, CD$_3$OD) δ ppm 1.47 (s, 9H), 2.14-2.29 (m, 2H), 3.12 (s, 1H), 3.36-3.67 (m, 4H), 5.24-5.30 (m, 1H); MS (DCI/NH$_3$) m/z 266 (M+H)$^+$, 283 (M+NH$_4$)$^+$.

Reference Example 5b (R)-tert-butyl 3-(piperidin-1-yl)pyrrolidine-1-carboxylate

A mixture of (S)-tert-butyl 3-(methylsulfonyloxy)pyrrolidine-1-carboxylate (Reference Example 5a, 12.15 g, 45.8 mmol) and piperidine (100 mL, 1.01568 mole) was stirred at 70° C. overnight. The residue was purified by silica gel chromatography (100% ethyl acetate to 97:3 ethyl acetate/methanol). Fractions containing product were combined and concentrated under reduced pressure to give (R)-tert-butyl 3-(piperidin-1-yl)pyrrolidine-1-carboxylate. ¹H NMR (300 MHz, CD$_3$OD) δ ppm 1.45 (s, 9H), 1.45-1.53 (m, 2H), 1.56-1.66 (m, 1H), 1.66-1.84 (m, 1H), 2.09-2.20 (m, 1H), 2.35-

2.60 (m, 4H), 2.73-2.89 (m, 1H), 3.06 (t, J=10 Hz, 1H), 3.17-3.29 (m, 1H), 3.51 (t, J=10 Hz, 1H), 3.58-3.66 (m, 1H); MS (DCI/NH$_3$) m/z 255 (M+H)$^+$.

Reference Example 5c (R)-1-(pyrrolidin-3-yl)piperidine dihydrochloride

A stirred, room temperature solution of (R)-tert-butyl 3-(piperidin-1-yl)pyrrolidine-1-carboxylate (Reference Example 5b, 6.87 g, 27.0 mmol) in methanol (100 mL) was treated with 4 N HCl in dioxane (67.5 mL, 0.2700 mole). The reaction mixture was stirred at room temperature overnight, then volatiles were removed under reduced pressure. The resulting solid was crystallized from methanol/ether to provide (R)-1-(pyrrolidin-3-yl)piperidine dihydrochloride. $^1$H NMR (300 MHz, CD$_3$OD) δ ppm 1.46-2.03 (m, 6H), 2.32-2.46 (m, 1H), 2.53-2.63 (m, 1H), 2.95-3.20 (m, 2H), 3.33-3.43 (m, 1H), 3.47-3.72 (m, 4H), 3.78-3.85 (m, 1H), 4.09 (pentet, J=8 Hz, 1H); MS (ESI) m/z 155 (M+H)$^+$.

Reference Example 6

(S)-1-(6-iodobenzo[d]thiazol-2-yl)pyrrolidin-3-ol

Reference Example 6a 6-iodobenzo[d]thiazole-2-thiol

A mixture of 2-fluoro-4-iodoaniline (24.19 g, 0.100 mole) and potassium ethylxanthogenate (35.27 g, 0.220 mole) in N,N-dimethylformamide (80 mL) was stirred at 95° C. for 5 hours. The reaction mixture was cooled to room temperature then diluted with water (150 mL) and 1 N aqueous HCl (200 mL). The mixture was stirred at room temperature overnight. The resulting precipitate was collected by filtration and rinsed with water. The solid was dried overnight at 85° C. in a vacuum oven to provide 6-iodobenzo[d]thiazole-2-thiol. $^1$H NMR (300 MHz, CD$_3$OD) δ ppm 7.09 (d, J=8 Hz, 1H), 7.70 (dd, J=2, 8 Hz, 1H), 8.10 (d, J=2 Hz, 1H), 13.82 (S$_{broad}$, 1H); MS (DCI/NH$_3$) m/z 294 (M+H)$^+$.

Reference Example 6b 6-iodo-2-(methylthio)benzo[d]thiazole

To a stirred, room temperature mixture of 6-iodobenzo[d]thiazole-2-thiol (Reference Example 6a, 1.5 g, 5.1 mmol) and potassium carbonate (0.707 g, 5.1 mmol) in tetrahydrofuran (30 mL) was added methyl iodide (0.35 mL, 5.6 mmol). The reaction mixture was stirred at room temperature overnight, then volatiles were removed under reduced pressure to give a solid. The solid was partitioned between saturated aqueous sodium carbonate and chloroform. The chloroform layer was dried (MgSO$_4$) and filtered. The filtrate was concentrated under reduced pressure to provide 6-iodo-2-(methylthio)benzo[d]thiazole. $^1$H NMR (300 MHz, CDCl$_3$) δ ppm 2.78 (s, 3H), 7.58 (d, J=9 Hz, 1H), 7.69 (dd, J=2, 9 Hz, 1H), 8.07 (d, J=2 Hz, 1H); MS (DCI/NH$_3$) m/z 308 (M+H)$^+$.

Reference Example 6c 6-iodo-2-(methylsulfonyl)benzo[d]thiazole

To a stirred, room temperature solution of 6-iodo-2-(methylthio)benzo[d]thiazole (Reference Example 6b, 1.22 g, 4.0 mmol) in acetic acid (100 mL) was added dropwise a solution of potassium permanganate (0.190 g, 1.2 mmol) in water (60 mL). The reaction mixture was stirred at room temperature for 68 hours, then quenched with aqueous sodium sulfite. The resulting mixture was vigorously stirred at room temperature overnight. The resulting precipitate was collected by filtration and rinsed with water. The solid was dissolved in ethyl acetate, dried (MgSO$_4$), and filtered. The filtrate was concentrated under reduced pressure to provide 6-iodo-2-(methylsulfonyl)benzo[d]thiazole. $^1$H NMR (300 MHz, CDCl$_3$) δ ppm 3.41 (s, 3H), 7.93 (d, J=1 Hz, 2H), 8.38 (t, J=1 Hz, 1H); MS(DCI/NH$_3$) m/z 340 (M+H)$^-$, 357 (M+NH$_4$)$^+$.

Reference Example 6d (S)-1-(6-iodobenzo[d]thiazol-2-yl)pyrrolidin-3-ol

A stirred mixture of 6-iodo-2-(methylsulfonyl)benzo[d]thiazole (Reference Example 6c, 1.50 g, 4.42 mmol), (S)-pyrrolidin-3-ol (0.500 g, 5.74 mmol), and potassium carbonate (1.222 g, 8.84 mmol) in N,N-dimethylformamide (21.5 mL) was heated to 150° C. under microwave irradiation for 10 minutes. The reaction mixture was cooled to room temperature, then poured into water (350 mL) to give a precipitate. The precipitate was collected by filtration, rinsed with water, and then dissolved in ethyl acetate. The ethyl acetate solution was dried (MgSO$_4$) and filtered. The filtrate was concentrated under reduced pressure to give a crude solid that was purified by silica gel chromatography (100% CHCl$_3$ to 97:3 CHCl$_3$/methanol). Fractions containing product were combined an concentrated under reduced pressure to provide (S)-1-(6-iodobenzo[d]thiazol-2-yl)pyrrolidin-3-ol. $^1$H NMR (300 MHz, CD$_3$OD) δ ppm 2.03-2.14 (m, 1H), 2.15-2.29 (m, 1H), 3.47-3.55 (m, 1H), 3.58-3.75 (m, 3H), 4.53-4.59 (m, 1H), 7.23 (d, J=8 Hz, 1H), 7.53-7.59 (m, 1H), 7.95-7.98 (m, 1H); MS (DCI/NH$_3$) m/z 347 (M+H)$^+$.

Reference Example 7

(S)-1-(6-bromobenzo[d]thiazol-2-yl)piperidin-3-ol

A mixture of 6-bromo-2-chlorobenzo[d]thiazole (1.0 g, 4.0 mmol) and (S)-piperidin-3-ol hydrochloride (0.609 g, 4.43 mmol), and N,N-diisopropylethylamine (3.51 mL, 0.02012 mole) in N,N-dimethylformamide (2.0 mL) was heated to 150° C. under microwave irradiation for 15 minutes. The reaction mixture was transferred to a 100 mL round bottom flask (methanol rinse) and volatiles were removed under reduced pressure. The residue was partitioned between CHCl$_3$ and saturated aqueous sodium carbonate. The organic layer was dried over MgSO$_4$. Drying agent was removed by filtration and the filtrate was concentrated under reduced pressure. The crude material was purified by column chromatography on an Analogix IntelliFlash-280 (Analogix SF15-12g, 100% CHCl$_3$ to 60:40 CHCl$_3$/ethyl acetate). Fractions containing product were combined and concentrated under reduced pressure to provide (S)-1-(6-bromobenzo[d]thiazol-2-yl)piperidin-3-ol.

$^1$H NMR (300 MHz, CD$_3$OD) δppm 1.52-1.70 (m, 1H), 1.84-2.09 (m, 2H), 3.17-3.26 (m, 1H), 3.33-3.42 (m, 1H), 3.69-3.82 (m, 2H), 3.92 (dd, J=4, 13 Hz, 1H), 7.31 (d, J=8 Hz, 1H), 7.37 (dd, J=2, 8 Hz, 1H), 7.75-7.77 (m, 1H); MS (DCI/NH$_3$) m/z 313 (M+H)$^+$.

TABLE 12

Reference Examples 8-9 were prepared by the method of Reference Example 7,
substituting the appropriate hydroxy-substituted amine for (S)-piperidin-3-ol hydrochloride.

| Reference Example Number | Hydroxy-substituted amine | Product | NMR and MS Data |
|---|---|---|---|
| 8 | (R)-pyrrolidin-3-ol | (R)-1-(6-bromobenzo[d]thiazol-2-yl)pyrrolidin-3-ol | $^1$H NMR (300 MHz, CD$_3$OD) δ ppm 2.03-2.14 (m, 1H), 2.15-2.29 (m, 1H), 3.47-3.55 (m, 1H), 3.58-3.75 (m, 3H), 4.53-4.59 (m, 1H), 7.34 (d, J = 8 Hz, 1H), 7.39 (dd, J = 2, 8 Hz, 1H), 7.79 (d, J = 2 Hz, 1H). MS (DCI/NH$_3$) m/z 299 (M + H)$^+$. |
| 9 | (R)-piperidin-3-ol hydrochloride | (R)-1-(6-bromobenzo[d]thiazol-2-yl)piperidin-3-ol | $^1$H NMR (300 MHz, CD$_3$OD) δ ppm 1.52-1.70 (m, 1H), 1.84-2.09 (m, 2H), 3.17-3.26 (m, 1H), 3.33-3.42 (m, 1H), 3.69-3.82 (m, 2H), 3.92 (dd, J = 4, 13 Hz, 1H), 7.31 (d, J = 8 Hz, 1H), 7.37 (dd, J = 2, 8 Hz, 1H), 7.75-7.77 (m, 1H). MS (DCI/NH$_3$) m/z 313 (M + H)$^+$. |

Reference Example 10

(S)-1-(6-bromobenzo[d]thiazol-2-yl)piperidin-3-yl methanesulfonate

In a 20 mL scintillation vial equipped with a magnetic stirbar was added (S)-1-(6-bromobenzo[d]thiazol-2-yl)piperidin-3-ol (Reference Example 7, 1.15 g, 3.67 mmol). Dichloromethane (10 mL) was then added to the reaction vial to give a solution. To this stirred solution was added 2.5 equivalents of triethylamine (1.279 mL, 9.18 mmol). The reaction vial was capped with a septum and vented to a bubbler. The vial was placed in an ice water bath. To this stirred, 0° C. solution was added dropwise 2.0 equivalents of methanesulfonyl chloride (0.572 mL, 7.34 mmol). The reaction mixture was stirred for 10 minutes at 0° C., then the ice bath was removed and stirring was continued at room temperature overnight. The reaction mixture was washed with water, then dried (MgSO$_4$) and filtered. The filtrate was concentrated under reduced pressure to give an oil that was purified by column chromatography on an Analogix IntelliFlash-280 (Analogix SF10-4g [2 connected in series], 100% dichloromethane). Fractions containing product were combined and concentrated under reduced pressure to give a solid that was treated with diethyl ether. This suspension was filtered to collect (S)-1-(6-bromobenzo[d]thiazol-2-yl)piperidin-3-yl methanesulfonate. $^1$H NMR (300 MHz, CDCl$_3$) δ ppm 1.68-1.81 (m, 1H), 1.94-2.16 (m, 3H), 3.06 (s, 3H), 3.51-3.68 (m, 2H), 3.85-3.90 (m, 2H), 4.86-4.93 (m, 1H), 7.37-7.39 (m, 2H), 7.69-7.71 (m, 1H); MS (DCI/NH$_3$) m/z 391 (M+H)$^+$.

TABLE 13

Reference Examples 11-12b were prepared by the method of Reference Example 10,
substituting the appropriate hydroxy-substituted amino-benzothiazole for (S)-1-(6-bromobenzo[d]thiazol-2-yl)piperidin-3-ol.

| Reference Example Number | Hydroxy-substituted amino-benzothiazole | Product | NMR and MS Data |
|---|---|---|---|
| 11 | Ref. Ex. 8: (R)-1-(6-bromobenzo[d]thiazol-2-yl)pyrrolidin-3-ol | (R)-1-(6-bromobenzo[d]thiazol-2-yl)pyrrolidin-3-yl methanesulfonate | $^1$H NMR (300 MHz, CDCl$_3$) δ ppm 2.31-2.45 (m, 1H), 2.47-2.57 (m, 1H), 3.07 (s, 3H), 3.72-3.79 (m, 2H), 3.85-4.00 (m, 2H), 5.43-5.48 (m, 1H), 7.40 (dd, J = 2, 8 Hz, 1H), 7.45 (d, J = 8 Hz, 1H), 7.73 (d, J = 2 Hz, 1H). MS (DCI/NH$_3$) m/z 377 (M + H)$^+$. |
| 12 | Ref. Ex. 9: (R)-1-(6-bromobenzo[d]thiazol-2-yl)piperidin-3-ol | (R)-1-(6-bromobenzo[d]thiazol-2-yl)piperidin-3-yl methanesulfonate | $^1$H NMR (300 MHz, CDCl$_3$) δ ppm 1.68-1.81 (m, 1H), 1.94-2.16 (m, 3H), 3.06 (s, 3H), 3.51-3.68 (m, 2H), 3.85-3.90 (m, 2H), 4.86-4.93 (m, 1H), 7.37-7.39 (m, 2H), 7.69-7.71 (m, 1H). MS (DCI/NH$_3$) m/z 391 (M + H)$^+$. |

TABLE 13-continued

Reference Examples 11-12b were prepared by the method of Reference Example 10, substituting the appropriate hydroxy-substituted amino-benzothiazole for (S)-1-(6-bromobenzo[d]thiazol-2-yl)piperidin-3-ol.

| Reference Example Number | Hydroxy-substituted amino-benzothiazole | Product | NMR and MS Data |
|---|---|---|---|
| 12b | Ref. Ex. 1: 1-(6-bromobenzo[d]thiazol-2-yl)azetidin-3-ol | 1-(6-bromobenzo[d]thiazol-2-yl)azetidin-3-yl methanesulfonate | Crude material used without characterization. |

Reference Example 13

(S)-1-(6-(4-cyanophenyl)benzo[d]thiazol-2-yl)pyrrolidin-3-yl methanesulfonate

Reference Example 13a (S)-1-(6-chlorobenzo[d]thiazol-2-yl)pyrrolidin-3-ol

A stirred mixture of 2,6-dichlorobenzo[d]thiazole (CAS #3622-23-9, 0.314 g, 3.00 mmol), (S)-pyrrolidin-3-ol (0.314 g, 3.60 mmol), and potassium carbonate (1.24 g, 9.00 mmol) in water/ethanol (10 mL/8 mL) was heated at 150° C. under microwave irradiation for 5 minutes. The reaction mixture was cooled to room temperature then partitioned between dichloromethane and saturated aqueous sodium carbonate. The organic layer was dried (MgSO$_4$) and filtered. The filtrate was concentrated under reduced pressure to give a crude solid that was purified by crystallization from ethyl acetate/hexane. Crystals were collected by filtration, then dried under vacuum to provide (S)-1-(6-chlorobenzo[d]thiazol-2-yl)pyrrolidin-3-ol. $^1$H NMR (300 MHz, CD$_3$OD) δ ppm 2.04-2.14 (m, 1H), 2.16-2.29 (m, 1H), 3.48-3.55 (m, 1H), 3.59-3.75 (m, 3H), 4.54-4.59 (m, 1H), 7.26 (dd, J=2, 8 Hz, 1H), 7.40 (d, J=8 Hz, 1H), 7.67 (d, J=2 Hz, 1H); MS (DCI/NH$_3$) m/z 255 (M+H)$^+$.

Reference Example 13b (S)-4-(2-(3-hydroxypyrrolidin-1-yl)benzo[d]thiazol-6-yl)benzonitrile A mixture of (S)-1-(6-chlorobenzo[d]thiazol-2-yl)pyrrolidin-3-ol (Reference Example 13a, 0.2547 g, 1.0 mmol), 4-cyanophenylboronic acid (CAS #126747-14-6, 0.2204 g, 1.5 mmol), palladium (II) acetate (2.2 mg, 0.01 mmol), 2-dicyclohexylphosphino-2',6'-dimethoxybiphenyl (CAS #657408-07-6, 0.0102 g, 0.025 mmol), and potassium phosphate (0.4246 g, 2.0 mmol) in toluene/isopropanol (2 mL/2 mL) was heated under microwave irradiation at 150° C. for 10 minutes. The reaction mixture was then cooled to room temperature and concentrated under reduced pressure. This residue was partitioned between ethyl acetate and saturated aqueous sodium carbonate. The organic layer was dried (MgSO$_4$) and filtered. The filtrate was concentrated under reduced pressure and the residue was purified by silica gel chromatography (80:20 to 60:40 hexane/isopropanol). Fractions containing product were combined and concentrated under reduced pressure to provide (S)-4-(2-(3-hydroxypyrrolidin-1-yl)benzo[d]thiazol-6-yl)benzonitrile. $^1$H NMR (300 MHz, DMSO-d$_6$) δ ppm 1.91-2.02 (m, 1H), 2.06-2.19 (m, 1H), 3.38-3.46 (m, 1H), 3.56-3.68 (m, 3H), 4.41-4.48 (m, 1H), 5.14 (d, J=4 Hz, 1H), 7.54 (d, J=8 Hz, 1H), 7.68 (dd, J=2, 8 Hz, 1H), 7.89 (s, 1H), 8.23 (d, J=2 Hz, 1H); MS (DCI/NH$_3$) m/z 322 (M+H)$^+$.

Reference Example 13c (S)-1-(6-(4-cyanophenyl)benzo[d]thiazol-2-yl)pyrrolidin-3-yl methanesulfonate A stirred, 0° C. solution of (S)-4-(2-(3-hydroxypyrrolidin-1-yl)benzo[d]thiazol-6-yl)benzonitrile (Reference Example 13b, 75 mg, 0.23 mmol) in pyridine (2.5 mL) was treated with methanesulfonyl chloride (0.022 mL, 0.280 mmol). The ice bath was removed and stirring was continued at room temperature overnight. The reaction mixture was concentrated under reduced pressure to give (S)-1-(6-(4-cyanophenyl)benzo[d]thiazol-2-yl)pyrrolidin-3-yl methanesulfonate that was used without further purification. $^1$H NMR (300 MHz, CDCl$_3$) δ ppm 2.36-2.50 (m, 1H), 2.53-2.63 (m, 1H), 3.10 (s, 3H), 3.84-4.15 (m, 4H), 5.47-5.52 (m, 1H), 7.60 (dd, J=2, 8 Hz, 1H), 7.67-7.75 (m, 4H), 7.79 (d, J=8 Hz, 1H), 7.85 (d, J=2 Hz, 1H); MS (DCI/NH$_3$) m/z 400 (M+H)$^+$.

Reference Example 14

(R)-1-(6-(4-cyanophenyl)benzo[d]thiazol-2-yl)pyrrolidin-3-yl methanesulfonate

Reference Example 14a (R)-4-(2-(3-hydroxypyrrolidin-1-yl)benzo[d]thiazol-6-yl)benzonitrile The title compound was prepared by the method of Example 13b, substituting (R)-1-(6-bromobenzo[d]thiazol-2-yl)pyrrolidin-3-ol (Reference Example 8) in place of (S)-1-(6-chlorobenzo[d]thiazol-2-yl)pyrrolidin-3-ol (Reference Example 13a) to give (R)-4-(2-(3-hydroxypyrrolidin-1-yl)benzo[d]thiazol-6-yl)benzonitrile. $^1$H NMR (300 MHz, DMSO-d$_6$) δ ppm 1.93-2.01 (m, 1H), 2.07-2.18 (m, 1H), 3.39-3.46 (m, 1H), 3.56-3.67 (m, 3H), 4.43-4.48 (m, 1H), 5.15 (d, J=6 Hz, 1H), 7.54 (d, J=8 Hz, 1H), 7.67 (dd, J=2, 8 Hz, 1H), 7.86-7.91 (m, 4H), 8.20 (d, J=2 Hz, 1H); MS (ESI) m/z 322 (M+H)$^+$.

Reference Example 14b (R)-1-(6-(4-cyanophenyl)benzo[d]thiazol-2-yl)pyrrolidin-3-yl methanesulfonate The title compound was prepared by the method of Example 13c, substituting (R)-4-(2-(3-hydroxypyrrolidin-1-yl)benzo[d]thiazol-6-yl)benzonitrile (Reference Example 14a) in place of (S)-4-(2-(3-hydroxypyrrolidin-1-yl)benzo[d]thiazol-6-yl)benzonitrile (Reference Example 13b) to give (R)-1-(6-(4-cyanophenyl)benzo[d]thiazol-2-yl)pyrrolidin-3-yl methanesulfonate. $^1$H NMR (300 MHz, CDCl$_3$) δ ppm 2.37-2.45 (m, 1H), 2.50-2.56 (m, 1H), 3.08 (s, 3H), 3.78-3.82 (m, 2H), 3.93 (dd, J=4, 12 Hz, 1H), 4.01 (d, J=12 Hz, 1H), 5.46-5.49 (m, 1H), 7.56 (dd, J=2, 8 Hz, 1H), 7.67 (d, J=8 Hz, 1H), 7.68-7.73 (m, 4H), 7.85 (d, J=2 Hz, 1H); MS (DCI/NH$_3$) m/z 400 (M+H)$^+$.

EXAMPLES

Example 1

6-(1-methyl-1H-pyrazol-4-yl)-2-(3-(piperidin-1-yl)azetidin-1-yl)benzo[d]thiazole A stirred solution of 1-(6-(1-methyl-1H-pyrazol-4-yl)benzo[d]thiazol-2-yl)azetidin-3-yl 4-nitrobenzenesulfonate (Reference Example 3, 38 mg, 0.08 mmol), and piperidine (0.024 mL, 0.24 mmol) in N,N-dimethylformamide (0.5 mL) was heated at 160° C. under microwave irradiation for 15 minutes. The mixture was cooled to room temperature then purified by silica gel chromatography (60:30:10 hexane/dichloromethane/2 M NH$_3$ in isopropanol). These product fractions were purified by silica gel chromatography again (79:20:1 to 70:25:5 hexane/dichloromethane/2 M NH$_3$ in isopropanol). A final silica gel chromatographic purification was performed by first eluting the column with 100% dichloromethane to 80:20 dichloromethane/ethyl acetate followed by elution with 99:1 to 96:4 dichloromethane/methanol to provide 6-(1-methyl-1H-pyrazol-4-yl)-2-(3-(piperidin-1-yl)azetidin-1-yl)benzo[d]thiazole. $^1$H NMR (300 MHz, CD$_3$OD) δ ppm 1.47-1.57 (m, 1H), 1.65 (pentet, J=5 Hz, 4H), 2.37-2.45 (m, 4H), 3.36-3.46 (m, 1H), 3.92 (s, 3H), 4.02-4.09 (m, 2H), 4.25 (t, J=8 Hz, 2H), 7.45 (d, J=8 Hz, 1H), 7.50 (dd, J=2, 8 Hz, 1H), 7.79 (s, 1H), 7.85 (d, J=2 Hz, 1H), 7.92 (s, 1H); MS (ESI) m/z 354 (M+H)$^+$.

Example 2

6-(1-methyl-1H-pyrazol-4-yl)-2-(3-(pyrrolidin-1-yl)azetidin-1-yl)benzo[d]thiazole A mixture of 1-(6-(1-methyl-1H-pyrazol-4-yl)benzo[d]thiazol-2-yl)azetidin-3-one (Reference Example 4, 17 mg, 0.06 mmol), pyrrolidine (0.015 mL, 0.18 mmol), and a catalytic amount of acetic acid (0.005 mL) in toluene (0.4 mL) was stirred at room temperature for 5 minutes, then sodium triacetoxyborohydride (38 mg, 0.18 mmol) was added. The reaction mixture was stirred at room temperature overnight. The reaction mixture was then quenched with 1 M aqueous K$_3$PO$_4$ (0.4 mL), and extracted twice with ethyl acetate. The combined organic layers were dried over sodium sulfate and concentrated. The crude product was purified by silica gel chromatography (60:40 dichloromethane/acetonitrile to 56:40:4 dichloromethane/acetonitrile/methanol) to give 6-(1-methyl-1H-pyrazol-4-yl)-2-(3-(pyrrolidin-1-yl)azetidin-1-yl)benzo[d]thiazole. $^1$H NMR (300 MHz, CD$_3$OD) δ ppm 1.84-1.90 (m, 4H), 2.59-2.66 (m, 4H), 3.59-3.68 (m, 1H), 3.92 (s, 3H), 4.06-4.12 (m, 2H), 4.26-4.32 (m, 2H), 7.45 (dd, J=1, 8 Hz, 1H), 7.50 (dd, J=2, 8 Hz, 1H), 7.79 (d, J=1 Hz, 1H), 7.85 (d, J=2 Hz, 1H), 7.92 (d, J=1 Hz, 1H); MS (ESI) m/z 340 (M+H)$^+$.

Example 3

2-(3-(azepan-1-yl)azetidin-1-yl)-6-(1-methyl-1H-pyrazol-4-yl)benzo[d]thiazole

The title compound was prepared by the method of Example 2, substituting hexamethyleneimine in place of pyrrolidine to give 2-(3-(azepan-1-yl)azetidin-1-yl)-6-(1-methyl-1H-pyrazol-4-yl)benzo[d]thiazole. $^1$H NMR (300 MHz, CD$_3$OD) δ ppm 1.63-1.77 (m, 7H), 2.59 (t, J=5 Hz, 4H), 3.64-3.73 (m, 1H), 3.92 (s, 3H), 3.97-4.03 (m, 2H), 4.24 (t, J=8 Hz, 2H), 7.45 (d, J=8 Hz, 1H), 7.50 (dd, J=2, 8 Hz, 1H), 7.79 (s, 1H), 7.85 (d, J=2 Hz, 1H), 7.92 (s, 1H); MS (ESI) m/z 368 (M+H)$^+$.

Example 4

(R)-6-(1-methyl-1H-pyrazol-4-yl)-2-(3-(2-methylpyrrolidin-1-yl)azetidin-1-yl)benzo[d]thiazole The title compound was prepared by the method of Example 2, substituting (R)-2-methylpyrrolidine in place of pyrrolidine to give (R)-6-(1-methyl-1H-pyrazol-4-yl)-2-(3-(2-methylpyrrolidin-1-yl)azetidin-1-yl)benzo[d]thiazole. $^1$H NMR (300 MHz, CD$_3$OD) δ ppm 1.12 (d, J=6 Hz, 3H), 1.42-1.55 (m, 1H), 1.75-1.88 (m, 2H), 1.96-2.08 (m, 1H), 2.48 (q, J=8 Hz, 1H), 2.55-2.68 (m, 1H), 3.04-3.12 (m, 1H), 3.91 (s, 3H), 4.12-4.27 (m, 3H), 4.36 (t, J=8 Hz, 1H), 7.45 (d, J=8 Hz, 1H), 7.50 (dd, J=2, 8 Hz, 1H), 7.79 (d, J=1 Hz, 1H), 7.85 (d, J=2 Hz, 1H), 7.91 (s, 1H); MS (ESI) m/z 354 (M+H)$^+$.

Example 5

6-(1-methyl-1H-pyrazol-4-yl)-2-(3-(2-methylpiperidin-1-yl)azetidin-1-yl)benzo[d]thiazole The title compound was prepared by the method of Example 2, substituting 2-methylpiperidine in place of pyrrolidine to give 6-(1-methyl-1H-pyrazol-4-yl)-2-(3-(2-methylpiperidin-1-yl)azetidin-1-yl)benzo[d]thiazole. $^1$H NMR (300 MHz, CD$_3$OD) δ ppm 1.06 (d, J=6 Hz, 3H), 1.35-1.50 (m, 2H), 1.55-1.75 (m, 4H), 2.14-2.24 (m, 1H), 2.48-2.57 (m, 1H), 2.77-2.86 (m, 1H), 3.74-3.84 (m, 1H), 3.92 (s, 3H), 4.08-4.15 (m, 2H), 4.18-4.32 (m, 2H), 7.45 (d, J=8 Hz, 1H), 7.50 (dd, J=2, 8 Hz, 1H), 7.79 (d, J=1 Hz, 1H), 7.86 (d, J=2 Hz, 1H), 7.92 (s, 1H); MS (ESI) m/z 368 (M+H)$^+$.

Example 6

N-ethyl-N-methyl-1-(6-(1-methyl-1H-pyrazol-4-yl)benzo[d]thiazol-2-yl)azetidin-3-amine The title compound was prepared by the method of Example 2, substituting N-ethylmethylamine in place of pyrrolidine to give N-ethyl-N-methyl-1-(6-(1-methyl-1H-pyrazol-4-yl)benzo[d]thiazol-2-yl)azetidin-3-amine. $^1$H NMR (300 MHz, CD$_3$OD) δ ppm 1.11 (t, J=7 Hz, 3H), 2.23 (s, 3H), 2.45 (q, J=7 Hz, 1H), 3.51-3.61 (m, 1H), 3.92 (s, 3H), 4.01-4.08 (m, 2H), 4.26 (t, J=8 Hz, 2H), 7.45 (d, J=8 Hz, 1H), 7.50

(dd, J=2, 8 Hz, 1H), 7.79 (d, J=1 Hz, 1H), 7.86 (d, J=2 Hz, 1H), 7.92 (s, 1H); MS (ESI) m/z 328 (M+H)+.

Example 7

2-(ethyl(1-(6-(1-methyl-1H-pyrazol-4-yl)benzo[d]thiazol-2-yl)azetidin-3-yl)amino)ethanol The title compound was prepared by the method of Example 2, substituting 2-(ethylamino)ethanol in place of pyrrolidine to give 2-(ethyl(1-(6-(1-methyl-1H-pyrazol-4-yl)benzo[d]thiazol-2-yl)azetidin-3-yl)amino)ethanol. $^1$H NMR (300 MHz, CD$_3$OD) δ ppm 1.08 (t, J=7 Hz, 3H), 2.65-2.75 (m, 4H), 3.64 (t, J=7 Hz, 1H), 3.92 (s, 3H), 3.93-4.03 (m, 1H), 4.06-4.12 (m, 2H), 4.26 (t, J=8 Hz, 2H), 7.45 (d, J=8 Hz, 1H), 7.50 (dd, J=2, 8 Hz, 1H), 7.79 (d, J=1 Hz, 1H), 7.86 (d, J=2 Hz, 1H), 7.92 (s, 1H); MS (ESI) m/z 358 (M+H)+.

Example 8

(S)-(1-(1-(6-(1-methyl-1H-pyrazol-4-yl)benzo[d]thiazol-2-yl)azetidin-3-yl)pyrrolidin-2-yl)methanol The title compound was prepared by the method of Example 2, substituting (S)-pyrrolidin-2-ylmethanol in place of pyrrolidine to give (S)-(1-(1-(6-(1-methyl-1H-pyrazol-4-yl)benzo[d]thiazol-2-yl)azetidin-3-yl)pyrrolidin-2-yl)methanol. $^1$H NMR (300 MHz, CD$_3$OD) δ ppm 1.63-2.01 (m, 4H), 2.53-2.65 (m, 1H), 2.71-2.81 (m, 1H), 3.04-3.13 (m, 1H), 3.42-3.55 (m, 2H), 3.92 (s, 3H), 3.94-4.03 (m, 1H), 4.07-4.35 (m, 4H), 7.45 (dd, J=1, 8 Hz, 1H), 7.50 (dd, J=2, 8 Hz, 1H), 7.79 (d, J=1 Hz, 1H), 7.85 (dd, J=1, 2 Hz, 1H), 7.91 (s, 1H); MS (ESI) m/z 370 (M+H)+.

Example 9

6-bromo-2-(3-(piperidin-1-yl)azetidin-1-yl)benzo[d]thiazole

A mixture of 1-(6-bromobenzo[d]thiazol-2-yl)azetidin-3-yl methanesulfonate (Reference Example 12b, 61.7 mg, 0.17 mmol), piperidine (0.250 mL, 2.5 mmol), and potassium carbonate (0.062 g, 0.44 mmol) in N,N-dimethylformamide (1 mL) was stirred at 90-95° C. for two days. The reaction mixture was cooled to room temperature, diluted with water (10 mL), and extracted with dichloromethane (2×4 mL). The combined organic extracts were washed with water (2×5 mL), then dried (Na$_2$SO$_4$) and filtered. The filtrate was concentrated under reduced pressure and the residue was purified by silica gel chromatography (90:10:0 to 88:10:2 dichloromethane/ethyl acetate/methanol). A second column was run with the same eluent gradient. Fractions containing product were combined and concentrated under reduced pressure to give 6-bromo-2-(3-(piperidin-1-yl)azetidin-1-yl)benzo[d]thiazole. $^1$H NMR (300 MHz, CD$_3$OD) δ ppm 1.47-1.58 (m, 2H), 1.64 (pentet, J=5 Hz, 1H), 2.35-2.45 (m, 4H), 3.36-3.46 (m, 1H), 4.02-4.08 (m, 2H), 4.24 (t, J=8 Hz, 2H), 7.35 (d, J=8 Hz, 1H), 7.42 (dd, J=2, 8 Hz, 1H), 7.83 (d, J=2 Hz, 1H); MS (ESI) m/z 352 (M+H)+.

Example 10

(R)-6-bromo-2-(3-(2-methylpyrrolidin-1-yl)azetidin-1-yl)benzo[d]thiazole

The title compound was prepared by the method of Example 9, substituting (R)-2-methylpyrrolidine in place of piperidine to give (R)-6-bromo-2-(3-(2-methylpyrrolidin-1-yl)azetidin-1-yl)benzo[d]thiazole. $^1$H NMR (300 MHz, CD$_3$OD) δ ppm 1.12 (d, J=6 Hz, 3H), 1.42-1.56 (m, 1H), 1.75-1.90 (m, 2H), 1.96-2.09 (m, 1H), 2.50 (q, J=9 Hz, 1H), 2.57-2.70 (m, 1H), 3.03-3.14 (m, 1H), 3.81-3.92 (m, 1H), 4.13-4.27 (m, 3H), 4.36 (t, J=8 Hz, 1H), 7.35 (d, J=8 Hz, 1H), 7.42 (dd, J=2, 8 Hz, 1H), 7.83 (d, J=2 Hz, 1H); MS (ESI) m/z 352 (M+H)+.

Example 11

4-(2-((2R,3'R)-2-methyl-1,3'-bipyrrolidin-1'-yl)benzo[d]thiazol-6-yl)benzonitrile A stirred solution of (S)-1-(6-(4-cyanophenyl)benzo[d]thiazol-2-yl)pyrrolidin-3-yl methanesulfonate (Reference Example 13c, 32 mg, 0.080 mmol), (R)-2-methylpyrrolidine (27.3 mg, 0.320 mmol), and N,N-diisopropylethylamine (0.17 mL, 0.961 mmol) in acetonitrile (2 mL) was heated to 150° C. under microwave irradiation for 20 minutes. The reaction mixture was cooled to room temperature then purified by silica gel chromatography (98:2:0 to 98:2:1 dichloromethane/methanol/aqueous NH$_4$OH). Fractions containing product were dried (MgSO$_4$) and filtered. The filtrate was concentrated under reduced pressure to give to give 4-(2-((2R,3'R)-2-methyl-1,3'-bipyrrolidin-1'-yl)benzo[d]thiazol-6-yl)benzonitrile.

$^1$H NMR (300 MHz, CD$_3$OD) δ ppm 1.17 (d, J=6 Hz, 3H), 1.45-1.57 (m, 1H), 1.73-1.90 (m, 2H), 1.98-2.20 (m, 2H), 2.24-2.35 (m, 1H), 2.62 (q, J=8 Hz, 1H), 2.83-2.96 (m, 1H), 2.99-3.08 (m, 1H), 3.36-3.62 (m, 3H), 3.69-3.78 (m, 1H), 3.86-3.93 (m, 1H), 7.57 (d, J=8 Hz, 1H), 7.65 (dd, J=2, 9 Hz, 1H), 7.80 (q, J=9 Hz, 4H), 8.03 (d, J=2 Hz, 1H); MS (DCI/NH$_3$) m/z 389 (M+H)+.

Example 12

(R)-4-(2-(1,3'-bipyrrolidin-1'-yl)benzo[d]thiazol-6-yl)benzonitrile

The title compound was prepared by the method of Example 11, substituting pyrrolidine in place of (R)-2-methylpyrrolidine to give (R)-4-(2-(1,3'-bipyrrolidin-1'-yl)benzo[d]thiazol-6-yl)benzonitrile. $^1$H NMR (300 MHz, CD$_3$OD) δ ppm 1.83-1.91 (m, 4H), 2.04-2.18 (m, 1H), 2.30-2.41 (m, 1H), 2.62-2.76 (m, 4H), 3.05-3.16 (m, 1H), 3.46-3.54 (m, 1H), 3.55-3.66 (m, 1H), 3.73-3.89 (m, 2H), 7.57 (d, J=9 Hz, 1H), 7.65 (dd, J=2, 9 Hz, 1H), 7.80 (q, J=9 Hz, 4H), 8.04 (d, J=2 Hz, 1H); MS (DCI/NH$_3$) m/z 375 (M+H)+.

Example 13

(R)-4-(2-(3-(piperidin-1-yl)pyrrolidin-1-yl)benzo[d]thiazol-6-yl)benzonitrile

The title compound was prepared by the method of Example 11, substituting piperidine in place of (R)-2-methylpyrrolidine to give (R)-4-(2-(3-(piperidin-1-yl)pyrrolidin-1-yl)benzo[d]thiazol-6-yl)benzonitrile. $^1$H NMR (300 MHz, CD$_3$OD) δ ppm 1.46-1.57 (m, 2H), 1.66 (pentet, J=5 Hz, 4H), 1.95-2.11 (m, 1H), 2.32-2.43 (m, 1H), 2.46-2.66 (m, 4H), 3.05-3.17 (m, 1H), 3.43 (t, J=9 Hz, 1H), 3.52-3.63 (m, 1H), 3.72-3.81 (m, 2H), 3.84-3.93 (m, 1H), 7.57 (d, J=9 Hz, 1H), 7.65 (dd, J=2, 9 Hz, 1H), 7.80 (q, J=9 Hz, 4H), 8.03 (d, J=2 Hz, 1H); MS (DCI/NH$_3$) m/z 389 (M+H)+.

Example 14

(R)-6-bromo-2-(3-(piperidin-1-yl)pyrrolidin-1-yl)benzo[d]thiazole

Example 14a

(R)-6-bromo-2-(3-(piperidin-1-yl)pyrrolidin-1-yl)benzo[d]thiazole

A stirred mixture of 2-chloro-6-bromobenzothiazole (2.48 g, 10.0 mmol), (R)-1-(pyrrolidin-3-yl)piperidine dihydrochloride (Reference Example 5c, 2.73 g, 0.0120 mole), and potassium carbonate (6.00 g, 0.04438 mole) in N,N-dimethylformamide (15 mL) was heated to 100° C. with an oil bath for 15 hours. The reaction mixture was cooled to room temperature then poured into water (300 mL). The resulting precipitate was collected by filtration and the filter cake was rinsed with water (600 mL). The solid was dissolved in dichloromethane and the solution was dried (MgSO$_4$) and filtered. The filtrate was concentrated under reduced pressure to give a solid that was crystallized from hot ethyl acetate to give (R)-6-bromo-2-(3-(piperidin-1-yl)pyrrolidin-1-yl)benzo[d]thiazole. $^1$H NMR (300 MHz, CD$_3$OD) δ ppm 1.46-1.55 (m, 2H), 1.65 (pentet, J=5 Hz, 4H), 1.92-2.07 (m, 1H), 2.29-2.39 (m, 1H), 2.43-2.64 (m, 4H), 3.00-3.12 (m, 1H), 3.33-3.41 (m, 1H), 3.46-3.57 (m, 1H), 3.66-3.75 (m, 1H), 3.77-3.86 (m, 1H), 4.07-4.35 (m, 4H), 7.35 (d, J=9 Hz, 1H), 7.40 (dd, J=2, 9 Hz, 1H), 7.81 (d, J=2 Hz, 1H); MS (DCI/NH$_3$) m/z 366 (M+H)$^+$.

Example 14b

Alternative Preparation

(R)-6-bromo-2-(3-(piperidin-1-yl)pyrrolidin-1-yl)benzo[d]thiazole

A solution of (R)-1-(pyrrolidin-3-yl)piperidine dihydrochloride (Reference Example 5c) in a minimum of water was treated with excess solid sodium hydroxide and sodium chloride. This mixture was extracted with dichloromethane. The organic layer was dried (MgSO$_4$) and filtered. The filtrate was concentrated under reduced pressure to give (R)-1-(pyrrolidin-3-yl)piperidine as the free base (308 mg, 2.0 mmol). This free base diamine was added to a stirred solution of 4-bromo-2-fluorophenylisothiocyanate (0.464 g, 2.0 mmol) in acetonitrile (20 mL). Cesium carbonate (2.6 g, 8.0 mmol) was added to the reaction mixture. The reaction mixture was then heated to 150° C. under microwave irradiation for 30 minutes. The reaction mixture was cooled to room temperature then diluted with water and extracted with chloroform. The organic layer was dried (MgSO$_4$) and filtered. The filtrate was concentrated under reduced pressure to give a residue that was purified by silica gel chromatography (100% dichloromethane to 50:50 dichloromethane/90% dichloromethane and 10% methanol). Fractions containing product were combined and concentrated under reduced pressure to give (R)-6-bromo-2-(3-(piperidin-1-yl)pyrrolidin-1-yl)benzo[d]thiazole.

Example 15

(R)-6-(2-methoxypyrimidin-5-yl)-²-(3-(piperidin-1-yl)pyrrolidin-1-yl)benzo[d]thiazole A stirred mixture of (R)-6-bromo-2-(3-(piperidin-1-yl)pyrrolidin-1-yl)benzo[d]thiazole (Example 14, 37.0 mg, 0.10 mmol), 2-methoxy-5-(4,4,5,5-tetramethyl-1,3,2-dioxaborolan-2-yl)pyrimidine (31 mg, 0.13 mmol), dichlorobis(triphenylphosphine)palladium (II) (7.0 mg, 0.01 mmol), (2-biphenyl)dicyclohexylphosphine (3.5 mg, 0.01 mmol) in 1:1 ethanol/dioxane (0.40 mL) was treated with 1 M aqueous sodium carbonate (0.150 mL, 0.15 mmol). The reaction tube was sealed and the stirred mixture was heated to 150° C. under microwave irradiation for 10 minutes. The reaction mixture was cooled to room temperature then diluted with dichloromethane (2 mL) and filtered through diatomaceous earth, followed by an acetonitrile/dichloromethane rinse (10 mL). The filtrate was dried (Na$_2$SO$_4$) and concentrated under reduced pressure and the residue was purified by silica gel chromatography (70:30:0 to 63:30:7 dichloromethane/acetonitrile/methanol). Fractions containing product were combined and concentrated under reduced pressure to give (R)-6-(2-methoxypyrimidin-5-yl)-2-(3-(piperidin-1-yl)pyrrolidin-1-yl)benzo[d]thiazole. $^1$H NMR (300 MHz, CD$_2$Cl$_2$) δ ppm 1.43-1.50 (m, 2H), 1.61 (pentet, J=5 Hz, 4H), 2.00 (pentet, J=10 Hz, 1H), 2.24-2.31 (m, 1H), 2.40-2.58 (m, 4H), 3.01 (pentet, J=8 Hz, 1H), 3.40 (t, J=9 Hz, 1H), 3.50-3.57 (m, 1H), 3.73 (t, J=9 Hz, 1H), 3.79-3.86 (m, 1H), 4.02 (s, 3H), 7.44 (dd, J=2, 8 Hz, 1H), 7.56 (d, J=8 Hz, 1H), 7.78 (d, J=2 Hz, 1H), 8.72 (s, 2H); MS (ESI) m/z 396 (M+H)$^+$.

Example 16

(R)-2-(3-(piperidin-1-yl)pyrrolidin-1-yl)-6-(pyrimidin-5-yl)benzo[d]thiazole The title compound was prepared by the method of Example 15, substituting pyrimidine-5-boronic acid in place of 2-methoxy-5-(4,4,5,5-tetramethyl-1,3,2-dioxaborolan-2-yl)pyrimidine to give (R)-2-(3-(piperidin-1-yl)pyrrolidin-1-yl)-6-(pyrimidin-5-yl)benzo[d]thiazole. $^1$H NMR (300 MHz, CD$_2$Cl$_2$) δ ppm 1.43-1.50 (m, 2H), 1.57-1.65 (m, 4H), 1.97-2.07 (m, 1H), 2.25-2.32 (m, 1H), 2.40-2.59 (m, 4H), 3.03 (pentet, J=8 Hz, 1H), (d, J=8 Hz, 1H), 7.85 (d, J=2 Hz, 1H), 8.95 (s, 2H), 9.10 (s, 1H); MS (ESI) m/z 366 (M+H)$^+$.

Example 17

(R)-6-(1-methyl-1H-pyrazol-4-yl)-2-(3-(piperidin-1-yl)pyrrolidin-1-yl)benzo[d]thiazole The title compound was prepared by the method of Example 15, substituting 1-methyl-4-(4,4,5,5-tetramethyl-1,3,2-dioxaborolan-2-yl)-1H-pyrazole in place of 2-methoxy-5-(4,4,5,5-tetramethyl-1,3,2-dioxaborolan-2-yl)pyrimidine to give (R)-6-(1-methyl-1H-pyrazol-4-yl)-2-(3-(piperidin-1-yl)pyrrolidin-1-yl)benzo[d]thiazole. $^1$H NMR (300 MHz, CD$_2$Cl$_2$) δ ppm 1.43-1.49 (m, 2H), 1.60 (pentet, J=5 Hz, 4H), 1.99 (pentet, J=10 Hz, 1H), 2.23-2.29 (m, 1H), 2.40-2.58 (m, 4H), 3.00 (pentet, J=8 Hz, 1H), 3.38 (t, J=9 Hz, 1H), 3.48-3.54 (m, 1H), 3.71 (t, J=9 Hz, 1H), 3.81 (t, J=8 Hz, 1H), 7.38 (dd, J=2, 8 Hz, 1H), 7.45 (d, J=8 Hz, 1H), 7.60 (s, 1H), 7.69 (s, 1H), 7.71 (d, J=2 Hz, 1H); MS (ESI) m/z 368 (M+H)$^+$.

Example 18

(R)-6-(2,6-dimethylpyridin-3-yl)-2-(3-(piperidin-1-yl)pyrrolidin-1-yl)benzo[d]thiazole The title compound was prepared by the method of Example 15, substituting 2,6-dimethyl-3-(4,4,5,5-tetramethyl-1,3,2-dioxaborolan-2-yl)pyridine in place of 2-methoxy-5-(4,4,5,5-tetramethyl-1,3,2-dioxaborolan-2-yl)pyrimidine to give (R)-6-(2,6-dimethylpyridin-3-yl)-2-(3-(piperidin-1-yl)pyrrolidin-1-yl)benzo[d]thiazole. $^1$H NMR (300 MHz, CD$_2$Cl$_2$) δ ppm 1.43-1.49 (m, 2H), 1.61 (pentet, J=5 Hz, 4H), 2.01 (pentet, J=10 Hz, 1H), 2.24-2.30 (m, 1H), 2.40-2.58 (m, 4H), 2.45 (s, 3H), 2.51 (s, 3H), 3.02 (pentet, J=8 Hz, 3.40 (t, J=9 Hz, 1H), 3.49-3.56 (m, 1H), 3.73 (t, J=9 Hz, 1H), 3.83 (t, J=8 Hz, 1H), 7.03 (d, J=8 Hz, 1H), 7.21 (dd, J=2, 8 Hz, 1H), 7.43 (d, J=8 Hz, 1H), 7.51 (d, J=8 Hz, 1H), 7.54 (d, J=2 Hz, 1H); MS (ESI) m/z 393 (M+H)$^+$.

Example 19

(R)-6-(6-methoxypyridin-3-yl)-2-(3-(piperidin-1-yl)pyrrolidin-1-yl)benzo[d]thiazole The title compound was prepared by the method of Example 15, substituting 2-methoxy-5-pyridineboronic acid in place of 2-methoxy-5-(4,4,5,5-tetramethyl-1,3,2-dioxaborolan-2-yl)pyrimidine to give (R)-6-(6-methoxypyridin-3-yl)-2-(3-(piperidin-1-yl)pyrrolidin-1-yl)benzo[d]thiazole. $^1$H NMR (300 MHz, CD$_2$Cl$_2$) δ ppm 1.43-1.49 (m, 2H), 1.56-1.64 (m, 4H), 1.99 (pentet, J=10 Hz, 1H), 2.24-2.30 (m, 1H), 2.40-2.57 (m, 4H), 3.01 (pentet, J=8 Hz, 1H), 3.39 (t, J=9 Hz, 1H), 3.49-3.56 (m, 1H), 3.73 (t, J=9 Hz, 1H), 3.83 (t, J=9 Hz, 1H), 3.95 (s, 3H), 6.80 (d, J=8 Hz, 1H), 7.45 (dd, J=2, 8 Hz, 1H), 7.53 (d, J=8 Hz, 1H), 7.78 (d, J=2 Hz, 1H), 7.81 (dd, J=3, 8 Hz, 1H), 8.37 (d, J=2 Hz, 1H); MS (ESI) m/z 395 (M+H)$^+$.

Example 20

(R)-2-(2-(3-(piperidin-1-yl)pyrrolidin-1-yl)benzo[d]thiazol-6-yl)pyridazin-3(2H)-one A mixture of (R)-6-bromo-2-(3-(piperidin-1-yl)pyrrolidin-1-yl)benzo[d]thiazole (Example 14, 0.792 g, 2.162 mmol), pyridazin-3(2H)-one (0.415 g, 4.32 mmol), copper powder (0.137 g, 2.16 mmol), copper(I) iodide (57.6 mg, 0.303 mmol), and potassium carbonate (0.896 g, 6.49 mmol) were combined into a large Biotage microwave vial equipped with a magnetic stirbar. The vial was crimp capped with a septum. Pyridine (17.3 mL) was introduced via syringe. The reaction mixture was purged (vacuum/nitrogen) three times, then N$^1$,N$^2$-dimethylethane-1,2-diamine (0.065 mL, 0.605 mmol) was added via syringe and the reaction mixture was stirred with heating at 117° C. for 24 hours. The reaction mixture was allowed to cool to room temperature then the vial was uncapped and the contents were transferred to a 100 mL round bottom flask (methanol rinse). Volatiles were removed under reduced pressure and the residue was partitioned between CHCl$_3$ and aqueous ammonium hydroxide. The organic layer was washed with brine then dried (MgSO$_4$) and filtered. The filtrate was concentrated under reduced pressure to give a solid that was treated with toluene and returned to the rotary evaporator in an attempt to remove residual pyridine. A solid was obtained. This was purified by column chromatography on an Analogix IntelliFlash-280 (Analogix SF65-220g, 100% CHCl$_3$ to 97:3 CHCl$_3$/methanol). Fractions containing product were combined and concentrated under reduced pressure to give a solid that was stirred with diethyl ether. The solid was collected by filtration and rinsed once with ethyl acetate and several times with hexane. This solid was crystallized from hot ethyl acetate. The first crystal batch was collected by filtration and dried in a vacuum oven at 84° C. for 5 hours. The filtrate was concentrated under reduced pressure and the solid residue was dissolved in hot ethyl acetate in a second crystallization attempt. The second crystal batch was collected by filtration and dried in the vacuum oven along with the first batch at 88° C. overnight. The two dried crystal batches combined gave (R)-2-(2-(3-(piperidin-1-yl)pyrrolidin-1-yl)benzo[d]thiazol-6-yl)pyridazin-3(2H)-one. $^1$H NMR (300 MHz, CD$_3$OD) δ ppm 1.51-1.59 (m, 2H), 1.70 (pentet, J=6 Hz, 4H), 1.99-2.15 (m, 1H), 2.36-2.47 (m, 1H), 2.56-2.77 (m, 4H), 3.17-3.31 (m, 1H), 3.47 (t, J=9 Hz, 1H), 3.53-3.64 (m, 1H), 3.73-3.82 (m, 1H), 3.87-3.96 (m, 1H), 7.09 (dd, J=2, 9 Hz, 1H), 7.45-7.51 (m, 1H), 7.57 (d, J=9 Hz, 1H), 7.89 (d, J=2 Hz, 1H), 8.04 (dd, J=2, 4 Hz, 1H); MS (DCI/NH$_3$) m/z 382 (M+H)$^+$.

Example 21

(R)-3-(2-(3-(piperidin-1-yl)pyrrolidin-1-yl)benzo[d]thiazol-6-yl)oxazolidin-2-one The title compound was prepared by the method of Example 20, substituting oxazolidin-2-one in place of pyridazin-3(2H)-one. The material was purified by column chromatography on an Analogix IntelliFlash-280 (Analogix SF10-4g, 100% dichloromethane to 97:3 dichloromethane/2 M NH$_3$ in methanol) to give (R)-3-(2-(3-(piperidin-1-yl)pyrrolidin-1-yl)benzo[d]thiazol-6-yl)oxazolidin-2-one. $^1$H NMR (300 MHz, CDCl$_3$) δ ppm 1.42-1.52 (m, 2H), 1.63 (pentet, J=6 Hz, 4H), 1.93-2.09 (m, 1H), 2.24-2.34 (m, 1H), 2.39-2.58 (m, 4H), 2.93-3.06 (m, 1H), 3.42 (t, J=9 Hz, 1H), 3.48-3.59 (m, 1H), 3.70-3.89 (m, 2H), 4.05-4.12 (m, 2H), 4.45-4.52 (m, 2H), 7.24 (dd, J=2, 9 Hz, 1H), 7.54 (d, J=9 Hz, 1H), 8.03 (d, J=2 Hz, 1H); MS (DCI/NH$_3$) m/z 373 (M+H)$^+$.

Example 22

(S)-3-hydroxy-1-(2-((R)-3-(piperidin-1-yl)pyrrolidin-1-yl)benzo[d]thiazol-6-yl)pyrrolidin-2-one The title compound was prepared by the method of Example 20, substituting (S)-3-hydroxypyrrolidin-2-one in place of pyridazin-3(2H)-one. The material was purified by column chromatography on an Analogix IntelliFlash-280 (Analogix SF15-12g, 100% dichloromethane to 97:3 dichloromethane/2 M NH$_3$ in methanol) to give (S)-3-hydroxy-1-(2-((R)-3-(piperidin-1-yl)pyrrolidin-1-yl)benzo[d]thiazol-6-yl)pyrrolidin-2-one. $^1$H NMR (300 MHz, CDCl$_3$) δ ppm 1.42-1.52 (m, 2H), 1.63 (pentet, J=6 Hz, 4H), 1.94-2.18 (m, 2H), 2.24-2.34 (m, 1H), 2.40-2.67 (m, 5H), 2.94-3.06 (m, 2H), 3.43 (t, J=9 Hz, 1H), 3.48-3.60 (m, 1H), 3.71-3.88 (m, 4H), 4.44-4.52 (m, 1H), 7.34 (dd, J=2, 9 Hz, 1H), 7.55 (d, J=9 Hz, 1H), 8.14 (d, J=2 Hz, 1H); MS (DCI/NH$_3$) m/z 387 (M+H)$^+$.

Example 23

4-(2-((3S)-3-(2-methylpiperidin-1-yl)pyrrolidin-1-yl)benzo[d]thiazol-6-yl)benzonitrile A stirred solution of (R)-1-(6-(4-cyanophenyl)benzo[d]thiazol-2-yl)pyrrolidin-3-yl methanesulfonate (Reference Example 14b, 20 mg, 0.050 mmol), 2-methylpiperidine (0.029 mL, 0.25 mmol), and N,N-dimethylformamide (0.01 mL) in isopropanol (0.50 mL) was heated at 150° C. under microwave irradiation for 15 minutes. The reaction mixture was cooled to room temperature, concentrated, and purified by silica gel chromatography (100:0 to 70:30 dichloromethane/ethyl acetate, then 98:2 to 92:8 dichloromethane/methanol). Fractions containing product were combined and concentrated under reduced pressure to give 4-(2-((3S)-3-(2- methylpiperidin-1-yl)pyrrolidin-1-yl)benzo[d]thiazol-6-yl) benzonitrile. $^1$H NMR (300 MHz, CD$_2$Cl$_2$) δ ppm 1.06-1.12 (m, 3H), 1.37-1.45 (m, 2H), 1.54-1.61 (m, 1H), 1.67-1.77 (m, 2H), 2.01-2.16 (m, 2H), 2.19-2.29 (m, 1H), 2.35-2.51 (m, 1H), 2.63-2.70 (m, 1H), 2.81-2.95 (m, 1H), 3.36-3.50 (m, 1H), 3.50-3.79 (m, 5H), 7.55 (s, 2H), 7.72 (s, 4H), 7.88 (s, 1H); MS (ESI) m/z 403 (M+H)$^+$.

Example 24

(S)-4-(2-(3-(piperidin-1-yl)pyrrolidin-1-yl)benzo[d]thiazol-6-yl)benzonitrile

The title compound was prepared by the method of Example 23, substituting piperidine in place of 2-methylpiperidine to give (S)-4-(2-(3-(piperidin-1-yl)pyrrolidin-1-yl)benzo[d]thiazol-6-yl)benzonitrile. $^1$H NMR (300 MHz, CD$_2$Cl$_2$) δ ppm 1.43-1.49 (m, 2H), 1.59 (pentet, J=5 Hz, 4H), 1.98 (pentet, J=10 Hz, 1H), 2.24-2.30 (m, 1H), 2.38-2.55 (m, 4H), 2.99 (pentet, J=8 Hz, 1H), 3.38 (t, J=9 Hz, 1H), 3.50-3.57 (m, 1H), 3.70-3.86 (m, 2H), 7.55 (s, 2H), 7.71 (s, 4H), 7.87 (s, 1H); MS (ESI) m/z 389 (M+H)$^+$.

Example 25

(S)-4-(2-(3-(azepan-1-yl)pyrrolidin-1-yl)benzo[d]thiazol-6-yl)benzonitrile

The title compound was prepared by the method of Example 23, substituting hexamethyleneimine in place of 2-methylpiperidine to give (S)-4-(2-(3-(azepan-1-yl)pyrrolidin-1-yl)benzo[d]thiazol-6-yl)benzonitrile. $^1$H NMR (300 MHz, CD$_2$Cl$_2$) δ ppm 1.58-1.69 (m, 8H), 1.94-2.04 (m, 1H), 2.21-2.28 (m, 1H), 2.65-2.77 (m, 4H), 3.34-3.46 (m, 2H), 3.49-3.56 (m, 1H), 3.67-3.85 (m, 2H), 7.55 (s, 2H), 7.71 (s, 4H), 7.88 (s, 1H); MS (ESI) m/z 403 (M+H)$^+$.

Example 26

4-(2-((3'S)-2-methyl-1,3'-bipyrrolidin-1'-yl)benzo[d]thiazol-6-yl)benzonitrile

The title compound was prepared by the method of Example 23, substituting 2-methylpyrrolidine in place of 2-methylpiperidine to give 4-(2-((3'S)-2-methyl-1,3'-bipyrrolidin-1'-yl)benzo[d]thiazol-6-yl)benzonitrile. $^1$H NMR (300 MHz, CD$_2$Cl$_2$) δ ppm 1.08-1.12 (m, 3H), 1.41-1.49 (m, 1H), 1.68-1.84 (m, 2H), 1.92-2.01 (m, 1H), 2.03-2.32 (m, 2H), 2.51-2.60 (m, 1H), 2.79-3.02 (m, 2H), 3.31-3.62 (m, 3H), 7.55 (s, 2H), 7.72 (s, 4H), 7.88 (s, 1H); MS (ESI) m/z 389 (M+H)$^+$.

Example 27

(S)-4-(2-(1,3'-bipyrrolidin-1'-yl)benzo[d]thiazol-6-yl)benzonitrile

The title compound was prepared by the method of Example 23, substituting pyrrolidine in place of 2-methylpiperidine to give (S)-4-(2-(1,3'-bipyrrolidin-1'-yl)benzo[d]thiazol-6-yl)benzonitrile. $^1$H NMR (300 MHz, CD$_2$Cl$_2$) δ ppm 1.76-1.82 (m, 4H), 2.02-2.11 (m, 1H), 2.20-2.27 (m, 1H), 2.53-2.62 (m, 4H), 2.91-2.99 (m, 1H), 3.43-3.48 (m, 1H), 3.52-3.59 (m, 1H), 3.68-3.82 (m, 2H), 7.55 (s, 2H), 7.71 (s, 4H), 7.87 (s, 1H); MS (ESI) m/z 375 (M+H)$^+$.

Example 28

4-(2-((2S,3'S)-2-(hydroxymethyl)-1,3'-bipyrrolidin-1'-yl)benzo[d]thiazol-6-yl)benzonitrile The title compound was prepared by the method of Example 23, substituting (S)-pyrrolidin-2-ylmethanol in place of 2-methylpiperidine to give 4-(2-((2S,3'S)-2-(hydroxymethyl)-1,3'-bipyrrolidin-1'-yl)benzo[d]thiazol-6-yl)benzonitrile. $^1$H NMR (300 MHz, CD$_2$Cl$_2$) δ ppm 1.71-1.80 (m, 3H), 1.84-2.02 (m, 2H), 2.06-2.16 (m, 1H), 2.25-2.32 (m, 1H), 2.56-2.62 (m, 1H), 2.95-3.01 (m, 1H), 3.07-3.14 (m, 1H), 3.35-3.39 (m, 1H), 3.44-3.62 (m, 4H), 3.69-3.83 (m, 2H), 7.56 (s, 2H), 7.72 (s, 4H), 7.88 (s, 1H); MS (ESI) m/z 405 (M+H)$^+$ Example 29

(S)-4-(2-(3-(diethylamino)pyrrolidin-1-yl)benzo[d]thiazol-6-yl)benzonitrile

The title compound was prepared by the method of Example 23, substituting diethylamine in place of 2-methylpiperidine to give (S)-4-(2-(3-(diethylamino)pyrrolidin-1-yl)benzo[d]thiazol-6-yl)benzonitrile. $^1$H NMR (300 MHz, CD$_2$Cl$_2$) δ ppm 1.03 (t, J=7 Hz, 6H), 2.00 (pentet, J=10 Hz, 1H), 2.20-2.27 (m, 1H), 2.61-2.72 (m, 4H), 3.36 (t, J=9 Hz, 1H), 3.42-3.56 (m, 2H), 3.67-3.86 (m, 2H), 7.55 (s, 2H), 7.71 (s, 4H), 7.87 (s, 1H). MS (ESI) m/z 377 (M+H)$^+$.

Example 30

(S)-4-(2-(3-(ethyl(methyl)amino)pyrrolidin-1-yl)benzo[d]thiazol-6-yl)benzonitrile The title compound was prepared by the method of Example 23, substituting N-ethylmethylamine in place of 2-methylpiperidine to give (S)-4-(2-(3-(ethyl(methyl)amino)pyrrolidin-1-yl)benzo[d]thiazol-6-yl)benzonitrile. $^1$H NMR (300 MHz, CD$_2$Cl$_2$) δ ppm 1.07 (t, J=7 Hz, 6H), 1.05 (pentet, J=10 Hz, 1H), 2.22-2.29 (m, 1H), 2.27 (s, 3H), 2.49-2.60 (m, 2H), 3.17 (pentet, J=7 Hz, 1H), 3.39 (t, J=9 Hz, 1H), 3.51-3.58 (m, 1H), 3.70-3.85 (m, 2H), 7.55 (s, 2H), 7.72 (s, 4H), 7.88 (s, 1H); MS (ESI) m/z 363 (M+H)$^+$.

Example 31

(S)-4-(2-(3-(isopropyl(methyl)amino)pyrrolidin-1-yl)benzo[d]thiazol-6-yl)benzonitrile The title compound was prepared by the method of Example 23, substituting N-isopropylmethylamine in place of 2-methylpiperidine to give (S)-4-(2-(3-(isopropyl(methyl)amino)pyrrolidin-1-yl)benzo[d]thiazol-6-yl)benzonitrile. $^1$H NMR (300 MHz, CD$_2$Cl$_2$) δ ppm 1.04 (d, J=6 Hz, 6H), 2.01 (pentet, J=10 Hz, 1H), 2.18-2.28 (m, 1H), 2.20 (s, 3H), 3.05 (septet, J=6 Hz, 1H), 3.30-3.41 (m, 2H), 3.50-3.57 (m, 1H), 3.71-3.87 (m, 2H), 7.55 (s, 2H), 7.71 (s, 4H), 7.87 (s, 1H); MS (ESI) m/z 377 (M+H)$^+$.

Example 32

(S)-2-(1,3'-bipyrrolidin-1'-yl)-6-bromobenzo[d]thiazole

A mixture of (R)-1-(6-bromobenzo[d]thiazol-2-yl)pyrrolidin-3-yl methanesulfonate (Reference Example 12, 0.50 g, 1.32 mmol), pyrrolidine (0.221 mL, 2.65 mmol), and potassium carbonate (0.549 g, 3.98 mmol) was placed in a 10 mL CEM microwave vial with a stirbar. N,N-Dimethylformamide (1.5 mL) was added, the vial was capped, and the reaction was heated to 100° C. under microwave irradiation for 15 minutes, then the cooling air was turned on and heating was continued at 70° C. for an additional 15 minutes. The reaction mixture was cooled to room temperature then partitioned between ethyl acetate and saturated aqueous sodium carbonate. The aqueous layer was extracted once more with ethyl acetate. The combined organic extracts were washed twice with brine, then dried (MgSO$_4$) and filtered. The filtrate was concentrated under reduced pressure to give an oil that solidified on trituration with diethyl ether. The solid was collected by filtration and rinsed with diethyl ether, then purified by column chromatography on an Analogix IntelliFlash-280 (Analogix SF15-12g, 100% dichloromethane to 98:2 dichloromethane/methanol). Fractions containing product were combined and concentrated under reduced pressure to give a solid that was dried overnight in a vacuum oven at 70° C. to give (S)-2-(1,3'-bipyrrolidin-1'-yl)-6-bromobenzo[d]thiazole. $^1$H NMR (300 MHz, CD$_3$OD) δ ppm 1.78-1.93 (m, 4H), 2.01-2.15 (m, 1H), 2.26-2.37 (m, 1H), 2.58-2.74 (m, 4H), 3.00-3.11 (m, 1H), 3.40-3.48 (m, 1H), 3.49-3.60 (m, 1H), 3.66-3.83 (m, 2H), 7.35 (d, J=9 Hz, 2H), 7.40 (dd, J=2, 9 Hz, 1H), 7.81 (d, J=2 Hz, 1H); MS (DCI/NH$_3$) m/z 352 (M+H)$^+$.

Example 33

(S)-2-(2-(1,3'-bipyrrolidin-1'-yl)benzo[d]thiazol-6-yl)pyridazin-3(2H)-one

The title compound was prepared by the method of Example 20, substituting (S)-2-(1,3'-bipyrrolidin-1'-yl)-6-bromobenzo[d]thiazole (Example 32) in place of (R)-6-bromo-2-(3-(piperidin-1-yl)pyrrolidin-1-yl)benzo[d]thiazole (Example 14) to give (S)-2-(2-(1,3'-bipyrrolidin-1'-yl)benzo[d]thiazol-6-yl)pyridazin-3(2H)-one. $^1$H NMR (300 MHz, CD$_3$OD) δ ppm 1.80-1.94 (m, 4H), 2.03-2.18 (m, 1H), 2.29-2.40 (m, 1H), 2.60-2.76 (m, 4H), 3.04-3.15 (m, 1H), 3.45-3.53 (m, 1H), 3.54-3.65 (m, 1H), 3.72-3.88 (m, 2H), 7.09 (dd, J=2, 9 Hz, 1H), 7.44-7.51 (m, 2H), 7.56 (d, J=9 Hz, 1H), 7.89 (d, J=9 Hz, 1H), 8.04 (dd, J=2, 4 Hz, 1H), MS (DCI/NH$_3$) m/z 368 (M+H)$^+$.

Example 34

(R)-2-(3-(azetidin-1-yl)piperidin-1-yl)-6-bromobenzo[d]thiazole

One equivalent of (S)-1-(6-bromobenzo[d]thiazol-2-yl)piperidin-3-yl methanesulfonate (Reference Example 10, 0.078 g, 0.2 mmol) and two equivalents of potassium carbonate (55.3 mg, 0.40 mmol) were weighed into a 2.5 mL Biotage microwave vial equipped with a magnetic stirbar. Acetonitrile (1 mL) was added, then 6 equivalents of azetidine (68.5 mg, 1.2 mmol) was weighed into the reaction mixture. The vial was sealed with a septum cap and the reaction mixture was stirred at 80° C. for 72 hours. The reaction mixture was transferred to a 100 mL round bottom flask (methanol rinse). Volatiles were removed under reduced pressure and the residue was partitioned between ethyl acetate and saturated aqueous sodium carbonate. The organic layer was dried (MgSO$_4$) and filtered. The filtrate was concentrated under reduced pressure to give an oil. The oil was purified by column chromatography on an Analogix IntelliFlash-280 (Analogix SF10-4g, 100% dichloromethane to 98:2 dichloromethane/2 M NH$_3$ in methanol). Fractions containing product were combined and concentrated under reduced pressure to give an oil that was dissolved in diethyl ether and dried (MgSO$_4$). The drying agent was removed by filtration and the filtrate was concentrated under reduced pressure to give a semi-solid that was triturated with diethyl ether/hexane to give (R)-2-(3-(azetidin-1-yl)piperidin-1-yl)-6-bromobenzo[d]thiazole as a solid. $^1$H NMR (300 MHz, CD$_3$OD) δ ppm 1.23-1.38 (m, 1H), 1.53-1.69 (m, 1H), 1.80-1.96 (m, 2H), 2.11 (pentet, J=7 Hz, 2H), 2.32-2.43 (m, 1H), 2.93-3.02 (m, 1H), 3.22-3.38 (m, 5H), 3.79 (dt, J=4, 13 Hz, 1H), 3.96 (dd, J=4, 13 Hz, 1H), 7.33 (d, J=9 Hz, 1H), 7.39 (dd, J=2, 9 Hz, 1H), 7.79 (d, J=2 Hz, 1H); MS (DCI/NH$_3$) m/z 352 (M+H)$^+$.

Example 35

(R)-6-bromo-2-(3-(pyrrolidin-1-yl)piperidin-1-yl)benzo[d]thiazole

The title compound was prepared by the method of Example 34, substituting pyrrolidine in place of azetidine to give (R)-6-bromo-2-(3-(pyrrolidin-1-yl)piperidin-1-yl)benzo[d]thiazole. $^1$H NMR (300 MHz, CD$_3$OD) δ ppm 1.47-1.75 (m, 2H), 1.77-1.95 (m, 5H), 2.11-2.20 (m, 1H), 2.28-2.39 (m, 1H), 2.67-2.76 (m, 4H), 3.06-3.25 (m, 2H), 3.87-3.96 (m, 1H), 4.25-4.32 (m, 1H), 7.33 (d, J=9 Hz, 1H), 7.39 (dd, J=2, 9 Hz, 1H), 7.79 (d, J=2 Hz, 1H); MS (DCI/NH$_3$) m/z 366 (M+H)$^+$.

Example 36

(R)-2-(1,3'-bipiperidin-1'-yl)-6-bromobenzo[d]thiazole

The title compound was prepared by the method of Example 34, substituting piperidine in place of azetidine to give (R)-2-(1,3'-bipiperidin-1'-yl)-6-bromobenzo[d]thiazole. $^1$H NMR (300 MHz, CD$_3$OD) δ ppm 1.45-1.55 (m, 2H), 1.56-1.73 (m, 6H), 1.82-1.95 (m, 1H), 2.04-2.12 (m, 1H), 2.46-2.57 (m, 1H), 2.59-2.74 (m, 4H), 3.04-3.18 (m, 2H), 3.96-4.05 (m, 1H), 4.22-4.30 (m, 1H), 7.33 (d, J=9 Hz, 1H), 7.39 (dd, J=2, 9 Hz, 1H), 7.79 (d, J=2 Hz, 1H); MS (DCI/NH$_3$) m/z 380 (M+H)$^+$.

Example 37

(R)-4-(1-(6-bromobenzo[d]thiazol-2-yl)piperidin-3-yl)morpholine

The title compound was prepared by the method of Example 34, substituting morpholine in place of azetidine to give (R)-4-(1-(6-bromobenzo[d]thiazol-2-yl)piperidin-3-yl)morpholine. $^1$H NMR (300 MHz, CD$_3$OD) δ ppm 1.75-2.01 (m, 2H), 2.02-2.14 (m, 1H), 2.32-2.43 (m, 1H), 3.29-3.48 (m, 3H), 3.50-3.73 (m, 4H), 3.80-3.96 (m, 3H), 4.03-4.19 (m, 2H), 4.56-4.65 (m, 1H), 7.33 (d, J=9 Hz, 1H), 7.39 (dd, J=2, 9 Hz, 1H), 7.79 (d, J=2 Hz, 1H); MS (DCI/NH$_3$) m/z 382 (M+H)$^+$.

Example 38

(R)-2-(3-(azepan-1-yl)piperidin-1-yl)-6-bromobenzo[d]thiazole

The title compound was prepared by the method of Example 34, substituting hexamethyleneimine in place of azetidine to give (R)-2-(3-(azepan-1-yl)piperidin-1-yl)-6- bromobenzo[d]thiazole. $^1$H NMR (300 MHz, CD$_3$OD) δ ppm 1.73-2.10 (m, 11H), 2.25-2.33 (m, 1H), 3.34-3.62 (m, 7H), 3.84-3.93 (m, 1H), 4.54-4.66 (m, 1H), 7.33 (d, J=9 Hz, 1H), 7.39 (dd, J=2, 9 Hz, 1H), 7.79 (d, J=2 Hz, 1H); MS (DCI/NH$_3$) m/z 394 (M+H)$^+$.

Example 39

(S)-2-(3-(azetidin-1-yl)piperidin-1-yl)-6-bromobenzo[d]thiazole

The title compound was prepared by the method of Example 34, substituting (R)-1-(6-bromobenzo[d]thiazol-2-yl)piperidin-3-yl methanesulfonate (Reference Example 12) in place of (S)-1-(6-bromobenzo[d]thiazol-2-yl)piperidin-3-yl methanesulfonate (Reference Example 10) to give (S)-2-(3-(azetidin-1-yl)piperidin-1-yl)-6-bromobenzo[d]thiazole. $^1$H NMR (300 MHz, CD$_3$OD) δ ppm 1.23-1.38 (m, 1H), 1.53-1.69 (m, 1H), 1.80-1.96 (m, 2H), 2.11 (pentet, J=7 Hz, 2H), 2.32-2.43 (m, 1H), 2.93-3.02 (m, 1H), 3.22-3.38 (m, 5H), 3.79 (dt, J=4, 13 Hz, 1H), 3.96 (dd, J=4, 13 Hz, 1H), 7.33 (d, J=9 Hz, 1H), 7.39 (dd, J=2, 9 Hz, 1H), 7.79 (d, J=2 Hz, 1H); MS (DCI/NH$_3$) m/z 352 (M+H)$^+$.

Example 40

(S)-6-bromo-2-(3-(pyrrolidin-1-yl)piperidin-1-yl)benzo[d]thiazole

The title compound was prepared by the method of Example 34, substituting (R)-1-(6-bromobenzo[d]thiazol-2-yl)piperidin-3-yl methanesulfonate (Reference Example 12) in place of (S)-1-(6-bromobenzo[d]thiazol-2-yl)piperidin-3-yl methanesulfonate (Reference Example 10) and substituting pyrrolidine in place of azetidine to give (S)-6-bromo-2-(3-(pyrrolidin-1-yl)piperidin-1-yl)benzo[d]thiazole. $^1$H NMR (300 MHz, CD$_3$OD) δ ppm 1.47-1.75 (m, 2H), 1.77-1.95 (m, 5H), 2.11-2.20 (m, 1H), 2.28-2.39 (m, 1H), 2.67-2.76 (m, 4H), 3.06-3.25 (m, 2H), 3.87-3.96 (m, 1H), 4.25-4.32 (m, 1H), 7.33 (d, J=9 Hz, 1H), 7.39 (dd, J=2, 9 Hz, 1H), 7.79 (d, J=2 Hz, 1H); MS (DCI/NH$_3$) m/z 366 (M+H)$^+$.

Example 41

(S)-2-(1,3'-bipiperidin-1'-yl)-6-bromobenzo[d]thiazole

The title compound was prepared by the method of Example 34, substituting (R)-1-(6-bromobenzo[d]thiazol-2-yl)piperidin-3-yl methanesulfonate (Reference Example 12) in place of (S)-1-(6-bromobenzo[d]thiazol-2-yl)piperidin-3-yl methanesulfonate (Reference Example 10) and substituting piperidine in place of azetidine to give (S)-2-(1,3'-bipiperidin-1'-yl)-6-bromobenzo[d]thiazole (0.018 g, 24% yield). $^1$H NMR (300 MHz, CD$_3$OD) δ ppm 1.45-1.55 (m, 2H), 1.56-1.73 (m, 6H), 1.82-1.95 (m, 1H), 2.04-2.12 (m, 1H), 2.46-2.57 (m, 1H), 2.59-2.74 (m, 4H), 3.04-3.18 (m, 2H), 3.96-4.05 (m, 1H), 4.22-4.30 (m, 1H), 7.33 (d, J=9 Hz, 1H), 7.39 (dd, J=2, 9 Hz, 1H), 7.79 (d, J=2 Hz, 1H); MS (DCI/NH$_3$) m/z 380 (M+H)$^+$.

Example 42

(S)-4-(1-(6-bromobenzo[d]thiazol-2-yl)piperidin-3-yl)morpholine

The title compound was prepared by the method of Example 34, substituting (R)-1-(6-bromobenzo[d]thiazol-2-yl)piperidin-3-yl methanesulfonate (Reference Example 12) in place of (S)-1-(6-bromobenzo[d]thiazol-2-yl)piperidin-3-yl methanesulfonate (Reference Example 10) and substituting morpholine in place of azetidine to give (S)-4-(1-(6-bromobenzo[d]thiazol-2-yl)piperidin-3-yl)morpholine. $^1$H NMR (300 MHz, CD$_3$OD) δ ppm 1.75-2.01 (m, 2H), 2.02-2.14 (m, 1H), 2.32-2.43 (m, 1H), 3.29-3.48 (m, 3H), 3.50-3.73 (m, 4H), 3.80-3.96 (m, 3H), 4.03-4.19 (m, 2H), 4.56-4.65 (m, 1H), 7.33 (d, J=9 Hz, 1H), 7.39 (dd, J=2, 9 Hz, 1H), 7.79 (d, J=2 Hz, 1H); MS (DCI/NH$_3$) m/z 382 (M+H)$^+$.

Example 43

(S)-2-(3-(azepan-1-yl)piperidin-1-yl)-6-bromobenzo[d]thiazole

The title compound was prepared by the method of Example 34, substituting (R)-1-(6-bromobenzo[d]thiazol-2-yl)piperidin-3-yl methanesulfonate (Reference Example 12) in place of (S)-1-(6-bromobenzo[d]thiazol-2-yl)piperidin-3-yl methanesulfonate (Reference Example 10) and substituting hexamethyleneimine in place of azetidine to give (S)-2-(3-(azepan-1-yl)piperidin-1-yl)-6-bromobenzo[d]thiazole (0.0712 g, 90% yield). $^1$H NMR (300 MHz, CD$_3$OD) δ ppm 1.73-2.10 (m, 11H), 2.25-2.33 (m, 1H), 3.34-3.62 (m, 7H), 3.84-3.93 (m, 1H), 4.54-4.66 (m, 1H), 7.33 (d, J=9 Hz, 1H), 7.39 (dd, J=2, 9 Hz, 1H), 7.79 (d, J=2 Hz, 1H); MS (DCI/NH$_3$) m/z 394 (M+H)$^+$.

Example 44

6-bromo-2-(4-(pyrrolidin-1-yl)piperidin-1-yl)benzo[d]thiazole

One equivalent of 6-bromo-2-chlorobenzo[d]thiazole (248 mg, 1.0 mmol) and 1.1 equivalents of 4-(pyrrolidin-1-yl)piperidine (0.170 g, 1.1 mmol) were weighed into a 10 mL CEM microwave vial equipped with a magnetic stirbar. N,N-Dimethylformamide (1.0 mL) and three equivalents of N,N-diisopropylethylamine (0.524 ml, 3.00 mmol) were added via syringe. The reaction mixture was heated to 150° C. under microwave irradiation with the cooling power on for 15 minutes. The reaction mixture was transferred to a 250 mL round bottom flask (methanol rinse) and volatiles were removed under reduced pressure. The residue was partitioned between saturated aqueous sodium carbonate and CHCl$_3$. The aqueous layer was extracted once more with CHCl$_3$, then the combined organic extracts were washed with brine, dried (MgSO$_4$), and filtered. The filtrate was concentrated under reduced pressure to give a solid. This crude solid was purified by column chromatography on an Analogix IF-280 (Analogix SF15-12g, 100% dichloromethane to 97:3 dichloromethane/2 M ammonia in methanol). Fractions containing product were combined and concentrated under reduced pressure to give a solid that was dissolved in hot ethyl acetate, dried (MgSO$_4$), and filtered. The filtrate was placed in a 0° C. freezer to promote crystallization. Crystals were collected by filtration and dried in a vacuum oven to give 6-bromo-2-(4-(pyrrolidin-1-yl)piperidin-1-yl)benzo[d]thiazole. $^1$H NMR (300 MHz, CD$_3$OD) δ ppm 1.51-1.66 (m, 2H), 1.78-1.88 (m, 4H), 2.04-2.14 (m, 2H), 2.34-2.46 (m, 1H), 2.63-2.72 (m, 4H), 3.16-3.27 (m, 2H), 4.06-4.15 (m, 2H), 7.33 (d, J=9 Hz, 1H), 7.39 (dd, J=2, 9 Hz, 1H), 7.79 (d, J=2 Hz, 1H); MS (DCI/NH$_3$) m/z 366 (M+H)$^+$.

Example 45

2-(1,4'-bipiperidin-1'-yl)-6-bromobenzo[d]thiazole

The title compound was prepared by the method of Example 44, substituting 4-piperidinopiperidine in place of 4-(pyrrolidin-1-yl)piperidine to give 2-(1,4'-bipiperidin-1'-yl)-6-bromobenzo[d]thiazole. ¹H NMR (300 MHz, CD₃OD) δ ppm 1.43-1.53 (m, 2H), 1.54-1.70 (m, 6H), 1.97-2.06 (m, 2H), 2.54-2.66 (m, 5H), 3.11-3.23 (m, 2H), 4.12-4.21 (m, 2H), 7.33 (d, J=9 Hz, 1H), 7.39 (dd, J=2, 9 Hz, 1H), 7.79 (d, J=2 Hz, 1H); MS (DCI/NH₃) m/z 380 (M+H)⁺.

Example 46

(R)-6-methoxy-2-(3-(piperidin-1-yl)pyrrolidin-1-yl)benzo[d]thiazole

One equivalent of 6-bromo-2-chlorobenzo[d]thiazole and 1.1 equivalents of (R)-1-(pyrrolidin-3-yl)piperidine (freebase of Reference Example 5C) are weighed into a 10 mL CEM microwave vial equipped with a magnetic stirbar. N,N-Dimethylformamide or 2-methoxyethanol is added to give approximately a 2 M solution followed by four equivalents of N,N-diisopropylethylamine. The reaction mixture was heated to 150° C. under microwave irradiation with the cooling power on for 20 minutes. The reaction mixture volatiles are then removed under reduced pressure. The residue is partitioned between saturated aqueous sodium carbonate and CHCl₃. The aqueous layer is extracted once more with CHCl₃, then the combined organic extracts are washed with brine, dried (MgSO₄), and filtered. The filtrate is concentrated under reduced pressure and the residue is purified by column chromatography on silica gel, eluting with 97:3 dichloromethane/2 M ammonia in methanol. Fractions containing product are combined and concentrated under reduced pressure to give a solid that is dissolved in hot ethyl acetate, dried (MgSO₄), and filtered. The filtrate is concentrated under reduced pressure to give (R)-6-methoxy-2-(3-(piperidin-1-yl)pyrrolidin-1-yl)benzo[d]thiazole.

Alternate Method of Preparation of Example 46

(R)-6-methoxy-2-(3-(piperidin-1-yl)pyrrolidin-1-yl)benzo[d]thiazole dihydrochloride A mixture of (R)-1-(pyrrolidin-3-yl)piperidine (freebase of Reference Example 5C, 0.721 g, 4.668 mmol), 2-chloro-6-methoxybenzo[d]thiazole (0.848 g, 4.244 mmol), and triethylamine (1.77 mL, 12.73 mmol) in N,N-dimethylformamide (10 mL) was heated to 150° C. under microwave irradiation for 1.5 hours. The reaction mixture was diluted with water (350 mL) and extracted with ethyl acetate (3×75 mL). The combined organic extracts were washed with brine (2×200 mL) then dried (MgSO₄) and filtered. The filtrate was concentrated under reduced pressure. The residue was purified by column chromatography on an Analogix IF-280 (Analogix SF40-120 g, 98:2 ethyl acetate/methanol). Fractions containing product were combined and concentrated under reduced pressure to give a solid. The solid was dissolved in hot ethyl acetate, dried (MgSO₄) and filtered. The filtrate was concentrated under reduced pressure and a crystallization attempt was set up with ethyl acetate and diethyl ether. A gummy solid formed. The remaining solution was decanted free of this solid and the decant was treated with excess 4 M HCl in dioxane to provide the title compound as a precipitate that was collected by filtration. ¹H NMR (300 MHz, CD₃OD) δ ppm 7.53 (d, J=5.8 Hz, 1H), 7.52 (s, 1H), 7.16 (dd, J=2.5, 9.0 Hz, 1H), 4.36-4.21 (m, 2H), 4.20-3.99 (m, 2H), 3.93-3.79 (m, 1H), 3.86 (s, 3H), 3.74-3.51 (m, 2H), 3.25-3.06 (m, 2H), 2.84-2.55 (m, 2H), 2.07-1.82 (m, 5H), 1.68-1.49 (m, 1H); MS (DCI/NH₃) m/z 318 (M+H)⁺.

Example 47

(R)-2-(3-(piperidin-1-yl)pyrrolidin-1-yl)benzo[d]thiazol-6-ol

A stirred solution of (R)-6-methoxy-2-(3-(piperidin-1-yl)pyrrolidin-1-yl)benzo[d]thiazole (Example 46) in N,N-dimethylformamide (~0.05 M) is chilled to −78° C. under a dry nitrogen atmosphere. A 1 M solution of boron tribromide in heptane (4 equivalents) is added dropwise. When the addition is complete, the reaction mixture is allowed to warm to ambient temperature and stirring is continued for 18 hours. Ice water is carefully added to the reaction mixture and stirring is continued for 15 minutes. The pH of the reaction mixture is then adjusted to 7 by the addition of aqueous sodium bicarbonate. After rapid stirring for ten minutes, the organic layer is isolated. The aqueous layer is saturated with sodium chloride and extracted with CHCl₃. The organic layers are combined, dried (MgSO₄), and filtered. The filtrate is concentrated under reduced pressure and the residue is purified by column chromatography on silica gel, eluting with 90:5:5 dichloromethane/acetonitrile/methanol. Fractions containing product are combined and concentrated under reduced pressure to give (R)-2-(3-(piperidin-1-yl)pyrrolidin-1-yl)benzo[d]thiazol-6-ol.

Alternate Method of Preparation of Example 47

(R)-2-(3-(piperidin-1-yl)pyrrolidin-1-yl)benzo[d]thiazol-6-ol

A stirred solution of (R)-6-methoxy-2-(3-(piperidin-1-yl)pyrrolidin-1-yl)benzo[d]thiazole (Example 46, 920 mg, 2.90 mmol) in dichloromethane (70 mL) was chilled to −78° C. with a dry ice/acetone bath under a dry nitrogen atmosphere. Boron tribromide, 1.0 M solution in heptane (11.600 mL, 11.60 mmol) was then added via syringe. The reaction mixture was stirred overnight while slowly warming to ambient temperature. A large quantity of precipitate had formed. The reaction mix was cooled to 0° C., then ice water containing 5 equivalents of sodium carbonate was added. The mixture was vigorously stirred for 30 minutes. The mixture was filtered free of an insoluble solid. The filtrate was extracted with CHCl₃. The solid was dissolved in 3 N aqueous sodium hydroxide. This basic aqueous solution was brought to ~pH 7 with aqueous citric acid, then extracted with CHCl₃. The two organic extracts were compared by TLC (1:1 dichloromethane/90% acetonitrile and 10% methanol). The second extract contained product, meaning the insoluble material that was collected by filtration was actually the product. That aqueous layer was adjusted to ~pH 7 again, saturated with sodium chloride and extracted again with CHCl₃. The combined organic extracts were dried (MgSO₄) and filtered. The filtrate was concentrated under reduced pressure to give a solid. The solid was purified by column chromatography on an Analogix IF-280 (Analogix SF15-12 g, 100% dichloromethane to 50:50 dichloromethane/90% acetonitrile and 10% methanol). Fractions containing product were combined and concentrated under reduced pressure to give a solid that was dissolved in hot 1:1 CHCl₃/tetrahydrofuran. This solution was dried (MgSO₄) and filtered. The filtrate was concentrated under reduced pressure. The resulting solid was dissolved in hot methanol and the resulting solution was filtered and then concentrated under reduced pressure. The concentrated methanol solution was scratched with a spatula inducing crystallization. The first crystal batch was dried overnight in a vacuum oven at 60° C. to provide the title compound as crystals. Additional title compound was obtained from the crystallization filtrate and other column fractions. $^1$H NMR (300 MHz, CD$_3$OD) δ ppm 7.30 (d, J=8.7 Hz, 1H), 7.07 (d, J=2.4 Hz, 1H), 6.78 (dd, J=2.5, 8.7 Hz, 1H), 3.85-3.74 (m, 1H), 3.74-3.63 (m, 1H), 3.56-3.43 (m, 1H), 3.41-3.33 (m, 1H), 3.16-3.01 (m, 1H), 2.67-2.45 (m, 4H), 2.40-2.28 (m, 1H), 2.07-1.91 (m, 1H), 1.72-1.60 (m, 4H), 1.57-1.45 (m, 2H); MS (DCI/NH$_3$) m/z 304 (M+H)$^+$.

Example 48

(R)—N-methyl-6-(2-(3-(piperidin-1-yl)pyrrolidin-1-yl)benzo[d]thiazol-6-yloxy)nicotinamide A mixture of (R)-2-(3-(piperidin-1-yl)pyrrolidin-1-yl)benzo[d]thiazol-6-ol (Example 47) in N,N-dimethylformamide (~0.06 M) under a dry nitrogen atmosphere is placed in a microwave vial and stirred. Sodium hydride or a 1 M solution of sodium bis(trimethylsilyl)amide in tetrahydrofuran (1.2 equivalents) is added to the reaction mixture and stirring is continued for 45 minutes. 6-Chloro-N-methyl-3-pyridinecarboxamide (CAS #54189-82-1, 1.2 equivalents) is added to the reaction mixture and stirring is continued for 2-3 hours at 100° C. under microwave irradiation with the cooling air remaining on for the duration of the heating cycle. The reaction mixture is cooled to ambient temperature, dried (MgSO$_4$), and filtered. The filtrate is concentrated under reduced pressure and the residue is purified by column chromatography on silica gel, eluting with 98:2 dichloromethane/2 M NH$_3$ in methanol. Fractions containing product are combined and concentrated under reduced pressure to give (R)—N-methyl-6-(2-(3-(piperidin-1-yl)pyrrolidin-1-yl)benzo[d]thiazol-6-yloxy)nicotinamide.

Example 49

(R)-6-(2-(3-(piperidin-1-yl)pyrrolidin-1-yl)benzo[d]thiazol-6-yloxy)nicotinamide The procedure of Example 48 is repeated, substituting 6-chloronicotinamide (CAS #6271-78-9) in place of 6-chloro-N-methyl-3-pyridinecarboxamide to give (R)-6-(2-(3-(piperidin-1-yl)pyrrolidin-1-yl)benzo[d]thiazol-6-yloxy)nicotinamide.

Example 50

(R)—N-methyl-5-(2-(3-(piperidin-1-yl)pyrrolidin-1-yl)benzo[d]thiazol-6-yloxy)pyrazine-2-carboxamide Methyl 5-chloro-2-pyridazinecarboxylate (CAS #33332-25-1) is hydrolyzed to the corresponding carboxylic acid, 5-chloropyrazine-2-carboxylic acid. This acid is then converted to the corresponding acid chloride, 5-chloropyrazine-2-carbonyl chloride, by treatment with either thionyl chloride or oxalyl chloride. This acid chloride is then treated with a 2 M solution of methylamine in tetrahydrofuran to provide 5-chloro-N-methylpyrazine-2-carboxamide. The procedure of Example 48 is then repeated, substituting 5-chloro-N-methylpyrazine-2-carboxamide in place of 6-chloro-N-methyl-3-pyridinecarboxamide to give (R)—N-methyl-5-(2-(3-(piperidin-1-yl)pyrrolidin-1-yl)benzo[d]thiazol-6-yloxy)pyrazine-2-carboxamide.

Example 51

(R)-5-bromo-2-(3-(piperidin-1-yl)pyrrolidin-1-yl)benzo[d]thiazole

A stirred mixture of 2-chloro-5-bromobenzothiazole (CAS #824403-26-1, catalog #20284, Daxian Chemical Institute Ltd., #179, 10169 New Hampshire Ave., Silver Spring, Md. 20903, 2.485 g, 0.0100 mole), (R)-1-(pyrrolidin-3-yl)piperidine dihydrochloride (Reference Example 5c, 2.73 g, 0.0120 mole), and potassium carbonate (6.00 g, 0.04438 mole) in N,N-dimethylformamide (15 mL) is heated to 100° C. with an oil bath for 15 hours. The reaction mixture is cooled to room temperature then poured into water (300 mL). The resulting precipitate is collected by filtration and the filter cake is rinsed with water (600 mL). The solid is dissolved in dichloromethane and the solution is dried (MgSO$_4$) and filtered. The filtrate is concentrated under reduced pressure to give a solid that is crystallized from hot ethyl acetate to give (R)-5-bromo-2-(3-(piperidin-1-yl)pyrrolidin-1-yl)benzo[d]thiazole.

Example 51b

Alternative Preparation (R)-5-bromo-2-(3-(piperidin-1-yl)pyrrolidin-1-yl)benzo[d]thiazole A solution of (R)-1-(pyrrolidin-3-yl)piperidine dihydrochloride (Reference Example 5c) in a minimum of water is treated with excess solid sodium hydroxide and sodium chloride. This mixture is extracted with dichloromethane. The organic layer is dried (MgSO$_4$) and filtered. The filtrate is concentrated under reduced pressure to give (R)-1-(pyrrolidin-3-yl)piperidine as the free base oil (308 mg, 2.0 mmol). This free base diamine is added to a stirred solution of 5-bromo-2-fluorophenylisothiocyanate (prepared from 5-bromo-2-fluoroaniline, CAS #2924-09-6, catalog #18297, Matrix Scientific, PO Box 25067, Columbia, S.C. 29224) (0.464 g, 2.0 mole) in acetonitrile (20 mL). Cesium carbonate (2.6 g, 8.0 mmol) is added to the reaction mixture. The reaction mixture is then heated to 150° C. under microwave irradiation for 30 minutes. The reaction mixture is cooled to room temperature then diluted with water and extracted with chloroform. The organic layer is dried (MgSO$_4$) and filtered. The filtrate is concentrated under reduced pressure to give a residue that is purified by silica gel chromatography (100% dichloromethane to 50:50 dichloromethane/90% dichloromethane and 10% methanol). Fractions containing product are combined and concentrated under reduced pressure to give (R)-5-bromo-2-(3-(piperidin-1-yl)pyrrolidin-1-yl)benzo[d]thiazole.

Example 52

(R)-2-(2-(3-(piperidin-1-yl)pyrrolidin-1-yl)benzo[d]thiazol-5-yl)pyridazin-3(2H)-one A mixture of (R)-5-bromo-2-(3-(piperidin-1-yl)pyrrolidin-1-yl)benzo[d]thiazole (Example 51, 0.792 g, 2.16 mmol), pyridazin-3(2H)-one (0.415 g, 4.32 mmol), copper powder (0.137 g, 2.16 mmol), copper(I) iodide (57.6 mg, 0.303 mmol), and potassium carbonate (0.896 g, 6.49 mmol) is weighed into a large Biotage microwave vial equipped with a magnetic stirbar. The vial is crimp capped with a septum. Pyridine (17.3 mL) is introduced via syringe. The reaction mixture is purged (vacuum/nitrogen) three times, then $N^1,N^2$-dimethylethane-1,2-diamine (0.065 mL, 0.605 mmol) is added via syringe and the reaction mixture is stirred with heating at 117° C. for 24 hours. The reaction mixture is allowed to cool to room temperature, then the vial is uncapped and the contents are transferred to a 100 mL round bottom flask (methanol rinse). Volatiles are removed under reduced pressure and the residue is partitioned between $CHCl_3$ and aqueous ammonium hydroxide. The organic layer is washed with brine then dried ($MgSO_4$) and filtered The filtrate is concentrated under reduced pressure to give a residue that is treated with toluene and returned to the rotary evaporator in an attempt to remove residual pyridine. This residue is purified by column chromatography on an Analogix IntelliFlash-280 (Analogix SF65-220g, 100% $CHCl_3$ to 97:3 $CHCl_3$/methanol). Fractions containing product are combined and concentrated under reduced pressure to give a solid that is stirred with diethyl ether. The solid is collected by filtration and rinsed once with ethyl acetate and several times with hexane. This solid is crystallized from hot ethyl acetate. The first crystal batch is collected by filtration and dried in a vacuum oven at 84° C. for 5 hours. The filtrate is concentrated under reduced pressure and the solid residue is dissolved in hot ethyl acetate in a second crystallization attempt. The second crystal batch is collected by filtration and dried in the vacuum oven along with the first batch at 88° C. overnight. The two dried crystal batches combined give (R)-2-(2-(3-(piperidin-1-yl)pyrrolidin-1-yl)benzo[d]thiazol-5-yl)pyridazin-3(2H)-one.

Example 53

(R)-ethyl 2-(3-(piperidin-1-yl)pyrrolidin-1-yl)benzo[d]thiazole-6-carboxylate

A mixture of ethyl 2-chlorobenzo[d]thiazole-6-carboxylate (1.62 g, 6.72 mmol), (R)-1-(pyrrolidin-3-yl)piperidine dihydrochloride (Reference Example 5c, 1.80 g, 7.94 mmol), and triethylamine (5.11 mL, 36.66 mmol) in N,N-dimethylformamide (19 mL) was stirred at ambient temperature for 17 hours. According to TLC (100% ethyl acetate) the spot for starting chloride was replaced by a much lower Rf, ninhydrin-positive spot. The reaction mixture was diluted with water (400 mL) and extracted with ethyl acetate (3×75 mL). The combined organic extracts were washed with brine (2×200 mL) then dried ($MgSO_4$) and filtered. The filtrate was concentrated under reduced pressure. The residue was purified by column chromatography on an Analogix IF-280 (Analogix SF40-120 g, 99:1 ethyl acetate/methanol). Fractions containing product were combined and concentrated under reduced pressure to provide the title compound. $^1$H NMR (300 MHz, $CD_3OD$) δ ppm 8.34 (d, J=1.7 Hz, 1H), 7.96 (dd, J=1.7 Hz, 8.5, 1H), 7.49 (d, J=8.6 Hz, 1H), 4.36 (q, J=7.1 Hz, 2H), 3.82 (dt, J=8.8, 18.3 Hz, 2H), 3.63-3.50 (m, 1H), 3.41 (t, J=9.3 Hz, 1H), 3.16-3.02 (m, 1H), 2.67-2.43 (m, 4H), 2.43-2.30 (m, 1H), 2.11-1.93 (m, 1H), 1.72-1.59 (m, 4H), 1.58-1.45 (m, 2H), 1.39 (t, J=7.1 Hz, 3H); MS (DCI/$NH_3$) m/z 360 (M+H)$^+$.

Example 54

(R)-2-(3-(piperidin-1-yl)pyrrolidin-1-yl)benzo[d]thiazole-6-carboxylic acid

A solution of (R)-ethyl 2-(3-(piperidin-1-yl)pyrrolidin-1-yl)benzo[d]thiazole-6-carboxylate (Example 53, 1.38 g, 3.85 mmol) in tetrahydrofuran (50 mL) and methanol (25 mL) was added to a stirred solution of lithium hydroxide monohydrate (0.504 g, 12.00 mmol) in water (20 mL). The reaction mixture was stirred at ambient temperature for 19 hours. An aliquot was checked by TLC (99:1 ethyl acetate/methanol). A lower Rf spot was apparent, however, considerable starting ester remained, so the reaction mixture was heated to 40° C. for 7 hours. Starting ester was still present so the reaction mixture was stirred at ambient temperature for approximately 65 hours. Starting ester appeared to be consumed so the reaction mixture was concentrated under reduced pressure. The residue was treated with methanol (100 mL), water (200 mL), and three equivalents (3.0 mL, 12.0 mmol) of 4 M HCl in dioxane. This mixture was stirred overnight at ambient temperature. A precipitate had formed overnight. Most of the methanol was removed under reduced pressure, then the mixture was diluted with additional water and the precipitate was collected by filtration. This solid was azeotroped with benzene to remove residual water then dried in a vacuum oven to provide the title compound as the dihydrate. $^1$H NMR (300 MHz, $CD_3OD$) δ ppm 8.27 (s, 1H), 7.95 (d, J=8.5 Hz, 1H), 7.45 (d, J=8.4 Hz, 1H), 3.96-3.83 (m, 1H), 3.81-3.68 (m, 1H), 3.62-3.36 (m, 3H), 2.94-2.69 (m, 4H), 2.51-2.36 (m, 1H), 2.23-2.06 (m, 1H), 1.83-1.68 (m, 4H), 1.66-1.50 (m, 2H); MS (DCI/$NH_3$) m/z 332 (M+H)$^+$.

Example 55

(R)-morpholino(2-(3-(piperidin-1-yl)pyrrolidin-1-yl)benzo[d]thiazol-6-yl)methanone (R)-2-(3-(piperidin-1-yl)pyrrolidin-1-yl)benzo[d]thiazole-6-carboxylic acid, the product of Example 54 (40 mg, 0.121 mmol), morpholine (12 μL, 0.133 mmol), and O-(7-azabenzotriazol-1-yl)-N,N,N',N'-tetramethyluronium hexafluorophosphate (51 mg, 0.133 mmol) were combined in dichloromethane (2 mL). Triethyl amine (52 μL, 0.374 mmol) was added and mixture was stirred overnight at room temperature. The mixture was diluted with dichloromethane and washed with a 1 N aqueous sodium hydroxide solution. The organic layer was absorbed on silica gel and the mixture was purified by column chromatography eluting with a gradient of methanol and dichloromethane (2-18%) to afford the title compound. $^1$H NMR (300 MHz, $CDCl_3$) δ ppm 1.41-1.54 (m, 2H) 1.59-1.70 (m, 4H) 1.94-2.12 (m, 1H) 2.24-2.38 (m, 1H) 2.39-2.60 (m, 4H) 2.95-3.11 (m, 1H) 3.37-3.48 (m, 1H) 3.49-3.61 (m, 1H) 3.61-3.80 (m, 9H) 3.81-3.93 (m, 1H) 7.33 (dd, J=8.31, 1.87 Hz, 1H) 7.55 (d, J=8.14 Hz, 1H) 7.73 (d, J=1.70 Hz, 1H); MS (ESI+) m/z 401.1 (M+H)$^+$.

Example 56

(R)—N-methyl-2-(3-(piperidin-1-yl)pyrrolidin-1-yl)benzo[d]thiazole-6-carboxamide The product of Example 54 (44 mg, 0.133 mmol), a 2.0 M solution of methyl amine in tetrahydrofuran (100 μL, 0.200 mmol), and O-(7-azabenzotriazol-1-yl)-N,N,N',N'-tetramethyluronium hexafluorophosphate (55 mg, 0.146 mmol) were combined in tetrahydrofuran (2 mL). Triethyl amine (57 μL, 0.412 mmol) was added and mixture was stirred overnight at room temperature. The mixture was diluted with dichloromethane and washed with a 1 N aqueous sodium hydroxide solution. The organic layer was absorbed on silica gel and the mixture was purified by column chromatography eluting with a gradient of methanol and dichloromethane (2-18%) to afford the title compound. $^1$H NMR (300 MHz, $CDCl_3$) δ ppm 1.41-1.53 (m, 2H) 1.58-1.71 (m, 4H) 1.92-2.13 (m, 1H) 2.22-2.37 (m, 1H) 2.38-2.60(m, 4H) 2.94-3.09

(m, 4 H) 3.44 (t, J=9.32 Hz, 1 H) 3.50-3.64 (m, 1 H) 3.69-3.94 (m, 2 H) 6.09 (d, J=3.97 Hz, 1 H) 7.51-7.58 (m, 1 H) 7.58-7.65 (m, 1 H) 8.13 (d, J=1.59 Hz, 1 H); MS (ESI+) m/z 345.0 (M+H)+.

Example 57

((S)-3-hydroxypyrrolidin-1-yl)(2-((R)-3-(piperidin-1-yl)pyrrolidin-1-yl)benzo[d]thiazol-6-yl)methanone The product of Example 54 (49 mg, 0.148 mmol) and (S)-pyrrolidin-3-ol (14 mg, 0.163 mmol) were treated under the conditions of Example 55 to afford the title compound.
$^1$H NMR (300 MHz, CDCl$_3$) δ ppm 1.39-1.53 (m, 2 H) 1.59-1.69 (m, 4 H) 1.72-1.86 (m, J=15.26, 7.12 Hz, 1 H) 1.91-2.12 (m, 3 H) 2.23-2.38 (m, 1 H) 2.37-2.60 (m, 4 H) 2.91-3.10 (m, 1 H) 3.37-3.49 (m, 1 H) 3.49-3.94 (m, 8 H) 4.53 (d, J=30.18 Hz, 1 H) 7.42-7.58 (m, 1 H) 7.85 (s, 1 H); MS (ESI+) m/z 401.1 (M+H)+.

Example 58

(R)—N-(2-hydroxy-2-methylpropyl)-2-(3-(piperidin-1-yl)pyrrolidin-1-yl)benzo[d]thiazole-6-carboxamide The product of Example 54 (45 mg, 0.136 mmol) and 1-amino-2-methylpropan-2-ol (13 mg, 0.149 mmol) were treated under the conditions of Example 55 to afford the title compound. $^1$H NMR (300 MHz, CDCl$_3$) δ ppm 1.30 (s, 6 H) 1.41-1.53 (m, 2 H) 1.58-1.70 (m, 4 H) 1.94-2.12 (m, 1 H) 2.24-2.62 (m, 6 H) 2.93-3.10 (m, 1 H) 3.38-3.52 (m, 3 H) 3.51-3.64 (m, 1 H) 3.71-3.94 (m, 2 H) 6.54 (t, J=5.76 Hz, 1 H) 7.51-7.60 (m, 1 H) 7.64-7.72 (m, 1 H) 8.15 (d, J=1.36 Hz, 1 H); MS (ESI+) m/z 403.1 (M+H)+.

Example 59

(R)—N-ethyl-N-methyl-2-(3-(piperidin-1-yl)pyrrolidin-1-yl)benzo[d]thiazole-6-carboxamide The product of Example 54 (47 mg, 0.142 mmol) and N-methylethanamine (13 μL, 0.156 mmol) were treated under the conditions of Example 55 to afford the title compound.
$^1$H NMR (300 MHz, CDCl$_3$) δ ppm 1.12-1.34 (m, 5 H) 1.56-1.79 (m, 4 H) 1.94-2.11 (m, 1 H) 2.29-2.42 (m, 1 H) 2.51-2.80 (m, 4 H) 2.95-3.10 (m, 4 H) 3.26 (s, 2 H) 3.43-3.58 (m, 2 H) 3.60-3.71 (m, 1 H) 3.83 (t, J=8.82 Hz, 1 H) 7.32 (dd, J=8.14, 1.70 Hz, 1 H) 7.55 (d, J=8.14 Hz, 1 H) 7.68 (d, J=1.36 Hz, 1 H); MS (ESI+) m/z 373.0 (M+H)+.

Example 60

(R)—N,N-dimethyl-2-(3-(piperidin-1-yl)pyrrolidin-1-yl)benzo[d]thiazole-6-carboxamide The product of Example 54 (48 mg, 0.145 mmol) and dimethylamine hydrochloride (13 mg, 0.159 mmol) were treated under the conditions of Example 55 to afford the title compound. $^1$H NMR (300 MHz, CDCl$_3$) δ ppm 1.44-1.57 (m, J=5.42 Hz, 2 H) 1.68 (t, J=4.07 Hz, 4 H) 1.94-2.11 (m, 1 H) 2.26-2.41 (m, 1 H) 2.49-2.74 (m, 4 H) 3.00-3.18 (m, 7 H) 3.24-3.40 (m, 1 H) 3.45-3.59 (m, 1 H) 3.63-3.75 (m, J=9.49, 9.49 Hz, 1 H) 3.83 (t, J=7.80 Hz, 1 H) 7.35 (dd, J=8.31, 1.86 Hz, 1 H) 7.55 (d, J=8.14 Hz, 1 H) 7.72 (d, J=1.36 Hz, 1 H); MS (ESI+) m/z 359.0 (M+H)+.

Example 61

(R)—N-ethyl-2-(3-(piperidin-1-yl)pyrrolidin-1-yl)benzo[d]thiazole-6-carboxamide

The product of Example 54 (48 mg, 0.145 mmol) and ethylamine hydrochloride (13 mg, 0.159 mmol) were treated under the conditions of Example 55 to afford the title compound. $^1$H NMR (300 MHz, CDCl$_3$) δ ppm 1.21-1.31 (m, 3 H) 1.43-1.52 (m, 2 H) 1.58-1.69 (m, 4 H) 1.93-2.11 (m, 1 H) 2.25-2.36 (m, 1 H) 2.38-2.59 (m, 4 H) 2.94-3.08 (m, 1 H) 3.38-3.63 (m, 4 H) 3.77 (t, J=9.15 Hz, 1 H) 3.82-3.92 (m, 1 H) 6.05 (t, J=4.92 Hz, 1 H) 7.51-7.57 (m, 1 H) 7.59-7.66 (m, 1 H) 8.13 (d, J=1.36 Hz, 1 H); MS (ESI+) m/z 359.0 (M+H)+.

Example 62

(R)—N-isopropyl-2-(3-(piperidin-1-yl)pyrrolidin-1-yl)benzo[d]thiazole-6-carboxamide The product of Example 54 (48 mg, 0.145 mmol) and isopropyl amine (16 μL, 0.188 mmol) were treated under the conditions of Example 55 to afford the title compound. $^1$H NMR (500 MHz, CDCl$_3$) δ ppm 1.27 (d, J=6.41 Hz, 6 H) 1.44-1.53 (m, 2 H) 1.59-1.68 (m, 4 H) 1.96-2.08 (m, 1 H) 2.26-2.34 (m, 1 H) 2.39-2.60 (m, 4 H) 2.95-3.08 (m, 1 H) 3.44 (t, J=9.15 Hz, 1 H) 3.50-3.61 (m, 1 H) 3.68-3.94 (m, J=49.43 Hz, 2 H) 4.24-4.36 (m, 1 H) 5.89 (d, J=7.63 Hz, 1 H) 7.51-7.58 (m, 1 H) 7.62 (dd, J=8.24, 1.83 Hz, 1 H) 8.12 (d, J=1.83 Hz, 1 H); MS (ESI+) m/z 373.0 (M+H)+.

Example 63

(R)—N-(2-fluoroethyl)-2-(3-(piperidin-1-yl)pyrrolidin-1-yl)benzo[d]thiazole-6-carboxamide To a solution of (25 mg, 0.075 mmol) of the compound of Example 54 ((R)-2-(3-(piperidin-1-yl)pyrrolidin-1-yl)benzo[d]thiazole-6-carboxylic acid) in N,N-dimethylformamide (1 mL) was added 2-fluoroethanamine hydrochloride (11.26 mg, 0.113 mmol), hydroxybenzotriazole (12.71 mg, 0.083 mmol), triethylamine (0.032 ml, 0.226 mmol) and 1-[3-(dimethylamino)propyl]-3-ethylcarbodiimide hydrochloride (15.91 mg, 0.083 mmol). The reaction mixture was stirred at room temperature overnight, and then N,N-dimethylformamide was removed under vacuum. The residue was treated with saturated aqueous NaHCO$_3$ and extracted with dichloromethane (4×2 mL). The organic phases were combined, dried and concentrated under vacuum, then purified via medium pressure liquid chromatography on silica gel column eluting with 10% methanol/dichloromethane), to give (R)—N-(2-fluoroethyl)-2-(3-(piperidin-1-yl)pyrrolidin-1-yl)benzo[d]thiazole-6-carboxamide.
$^1$H NMR (300 MHz, CDCl$_3$) δ 68.14 (d, J=1.7, 1H), 7.67 (dd, J=1.9, 8.5, 1H), 7.56 (d, J=8.5, 1H), 6.47 (br t, J=5.9, 1H), 4.70 (t, J=4.7, 1H), 4.54 (t, J=4.7, 1H), 3.88 (m, 1H), 3.84 (dd, J=5.0, 10.3, 1H), 3.75 (dd, J=5.1, 10.2, 1H), 3.57 (td, J=6.8, 9.9, 1H), 3.45 (t, J=9.3, 1H), 3.03 (dt, J=5.5, 16.6, 1H), 2.58-2.40 (m, 3H), 2.37-2.27 (m, 1H), 2.12-1.95 (m, 1H), 1.66-1.60 (m, 6H), 1.54-1.41 (m, 2H); MS(DCI/NH$_3$) m/z 337.3 (M+H)+.

Example 64

(R)-isopropyl 6-(2-(3-(piperidin-1-yl)pyrrolidin-1-yl)benzo[d]thiazol-6-yl)picolinate

Example 64A (R)-2-(3-(piperidin-1-yl)pyrrolidin-1-yl)-6-(4,4,5 5-tetramethyl-1,3,2-dioxaborolan-2-yl)benzo[d]thiazole A mixture of (R)-6-bromo-2-(3-(piperidin-1-yl)pyrrolidin-1-yl)benzo[d]thiazole (the product of Example 14, 123 mg, 0.336 mmol), bis(pinacolato)diboron (119 mg, 0.470 mmol), [1,1'-bis(diphenylphosphino)ferrocene]dichloropalladium(II) dichloromethane complex (27.4 mg, 0.034 mmol) and anhydrous potassium acetate (KOAc, 66 mg, 0.67 mmol) in tetrahydrofuran (1 mL) was heated to 70° C. over night in a vial. The mixture was cooled and partitioned between 1 M NaOH (5 mL) and $CH_2Cl_2$ (25 mL). The layers were separated and the aqueous layer was extracted with $CH_2Cl_2$ (25 mL). The combined $CH_2Cl_2$ layers were dried ($MgSO_4$), filtered, concentrated and chromatographed on silica gel eluting with a gradient of 2 to 10% (9:1 methanol:ammonium hydroxide) in $CH_2Cl_2$ to provide the title compound. $^1H$ NMR (300 MHz, $CDCl_3$) δ ppm 1.35 (s, 12H) 1.42-1.52 (m, 2H) 1.57-1.68 (m, 4H) 1.96-2.08 (m, 1H) 2.23-2.34 (m, 1H) 2.39-2.57 (m, 4H) 2.93-3.07 (m, 1H) 3.43 (t, 1H) 3.55 (dt, J=10.3, 7.0 Hz, 1H) 3.76 (t, J=9.3 Hz, 1H) 3.82-3.91 (m, 1H) 7.55 (d, J=8.1 Hz, 1H) 7.73 (dd, J=8.0, 1.2 Hz, 1H) 8.06 (t, J=0.7 Hz, 1H); MS (DCI/$NH_3$) m/z 414 (M+H)$^+$.

Example 64B (R)-isopropyl 6-(2-(3-(piperidin-1-yl)pyrrolidin-1-yl)benzo[d]thiazol-6-yl)picolinate A vial containing (R)-2-(3-(piperidin-1-yl)pyrrolidin-1-yl)-6-(4,4,5,5-tetramethyl-1,3,2-dioxaborolan-2-yl)benzo[d]thiazole (Example 64A, 31 mg, 0.074 mmol), methyl 6-bromo-2-pyridinecarboxylate (16 mg, 0.074 mmol), $K_2CO_3$ (31 mg, 0.22 mmol) and bis(triphenylphosphine)palladium(II) chloride (5 mg, 7 μmol) suspended in isopropanol (1 mL) was heated to 80° C. for 2 hours. The mixture was allowed to stand at room temperature over night. The mixture was partitioned between 1 M NaOH (5 mL) and $CH_2Cl_2$ (25 mL). The layers were separated and the aqueous layer was extracted with $CH_2Cl_2$ (25 mL). The combined $CH_2Cl_2$ layers were dried ($MgSO_4$), filtered, concentrated and chromatographed on silica gel eluting with a gradient of 2% to 10% (9:1 methanol:ammonium hydroxide) in $CH_2Cl_2$ and then rechromatographed on silica gel eluting with a gradient of 10:1:1 to 7:1:1 ethyl acetate:$HCO_2H$:$H_2O$. The residue was partitioned between 1 M NaOH and $CH_2Cl_2$. This $CH_2Cl_2$ layer was dried ($MgSO_4$), filtered and concentrated to provide the title compound. $^1H$ NMR (300 MHz, $CDCl_3$) δ ppm 1.42-1.52 (m, 2H), 1.44 (d, J=6.3 Hz, 6H), 1.59-1.68 (m, 4H), 1.96-2.11 (m, 1H), 2.26-2.36 (m, 1H), 2.41-2.59 (m, 4H), 2.95-3.08 (m, 1H), 3.46 (t, J=9.3 Hz, 1H), 3.53-3.63 (m, 1H), 3.75-3.84 (m, 1H), 3.85-3.94 (m, 1H), 5.29-5.39 (m, 1H), 7.64 (d, J=8.7 Hz, 1H), 7.80-7.99 (m, 4H), 8.50 (d, J=1.2 Hz, 1H); MS (DCI/$NH_3$) m/z 451 (M+H)$^+$.

Example 65

(R)-6-(2-(3-(piperidin-1-yl)pyrrolidin-1-yl)benzo[d]thiazol-6-yl)picolinic acid

A vial containing (R)-2-(3-(piperidin-1-yl)pyrrolidin-1-yl)-6-(4,4,5,5-tetramethyl-1,3,2-dioxaborolan-2-yl)benzo[d]thiazole (Example 64A, 23 mg, 0.056 mmol), methyl 6-bromo-2-pyridinecarboxylate (12 mg, 0.056 mmol), bis(triphenylphosphine)palladium(II) chloride (5 mg, 7 μmol), and $K_2CO_3$ (23 mg, 0.17 mmol) in methanol (0.5 mL) was heated to 80° C. for 2 hours and cooled. The mixture was filtered and concentrated. The residue was purified by preparative HPLC on a Phenomenex Luna C8(2) 5 um 100 Å AXIA column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A). Samples were injected in 1.5 mL dimethyl sulfoxide:methanol (1:1). A custom purification system was used, consisting of the following modules: Waters LC4000 preparative pump; Waters 996 diode-array detector; Waters 717+ autosampler; Waters SAT/IN module, Alltech Varex III evaporative light-scattering detector; Gilson 506C interface box; and two Gilson FC204 fraction collectors. The system was controlled using Waters Millennium32 software. Fractions were collected based upon UV signal threshold and selected fractions subsequently analyzed by flow injection analysis mass spectrometry using positive APCI ionization on a Finnigan LCQ using 70:30 methanol: 10 mM $NH_4OH$(aqueous) at a flow rate of 0.8 mL/minute. Loop-injection mass spectra were acquired using a Finnigan LCQ running LCQ Navigator 1.2 software and a Gilson 215 liquid handler for fraction injection. The title compound was obtained as the bis trifluoroacetate salt. $^1H$ NMR (300 MHz, $CD_3OD$) δ ppm 1.52-1.68 (m, 1H), 1.74-1.93 (m, 3H), 1.95-2.09 (m, 2H), 2.32-2.47 (m, 1H), 2.64-2.75 (m, 1H), 3.02-3.23 (m, 2H), 3.51-3.76 (m, 3H), 3.79-3.95 (m, 2H), 4.08-4.22 (m, 2H), 7.64 (d, J=8.5 Hz, 1H), 7.99-8.09 (m, 2H), 8.10-8.17 (m, 2H), 8.62 (d, J=1.7 Hz, 1H); MS (DCI/$NH_3$) m/z 409 (M+H)$^+$.

Example 66

(R)-methyl 6-(2-(3-(piperidin-1-yl)pyrrolidin-1-yl)benzo[d]thiazol-6-yl)picolinate A vial containing (R)-2-(3-(piperidin-1-yl)pyrrolidin-1-yl)-6-(4,4,5,5-tetramethyl-1,3,2-dioxaborolan-2-yl)benzo[d]thiazole (Example 64A, 30 mg, 0.072 mmol), methyl 6-bromo-2-pyridinecarboxylate (16 mg, 0.072 mmol), $K_2CO_3$ (30 mg, 0.22 mmol) and bis(triphenylphosphine)palladium(II) chloride (5 mg, 7 μmol) in tert-butanol (0.5 mL) was heated to 80° C. for 1 hour and cooled. The mixture was diluted with $CH_2Cl_2$ (5 mL), filtered, and concentrated. The residue was purified by preparative HPLC on a Phenomenex Luna C8(2) 5 um 100 Å AXIA column (30 mm×75 mm) as described in Example 65. The title compound was obtained as the bis trifluoroacetate salt. $^1H$ NMR (300 MHz, $CD_3OD$) δ ppm 1.52-1.65 (m, 1H), 1.74-1.93 (m, 3H), 1.96-2.09 (m, 2H), 2.34-2.48 (m, 1H), 2.63-2.76 (m, 1H), 3.04-3.20 (m, 2H), 3.52-3.77 (m, 3H), 3.81-3.95 (m, 2H), 4.01 (s, 3H), 4.08-4.21 (m, 2H), 7.64 (d, J=8.5 Hz, 1H), 7.98-8.07 (m, 2H), 8.08-8.15 (m, 2H), 8.57 (d, J=1.7 Hz, 1H); MS (DCI/$NH_3$) m/z 423 (M+H)$^+$.

Example 67

(R)-methyl 5-(2-(3-(piperidin-1-yl)pyrrolidin-1-yl)benzo[d]thiazol-6-yl)picolinate The title compound was prepared by the method of Example 66, substituting methyl 5-bromopyridine-2-carboxylate for methyl 6-bromo-2-pyridinecarboxylate. $^1H$ NMR (300 MHz, CD$_3$OD) δ ppm 1.53-1.66 (m, 1H), 1.74-1.91 (m, 3H), 1.96-2.10 (m, 2H), 2.31-2.45 (m, 1H), 2.63-2.75 (m, 1H), 3.04-3.20 (m, 2H), 3.51-3.75 (m, 3H), 3.78-3.94 (m, 2H), 4.01 (s, 3H), 4.08-4.23 (m, 2H), 7.66 (d, J=8.5 Hz, 1H), 7.76 (dd, J=8.5, 2.0 Hz, 1H), 8.17 (d, J=2.0 Hz, 1H), 8.22 (dd, J=8.1, 0.7 Hz, 1H), 8.29 (dd, J=8.1, 2.4 Hz, 1H), 8.97 (dd, J=2.0, 0.7 Hz, 1H); MS (DCI/NH$_3$) m/z 423 (M+H)$^+$.

Example 68

(R)-6-(6-methoxypyridazin-3-yl)-²-(3-(piperidin-1-yl)pyrrolidin-1-yl)benzo[d]thiazole The title compound was prepared by the method of Example 66, substituting 3-chloro-6-methoxypyridazine for methyl 6-bromo-2-pyridinecarboxylate and substituting isopropyl alcohol for tert-butanol. $^1$H NMR (300 MHz, CD$_3$OD) δ ppm 1.53-1.67 (m, 1H), 1.73-1.92 (m, 3H), 1.96-2.09 (m, 2H), 2.33-2.48 (m, 1H), 2.63-2.75 (m, 1H), 3.04-3.20 (m, 2H), 3.51-3.76 (m, 3H), 3.80-3.96 (m, 2H), 4.09-4.24 (m, 2H), 4.16 (s, 3H), 7.45 (d, J=9.5 Hz, 1H), 7.67 (d, J=8.8 Hz, 1H), 7.97 (dd, J=8.6, 1.9 Hz, 1H), 8.22 (d, J=9.5 Hz, 1H), 8.39 (d, J=1.4 Hz, 1H); MS (DCI/NH$_3$) m/z 396 (M+H)$^+$.

Example 69

(R)—N-methyl-6-(2-(3-(piperidin-1-yl)pyrrolidin-1-yl)benzo[d]thiazol-6-yl)picolinamide

Example 69A 6-bromopicolinoyl chloride

A mixture of 6-bromo-2-pyridinecarboxylic acid (1 g, 5 mmol) in SOCl$_2$ (10 ml, 140 mmol) was heated to 70° C. for 6 hours and concentrated to dryness to provide the title compound.

Example 69B 6-bromo-N-methylpicolinamide

A solution of 6-bromopicolinoyl chloride (Example 69A, 350 mg, 1.6 mmol) in tetrahydrofuran (4 mL) was added in portions via a pipette over 2 minutes to a solution of methylamine (40 wt. % in water, 4 mL, 46.2 mmol) in tetrahydrofuran (6 mL). The mixture was stirred for 15 minutes and partitioned between water (5 mL) and CH$_2$Cl$_2$ (25 mL). The layers were separated and the aqueous layer was extracted with CH$_2$Cl$_2$ (25 mL). The combined CH$_2$Cl$_2$ layers were dried (MgSO$_4$), filtered and concentrated to provide the desired product, 6-bromo-N-methylpicolinamide. $^1$H NMR (300 MHz, CDCl$_3$) δ ppm 3.03 and 3.04 (s and s, 3H), 7.45 and 7.60 (dd and dd, J=8.1, 1.0 Hz, 1H), 7.71 and 7.82 (t, J=7.8 Hz, 1H), 7.75-7.88 (bs, 1H), 8.11-8.18 (m, 1H); MS (DCI/NH$_3$) m/z 215 (M+H)$^+$.

Example 69C (R)—N-methyl-6-(2-(3-(piperidin-1-yl)pyrrolidin-1-yl)benzo[d]thiazol-6-yl)picolinamide The title compound was prepared by the method of Example 66, substituting 6-bromo-N-methylpicolinamide (Example 69B) for methyl 6-bromo-2-pyridinecarboxylate and substituting isopropyl alcohol for tert-butanol. $^1$H NMR (300 MHz, CD$_3$OD) δ 1.51-1.67 (m, 1H), 1.71-1.94 (m, 3H), 1.97-2.11 (m, 2H), 2.32-2.47 (m, 1H), 2.64-2.76 (m, 1H), 3.03 (s, 3H), 3.05-3.20 (m, 2H), 3.53-3.76 (m, 3H), 3.78-3.96 (m, 2H), 4.09-4.23 (m, 2H), 7.63 (d, J=8.7 Hz, 1H), 7.95-8.04 (m, 2H), 8.03-8.11 (m, 1H), 8.18 (dd, J=8.5, 1.8 Hz, 1H), 8.69 (d, J=1.6 Hz, 1H); MS (DCI/NH$_3$) m/z 422 (M+H)$^+$.

Example 70

(R)—N-methyl-2-(2-(3-(piperidin-1-yl)pyrrolidin-1-yl)benzo[d]thiazol-6-yl)isonicotinamide

Example 70A 2-bromo-N-methylisonicotinamide

The title compound was prepared by the methods of Example 69A and Example 69B, substituting 2-bromo-4-pyridinecarboxylic acid for 6-bromo-2-pyridinecarboxylic acid. $^1$H NMR (300 MHz, CDCl$_3$) δ ppm 3.03 and 3.05 (d and d, J=1 Hz, 1H), 6.22 (bs, 1H), 7.52 and 7.55 (dd and dd, J=5, 1 Hz, 1H)) 7.65 and 7.80(m and m, 1H), 8.50 (t, J=5.6 Hz, 1H); MS (DCI/NH$_3$) m/z 215 (M+H)$^+$.

Example 70B (R)—N-methyl-2-(2-(3-(piperidin-1-yl)pyrrolidin-1-yl)benzo[d]thiazol-6-yl)isonicotinamide The title compound was prepared by the method of Example 66, substituting 2-bromo-N-methylisonicotinamide (Example 70A) for methyl 6-bromo-2-pyridinecarboxylate and substituting isopropyl alcohol for tert-butanol. The product was further purified by chromatography on silica gel eluting with a gradient of 2 to 10% (9:1 methanol:ammonium hydroxide) in CH$_2$Cl$_2$. $^1$H NMR (300 MHz, CD$_3$OD) δ ppm 1.47-1.56 (m, 2H), 1.61-1.71 (m, 4H), 1.94-2.09 (m, 1H), 2.31-2.42 (m, 1H), 2.46-2.55 (m, 2H), 2.55-2.65 (m, 2H), 2.97 (s, 3H), 3.02-3.15 (m, 1H), 3.38-3.46 (m, 1H), 3.51-3.61 (m, 1H), 3.71-3.80 (m, 1H), 3.82-3.91 (m, 1H), 7.58 (d, J=8.8 Hz, 1H), 7.62 (dd, J=5.1, 1.4 Hz, 1H), 7.99 (dd, J=8.5, 2.0 Hz, 1H), 8.20 (dd, J=1.5, 0.8 Hz, 1H), 8.37 (d, J=1.7 Hz, 1H), 8.70 (dd, J=5.1, 0.7 Hz, 1H); MS (DCI/NH$_3$) m/z 422 (M+H)$^+$.

Example 71

(R)—N-methyl-6-(2-(3-(piperidin-1-yl)pyrrolidin-1-yl)benzo[d]thiazol-6-yl)nicotinamide

Example 71A 6-chloro-N-methylnicotinamide

The title compound was prepared by the methods of Example 69A and Example 69B, substituting 6-chloronicotinic acid for 6-bromo-2-pyridinecarboxylic acid. $^1$H NMR (300 MHz, CDCl$_3$) δ ppm 3.04 (d, J=5.1 Hz, 3H), 6.25 (bs, 1H), 7.41 (dd, J=8.1, 0.7 Hz, 1H), 8.09 (dd, J=8.3, 2.5 Hz, 1H), 8.73 (dd, J=2.4, 0.7 Hz, 1H); MS (DCI/NH$_3$) m/z 171 (M+H)$^+$.

Example 71B (R)—N-methyl-6-(2-(3-(piperidin-1-yl)pyrrolidin-1-yl)benzo[d]thiazol-6-yl)nicotinamide The title compound was prepared by the method of Example 66, substituting 6-chloro-N-methylnicotinamide (Example 71A) for methyl 6-bromo-2-pyridinecarboxylate and substituting isopropyl alcohol for tert-butanol. The product was further purified by chromatography on silica gel eluting with a gradient of 2 to 10% (9:1 methanol:ammonium hydroxide) in CH$_2$C$_2$. $^1$H NMR (300 MHz, CD$_3$OD) δ ppm 1.46-1.57 (m, 2H), 1.59-1.73 (m, 4H), 1.97-2.10 (m, 1H), 2.32-2.43 (m, 1H), 2.45-2.65 (m, 4H), 2.95 (s, 3H), 3.03-3.16 (m, 1H), 3.38-3.47 (m, 1H), 3.52-3.63 (m, 1H), 3.72-3.81 (m, 1H), 3.83-3.92 (m, 1H), 7.57 (d, J=8.5 Hz, 1H), 7.95 (none, 1H), 7.95 (d, J=8.5 Hz, 1H), 8.01 (dd, J=8.6, 1.9 Hz, 1H), 8.22 (dd, J=8.5, 2.4 Hz, 1H), 8.40 (d, J=1.7 Hz, 1H), 9.00 (d, J=1.7 Hz, 1H); MS (DCI/NH$_3$) m/z 422 (M+H)$^+$.

Example 72

(R)-6-(2-(3-(piperidin-1-yl)pyrrolidin-1-yl)benzo[d]thiazol-6-yl)pyridazin-3-ol A solution of (R)-6-(6-methoxypyridazin-3-yl)-2-(3-(piperidin-1-yl)pyrrolidin-1-yl)benzo[d]thiazole (Example 68, 19.8 mg, 0.032 mmol) in hydrobromic acid (48 wt. % in water, 0.25 mL, 2.210 mmol) was heated to 80° C. for 1 hour, concentrated with a stream of nitrogen and chromatographed on silica gel eluting with a gradient of 2 to 10% (9:1 methanol:ammonium hydroxide) in CH$_2$Cl$_2$ to provide the desired product, (R)-6-(2-(3-(piperidin-1-yl)pyrrolidin-1-yl)benzo[d]thiazol-6-yl)pyridazin-3-ol. $^1$H NMR (300 MHz, CD$_3$OD) δ ppm 1.47-1.57 (m, 2H), 1.61-1.72 (m, 4H), 1.95-2.10 (m, 1H), 2.32-2.43 (m, 1H), 2.46-2.66 (m, 4H), 3.05-3.18 (m, 1H), 3.38-3.47 (m, 1H), 3.52-3.63 (m, 1H), 3.72-3.81 (m, 1H), 3.84-3.92 (m, 1H), 7.05 (d, J=9.8 Hz, 1H), 7.54 (d, J=8.5 Hz, 1H), 7.83 (dd, J=8.5, 2.0 Hz, 1H), 8.06 (d, J=9.8 Hz, 1H), 8.21 (d, J=1.7 Hz, 1H); MS (DCI/NH$_3$) m/z 382 (M+H)$^+$.

Example 73

(R)-5-(2-(3-(piperidin-1-yl)pyrrolidin-1-yl)benzo[d]thiazol-6-yl)pyrimidin-2-ol A solution of (R)-6-(2-methoxypyrimidin-5-yl)-2-(3-(piperidin-1-yl)pyrrolidin-1-yl)benzo[d]thiazole (Example 15, 20 mg, 0.051 mmol) in hydrobromic acid (48 wt. % in water, 0.25 mL, 2.2 mmol) was heated to 80° C. for 1 hour, concentrated with a stream of nitrogen and chromatographed on silica gel eluting with 2 to 20% (9:1 methanol:ammonium hydroxide) in CH$_2$Cl$_2$ to provide the desired product. $^1$H NMR (300 MHz, CD$_3$OD) δ ppm 1.48-1.57 (m, 2H), 1.62-1.72 (m, 4H), 1.98-2.10 (m, 1H), 2.32-2.43 (m, 1H), 2.47-2.67 (m, 4H), 3.05-3.19 (m, 1H), 3.39-3.46 (m, 1H), 3.52-3.62 (m, 1H), 3.71-3.80 (m, 1H), 3.84-3.92 (m, 1H), 7.49 (dd, J=8.5, 1.7 Hz, 1H), 7.55 (d, J=8.5 Hz, 1H), 7.90 (d, J=1.4 Hz, 1H), 8.59 (s, 2H); MS (DCI/NH$_3$) m/z 382 (M+H)$^+$.

Example 74

(R)-5-(2-(3-(piperidin-1-yl)pyrrolidin-1-yl)benzo[d]thiazol-6-yl)pyridin-2-ol The title compound was prepared by the method of Example 73, substituting (R)-6-(6-methoxypyridin-3-yl)-2-(3-(piperidin-1-yl)pyrrolidin-1-yl)benzo[d]thiazole (Example 19) in place of (R)-6-(2-methoxypyrimidin-5-yl)-2-(3-(piperidin-1-yl)pyrrolidin-1-yl)benzo[d]thiazole (Example 15). $^1$H NMR (300 MHz, CD$_3$OD) δ ppm 1.47-1.56 (m, 2H), 1.61-1.72 (m, 4H), 1.96-2.09 (m, 1H), 2.31-2.42 (m, 1H), 2.46-2.65 (m, 4H), 3.03-3.16 (m, 1H), 3.37-3.45 (m, 1H), 3.50-3.61 (m, 1H), 3.70-3.79 (m, 1H), 3.83-3.90 (m, 1H), 6.64 (dd, J=9.5, 0.7 Hz, 1H), 7.45 (dd, J=8.5, 1.7 Hz, 1H), 7.52 (d, J=8.5 Hz, 1H), 7.67 (d, J=2.0 Hz, 1H), 7.84 (d, J=2.0 Hz, 1H), 7.96 (dd, J=9.5, 2.7 Hz, 1H); MS (DCI/NH$_3$) m/z 381 (M+H)$^+$.

Example 75

(R)—N-methyl-5-(2-(3-(piperidin-1-yl)pyrrolidin-1-yl)benzo[d]thiazol-6-yl)picolinamide

Example 75A

5-bromo-N-methylpicolinamide

The title compound was prepared by the methods of Example 69A and Example 69B, substituting 5-bromopyridine-2-carboxylic acid for 6-bromo-2-pyridinecarboxylic acid. $^1$H NMR (300 MHz, CDCl$_3$) δ ppm 3.03 (d, J=5.1 Hz, 3H), 7.88 (bs, 1H), 7.97 (dd, J=8.3, 2.2 Hz, 1H), 8.09 (dd, J=8.5, 0.7 Hz, 1H), 8.60 (dd, J=2.4, 0.7 Hz, 1H); MS (DCI/NH$_3$) m/z 215 (M+H)$^+$.

Example 75B

(R)—N-methyl-5-(2-(3-(piperidin-1-yl)pyrrolidin-1-yl)benzo[d]thiazol-6-yl)picolinamide The title compound was prepared by the method of Example 66, substituting 5-bromo-N-methylpicolinamide (Example 75A) for methyl 6-bromo-2-pyridinecarboxylate and substituting isopropyl alcohol for tert-butanol. The product was further purified by chromatography on silica gel eluting a gradient of 2 to 10% (9:1 methanol:ammonium hydroxide) in CH$_2$Cl$_2$. $^1$H NMR (300 MHz, CDCl$_3$) δ ppm 1.43-1.53 (m, 2H), 1.58-1.70 (m, 4H), 1.97-2.12 (m, 1H), 2.26-2.37 (m, 1H), 2.40-2.60 (m, 4H), 2.97-3.11 (m, 1H), 3.06 (d, J=5.1 Hz, 3H), 3.42-3.50 (m, J=9.2, 9.2 Hz, 1H), 3.53-3.64 (m, 1H), 3.74-3.83 (m, 1H), 3.85-3.93 (m, 1H), 7.55 (dd, J=8.5, 1.7 Hz, 1H), 7.67 (d, J=8.8 Hz, 1H), 7.85 (d, J=2.0 Hz, 1H), 8.01 (bs, 1H), 8.03 (dd, J=8.3, 2.2 Hz, 1H), 8.24 (dd, J=8.1, 0.7 Hz, 1H), 8.77 (dd, J=2.2, 0.8 Hz, 1H); MS (DCI/NH$_3$) m/z 422 (M+H)$^+$.

Example 76

(R)—N-methyl-2-(2-(3-(piperidin-1-yl)pyrrolidin-1-yl)benzo[d]thiazol-6-yl)thiazole-5-carboxamide

Example 76A

2-chloro-N-methylthiazole-5-carboxamide

The title compound was prepared by the methods of Example 69A and Example 69B, substituting 2-bromo-5-thiazolecarboxylic acid for 6-bromo-2-pyridinecarboxylic acid. $^1$H NMR (300 MHz, CDCl$_3$) δ ppm 3.00 (d, J=4.7 Hz, 3H), 6.00 (bs, 1H), 7.85 (s, 1H); MS (DCI/NH$_3$) m/z 177 (M+H)$^+$.

Example 76B

(R)—N-methyl-2-(2-(3-(piperidin-1-yl)pyrrolidin-1-yl)benzo[d]thiazol-6-yl)thiazole-5-carboxamide The title compound was prepared by the method of Example 66, substituting 2-chloro-N-methylthiazole-5-carboxamide (Example 76A) for methyl 6-bromo-2-pyridinecarboxylate and substituting isopropyl alcohol for tert-butanol. Instead of HPLC purification, the residue was chromatographed on silica gel eluting with a gradient of 2-10% (9:1 methanol:ammonium hydroxide) in $CH_2Cl_2$ and then rechromatographed on silica gel eluting with a gradient of 22:1:1 to 4:1:1 ethyl acetate:$HCO_2H$:$H_2O$. $^1H$ NMR (300 MHz, $CDCl_3$) δ ppm 1.43-1.53 (m, 2H), 1.58-1.68 (m, 4H), 1.95-2.11 (m, 1H), 2.26-2.37 (m, 1H), 2.39-2.58 (m, 4H), 2.96-3.08 (m, 1H), 3.03 (d, J=5.1 Hz, 3H), 3.45 (t, J=9.3 Hz, 1H), 3.51-3.63 (m, 1H), 3.73-3.93 (m, 2H), 5.89-5.97 (m, 1H), 7.58 (d, J=8.5 Hz, 1H), 7.85 (dd, J=8.5, 1.7 Hz, 1H), 8.10 (s, 1H), 8.26 (d, J=1.7 Hz, 1H); MS (DCI/$NH_3$) m/z 428 $(M+H)^+$.

Example 77

(R)—N-methyl-5-(2-(3-(piperidin-1-yl)pyrrolidin-1-yl)benzo[d]thiazol-6-yl)nicotinamide Example 77A 5-bromo-N-methylnicotinamide The title compound was prepared by the methods of Example 69A and Example 69B, substituting 5-bromonicotinic acid for 6-bromo-2-pyridinecarboxylic acid. $^1H$ NMR (300 MHz, $CDCl_3$) δ ppm 3.05 (d, J=5.1 Hz, 3H), 6.17 (s, 1H), 8.27 (t, J=2.2 Hz, 1H), 8.79 d, J=2.4 Hz, 1H), 8.85 (d, J=2.0 Hz, 1H); MS (DCI/$NH_3$) m/z 215 $(M+H)^+$.

Example 77B (R)—N-methyl-5-(2-(3-(piperidin-1-yl)pyrrolidin-1-yl)benzo[d]thiazol-6-yl)nicotinamide The title compound was prepared by the method of Example 66 substituting 5-bromo-N-methylnicotinamide for methyl 6-bromo-2-pyridinecarboxylate and substituting isopropyl alcohol for tert-butanol. Instead of HPLC purification, the residue was chromatographed on silica gel eluting with a gradient of 2-10% (9:1 methanol:ammonium hydroxide) in $CH_2Cl_2$ and then rechromatographed on silica gel eluting with a gradient of 22:1:1 to 4:1:1 ethyl acetate:$HCO_2H$:$H_2O$. $^1H$ NMR (300 MHz, $CDCl_3$) δ ppm 1.43-1.53 (m, 2H), 1.58-1.69 (m, 4H), 1.96-2.11 (m, 1H), 2.26-2.38 (m, 1H), 2.41-2.59 (m, 4H), 2.96-3.10 (m, 1H), 3.07 (d, J=4.7 Hz, 3H), 3.46 (t, J=9.2 Hz, 1H), 3.58 (dt, J=10.2, 7.1 Hz, 1H), 3.74-3.94 (m, 2H), 6.20-6.28 (m, 1H), 7.55 (dd, J=8.5, 2.0 Hz, 1H), 7.66 (d, J=8.5 Hz, 1H), 7.85 (d, J=2.0 Hz, 1H), 8.31 (t, J=2.2 Hz, 1H), 8.86 (d, J=2.0 Hz, 1H), 8.96 (d, J=2.4 Hz, 1H); MS (DCI/$NH_3$) m/z 422 $(M+H)^+$.

Example 78

Alternative Preparation of (R)—N-methyl-6-(2-(3-(piperidin-1-yl)pyrrolidin-1-yl)benzo[d]thiazol-6-yloxy)nicotinamide A mixture of (R)-2-(3-(piperidin-1-yl)pyrrolidin-1-yl)benzo[d]thiazol-6-ol (Example 47, 20 mg, 0.066 mmol), 6-chloro-N-methylnicotinamide (Example 71A, 11 mg, 0.066 mmol) and $K_2CO_3$ (27 mg, 0.20 mmol) in N,N-dimethylformamide (0.25 mL) was heated to 100° C. for 1 hour, cooled, diluted with $CH_2Cl_2$, filtered, and concentrated. The residue was purified by HPLC as described in Example 66. The product was further purified by chromatography on silica gel eluting with a gradient of 2 to 10% (9:1 methanol:ammonium hydroxide) in $CH_2Cl_2$ to provide the title compound. $^1H$ NMR (300 MHz, $CDCl_3$) δ ppm 1.44-1.53 (m, 2H), 1.59-1.67 (m, 4H), 1.94-2.10 (m, 1H), 2.24-2.34 (m, 1H), 2.39-2.57 (m, 4H), 2.95-3.06 (m, 1H), 3.01 (d, J=4.7 Hz, 3H), 3.43 (t, J=9.3 Hz, 1H), 3.48-3.60 (m, 1H), 3.70-3.89 (m, 2H), 6.09-6.18 (m, 1H), 6.92 (dd, J=8.5, 0.7 Hz, 1H), 7.07 (dd, J=8.5, 2.4 Hz, 1H), 7.40 (d, J=2.4 Hz, 1H), 7.58 (d, J=8.8 Hz, 1H), 8.12 (dd, J=8.6, 2.5 Hz, 1H), 8.53 (dd, J=2.7, 0.7 Hz, 1H); MS (DCI/$NH_3$) m/z 438 $(M+H)^+$.

Example 79

(R)—N-methyl-6-(2-(3-(piperidin-1-yl)pyrrolidin-1-yl)benzo[d]thiazol-6-yloxy)picolinamide The title compound was prepared by the method of Example 78, substituting 6-bromo-N-methylpicolinamide (Example 69B) for 6-chloro-N-methylnicotinamide. $^1H$ NMR (300 MHz, $CDCl_3$) δ 1.43-1.53 (m, 2H), 1.59-1.69 (m, 4H), 1.95-2.11 (m, 1H), 2.26-2.37 (m, 1H), 2.40-2.59 (m, 4H), 2.90 (d, J=5.2 Hz, 3H), 2.95-3.07 (m, 1H), 3.44 (t, J=9.1 Hz, 1H), 3.56 (dt, J=10.2, 6.9 Hz, 1H), 3.77 (t, J=9.1 Hz, 1H), 3.83-3.91 (m, 1H), 7.00 (d, J=8.3 Hz, 1H), 7.08 (dd, J=8.7, 2.4 Hz, 1H), 7.39 (d, J=2.4 Hz, 1H), 7.44-7.53 (m, 1H), 7.59 (d, J=8.7 Hz, 1H), 7.81 (t, J=7.7 Hz, 1H), 7.89 (d, J=6.7 Hz, 1H); MS (DCI/$NH_3$) m/z 438 $(M+H)^+$.

Example 80

(R)—N-methyl-2-(2-(3-(piperidin-1-yl)pyrrolidin-1-yl)benzo[d]thiazol-6-yloxy)isonicotinamide The title compound was prepared by the method of Example 78, substituting 2-bromo-N-methylisonicotinamide (Example 70A) for 6-chloro-N-methylnicotinamide. $^1H$ NMR (300 MHz, $CDCl_3$) δ 1.42-1.52 (m, 2H), 1.56-1.67 (m, 4H), 1.93-2.10 (m, 1H), 2.23-2.36 (m, 1H), 2.38-2.59 (m, 4H), 2.94-3.07 (m, 1H), 3.01 (d, J=4.8 Hz, 3H), 3.42 (t, J=9.1 Hz, 1H), 3.54 (dt, J=10.1, 7.1 Hz, 1H), 3.74 (t, J=9.1 Hz, 1H), 3.81-3.89 (m, 1H), 6.24-6.32 (m, 1H), 7.06 (dd, J=8.7, 2.4 Hz, 1H), 7.16 (t, J=0.8 Hz, 1H), 7.25-7.28 (m, 1H), 7.39 (d, J=2.4 Hz, 1H), 7.57 (d, J=8.7 Hz, 1H), 8.28 (d, J=5.2 Hz, 1H); MS (DCI/$NH_3$) m/z 438 $(M+H)^+$.

Example 81

(R)—N-methyl-5-(2-(3-(piperidin-1-yl)pyrrolidin-1-yl)benzo[d]thiazol-6-yloxy)picolinamide The title compound was prepared by the method of Example 78, substituting 5-bromo-N-methylpicolinamide (Example 75A) for 6-chloro-N-methylnicotinamide. $^1H$ NMR (300 MHz, $CDCl_3$) δ ppm 1.44-1.53 (m, 2H), 1.59-1.68 (m, 4H), 1.96-2.11 (m, 1H), 2.26-2.38 (m, 1H), 2.39-2.59 (m, 4H), 2.95-3.08 (m, 1H), 3.02 (d, J=5.1 Hz, 3H), 3.43 (t, J=9.3 Hz, 1H), 3.55 (dt, J=10.3, 7.0 Hz, 1H), 3.76 (t, J=9.0 Hz, 1H), 3.81-3.90 (m, 1H), 7.03 (dd, J=8.8, 2.4 Hz, 1H), 7.29 (dd, J=8.8, 3.1 Hz, 1H), 7.34 (d, J=2.4 Hz, 1H), 7.58 (d, J=8.8 Hz, 1H), 7.81-7.88 (m, 1H), 8.12 (d, J=9.2 Hz, 1H), 8.26 (dd, J=2.7, 0.7 Hz, 1H); MS (DCI/$NH_3$) m/z 438 $(M+H)^+$.

Example 82

(R)—N-methyl-2-(2-(3-(piperidin-1-yl)pyrrolidin-1-yl)benzo[d]thiazol-6-yloxy)thiazole-5-carboxamide The title compound was prepared by the method of Example 78, substituting 2-chloro-N-methylthiazole-5-carboxamide (Example 76A) for 6-chloro-N-methylnicotinamide.

¹H NMR (300 MHz, CDCl₃) δ ppm 1.43-1.52 (m, 2H), 1.58-1.68 (m, 4H), 1.95-2.10 (m, 1H), 2.24-2.37 (m, 1H), 2.40-2.58 (m, 4H), 2.95 (d, J=5.1 Hz, 3H), 2.98-3.08 (m, 1H), 3.43 (t, J=8.8, 8.8 Hz, 1H), 3.54 (dt, J=10.2, 7.1 Hz, 1H), 3.75 (t, J=9.0 Hz, 1H), 3.81-3.89 (m, 1H), 5.91-5.99 (m, 1H), 7.19 (dd, J=8.8, 2.4 Hz, 1H), 7.53 (d, J=2.4 Hz, 1H), 7.57 (d, J=8.1 Hz, 1H), 7.59 (s, 1H); MS (DCI/NH₃) m/z 444 (M+H)⁺.

Example 83

(R)-6-(6-methoxypyridazin-3-yloxy)-2-(3-(piperidin-1-yl)pyrrolidin-1-yl)benzo[d]thiazole A mixture of (R)-2-(3-(piperidin-1-yl)pyrrolidin-1-yl)benzo[d]thiazol-6-ol (Example 47, 40 mg, 0.132 mmol), 3-chloro-6-methoxypyridazine (28.6 mg, 0.198 mmol), palladium(II) acetate (2.96 mg, 0.013 mmol), and potassium phosphate tribasic (84 mg, 0.40 mmol) in toluene (1 mL) was heated at 100° C. over night, cooled, diluted with 1 M NaOH (5 mL) and extracted with CH₂Cl₂ (2×25 mL). The combined CH₂Cl₂ layers were dried (MgSO₄), filtered, concentrated and chromatographed on silica gel eluting with a gradient of 2-10% (9:1 methanol:ammonium hydroxide) in CH₂Cl₂ to provide the title compound. ¹H NMR (300 MHz, CDCl₃) δ ppm 1.43-1.53 (m, 2H), 1.58-1.69 (m, 4H), 1.94-2.09 (m, 1H), 2.25-2.36 (m, 1H), 2.40-2.59 (m, 4H), 2.95-3.07 (m, 1H), 3.42 (t, J=9.2 Hz, 1H), 3.54 (dt, J=10.2, 6.8 Hz, 1H), 3.75 (t, J=8.8 Hz, 1H), 3.81-3.89 (m, 1H), 4.04 (s, 3H), 7.02 (d, J=9.2 Hz, 1H), 7.11 (dd, J=8.5, 2.4 Hz, 1H), 7.13 (d, J=9.5 Hz, 1H), 7.49 (d, J=2.7 Hz, 1H), 7.56 (d, J=8.8 Hz, 1H); MS (DCI/NH₃) m/z 412 (M+H)⁺.

Example 84

(R)-6-(6-methoxypyridin-2-yloxy)-2-(3-(piperidin-1-yl)pyrrolidin-1-yl)benzo[d]thiazole The title compound was prepared by the method of Example 83, substituting bromo-6-methoxypyridine for 3-chloro-6-methoxypyridazine. ¹H NMR (300 MHz, CDCl₃) δ ppm 1.43-1.52 (m, 2H), 1.59-1.70 (m, 4H), 1.94-2.10 (m, 1H), 2.26-2.36 (m, 1H), 2.40-2.58 (m, 4H), 2.94-3.06 (m, 1H), 3.43 (t, 1H), 3.55 (dt, J=10.2, 7.1 Hz, 1H), 3.71-3.79 (m, 1H), 3.81 (s, 3H), 3.83-3.89 (m, 1H), 6.25 (d, J=7.5 Hz, 1H), 6.42 (d, J=7.5 Hz, 1H), 7.10 (dd, J=8.8, 2.4 Hz, 1H), 7.41 (d, J=2.4 Hz, 1H), 7.51 (t, J=7.8 Hz, 1H), 7.56 (d, J=8.5 Hz, 1H); MS (DCI/NH₃) m/z 411 (M+H)⁺.

Example 85

(R)-6-(2-(3-(piperidin-1-yl)pyrrolidin-1-yl)benzo[d]thiazol-6-yloxy)pyridazin-3-ol The title compound was prepared by the method of Example 73, substituting (R)-6-(6-methoxypyridazin-3-yloxy)-2-(3-(piperidin-1-yl)pyrrolidin-1-yl)benzo[d]thiazole (Example 83) in place of (R)-6-(2-methoxypyrimidin-5-yl)-2-(3-(piperidin-1-yl)pyrrolidin-1-yl)benzo[d]thiazole. The product was further purified by chromatography on silica gel eluting with a gradient of 10:1:1 to 4:1:1 ethyl acetate:HCO₂H:H₂O. ¹H NMR (300 MHz, CDCl₃) δ ppm 1.42-1.51 (m, 2H), 1.58-1.68 (m, 4H), 1.94-2.10 (m, 1H), 2.23-2.35 (m, 1H), 2.40-2.57 (m, 4H), 2.95-3.07 (m, 1H), 3.42 (t, 1H), 3.53 (dt, J=10.2, 7.1 Hz, 1H), 3.74 (t, J=8.8 Hz, 1H), 3.84 (dd, J=9.5, 7.5 Hz, 1H), 7.00 (d, J=9.8 Hz, 1H), 7.06 (dd, J=8.8, 2.4 Hz, 1H), 7.19 (d, J=9.8 Hz, 1H), 7.39 (d, J=2.4 Hz, 1H), 7.56 (d, J=8.8 Hz, 1H), 10.11 (bs, 1H); MS (DCI/NH₃) m/z 398 (M+H)⁺.

Example 86

3-[2-((R)-3-piperidin-1-yl-pyrrolidin-1-yl)-benzothiazol-6-yl]-3H-pyrimidin-4-one A solution of (R)-6-bromo-2-(3-(piperidin-1-yl)pyrrolidin-1-yl)benzo[d]thiazole (Example 14, 80 mg, 0.218 mmol), pyrimidin-4(3H)-one (31.5 mg, 0.328 mmol), (1R,2R)—N¹,N²-dimethylcyclohexane-1,2-diamine (31.1 mg, 0.218 mmol), copper (27.8 mg, 0.437 mmol) and copper(I) iodide (8.32 mg, 0.044 mmol) in pyridine (3 ml) was heated in a microwave reactor to 200° C. for 30 minutes. The mixture was diluted with ether (20 mL) and washed with water, a small amount of aqueous NH₄OH and brine. The organic layer was separated and dried with MgSO₄ and concentrated under reduced pressure. The residue obtained was chromatographed on silica gel column eluting with 3% (9:1 methanol:concentrated NH₄OH) in dichloromethane to provide the title compound. ¹H NMR (300 MHz, CDCl₃) δ ppm 1.43-1.52 (m, 2H), 1.58-1.69 (m, 4H), 1.94-2.11 (m, 1H), 2.25-2.37 (m, 1H), 2.39-2.58 (m, 4H), 2.96-3.09 (m, 1H), 3.40-3.63 (m, 2H), 3.72-3.92 (m, 2H), 6.56 (d, J=6.74 Hz, 1H), 7.22 (dd, J=8.72, 2.38 Hz, 1H), 7.62 (d, J=2.38 Hz, 1H), 7.65 (d, J=8.33 Hz, 1H), 7.94 (d, J=6.74 Hz, 1H), 8.20 (s, 1H); MS (DCI/NH₃) m/z 382 (M+H)⁺.

Example 87

6-methyl-3-[2-((R)-3-piperidin-1-yl-pyrrolidin-1-yl)-benzothiazol-6-yl]-3H-pyrimidin-4-one The title compound was prepared using the procedures described in Example 86 substituting 6-methylpyrimidin-4(3H)-one for pyrimidin-4(3H)-one. ¹H NMR (300 MHz, CDCl₃) δ ppm 1.45-1.52 (m, 2H), 1.59-1.68 (m, 4H), 1.97-2.12 (m, 1H), 2.23-2.33 (m, 1H), 2.34-2.37 (m, 3H), 2.40-2.58 (m, 4H), 2.96-3.09 (m, 1H), 3.38-3.62 (m, 2H), 3.71-3.92 (m, 2H), 6.39 (s, 1H), 7.21 (dd, J=8.48, 2.37 Hz, 1H), 7.60 (d, J=2.03 Hz, 1H), 7.64 (d, J=8.81 Hz, 1H), 8.13 (s, 1H); MS (DCI/NH₃) m/z 396 (M+H)⁺.

Example 88

4-[2-((R)-3-piperidin-1-yl-pyrrolidin-1-yl)-benzothiazol-6-yl]-morpholin-3-one

The title compound was prepared using the procedures described in Example 86 substituting morpholin-3-one for pyrimidin-4(3H)-one. ¹H NMR (300 MHz, CDCl₃) δ ppm 1.43-1.53 (m, 2H), 1.59-1.68 (m, 4H), 1.96-2.10 (m, 1H), 2.23-2.36 (m, 1H), 2.39-2.58 (m, 4H), 2.95-3.08 (m, 1H), 3.38-3.60 (m, 2H), 3.70-3.80 (m, 3H), 3.81-3.89 (m, 1H), 4.01-4.06 (m, 2H), 4.33-4.37 (m, 2H), 7.18 (dd, J=8.48, 2.03 Hz, 1H), 7.55-7.60 (m, 2H); MS (DCI/NH₃) m/z 387 (M+H)⁺.

Example 89

2-methyl-3-[2-((R)-3-piperidin-1-yl-pyrrolidin-1-yl)-benzothiazol-6-yl]-3H-quinazolin-4-one Example 89A (R)-2-(3-(piperidin-1-yl)pyrrolidin-1-yl)benzo[d]thiazol-6-amine A solution of (R)-6-bromo-2-(3-(piperidin-1-yl)pyrrolidin-1-yl)benzo[d]thiazole (Example 14, 100 mg, 0.273 mmol), tri-tert-butylphosphine (66.3 mg, 0.033 mmol), tris (dibenxylideneacetone)dipalladium(0) (12.5 mg, 0.014 mmol) and lithium bis(trimethylsilyl)amide (63.9 mg, 0.382 mmol) in toluene (1 ml) was heated in a microwave reactor to 160° C. for 30 minutes. The mixture was treated with HCl (1 N, 1 mL) and stirred for 5 minutes. It was then basified with NaOH (10%), diluted with ether and partitioned. The organic was separated, dried with $MgSO_4$ and concentrated under reduced pressure. The residue was chromatographed on silica gel column eluting with 2% (9:1 methanol:concentrated $NH_4OH$) in dichloromethane to provide the title compound. $^1H$ NMR (300 MHz, $CDCl_3$) δ ppm 1.43-1.52 (m, 2H), 1.58-1.68 (m, 4H), 1.91-2.07 (m, 1H), 2.20-2.34 (m, 1H), 2.39-2.56 (m, 4H), 2.90-3.05 (m, 1H), 3.39 (t, J=9.12 Hz, 1H), 3.46-3.58 (m, 3H), 3.66-3.76 (m, 1H), 3.82 (dd, J=9.52, 7.54 Hz, 1H), 6.69 (dd, J=8.33, 2.38 Hz, 1H), 6.96 (d, J=1.98 Hz, 1H), 7.39 (d, J=8.33 Hz, 1H); MS (DCI/$NH_3$) m/z 303 (M+H)+.

Example 89B 2-methyl-4H-benzo[d][1,3]oxazin-4-one

A solution of 2-aminobenzoic acid (300mg, 1.46 mmol) in acetic anhydride (2 mL) was heated to 130° C. for 16 hours. The mixture was concentrated under reduced pressure. The residue was chromatographed on silica gel eluting with 20% ethyl acetate in hexanes to provide the title compound. $^1H$ NMR (300 MHz, $CDCl_3$) δ ppm 2.44-2.52 (m, 3H), 7.44-7.60 (m, 2H), 7.76-7.87 (m, 1H), 8.20 (dd, J=7.97, 1.53 Hz, 1H); MS (DCI/$NH_3$) m/z 162 (M+H)+.

Example 89C 2-methyl-3-[2-((R)-3-piperidin-1-yl-pyrrolidin-1-yl)-benzothiazol-6-yl]-3H-quinazolin-4-one A solution of (R)-2-(3-(piperidin-1-yl)pyrrolidin-1-yl)benzo[d]thiazol-6-amine (Example 89A, 27mg, 0.089 mmol) and 2-methyl-4H-benzo[d][1,3]oxazin-4-one (Example 89B, 14.39 mg, 0.089 mmol) in acetic acid (1 mL) was heated in a microwave reactor to 160° C. for 20 minutes. The mixture was concentrated under reduced pressure and chromatographed on silica gel column eluting with 2% (9:1 methanol:concentrated $NH_4OH$) in dichloromethane to provide the title compound. $^1H$ NMR (300 MHz, $CDCl_3$) δ ppm 1.45-1.53 (m, 2H), 1.58-1.70 (m, 4H), 1.98-2.12 (m, 1H), 2.26-2.30 (m, J=1.36 Hz, 3H), 2.29-2.37 (m, 1H), 2.42-2.58 (m, 4H), 2.94-3.10 (m, J=8.48 Hz, 1H), 3.39-3.51 (m, 1H), 3.52-3.64 (m, 1H), 3.71-3.94 (m, 2H), 7.14 (dd, 1H), 7.43-7.51 (m, 2H), 7.66-7.72 (m, 2H), 7.74-7.81 (m, 1H), 8.24-8.31 (m, 1H); MS (DCI/$NH_3$) m/z 387 (M+H)+.

Example 90

2,8-dimethyl-3-[2-((R)-3-piperidin-1-yl-pyrrolidin-1-yl)-benzothiazol-6-yl]-3H-quinazolin-4-one Example 90A 2,8-dimethyl-4H-benzo[d][1,3]oxazin-4-one The title compound was prepared using the procedures described in Example 89B substituting 2-amino-3-methylbenzoic acid for 2-aminobenzoic acid.

Example 90B 2,8-Dimethyl-3-[2-((R)-3-piperidin-1-yl-pyrrolidin-1-yl)-benzothiazol-6-yl]-3H-quinazolin-4-one The title compound was prepared using the procedures described in Example 89C substituting 2,8-dimethyl-4H-benzo[d][1,3]oxazin-4-one for 2-methyl-4H-benzo[d][1,3]oxazin-4-one. $^1H$ NMR (300 MHz, $CDCl_3$) δ ppm 1.44-1.53 (m, 2H), 1.59-1.69 (m, 4H), 1.95-2.12 (m, 1H), 2.27-2.30 (m, 3H), 2.30-2.37 (m, 1H), 2.42-2.58 (m, 4H), 2.64 (s, 3H), 2.97-3.10 (m, 1H), 3.40-3.51 (m, 1H), 3.53-3.63 (m, 1H), 3.73-3.93 (m, 2H), 7.13 (dd, J=8.48, 2.03 Hz, 1H), 7.35 (d, J=7.80 Hz, 1H), 7.47 (d, J=2.37 Hz, 1H), 7.57-7.64 (m, 1H), 7.69 (d, J=8.48 Hz, 1H), 8.13 (d, J=8.14 Hz, 1H); MS (DCI/$NH_3$) m/z 460 (M+H)+.

Example 91

2-Methyl-3-[2-((R)-3-piperidin-1-yl-pyrrolidin-1-yl)-benzothiazol-6-yl]-8-trifluoromethyl-3H-quinazolin-4-one Example 91A 2-methyl-8-(trifluoromethyl)-4H-benzo[d][1,3]oxazin-4-one The title compound was prepared using the procedures described in Example 89B substituting 2-amino-3-(trifluoromethyl)benzoic acid for 2-aminobenzoic acid.

Example 91B 2-methyl-3-[2-((R)-3-piperidin-1-yl-pyrrolidin-1-yl)-benzothiazol-6-yl]-8-trifluoromethyl-3H-quinazolin-4-one The title compound was prepared using the procedures described in Example 89C substituting 2-methyl-8-(trifluoromethyl)-4H-benzo[d][1,3]oxazin-4-one (Example 91A) for 2-methyl-4H-benzo[d][1,3]oxazin-4-one. $^1H$ NMR (300 MHz, $CDCl_3$) δ ppm 1.45-1.53 (m, 2H), 1.62-1.71 (m, 4H), 1.99-2.13 (m, 1H), 2.30-2.35 (m, J=1.36 Hz, 3H), 2.34-2.38 (m, 1H), 2.41-2.62 (m, 4H), 2.97-3.13 (m, 1H), 3.53 (s, 1H), 3.54-3.64 (m, 1H), 3.79 (d, J=9.15 Hz, 2H), 7.13 (dd, J=8.48, 2.03 Hz, 1H), 7.47 (d, J=2.03 Hz, 1H), 7.50-7.55 (m, 1H), 7.70 (d, J=8.48 Hz, 1H), 8.07 (d, J=6.78 Hz, 1H), 8.47 (d, J=7.80 Hz, 1H); MS (DCI/$NH_3$) m/z 514 (M+H)+.

Example 92

(R)—N,N-dimethyl-2-(3-(piperidin-1-yl)pyrrolidin-1-yl)benzo[d]oxazole-6-carboxamide Example 92A Methyl 2-thioxo-2,3-dihydrobenzo[d]oxazole-6-carboxylate Methyl 4-amino-3-hydroxybenzoate (16.7 g, 100 mmol, Chemical Abstracts number 63435-16-5, available from Alfa Chemicals, 26 Parkridge Rd, Ward Hill, Mass. 01835-8099) and potassium O-ethyl carbonodithioate (20.8 g, 130 mmol) were combined in pyridine (100 mL) and refluxed for two hours. The reaction mixture was cooled to ambient temperature and the product was filtered, washed with water, and dried in a vacuum oven overnight at 45° C. to afford the title compound. ¹H NMR (300 MHz, DMSO-d₆) δ ppm 3.87 (d, 3 H) 7.34 (d, J=8.33 Hz, 1 H) 7.92 (d, J=1.59 Hz, 1 H) 7.97 (dd, J=12.69, 1.59 Hz, 1 H); MS (ESI–)m/z 207.9 (M–H)⁻.

Example 92B 2-thioxo-2,3-dihydrobenzo[d]oxazole-6-carboxylic acid

Methyl 2-thioxo-2,3-dihydrobenzo[d]oxazole-6-carboxylate (Example 92A, 470 mg, 2.25 mmol) and potassium hydroxide (1.26 g, 22.5 mmol) were combined in a 11.6 mL mixture of tetrahydrofuran, methanol, and water (10:1:1) and stirred at 45° C. for three hours. The reaction mixture was diluted with ethyl acetate, washed with a 1 N aqueous solution of hydrochloric acid, dried over sodium sulfate, and concentrated under reduced pressure to afford the title compound. MS (ESI–) m/z 193.8 (M–H)⁻.

Example 92C

N,N-dimethyl-2-thioxo-2,3-dihydrobenzo[d]oxazole-6-carboxamide

2-Thioxo-2,3-dihydrobenzo[d]oxazole-6-carboxylic acid (Example 92B, 394 mg, 2.02 mmol), dimethylamine hydrochloride (181 mg, 2.22 mmol), and O-(7-azabenzotriazol-1-yl)-N,N,N',N'-tetramethyluronium hexafluorophosphate (844 mg, 2.22 mmol) were combined in tetrahydrofuran (20 mL) and dimethylformamide (2 mL). Diisopropylethylamine (1.5 mL, 8.68 mmol) was added and the mixture was stirred at ambient temperature overnight. The mixture was diluted with dichloromethane, washed with a 1 N aqueous solution of hydrochloric acid, and absorbed on silica gel. The crude mixture was purified with silica gel chromatography eluting with a gradient of methanol in dichloromethane (2-20%) to afford the title compound. MS (ESI+) m/z 222.9 (M+H)⁺.

Example 92D (R)—N,N-dimethyl-2-(3-(piperidin-1-yl)pyrrolidin-1-yl)benzo[d]oxazole-6-carboxamide N,N-Dimethyl-2-thioxo-2,3-dihydrobenzo[d]oxazole-6-carboxamide (Example 92C, 44 mg, 0.119 mmol) and (R)-1-(pyrrolidin-3-yl)piperidine dihydrochloride (Reference Example 5c, 54 mg, 0.238 mmol) were combined in xylene (1 mL) and heated to 150° C. for 30 minutes. The mixture was diluted with dichloromethane, washed with water, and the organic layer was absorbed on silica gel. The crude mixture was purified by silica gel chromatography eluting with a gradient of methanol in dichloromethane (2-20%) to afford the title compound. ¹H NMR (300 MHz, CDCl₃) δ ppm 1.43-1.53 (m, 2 H) 1.59-1.70 (m, 4 H) 1.91-2.07 (m, 1 H) 2.23-2.35 (m, 1 H) 2.40-2.62 (m, 4 H) 2.93-3.13 (m, 7 H) 3.41-3.51 (m, 1 H) 3.55-3.66 (m, 1 H) 3.80-3.90 (m, 1 H) 3.96 (dd, J=10.00, 7.29 Hz, 1 H) 7.22-7.28 (m, 1 H) 7.30-7.35 (m, 1 H) 7.37-7.40 (m, 1 H); MS (ESI+) m/z 343.0 (M+H)⁺.

Example 93

(R)—N-ethyl-2-(3-(piperidin-1-yl)pyrrolidin-1-yl)benzo[d]oxazole-6-carboxamide

Example 93A

N-ethyl-2-thioxo-2,3-dihydrobenzo[d]oxazole-6-carboxamide

2-Thioxo-2,3-dihydrobenzo[d]oxazole-6-carboxylic acid (Example 92B, 424 mg, 2.17 mmol), ethanamine hydrochloride (266 mg, 3.26 mmol), and O-(7-azabenzotriazol-1-yl)-N,N,N',N'-tetramethyluronium hexafluorophosphate (991 mg, 2.61 mmol) were combined in tetrahydrofuran (5 mL). Triethylamine (1.4 mL, 977 mmol) was added and the mixture was stirred at room temperature overnight. The reaction mixture was diluted with dichloromethane, washed with a 1 N aqueous solution of hydrochloric acid, and absorbed on silica gel. The crude mixture was purified with silica gel chromatography eluting with a gradient of methanol in dichloromethane (2-20%). The chromatographed material was triturated with dichloromethane to afford the title compound. MS (ESI–) m/z 220.9 (M–H)⁻.

Example 93B (R)—N-ethyl-2-(3-(piperidin-1-yl)pyrrolidin-1-yl)benzo[d]oxazole-6-carboxamide N-Ethyl-2-thioxo-2,3-dihydrobenzo[d]oxazole-6-carboxamide (Example 93A, 56 mg, 0.253 mmol) and (R)-1-(pyrrolidin-3-yl)piperidine (Reference Example 5c, 39 mg, 253 mmol) were combined in toluene (1 mL) and heated to 130° C. for one hour. The reaction mixture was diluted with dichloromethane, washed with a 1 N aqueous solution of sodium hydroxide, and the organic layer was absorbed on silica gel. The crude mixture was purified using silica gel chromatography (12 g column) eluting with a gradient of methanol/dichloromethane (1-18%) to afford the title compound. ¹H NMR (300 MHz, CDCl₃) δ ppm 1.26 (t, J=7.34 Hz, 3 H) 1.40-1.53 (m, 2 H) 1.59-1.69 (m, 4 H) 1.89-2.07 (m, 1 H) 2.22-2.35 (m, 1 H) 2.36-2.60 (m, 4 H) 2.89-3.03 (m, 1 H) 3.42-3.58 (m, 3 H) 3.59-3.68 (m, 1 H) 3.82-3.92 (m, 1 H) 3.97 (dd, J=10.11, 7.34 Hz, 1 H) 5.98-6.11 (m, 1 H) 7.31 (d, J=8.33 Hz, 1 H) 7.53 (dd, J=8.33, 1.59 Hz, 1 H) 7.78 (d, J=1.59 Hz, 1 H); MS (ESI+) m/z 343.1 (M+H)⁺.

Example 94 methyl 2-(1,4'-bipiperidin-1'-yl)benzo[d]oxazole-5-carboxylate

Example 94A methyl 2-thioxo-2,3-dihydrobenzo[d]oxazole-5-carboxylate

Methyl 3-amino-4-hydroxybenzoate (5.09 g, 30.4 mmol) and potassium O-ethyl carbonodithioate (6.35 g, 39.6 mmol) were combined in pyridine (50 mL) and heated to reflux for two hours. The reaction mixture was cooled to ambient temperature. The mixture was filtered, washed with a 1 N aqueous hydrochloric acid solution, and dried on a vacuum filter overnight to afford the title compound. ¹H NMR (300 MHz, DMSO-d₆) δ ppm 3.88 (s, 3 H) 7.63 (d, J=8.48 Hz, 1 H) 7.69 (d, J=1.70 Hz, 1 H) 7.89 (dd, J=8.82, 1.70 Hz, 1 H); MS (ESI–) m/z 207.87 (M–H)⁻.

Example 94B methyl 2-(1,4'-bipiperidin-1'-yl)benzo[d]oxazole-5-carboxylate

Methyl 2-thioxo-2,3-dihydrobenzo[d]oxazole-5-carboxylate (Example 94A, 300 mg, 1.43 mmol) and 1,4'-bipiperidine (483 mg, 2.87 mmol) were combined in xylene (2 mL). The mixture was heated in a microwave to 130° C. for 20 minutes. The reaction mixture was diluted with dichloromethane, washed with water, and the organic layer was absorbed on silica gel. The crude mixture was purified using silica gel chromatography (40 g column) eluting with a gradient of methanol/dichloromethane (3-18%) to afford the title compound. $^1$H NMR (300 MHz, CDCl$_3$) δ ppm 1.38-1.50 (m, 2 H) 1.54-1.72 (m, 5 H) 1.95 (d, J=12.89 Hz, 2 H) 2.46-2.59 (m, 6 H) 3.03-3.16 (m, 2 H) 3.91 (s, 3 H) 4.32-4.36 (m, 1 H) 4.36-4.41 (m, 1 H) 7.25 (d, 1 H) 7.79 (dd, J=8.48, 1.70 Hz, 1 H) 8.00 (d, J=1.70 Hz, 1 H); MS (ESI+) m/z 344.3 (M+H)$^+$.

Example 95

2-(1,4'-bipiperidin-1'-yl)-N-ethylbenzo[d]oxazole-5-carboxamide

Example 95A 2-(1,4'-bipiperidin-1'-yl)benzo[d]oxazole-5-carboxylic acid

Methyl 2-(1,4'-bipiperidin-1'-yl)benzo[d]oxazole-5-carboxylate (Example 94, 220 mg, 0.641 mmol) and potassium hydroxide were combined in a mixture of tetrahydrofuran, methanol, and water (9:1:1, 7 mL) and stirred at 40° C. overnight. The mixture was neutralized with concentrated hydrochloric acid, concentrated under reduced pressure, and triturated with chloroform to afford the title compound. MS (ESI+) m/z 330.2 (M+H)$^+$.

Example 95B 2-(1,4'-bipiperidin-1'-yl)-N-ethylbenzo[d]oxazole-5-carboxamide 2-(1,4'-Bipiperidin-1'-yl)benzo[d]oxazole-5-carboxylic acid (Example 95A, 40 mg, 0.121 mmol), ethanamine hydrochloride (15 mg, 0.182 mmol), and O-(7-azabenzotriazol-1-yl)-N,N,N',N'-tetramethyluronium hexafluorophosphate (55 mg, 0.146 mmol) were combined in tetrahydrofuran (3 mL). Triethylamine (51 µL, 0.364 mmol) was added and the mixture was stirred at 45° C. overnight. The reaction mixture was diluted with dichloromethane, washed with a 1 N aqueous solution of sodium hydroxide, and absorbed on silica gel. The crude mixture was purified with silica gel chromatography eluting with a gradient of methanol in dichloromethane (3-18%) to afford the title compound. $^1$H NMR (300 MHz, CDCl$_3$) δ ppm 1.25 (t, J=7.29 Hz, 3 H) 1.39-1.51 (m, 2 H) 1.52-1.75 (m, 7 H) 1.96 (d, J=12.89 Hz, 2 H) 2.44-2.61 (m, J=4.75 Hz, 4 H) 3.01-3.15 (m, 2 H) 3.43-3.58 (m, 2 H) 4.29-4.41 (m, 2 H) 6.01 (s, 1 H) 7.21-7.28 (m, 1 H) 7.50 (dd, J=8.31, 1.86 Hz, 1 H) 7.66 (d, J=1.36 Hz, 1 H); MS (ESI+) m/z 357.0 (M+H)$^+$.

Determination of Biological Activity

To determine the effectiveness of representative compounds of this invention as histamine-3 receptor ligands (H$_3$ receptor ligands), the following tests were conducted according to previously described methods (see European Journal of Pharmacology, 188:219-227 (1990); Journal of Pharmacology and Experimental Therapeutics, 275:598-604 (1995); Journal of Pharmacology and Experimental Therapeutics, 276:1009-1015 (1996); and Biochemical Pharmacology, 22:3099-3108 (1973)).

The rat H$_3$ receptor was cloned and expressed in cells, and competition binding assays carried out, according to methods previously described (see Esbenshade, et al. Journal of Pharmacology and Experimental Therapeutics, vol. 313:165-175, 2005; Esbenshade et al., Biochemical Pharmacology 68 (2004) 933-945; Krueger, et al. Journal of Pharmacology and Experimental Therapeutics, vol. 314:271-281, 2005). Membranes were prepared from C6 or HEK293 cells, expressing the rat histamine H$_3$ receptor, by homogenization on ice in TE buffer (50 mM Tris-HCl buffer, pH 7.4, containing 5 mM EDTA), 1 mM benzamidine, 2 µg/ml aprotinin, 1 µg/ml leupeptin, and 1 µg/ml pepstatin. The homogenate was centrifuged at 40,000 g for 20 minutes at 4° C. This step was repeated, and the resulting pellet was resuspended in TE buffer. Aliquots were frozen at −70° C. until needed. On the day of assay, membranes were thawed and diluted with TE buffer.

Membrane preparations were incubated with [$^3$H]—N-α-methylhistamine (0.5-1.0 nM) in the presence or absence of increasing concentrations of ligands for H$_3$ receptor competition binding. The binding incubations were conducted in a final volume of 0.5 ml TE buffer at 25° C. and were terminated after 30 minutes. Thioperamide (30 µM) was used to define non-specific binding. All binding reactions were terminated by filtration under vacuum onto polyethylenimine (0.3%) presoaked Unifilters (Perkin Elmer Life Sciences) or Whatman GF/B filters followed by three brief washes with 2 ml of ice-cold TE buffer. Bound radiolabel was determined by liquid scintillation counting. For all of the radioligand competition binding assays, IC$_{50}$ values and Hill slopes were determined by Hill transformation of the data and pK$_i$ values were determined by the Cheng-Prusoff equation. The general method for determining potency in competition binding assays is also suitable for determining the potency of compounds at the human H$_3$ receptor, as specifically described in Esbenshade, et al. Journal of Pharmacology and Experimental Therapeutics, vol. 313:165-175, 2005.

Generally, representative compounds of the invention demonstrated binding affinities at the histamine H$_3$ receptor range from about 0.1 nM to about 3,100 nM. Preferred compounds of the invention bound to histamine-3 receptors with binding affinities from about 0.1 nM to about 500 nM. More preferred compounds of the invention bound to histamine-3 receptors with binding affinities from about 0.1 nM to about 100 nM.

Compounds of the invention are histamine-3 receptor ligands that modulate function of the histamine-3 receptor by altering the activity of the receptor. These compounds may be inverse agonists that inhibit the basal activity of the receptor or they may be antagonists that completely block the action of receptor-activating agonists. These compounds may also be partial agonists that partially block or partially activate the histamine-3 receptor or they may be agonists that activate the receptor.

In addition to the utility of in vitro methods for characterizing the potency of compounds at the H$_3$ receptor, there are animal disease models available which demonstrate the utility of compounds. There are a number of methods to test the activity of compounds in different pain models that are well known to those skilled in the art. Pain states are exhibited by humans and other animals, and there are numerous animal models of pain; a review of animal models of pain is found in Joshi and Honore, Expert Opinion in Drug Discovery (2004) 1, pp. 323-334. A description of the formalin test in rats, neuropathic pain models in rats, general descriptions of methods of testing and descriptions of pain models are found in the book 'Drug Discovery and Evaluation, 2$^{nd}$ edition' (H. Gerhard Vogel, editor; Springer-Verlag, New York, 2002; pp. 702-706).

Determination of Analgesic Effect Against Neuropathic Pain

Animals were prepared for testing, by use of a surgical procedure that induces neuropathic pain in one paw. Male Sprague Dawley rats were purchased from Charles River (Portage, Mich.). Prior to surgery, animals were housed in groups and maintained in a temperature-regulated environment. Following nerve ligation surgery, animals were housed in groups, and had access to food and water ad libitum.

The L5 and L6 spinal nerves of anesthetized rats were tightly ligated in a manner described previously (see Kim and Chung, Pain (1992) vol. 50 pp. 355-363). An incision was made on the dorsal portion of the hip and the muscle was blunt-dissected to reveal the spinal processes. The L6 transverse process was removed, and the left side L5 and L6 spinal nerves were tightly ligated with 5.0 braided silk suture. The wound was cleaned, the membrane sewn with 4.0 dissolvable Vicryl suture and the skin closed with wound clips. The paw affected by the surgical procedure (the left paw) develops an allodynic response, a hypersensitivity to mechanical and other stimuli; neuropathic pain is assessed as an increased sensitivity in the surgically affected (left) allodynic paw compared to the control paw on the right side, and measured by comparing the response of the (left side) allodynic paw to the response of the unaffected right side control paw.

For the assessment of neuropathic pain, mechanical allodynia in the affected paw of animals that had undergone spinal nerve ligation was evaluated using testing with von Frey filaments. As described previously by S. R. Chaplan, et al ("Quantitative assessment of tactile allodynia in the rat paw" J. Neurosci. Meth. (1994) vol. 53 pp. 55-63), two weeks following surgery rats were acclimated to a testing box constructed of plexiglass with a wire mesh floor which allowed access to the plantar surface of the animal's hindpaws. Using an Up-Down method (Dixon, Annual Rev. Pharmacol. Toxicol. (1980) vol. 20, pp. 441-462; Chaplan et al. "Quantitative assessment of tactile allodynia in the rat paw" J. Neuroscience Methods (1994) vol. 53 pp. 55-63), von Frey filaments of increasing stiffness were applied to the plantar surface of the hindpaws and the withdrawal response of the animals was observed; for the surgically affected paw with neuropathic pain (the left side paw) the baseline level of allodynia has a withdrawal threshold of $\leq 4$ g of pressure. By comparison, for the control paw without allodynia (in this case the right side paw), the typical withdrawal pressure is around 15 g. Representative compounds of the invention, administered intraperitoneally 30 minutes before testing, are able to reduce the symptoms of neuropathic pain and induce a dose-dependent increase in the withdrawal threshold for allodynic (left side) limb, up to a maximum effect of 15 g. The efficacy of the compound in reducing neuropathic pain at different doses is determined by comparing response in the surgery-affected paw versus the response in the control paw. This is expressed as the MPE (maximum percent effect), or 100 times the withdrawal threshold of the allodynic (left side) divided by the withdrawal threshold of the control (right side). In this model, the compound of Example 20 ((R)-2-(2-(3-(piperidin-1-yl)pyrrolidin-1-yl)benzo[d]thiazol-6-yl)pyridazin-3(2H)-one) was very effective, producing a 40% reduction (p<0.01) in the withdrawal threshold at a dose of 3 mg/kg, administered by intraperitoneal injection. No complicating adverse effects were observed.

Activity in an Osteoarthritis Model

Unilateral knee joint osteoarthritis was induced in rats by a single intra-articular (i.a.) injection of sodium monoiodoacetate (MIA) (Sigma-Aldrich, St. Louis, Mo.) (3 mg in 50 µl sterile isotonic saline) into the right knee joint cavity under light (1-3%) isoflurane anesthesia.

Pain behavior was assessed by measurement of hind limb grip force (GF) in adult osteoarthritic rats. Following the unilateral injection of MIA (male Sprague Dawley, 325-350 g, tested at 20 days following MIA injection), a behavioral measure of activity-induced pain was carried out. Measurements of the peak hind limb grip force were conducted by recording the maximum compressive force ($CF_{max}$), in grams of force, exerted on a hind limb strain gauge setup, in a commercially available grip force measurement system (Columbus Instruments, Columbus, Ohio).

During testing, each rat was gently restrained by grasping it around its rib cage and then allowed to grasp the wire mesh frame attached to the strain gauge. The experimenter then moved the animal in a rostral-to-caudal direction until the grip was broken. Each rat was sequentially tested twice at approximately 2-3 min interval to obtain a raw mean grip force ($CF_{max}$). This raw mean grip force data was in turn converted to a maximum hindlimb cumulative compressive force ($CF_{max}$), as the grams of force/kg of body weight, for each animal.

For evaluating the compound effects, the hind limb grip force was conducted 20 days following the intra-articular injection of MIA. A group of age-matched naïve (not injected with MIA) animals was added as a comparator to the drug-dosed groups. The vehicle control response for each group of MIA-treated animals was defined as the 0% response (0% effect), whereas the naïve control group was defined as the normal response and as 100% effect. The % effects for each dose group was expressed as % return of reponse to normalcy, compared to the naïve group. That is, the % effect=(Treatment $CF_{max}$–Vehicle $CF_{max}$)/Vehicle $CF_{max}$×100). All experiments evaluating drug effects in this model were conducted in a randomized blinded fashion. In this model, the compound of Example 20, ((R)-2-(2-(3-(piperidin-1-yl)pyrrolidin-1-yl)benzo[d]thiazol-6-yl)pyridazin-3(2H)-one), was very effective, producing a 69% reduction (p<0.01) in the withdrawal threshold at a dose of 3 mg/kg, and a 49% reduction (p<0.01) in the withdrawal threshold at a dose of 1 mg/kg, administered by intraperitoneal injection. No complicating adverse effects were observed.

The ability of compounds to treat diseases with deficits in memory and cognition such as Alzheimer's disease, dementia, age-related cognitive impairment, schizophrenia, and cognitive deficits of schizophrenia can be assessed in animal models. One model assessing the capability of a compound to enhance memory is the single trial 24-hour inhibitory avoidance model, described in Tietje et al. (Tietje, K. R., et al. "Preclinical Characterization of A-582941: A Novel α7 Neuronal Nicotinic Receptor Agonist with Broad Spectrum Cognition-Enhancing Properties" CNS Neuroscience and Therapeutics 2008 v14 pp. 65-82). In this mouse model, at a dose of 0.03 mg/kg, administered by intraperitoneal injection, the compound of Example 20 ((R)-2-(2-(3-(piperidin-1-yl)pyrrolidin-1-yl)benzo[d]thiazol-6-yl)pyridazin-3(2H)-one) achieved full efficacy, (p<0.01 versus vehicle injected control mice).

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, deriva-

What is claimed is:
1. A compound of formula:

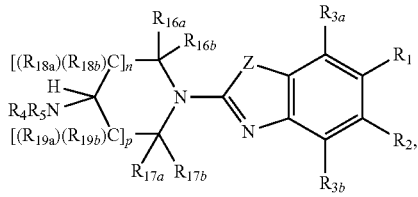
(I)

or a pharmaceutically acceptable salt, ester, or amide-thereof, wherein:

Z is sulfur;

n is an integer from 0 to 2;

p is an integer from 0 to 1;

one of $R_1$ and $R_2$ is a group of the formula -L-$R_6$ or a group of -$L_{2a}$-$R_{6a}$-$L_{2b}$-$R_{6b}$;

the other of $R_1$ and $R_2$ is selected from hydrogen, chloro, cyano, alkoxy, alkoxyalkyl, alkyl, alkylthio, cycloalkyl, fluoro, fluoroalkyl, fluoroalkoxy, hydroxyalkyl, —$SO_2N(R_{14a})(R_{14b})$, and —$N(R_{14a})SO_2(R_{14b})$;

$R_{3a}$ and $R_{3b}$ are each independently selected from hydrogen, cyano, halogen, alkyl, cycloalkyl, fluoroalkyl, alkoxy, alkoxyalkyl, fluoroalkoxy, alkylthio, —$SO_2N(R_{14a})(R_{14b})$, and —$N(R_{14a})SO_2(R_{14b})$;

$R_4$ and $R_5$ are each independently selected from alkyl, fluoroalkyl, hydroxyalkyl, alkoxyalkyl, and cycloalkyl; or $R_4$ and $R_5$ taken together with the nitrogen atom to which each is attached form a non-aromatic ring of the formula:

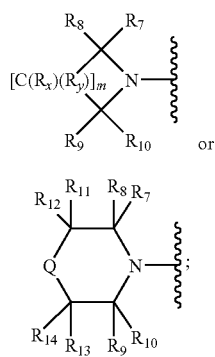
(a)

(b)

$R_7$, $R_8$, $R_9$, and $R_{10}$ at each occurrence are each independently selected from hydrogen, hydroxyalkyl, fluoroalkyl, cycloalkyl, and alkyl;

$R_{11}$, $R_{12}$, $R_{13}$, and $R_{14}$ are each independently selected from hydrogen, hydroxyalkyl, alkyl, and fluoroalkyl;

$R_x$ and $R_y$ at each occurrence are independently selected from the group consisting of hydrogen, hydroxy, hydroxyalkyl, alkyl, alkoxy, alkylamino, fluoro, and dialkylamino;

Q is selected from O and S;

m is an integer from 1 to 5:

$R_6$ is an unsubstituted or substituted group selected from aryl, a 5- to 6-membered heteroaryl ring, an 8- to 12-membered bicyclic heteroaryl ring, and a 4- to 12-membered heterocyclic ring containing two, three, four, or five heteroatoms;

$R_{6a}$ is an unsubstituted or substituted group selected from a divalent 5- to 6-membered heteroaryl ring, a divalent cyanophenyl, a divalent 8- to 12-membered bicyclic heteroaryl ring, and a divalent 4- to 12-membered heterocyclic ring containing two, three, four, or five heteroatoms:

$R_{6b}$ is hydrogen or an unsubstituted or substituted group selected from a 5- to 6-membered heteroaryl ring, an aryl ring, an 8- to 12-membered bicyclic heteroaryl ring, and a 4- to 12-membered heterocyclic ring;

L, $L_{2a}$, $L_{2b}$ are each independently selected from a bond, —O—, alkylene, —C(=O)—, —S—, —$SO_2N(R_{14a})$—, —$N(R_{14a})SO_2$—, and —$C(O)N(R_{14a})$;

$R_{14a}$ and $R_{14b}$ are each independently selected at each occurrence from hydrogen, alkyl, and cycloalkyl;

$R_{16a}$, $R_{16b}$, $R_{17a}$, $R_{17b}$, $R_{18a}$ $R_{18b}$, $R_{19a}$, and $R_{19b}$ are independently selected at each occurrence from hydrogen and lower alkyl; and $R_A$ and $R_B$ are independently selected from hydrogen, alkyl, haloalkyl, alkoxycarbonyl, cycloalkyl, and formyl:

wherein, when substituted, aryl and heteroaryl rings are substituted with one or more substituents selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkyl, fluoroalkoxy, formyl, haloalkoxy, haloalkyl, halogen, hydroxy, hydroxyalkyl, mercapto, nitro, alkylthio, —$NR_AR_B$, ($NR_AR_B$)carbonyl, —$SO_2N(R_{14a})(R_{14b})$, and, —$N(R_{14a})SO_2(R_{14b})$ and;

wherein, when substituted, heterocyclic rings are substituted with 0, 1, 2, 3, 4, 5, 6, 7, 8, or 9 substituents selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkyl, fluoroalkoxy, formyl, haloalkoxy, haloalkyl, halogen, hydroxy, hydroxyalkyl, mercapto, nitro, oxo, alkylthio, —$NR_AR_B$, ($NR_AR_B$)carbonyl-, —$SO_2N(R_{14a})(R_{14b})$, and, —$N(R_{14a})SO_2)(R_{14b})$.

2. The compound of claim 1, wherein $R_1$ is -L-$R_6$, wherein L is a bond and $R_6$ is as defined in claim 1.

3. The compound of claim 1 wherein $R_6$ is an unsubstituted or substituted group selected from furyl, imidazolyl, imidazolidin-2-onyl, isoxazolyl, isothiazolyl, oxazolyl, pyrazinyl, pyrazolyl, pyridazinyl, pyridinyl, pyrimidinyl, pyrrolyl, tetrazolyl, thiadiazolyl, thiadiazolonyl, thiadiazinonyl, oxadiazolyl, oxadiazolonyl, oxadiazinonyl, oxazolidin-2-onyl, thiazolyl, thienyl, triazinyl, triazolyl, pyridazinonyl, pyridonyl, pyrimidinonyl, indolyl, benzothienyl, benzofuranyl, indazolyl, benzimidazolyl, benzothiazolyl, benzoxazolyl, benzoisothiazolyl, benzoisoxazolyl, quinolinyl, isoquinolinyl, quinazolinyl, quinoxalinyl, phthalazinyl, pteridinyl, purinyl, naphthyridinyl, cinnolinyl, thieno[2,3-d]imidazole, pyrrolopyrimidinyl, morpholinyl, piperazinyl, dihydrothiazolyl, thiomorpholinyl, dioxanyl, dithianyl, [1,3]dioxolanyl, quinazolin-4-onyl, and phenyl.

4. The compound of claim 3, wherein $R_6$ is a group selected from cyanophenyl, pyrazolyl, pyrimidinyl, pyrimidinonyl, pyridinyl, pyridazinonyl, imidazolidin-2-onyl, oxazolidin-2-onyl, pyridazinyl, thiazolyl, morpholinyl, and quinazolin-4- onyl, wherein each group is substituted with 0, 1, or 2 substituents selected from hydroxy, methoxy, oxo, amido, alkoxycarbonyl, carboxy, haloalkyl, and methyl.

5. The compound of claim 1, wherein $R_{3a}$ and $R_{3b}$ are hydrogen.

6. The compound of claim 1, wherein $R_4$ and $R_5$ taken together with the nitrogen atom to which each is attached form a non-aromatic ring of formula (a) or formula (b) that is a 4- to 9-membered non-aromatic ring.

7. The compound of claim 1, wherein $R_4$ and $R_5$ are taken together with the nitrogen atom to which each is attached to form a ring selected from azepanyl, azetidinyl, azocanyl, morpholinyl, piperidinyl, and pyrrolidinyl, and wherein each ring is substituted with 0, 1, or 2 substituents selected from alkyl, hydroxyalkyl, and fluoroalkyl.

8. The compound of claim 1, wherein the compound has the formula (II):

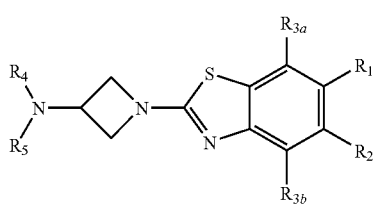

(II)

wherein $R_1, R_2, R_{3a}, R_{3b}, R_4$, and $R_5$ are as defined in claim 1.

9. The compound of claim 1, wherein the compound has the formula (III):

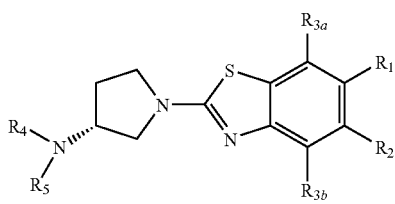

(III)

wherein $R_1, R_2, R_{3a}, R_{3b}, R_4$, and $R_5$ are as defined in claim 1.

10. The compound of claim 1, wherein the compound has the formula (IV):

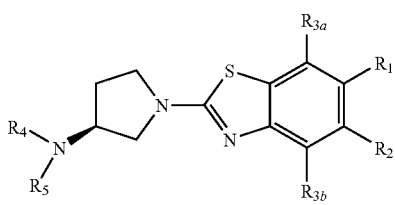

(IV)

wherein $R_1, R_2, R_{3a}, R_{3b}, R4$, and $R_5$ are as defined in claim 1.

11. The compound of claim 1, wherein the compound has the formula (V):

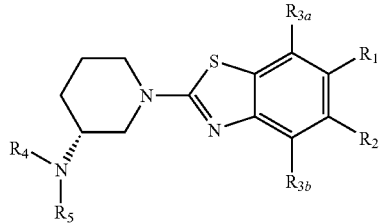

(V)

wherein $R_1, R_2, R_{3a}, R_{3b}, R_4$, and $R_5$ are as defined in claim 1.

12. The compound of claim 1, wherein the compound has the formula (VI):

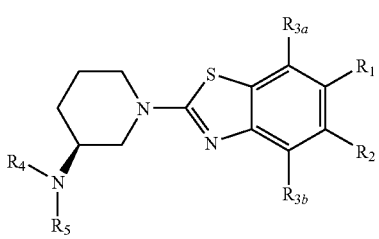

(VI)

wherein $R_1, R_2, R_{3a}, R_{3b}, R_4$, and $R_5$ are as defined in claim 1.

13. The compound of claim 1, wherein the compound has the formula (VII):

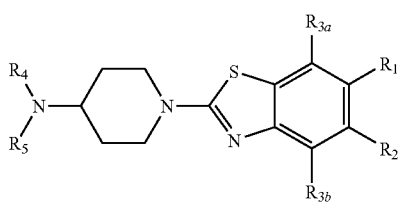

(VII)

wherein $R_1, R_2, R_{3a}, R_{3b}, R_4$, and $R_5$ are as defined in claim 1.

14. The compound of claim 1, wherein one of $R_1$ and $R_2$ is -L-$R_6$, L is a bond, and $R_6$ is a structure of formula:

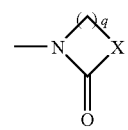

(c)

wherein
X is selected from oxygen, and $NR_{20}$;
q is an integer from 1 to 4; and
$R_{20}$ is selected from hydrogen and lower alkyl.

15. The compound of claim 1, selected from:
6-(1-methyl-1H-pyrazol-4-yl)-2-(3-(piperidin-1-yl)azetidin-1-yl)benzo[d]thiazole;
6-(1-methyl-1H-pyrazol-4-yl)-2-(3-(pyrrolidin-1-yl)azetidin-1-yl)benzo[d]thiazole;
2-(3-(azepan-1-yl)azetidin-1-yl)-6-(1-methyl-1H-pyrazol-4-yl)benzo[d]thiazole;

(R)-6-(1-methyl-1H-pyrazol-4-yl)-2-(3-(2-methylpyrrolidin-1-yl)azetidin-1-yl)benzo[d]thiazole;
6-(1-methyl-1H-pyrazol-4-yl)-2-(3-(2-methylpiperidin-1-yl)azetidin-1-yl)benzo[d]thiazole;
N-ethyl-N-methyl-1-(6-(1-methyl-1H-pyrazol-4-yl)benzo[d]thiazol-2-yl)azetidin-3-amine;
2-(ethyl(1-(6-(1-methyl-1H-pyrazol-4-yl)benzo[d]thiazol-2-yl)azetidin-3-yl)amino)ethanol;
(S)-(1-(1-(6-(1-methyl-1H-pyrazol-4-yl)benzo[d]thiazol-2-yl)azetidin-3-yl)pyrrolidin-2-yl)methanol;
4-(2-((2R,3'R)-2-methyl-1,3'-bipyrrolidin-1'-yl)benzo[d]thiazol-6-yl)benzonitrile;
(R)-4-(2-(1,3'-bipyrrolidin-1'-yl)benzo[d]thiazol-6-yl)benzonitrile;
(R)-4-(2-(3-(piperidin-1-yl)pyrrolidin-1-yl)benzo[d]thiazol-6-yl)benzonitrile;
(R)-6-(2-methoxypyrimidin-5-yl)-2-(3-(piperidin-1-yl)pyrrolidin-1-yl)benzo[d]thiazole;
(R)-2-(3-(piperidin-1-yl)pyrrolidin-1-yl)-6-(pyrimidin-5-yl)benzo[d]thiazole;
(R)-6-(1-methyl-1H-pyrazol-4-yl)-2-(3-(piperidin-1-yl)pyrrolidin-1-yl)benzo[d]thiazole;
(R)-6-(2,6-dimethylpyridin-3-yl)-2-(3-(piperidin-1-yl)pyrrolidin-1-yl)benzo[d]thiazole;
(R)-6-(6-methoxypyridin-3-yl)-2-(3-(piperidin-1-yl)pyrrolidin-1-yl)benzo[d]thiazole;
(R)-2-(2-(3-(piperidin-1-yl)pyrrolidin-1-yl)benzo[d]thiazole-6-yl)pyridazin-3(2H)-one;
(R)-3-(2-(3-(piperidin-1-yl)pyrrolidin-1-yl)benzo[d]thiazol-6-yl)oxazolidin-2-one;
4-(2-((3S)-3-(2-methylpiperidin-1-yl)pyrrolidin-1-yl)benzo[d]thiazol-6-yl)benzonitrile;
(S)-4-(2-(3-(piperidin-1-yl)pyrrolidin-1-yl)benzo[d]thiazol-6-yl)benzonitrile;
(S)-4-(2-(3-(azepan-1-yl)pyrrolidin-1-yl)benzo[d]thiazol-6-yl)benzonitrile;
4-(2-(3'S)-2-methyl-1.3'-bipyrrolidin-1'-yl)benzo[d]thiazol-6-yl)benzonitrile;
(S)-4-(2-(1,3'-bipyrrolidin-1'-yl)benzo[d]thiazol-6-yl)benzonitrile;
4-(2-((2S,3'S)-2-(hydroxymethyl)-1,3'-bipyrrolidin-1'-yl)benzo[d]thiazol-6-yl)benzonitrile;
(S)-4-(2-(3-(diethylamino)pyrrolidin-1-yl)benzo[d]thiazol-6-yl)benzonitrile;
(S)-4-(2-(3-(ethyl(methy)amino)pyrrolidin-1-yl)benzo[d]thiazol-6-yl)benzonitrile;
(S)-4-(2-(3-(isopropyl(methyl)amino)pyrrolidin-1-yl)benzo[d]thiazol-6-yl)benzonitrile;
(S)-2-(2-(1.3'-bipyrrolidin-1'-yl)benzo[d]thiazol-6-yl)pyridazin-3(2H)-one;
(R)-6-(2-(3-(piperidin-1-yl)pyrrolidin-1-yl)benzo[d]thiazol-6-yloxy)nicotinamide;
(R)-N-methyl-5-(2-(3-(piperidin-1-yl)pyrrolidin-1-yl)benzo[d]thiazol-6-yloxy)pyrazine-2-carboxamide;
(R)-2-(2-(3-(piperidin-1-yl)pyrrolidin-1-yl)benzo[d]thiazol-5-yl)pyridazin-3(2H)-one;
(R)-morpholino(2-(3-(piperidin-1-yl)pyrrolidin-1-yl)benzo[d]thiazol-6-yl)methanone;
(R)-isopropyl6-(2-(3-(piperidin-1-yl)pyrrolidin-1-yl)benzo[d]thiazol-6-yl)picolinate;
(R)-6-(2-(3-(piperidin-1-yl)pyrrolidin-1-yl)benzo[d]thiazol-6-yl)picolinic acid;
(R)-methyl6-(2-(3-(piperidin-1-yl)pyrrolidin-1-yl)benzo[d]thiazol-6-yl)picolinate;
(R)-methyl5-(2-(3-(piperidin-1-yl)pyrrolidin-1-yl)benzo[d]thiazol-6-yl)picolinate;
(R)-6-(6-methoxypyridazin-3-yl)-2-(3-(piperidin-1-yl)pyrrolidin-1-yl)benzo[d]thiazole;
(R)-N-methyl-6-(2-(3-(piperidin-1-yl)pyrrolidin-1-yl)benzo[d]thiazol-6-yl)picolinamide;
(R)-N-methyl-2-(2-(3-(piperidin-1-yl)pyrrolidin-1-yl)benzo[d]thiazol-6-yl)isonicotinamide;
(R)-N-methyl-6-(2-(3-(piperidin-1-yl)pyrrolidin-1-yl)benzo[d]thiazol-6-yl)nicotinamide;
(R)-6-(2-(3-(piperidin-1-yl)pyrrolidin-1-yl)benzo[d]thiazol-6-yl)pyridazin-3-ol;
(R)-5-(2-(3-(piperidin-1-yl)pyrrolidin-1-yl)benzo[d]thiazol-6-yl)pyrimidin-2-ol;
(R)-5-(2-(3-(piperidin-1-yl)pyrrolidin-1-yl)benzo[d]thiazol-6-yl)pyridin-2-ol;
(R)-N-methyl-5-(2-(3-(piperidin-1-yl)pyrrolidin-1-yl)benzo[d]thiazol-6-yl)picolinamide;
(R)-N-methyl-2-(2-(3-(piperidin-1-yl)pyrrolidin-1-yl)benzo[d]thiazol-6-yl)thiazole-5-carboxamide;
(R)-N-methyl-5-(2-(3-(piperidin-1-yl)pyrrolidin-1-yl)benzo[d]thiazol-6-yl)nicotinamide;
(R)-N-methyl-6-(2-(3-(piperidin-1-yl)pyrrolidin-1-yl)benzo[d]thiazol-6-yloxy)nicotinamide;
(R)-N-methyl-6-(2-(3-(piperidin-1-yl)pyrrolidin-1-yl)benzo[d]thiazol-6-yloxy)picolinamide;
(R)-N-methyl-2-(2-(3-(piperidin-1-yl)pyrrolidin-1-yl)benzo[d]thiazol-6-yloxy)isonicotinamide;
(R)-N-methyl-5-(2-(3-(piperidin-1-yl)pyrrolidin-1-yl)benzo[d]thiazol-6-yloxy)picolinamide;
(R)-N-methyl-2-(2-(3-(piperidin-1-yl)pyrrolidin -1-yl)benzo[d]thiazol-6-yloxy)thiazole-5-carboxamide;
(R)-6-(6-methoxypyridazin-3-yloxy)-2-(3-(piperidin-1-yl)pyrrolidin-1-yl)benzo[d]thiazole;
(R)-6-(6-methoxypyridin-2-yloxy)-2-(3-(piperidin-1-yl)pyrrolidin-1-yl)benzo[d]thiazole;
(R)-6-(2-(3-(piperidin-1-yl)pyrrolidin-1-yl)benzo[d]thiazol-6-yloxy)pyridazin-3-ol;
3-[2-((R)-3-piperidin-1-yl-pyrrolidin-1-yl)-benzothiazol-6-yl]-3H-pyrimidin-4-one;
6-methyl-3-[2-((R)-3-piperidin-1-yl-pyrrolidin-1-yl)-benzothiazol-6-yl]-3H-pyrimidin-4-one;
4-[2-((R)-3-piperidin-1-yl-pyrrolidin-1-yl)-benzothiazol-6-yl]-morpholin-3-one;
2-methyl-3-[2-((R)-3-piperidin-1-yl-pyrrolidin-1-yl)-benzothiazol-6-yl]-3H-quinazolin-4-one;
2,8-dimethyl-3-[2-((R)-3-piperidin-1-yl-pyrrolidin-1-yl)-benzothiazol-6-yl]-3H -quinazolin-4-one; and 2-methyl-3-[2-((R)-3-piperidin-1-yl)-pyrrolidin-1-yl)-benzothiazol-6-yl]-8-trifluoromethyl-3 H-quinazol in-4-one.

16. A pharmaceutical composition comprising a therapeutically effective amount of a compound of claim 1 in combination with a pharmaceutically acceptable carrier.

\* \* \* \* \*